United States Patent
Miyake et al.

(10) Patent No.: US 10,968,168 B2
(45) Date of Patent: Apr. 6, 2021

(54) ISOCYANATE PRODUCTION METHOD

(71) Applicant: ASAHI KASEI KABUSHIKI KAISHA, Tokyo (JP)

(72) Inventors: Nobuhisa Miyake, Tokyo (JP); Koichi Nakaoka, Tokyo (JP); Tsubasa Uematsu, Tokyo (JP); Yusuke Sakurai, Tokyo (JP); Yusuke Ishii, Tokyo (JP); Kazuhiro Takagaki, Tokyo (JP); Takeharu Sasaki, Tokyo (JP); Yuji Kosugi, Tokyo (JP); Atsushi Ohkubo, Tokyo (JP); Masaaki Shinohata, Tokyo (JP)

(73) Assignee: Asahi Kasei Kabushiki Kaisha, Tokyo (JP)

( * ) Notice: Subject to any disclaimer, the term of this patent is extended or adjusted under 35 U.S.C. 154(b) by 0 days.

(21) Appl. No.: 16/610,404

(22) PCT Filed: May 15, 2018

(86) PCT No.: PCT/JP2018/018830
§ 371 (c)(1),
(2) Date: Nov. 1, 2019

(87) PCT Pub. No.: WO2018/212208
PCT Pub. Date: Nov. 22, 2018

(65) Prior Publication Data
US 2020/0115327 A1 Apr. 16, 2020

(30) Foreign Application Priority Data

| May 15, 2017 | (JP) | JP2017-096766 |
|---|---|---|
| May 15, 2017 | (JP) | JP2017-096767 |
| May 15, 2017 | (JP) | JP2017-096768 |
| May 15, 2017 | (JP) | JP2017-096769 |
| May 15, 2017 | (JP) | JP2017-096770 |
| May 15, 2017 | (JP) | JP2017-096771 |
| May 15, 2017 | (JP) | JP2017-096772 |
| May 15, 2017 | (JP) | JP2017-096773 |
| May 15, 2017 | (JP) | JP2017-096774 |
| May 15, 2017 | (JP) | JP2017-096775 |
| May 15, 2017 | (JP) | JP2017-096776 |
| May 15, 2017 | (JP) | JP2017-096781 |

(51) Int. Cl.
C07C 263/20 (2006.01)
C07D 263/04 (2006.01)
C07C 263/04 (2006.01)

(52) U.S. Cl.
CPC .......... *C07C 263/04* (2013.01); *C07C 263/20* (2013.01)

(58) Field of Classification Search
CPC ................. C07C 263/04; C07C 263/20
See application file for complete search history.

(56) References Cited

U.S. PATENT DOCUMENTS

| 3,939,200 A | 2/1976 | Emmons et al. |
|---|---|---|
| 3,992,430 A | 11/1976 | Bacskai |
| 5,633,396 A | 5/1997 | Bischof et al. |
| 5,731,458 A | 3/1998 | Dahmer et al. |
| 6,333,427 B1 | 12/2001 | Miyake et al. |
| 2003/0125579 A1 | 7/2003 | Yoshida et al. |
| 2007/0015932 A1 | 1/2007 | Fujita et al. |
| 2010/0069665 A1 | 3/2010 | Shinohata et al. |
| 2011/0054211 A1 | 3/2011 | Shinohata et al. |
| 2011/0133121 A1 | 6/2011 | Shinohata et al. |
| 2013/0184488 A1 | 7/2013 | Shinohata et al. |
| 2015/0197483 A1 | 7/2015 | Harrington et al. |

FOREIGN PATENT DOCUMENTS

| EP | 0044363 A1 | 1/1982 |
|---|---|---|
| JP | 53-135931 A | 11/1978 |
| JP | 55-105649 A | 8/1980 |
| JP | 55-105650 A | 8/1980 |
| JP | 56-100752 A | 8/1981 |
| JP | 60-188356 A | 9/1985 |
| JP | 60-222450 A | 11/1985 |
| JP | 60-231640 A | 11/1985 |

(Continued)

OTHER PUBLICATIONS

Hoffmann, "On the Aromatic Cyanates," Berlin University Laboratory, Berichte der Deutechen Chemischen Gesellschaft, vol. 3, pp. 653-658, 1870.
Dyer et al., "Thermal Degradation of Alkyl N-Phenylcarbamates," Journal of American Chemical Society, vol. 81, pp. 2138-2143, 1959.
International Search Report issued in International Application No. PCT/JP2018/018830 dated Aug. 14, 2018.
Written Opinion of the International Searching Authority issued in International Application No. PCT/JP2018/018830 dated Aug. 14, 2018.

*Primary Examiner* — Shawquia Jackson
(74) *Attorney, Agent, or Firm* — Morgan, Lewis & Bockius LLP

(57) ABSTRACT

An isocyanate production method according to the present invention is a method in which an isocyanate is produced by subjecting a carbamate to thermal decomposition, and includes: a step of preparing a mixture liquid containing the carbamate, an inactive solvent and a polyisocyanate compound; a step of conducting a thermal decomposition reaction of the carbamate by continuously introducing the mixture liquid into a thermal decomposition reactor; a step of collecting a low-boiling decomposition product by continuously extracting the low-boiling decomposition product in a gaseous state from the reactor, the low-boiling decomposition product having a boiling point lower than the polyisocyanate compound; and a step of collecting a high-boiling component by continuously extracting, from the reactor, a liquid phase component which is not collected in a gaseous state at the step of collecting the low-boiling decomposition product.

19 Claims, 2 Drawing Sheets

(56) References Cited

FOREIGN PATENT DOCUMENTS

| | | | |
|---|---|---|---|
| JP | 61-53248 | A | 3/1986 |
| JP | 61-053249 | A | 3/1986 |
| JP | 61-053254 | A | 3/1986 |
| JP | 01-121259 | A | 5/1989 |
| JP | 01-230550 | A | 9/1989 |
| JP | 05-065253 | A | 3/1993 |
| JP | 06-192207 | A | 7/1994 |
| JP | 08-157431 | A | 6/1996 |
| JP | 09-12525 | A | 1/1997 |
| JP | 09-249632 | A | 9/1997 |
| JP | 11-171929 | A | 6/1999 |
| JP | 2001-199951 | A | 7/2001 |
| JP | 2003-252840 | A | 9/2003 |
| JP | 2003-252846 | A | 9/2003 |
| JP | 2007-22932 | A | 2/2007 |
| JP | 2012-233014 | A | 11/2012 |
| JP | 2013-517312 | A | 5/2013 |
| JP | 2013-107909 | A | 6/2013 |
| WO | 2009-139061 | A1 | 11/2009 |
| WO | 2011-021257 | A1 | 2/2011 |
| WO | 2012-046734 | A1 | 4/2012 |
| WO | 2013-008891 | A1 | 1/2013 |

ISOCYANATE PRODUCTION METHOD

TECHNICAL FIELD

The present invention relates to an isocyanate production method.

The present invention claims priority on the basis of Japanese Patent Application No. 2017-096776, Japanese Patent Application No. 2017-096766, Japanese Patent Application No. 2017-096767, Japanese Patent Application No. 2017-096768, Japanese Patent Application No. 2017-096769, Japanese Patent Application No. 2017-096770, Japanese Patent Application No. 2017-096771, Japanese Patent Application No. 2017-096772, Japanese Patent Application No. 2017-096773, Japanese Patent Application No. 2017-096774, Japanese Patent Application No. 2017-096775, and Japanese Patent Application No. 2017-096781, filed in Japan on May 15, 2017, the contents of which are incorporated herein by reference.

BACKGROUND OF THE INVENTION

An isocyanate is widely used as a raw material to prepare a polyurethane foam, a coating material, an adhesive agent or the like. The major industrial production method of an isocyanate is a method in which an amine compound and a phosgene are reacted (phosgene method), and almost all global production thereof is produced by the phosgene method. However, the phosgene method causes many problems.

As the first problem, a large amount of phosgene is used as a starting material. Phosgene has excessively high toxicity, and therefore requires particular attention to prevent exposure thereof to engaged persons, as well as particular equipments to remove wastage.

As the second problem, a large amount of hydrogen chloride having high corrosiveness is produced as a by-product, and therefore a process to remove the hydrogen chloride is required. In addition, the resultant isocyanate often contains hydrolyzable chlorine. Accordingly, there is a case where the use of the isocyanate produced by the phosgene method causes adverse effects on the weather-resistance or the heat-resistance of polyurethane products.

In view of such a background, a production method of an isocyanate compound in which no phosgene is used has been desired. As one of the production methods of an isocyanate compound in which no phosgene is used, a method in which a carbamic acid ester is subjected to thermal decomposition has been proposed. It is conventionally known that the thermal decomposition of the carbamic acid ester produces an isocyanate and a hydroxy compound (see, for example, Non-Patent Document 1). The basic reaction is illustrated by the following formula.

$$R(NHCOOR')a \rightarrow R(NCO)a + aR'OH \quad (1)$$

In the formula, R represents an organic residual group with a valency of a, R' represents a monovalent organic residual group, and a represents an integer of 1 or more.

Patent Document 1 discloses a method for preparing an isocyanate by subjecting carbamate to thermal decomposition in the presence of an inactive solvent in a flask.

In contrast, the thermal decomposition reaction of a carbamic acid ester easily causes various irreversible side reactions such as an unfavorable thermal denaturation reaction of a carbamic acid ester, or a condensation reaction of an isocyanate produced by the thermal decomposition. Examples of the side reactions include: a reaction in which a urea bond is formed; a reaction in which carbodiimides are formed; and a reaction in which isocyanurates are formed (see, for example, Non-Patent Documents 1 and 2).

Such side reactions not only cause a decrease in the yield or selectivity of a target isocyanate, but also may cause precipitation of polymeric solid content particularly in isocyanate production, which causes difficulty in long-term operation by clogging a reactor or the like.

DOCUMENTS OF RELATED ART

Patent Documents

Patent Document 1: Japanese Unexamined Patent Application Publication No. 2003-252846

Non-Patent Documents

Non-Patent Document 1: Berchte der Deutechen Chemischen Gesellschaft, volume 3, page 653, 1870
Non-Patent Document 2: Journal of American Chemical Society, volume 81, page 2138, 1959

SUMMARY OF THE INVENTION

Problems to be Solved by the Invention

Although the above-mentioned Patent Document 1 discloses a method in which a carbamate is supplied to a reactor to conduct the thermal decomposition while extracting the resultant isocyanate, the mechanism that realizes extraction of high-boiling components produced by side reaction is absent, and therefore it is difficult to produce isocyanate continuously for a long time.

The present invention is made in view of the above-mentioned circumstances, and aims to provide an isocyanate production method continuously while suppressing the occurrence of side reactions.

Means to Solve the Problems

The present invention encompasses [1] to [12] mentioned below.
[1] An isocyanate production method in which an isocyanate is produced by thermal decomposition of a carbamate, including:
a step of preparing a mixture liquid containing the carbamate and a polyisocyanate compound;
a step of conducting a thermal decomposition reaction of the carbamate by continuously introducing the mixture liquid into a thermal decomposition reactor:
a step of collecting a low-boiling decomposition product by continuously extracting the low-boiling decomposition product in a gaseous state from the thermal decomposition reactor, the low-boiling decomposition product having a standard boiling point lower than the polyisocyanate compound; and
a step of collecting a high-boiling component by continuously extracting, from the thermal decomposition reactor, a liquid phase component which is not collected in a gaseous state at the step of collecting the low-boiling decomposition product, as the high-boiling component.
[2] The isocyanate production method according to [1], wherein the mixture liquid contains an inactive solvent,
the inactive solvent is continuously extracted in a gaseous state from the thermal decomposition reactor together with the low-boiling decomposition product having a boiling point lower than the polyisocyanate compound in the step of collecting the low-boiling decomposition product, and the inactive solvent is substantially inactive under thermal decomposition reaction conditions, and has a boiling point between a boiling point of the isocyanate produced by thermal decomposition and a boiling point of a hydroxy compound.

[3] The method according to [1] or [2], wherein the carbamate is a carbamate of formula (20).

(20)

In the formula (20), c represents an integer of 1 or more, $R^1$ represents an organic group having a valency of c, $R^3$ represents a residual group obtained by removing one hydroxy group from a hydroxy compound, and plural $R^3$ are identical to or different from each other.

[4] The method according to any one of [1] to [3], wherein the thermal decomposition reactor is a tubular reactor.

[5] The method according to any one of [1] to [4], wherein the low-boiling decomposition product extracted from the thermal decomposition reactor in a gaseous state contains an isocyanate compound, and the method further including a step in which the low-boiling decomposition product is supplied in a gaseous state to a distillation column and the isocyanate is separated in the distillation column.

[6] The method according to any one of [1] to [5], wherein the step of conducting the thermal decomposition reaction includes:

a step of preparing the liquid phase component in which the mixture liquid is continuously introduced into a first reactor containing a vertical tubular reactor to conduct a first decomposition reaction while allowing the mixture liquid to fall down inside the first reactor, and the liquid phase component is obtained from a bottom of the first reactor; and a decomposition step in which the liquid phase component is introduced into a second reactor containing a tank reactor and a second decomposition reaction is conducted to decompose the carbamate into the isocyanate and a hydroxy compound;

wherein, in the step of collecting the low-boiling decomposition product, the low-boiling decomposition product is extracted continuously in a gaseous state from the first reactor or both the first reactor and the second reactor, in the step of collecting the high-boiling component, the liquid phase component contains a high-boiling decomposition product having a standard boiling point higher than a standard boiling point of the low-boiling decomposition product, and the high-boiling decomposition product is extracted continuously from the second reactor together with the polyisocyanate compound, the isocyanate is contained in the low-boiling decomposition product and the high-boiling decomposition product, and a difference between a temperature in the first reactor and a temperature in the second reactor is 50° C. or lower.

[7] The isocyanate production method according to [6], further including a recycle step in which, in the step of collecting the low-boiling decomposition product, an inactive solvent vapor is extracted continuously in a gaseous state together with the low-boiling decomposition product from the first reactor or both the first reactor and the second reactor, the gas component extracted continuously is introduced into a partial condenser in which a temperature thereof is maintained at a temperature which allows partial or entire condensation of the inactive solvent vapor but does not allow partial or entire condensation of the low-boiling decomposition product to separate the gas component into a gaseous component mainly containing the low-boiling decomposition product and a liquid-form component mainly containing the inactive solvent, and then the liquid-form component is partially or entirely returned to the first reactor or both the first reactor and the second reactor.

[8] The isocyanate production method according to [6] or [7], wherein a tubular reactor, an inside of which is filled with either a solid filler content or a solid catalyst or both thereof, is used as the first reactor.

[9] The isocyanate production method according to [6] or [7], wherein a tubular reactor in which a tray is placed is used as the first reactor.

[10] The isocyanate production method according to [6] or [7], wherein a tubular reactor in which a tray is placed, the tubular reactor being filled with either a solid filler content or a solid catalyst or both thereof, is used as the first reactor.

[11] The isocyanate production method according to any one of [6] to [10], wherein the gas component generated in the second reactor is introduced into the first reactor from a bottom thereof.

[12] The isocyanate production method according to any one of [6] to [11], wherein a carrier agent in a gaseous state, which is substantially inactive under thermal decomposition reaction conditions, is introduced into either the first reactor or the second reactor or both thereof from a bottom thereof, and a gas component is extracted from a top thereof.

[13] The isocyanate production method according to any one of [6] to [12], wherein a carrier agent is introduced into a liquid in the second reactor.

Effects of the Invention

According to the present invention, an isocyanate production method by which an isocyanate is produced continuously while suppressing occurrence of a side reaction is provided.

BRIEF DESCRIPTION OF DRAWINGS

FIG. 1 indicates a thermal decomposition reactor used in Example 1 and the like.

FIG. 2 indicates a thermal decomposition reactor used in Example 81 and the like.

FIG. 3 indicates a thermal decomposition reactor used in Example 161 and the like.

EMBODIMENTS FOR CARRYING OUT THE INVENTION

Figure 1:
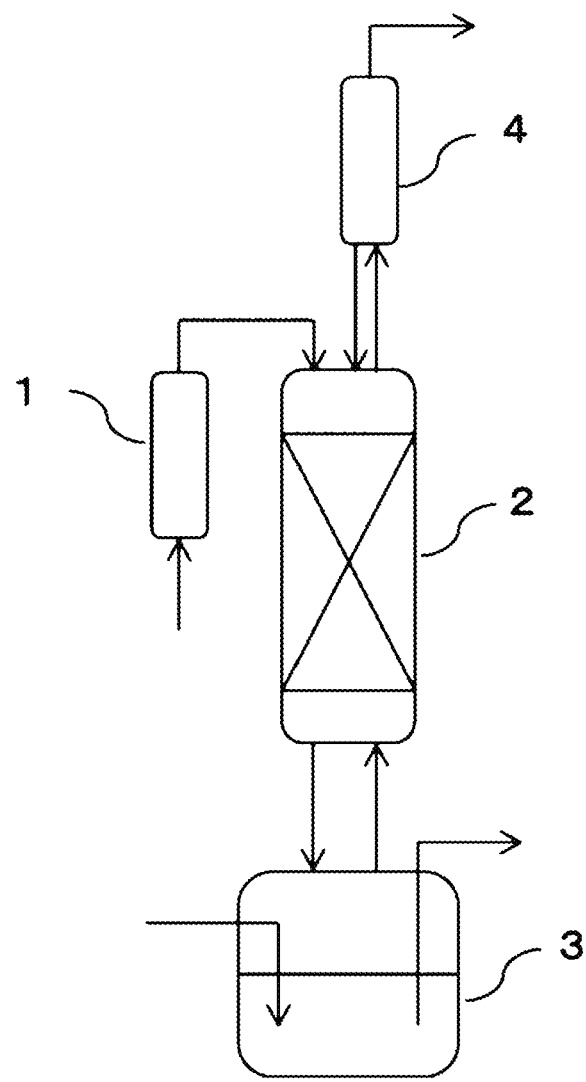

Embodiments for carrying out the present invention (hereinafter, referred to as "present embodiment") will be specifically described below. The below-mentioned present embodiments are examples to explain the present invention, and are not intended to limit the present invention to the below-mentioned present embodiments. The present invention may be modified in various ways within the summary thereof.

<Isocyanate Production Method>

The present embodiment is a method for producing an isocyanate by subjecting a carbamate to thermal decomposition.

The isocyanate production method according to the present embodiment includes:

a step of preparing a mixture liquid containing a carbamate and a polyisocyanate compound;

a step of conducting a thermal decomposition reaction of the carbamate by continuously introducing the mixture liquid into a thermal decomposition reactor;

a step of collecting a low-boiling decomposition product by continuously extracting the low-boiling decomposition product in a gaseous state from the reactor, the low-boiling decomposition product having a boiling point lower than the polyisocyanate compound; and a step of collecting a high-boiling component by continuously extracting, from the reactor, a liquid phase component which is not collected in a gaseous state at the step of collecting the low-boiling decomposition product.

<Isocyanate>

An isocyanate produced according to the present embodiment is a compound corresponding to "its hydrocarbonyl derivatives: RN=C=O" in the last half of "The isocyanic acid tautomer, HN=C=O, of cyanic acid, HOC=N and its hydrocarbonyl derivative: RN=C=O." in the section "isocyanates" in Rule C-8 stipulated by Nomenclature (IUPAC Nomenclature of Organic Chemistry) defined in IUPAC (The International Union of Pure and Applied Chemistry), and preferably a compound of formula (2) shown below.

$$R^1\text{-}(NCO)_c \quad (2)$$

In the formula (2), c represents an integer of 1 or more, preferably 2 to 10, more preferably 2 to 4, and even more preferably 2 or 3. $R^1$ represents an organic group having a valency of c.

In the formula (2), $R^1$ preferably represents a C3-85 organic group, and more preferably a C3-30 organic group.

$R^1$ preferably represents an aliphatic group, an aromatic group, or a group formed by bonding an aliphatic group and an aromatic group. Specific examples of $R^1$ include: cyclic groups such as cyclic hydrocarbon groups (monocyclic hydrocarbon groups, condensed polycyclic hydrocarbon groups, cross-linked cyclic hydrocarbon groups, spiro hydrocarbon groups, ring-assembly hydrocarbon groups, side chain-containing cyclic hydrocarbon groups), heterocyclic groups, heterocyclic spiro groups, and hetero cross-linked cyclic groups; acyclic hydrocarbon groups, groups formed by bonding an acyclic hydrocarbon group and at least one cyclic group, and groups formed by bonding the above-mentioned group and a specific nonmetallic atom (carbon, oxygen, nitrogen, sulfur or silicon) via a covalent bond.

The covalent bond with the specific nonmetallic atom may generate the state, for example, in which the above-mentioned group is bonded with any of groups of formulae (3) to (15) via a covalent bond.

  (3)

  (4)

  (5)

  (6)

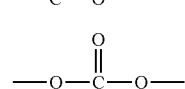  (7)

(8)

  (9)

  (10)

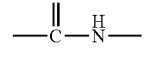  (11)

  (12)

  (13)

  (14)

  (15)

Among these, $R^1$ preferably represents an aliphatic hydrocarbon group, an aromatic hydrocarbon group, or a group formed by bonding a single kind or plural kinds of aliphatic hydrocarbon groups and/or aromatic hydrocarbon groups via an ether bond (—O—), a thioether bond (—S—), an ester bond (—COO—), or an amide bond (—CONH—), and more preferably represents an aliphatic hydrocarbon group, an aromatic hydrocarbon group, or a group formed by bonding a single kind or plural kinds of aliphatic hydrocarbon groups and/or aromatic hydrocarbon groups via an ester bond. The number of carbon atoms constituting $R^1$ is preferably 1 to 30.

As an isocyanate produced by the method according to the present embodiment, c in the formula (2) is preferably an integer of 2 to 5, more preferably 2 or 3, and even more preferably 3, from the viewpoint of ease of production or handling. An isocyanate having a bond of formula (3) to (5), (7), (9), (11) or (12) is preferable, and an isocyanate having a bond of formula (7), (9) or (12) is more preferable.

Examples of monofunctional isocyanate compounds in which c in the formula (2) is 1 include: C1-30 aliphatic isocyanates, C6-30 alicyclic isocyanates, and C6-30 aromatic group-containing isocyanates.

Examples of monofunctional isocyanate compounds in which c in the formula (2) is 1 further include isocyanates having: an ester bond or an amide bond of formula (A-2) mentioned below; and one isocyanate group.

Examples of difunctional diisocyanate compounds in which c in the formula (2) is 2 include C4-30 aliphatic diisocyanates, C8-30 alicyclic diisocyanates, and C8-30 aromatic group-containing diisocyanates.

Examples of C4-30 aliphatic diisocyanates include 1,4-tetramethylene diisocyanate, 1,5-pentamethylene diisocyanate, 1,4-diisocyanato-2-methylbutane, 1,6-hexamethylene diisocyanate, 1,6-diisocyanato-2,5-dimethylhexane, 2,2,4-trimethyl-1,6-hexamethylene diisocyanate, lysine methyl ester diisocyanate, and lysine ethyl ester diisocyanate.

Examples of C8-30 alicyclic diisocyanates include isophorone diisocyanate, 1,3-bis(isocyanatemethyl)-cyclohexane, 4,4'-dicyclohexylmethane diisocyanate, hydrogenated tetramethylxylylene diisocyanate, and norbornene diisocyanate.

Examples of C8-30 aromatic group-containing diisocyanates include 4,4'-diphenylmethane diisocyanate, 2,6-tolylene diisocyanate, xylylene diisocyanate, tetramethylxylylene diisocyanate, and naphthalene diisocyanate.

In the case where the above-mentioned compound has structural isomers, the structural isomers are encompassed in the above-mentioned examples.

Examples of difunctional diisocyanate compounds in which c in the formula (2) is 2 further include isocyanates having: an ester bond or an amide bond of formula (A-1) or (A-2) mentioned below; and two isocyanate groups.

As a trifunctional isocyanate in which c in the formula (2) is 3, an isocyanate of formula (16) shown below is preferable.

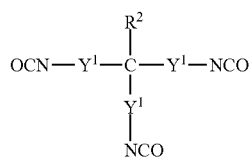

(16)

In the formula (16), plural $Y^1$ each independently represent a single bond, or a C1-20 divalent hydrocarbon group which may have a bond selected from the group consisting of an ester bond, an ether bond and an amide bond, and $R^2$ represents a hydrogen atom or a C1-12 monovalent hydrocarbon group.

$R^2$ in the formula (16) is preferably a hydrogen atom, a C1-10 aliphatic group, or a C6-10 aromatic group, and specific examples thereof include: aliphatic groups such as a methyl group, an ethyl group, a propyl group, a butyl group, a pentyl group, a hexyl group, and a decyl group; and aromatic groups such as a phenyl group, a methylphenyl group, an ethylphenyl group, a butylphenyl group, a dimethylphenyl group, and a diethylphenyl group.

In the formula (16), $Y^1$ preferably represents a single bond, a C1-20 divalent aliphatic group, a C6-20 divalent aromatic group, a C2-20 divalent group formed by bonding aliphatic groups via an ester bond, a C2-20 divalent group formed by bonding an aliphatic group and an aliphatic group via an ether bond, a C7-20 divalent group formed by bonding an aliphatic group and an aromatic group via an ester bond, a C7-20 divalent group formed by bonding an aliphatic group and an aromatic group via an ether bond, a C14-20 divalent group formed by bonding an aromatic group and an aromatic group via an ester bond, or a C14-20 divalent group formed by bonding an aromatic group and an aromatic group via an ether bond.

Further specific examples of the isocyanate compound of the formula (16) include: compounds in which $Y^1$ in the formula (16) is a C1-20 divalent aliphatic group or a C6-20 divalent aromatic group; compounds of formula (17), (18) or (19), shown below: and isocyanates having an ester bond or an amide bond of formula (A-2) mentioned below and three isocyanate groups.

Examples of the compounds in which $Y^1$ in the formula (16) is a C1-20 divalent aliphatic group and/or a C6-20 divalent aromatic group include 1,2,3-propane triisocyanate, 1,8-diisocyanate-4-isocyanate methyloctane, 1,3,6-triisocyanate hexane, 1,8-diisocyanato-4-(isocyanatomethyl)-2,4,7-trimethyloctane, 1,5-diisocyanato-3-(isocyanatomethyl) pentane, 1,6,11-triisocyanatoundecane, 1,4,7-triisocyanatoheptane, 1,2,2-triisocyanatobutane, 1,2,6-triisocyanatohexane, 1-isocyanato-2,2-bis (isocyanatomethyl)butane, 1,3,5-triisocyanatocyclohexane, 1,7-diisocyanato-4-(3-isocyanatopropyl)heptane, 1,3-diisocyanato-2-(isocyanatomethyl)-2-methylpropane, 1,3,5-triisocyanatobenzene, 1,3,5-triisocyanato-2-methylbenzene, 1,3,5-tris(1-isocyanatopropane-2-yl)benzene, 1,3,5-tris(1-isocyanatopropane-2-yl)-2-methylbenzene, 1,3,5-tris(1-isocyanatomethyl)-2-methylbenzene, and 2,2'-((2-isocyanato-1,3-phenylene)bis(methylene))bis(isocyanatebenzene).

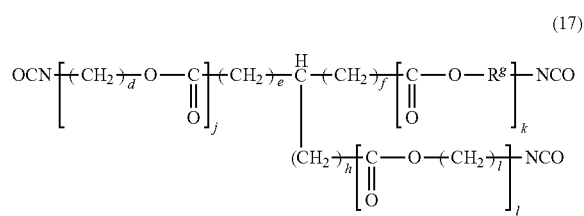

(17)

In the formula (17), $R^g$ represents a C1-10 aliphatic hydrocarbon group, d and I each independently represent an integer of 1 to 4, e, f, and h each independently represent an integer of 0 to 5, j, k and l each independently represent 0 or 1, and the sum of j, k, and l is 1 to 3.

Specific examples of the compound of the formula (17) include: 2-isocyanatoethyl-2,5-diisocyanatopentanoate in which e is 3, f and h are 0, j and l are 0, k is 1, and $R^g$ is an ethylene group; 2-isocyanatoethyl-2,6-diisocyanatohexanoate in which e is 4, f and h are 0, j and l are 0, k is 1, and $R^g$ is an ethylene group; bis(2-isocyanatoethyl)-2-isocyanatobutanedioate in which d is 2, e is 1, f and h are 0, j and k are 1, l is 0, and $R^g$ is an ethylene group; bis(2-isocyanatoethyl)-2-isocyanatopentanedioate in which d is 2, $R^g$ is an ethylene group, e is 2, f and h are 0, j and k are 1, and l is 0; and tris(2-isocyanatoethyl)hexane-1,3,6-tricarboxylate in which d and i are 2, $R^g$ is an ethylene group, j, k and l are 1, e is 3, f is 2, and h is 0.

Among these, a method for producing an aliphatic isocyanate of formula (I) shown below is preferable.

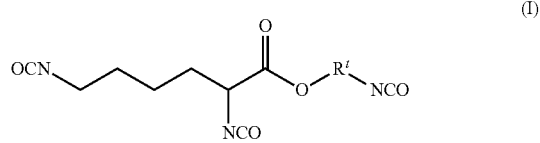

(I)

In the formula (I), $R^t$ represents an alkylene group.
The alkylene group in the formula (I) is preferably a C1-6 linear or branched alkylene group, and more preferably a C2-4 linear or branched alkylene group, and specific examples thereof include an ethylene group, a propylene group, a butylene group, an isobutylene group, and a pentylene group. Among these, an ethylene group is preferable.

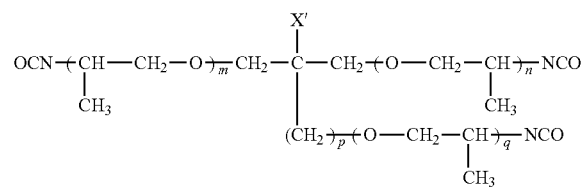
(18)

In the formula (18), X' represents a C1-4 hydrocarbon group, m, n, and q each represent an integer of 1 or more, the sum of m, n, and q is 3 to 99, and p represents an integer of 0 to 3.

A compound of formula (19) shown below is also preferable as an isocyanate compound produced according to the present embodiment.

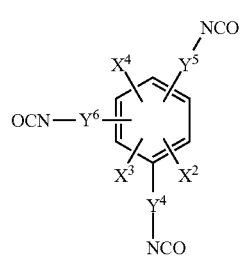
(19)

In the formula (19), $X^2$ to $X^4$ each independently represent a hydrogen atom or a C1-12 monovalent hydrocarbon group, and $Y^4$ to $Y^6$ each independently represent a C1-20 divalent hydrocarbon group which may have an ester bond and/or an ether bond, or a single bond.

In the formula (19), $X^2$ to $X^4$ preferably represent a group defined as $R^2$ in the formula (16), and more preferably a hydrogen atom.

$Y^4$ to $Y^6$ preferably represent a single bond, a C1-20 divalent aliphatic group, a C6-20 divalent aromatic group, a C2-20 divalent group formed by bonding an aliphatic group and an aliphatic group via an ester bond, a C2-20 divalent group formed by bonding an aliphatic group and an aliphatic group via an ether bond, a C7-20 divalent group formed by bonding an aliphatic group and an aromatic group via ester bond, a C7-20 divalent group formed by bonding an aliphatic group and an aromatic group via an ether bond, a C14-20 divalent group formed by bonding an aromatic group and an aromatic group via an ester bond, or a C14-20 divalent group formed by bonding an aromatic group and an aromatic group via an ether bond, and more preferably a single bond, a C1-20 divalent aliphatic group, or a C6-20 divalent aromatic group.

In addition, the trifunctional isocyanate may be a compound formed by trimerization of three molecules of difunctional isocyanates via an isocyanurate ring structure or a biuret bond.

Specific examples of the compound of formula (19) include 1,3,5-triisocyanatobenzene, 1,3,5-triisocyanato-2-methylbenzene, 1,3,5-tris(1-isocyanatopropane-2-yl)benzene, 1,3,5-tris(1-isocyanatopropane-2-yl)-2-methylbenzene, 1,3,5-tris(1-isocyanatomethyl)-2-methylbenzene, and 2,2'-((2-isocyanato-1,3-phenylene)bis(methylene))bis(isocyanatebenzene).

The isocyanate according to the present embodiment may also be a compound of formula (A-1) or (A-2) shown below.

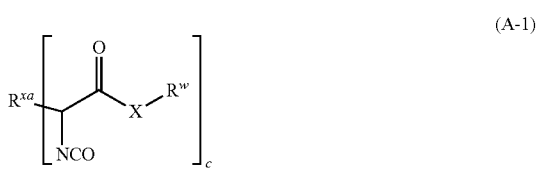
(A-1)

In the formula, $R^{xa}$ represents an aliphatic group having a carbon number of 1 or more or an aromatic group having a carbon number of 6 or more, which may contain an isocyanate group, a sulfur atom, an oxygen atom, or a halogen atom.

X represents an oxygen atom or a secondary amino group (—NH—), and preferably an oxygen atom.

$R^w$ represents a C1-15 aliphatic group, a C6-15 aromatic group or a hydrogen atom.

c represents 2 or 3.

In the formula (A-1), $R^{xa}$ preferably represents a structure formed by removing a —NHCOOH group from an amino acid, and more preferably a C1-15 aliphatic group or a C6-15 aromatic group.

Preferable examples of the compound of the formula (A-1) include compounds of below-shown formulae.

α-amino acids have two possible sterically binding modes of an amino group or a carboxyl group to an a carbon, and are respectively distinguished as D-type or L-type photoisomer. The amino acid (and a compound having an amino acid skeleton) available in the present embodiment may be D-type, L-type, a mixture thereof, or a racemic body. Many industrially inexpensively available amino acids are amino acids produced by fermentation, and are almost all L-type, which are preferably used. Although the steric configuration is not shown in the present specification, the steric configuration is either D-type or L-type.

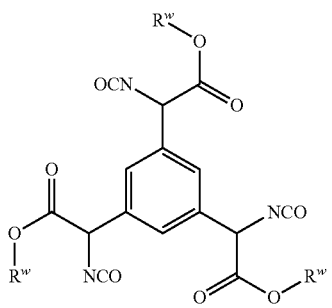

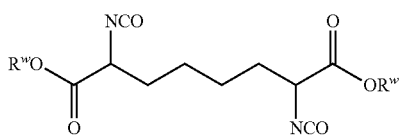

-continued

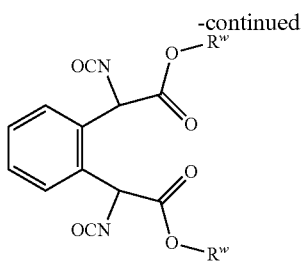

In the formulae, R$^w$ preferably represents a methyl group.

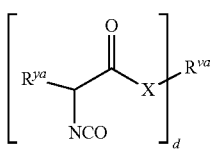 (A-2)

In the formula, X represents a group defined in the formula (A-1),

R$^{ya}$ represents an aliphatic group having a carbon number of 1 or more or an aromatic group having a carbon number of 6 or more, which may contain an isocyanate group, a sulfur atom, an oxygen atom, or a halogen atom, or a hydrogen atom, R$^{va}$ represents a C1-15 aliphatic group or a C6-15 aromatic group, which may have an isocyanate group, or a hydrogen atom, and d represents an integer of 1 to 4.

In the formula (A-2), R$^{ya}$ represents a C1-15 aliphatic group which may have a group selected from the group consisting of groups of formulae (i-1) to (ii-1) and (iii-1) to (iv-1); a C6-15 aromatic group which may have a group selected from the group consisting of groups formulae (i-1) to (ii-1) and (iii-1) to (iv-1); a C7-15 group formed by bonding an aliphatic group and an aromatic group, which may have a group selected from the group consisting of groups formulae (i-1) to (ii-1) and (iii-1) to (iv-1); a group of one of formulae (IV-1) to (V-1), or a hydrogen atom.

—O— (i-1)

—S— (ii-1)

—NCO (iii-1)

—S—S— (iv-1)

In the formulae (i-1) to (iv-1), an atom to which a nitrogen atom or a sulfur atom bonds is a carbon atom.

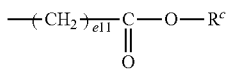 (IV-1)

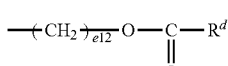 (V-1)

In the formula (IV-1), e11 represents an integer of 0 to 5, and R$^c$ represents a group of formula (I-1), (II-1) or (III-1), or a C1-10 aliphatic hydrocarbon group.

In the formula (V-1), e12 represents an integer of 0 to 5, and R$^d$ represents a C1-15 aliphatic hydrocarbon group or a C6-15 aromatic hydrocarbon group.

 (I-1)

 (II-1)

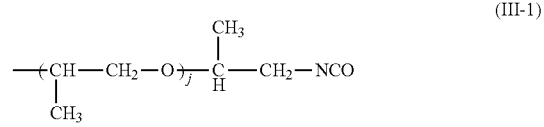 (III-1)

In the formulae, R$^g$ represents a C1-10 aliphatic hydrocarbon group, h represents an integer of 1 to 9, and j represents an integer of 0 to 9.

In the formula (IV-1), R$^c$ preferably represents a group of formula (I-1).

As an isocyanate according to the present embodiment, compounds of below-shown formulae may also be mentioned.

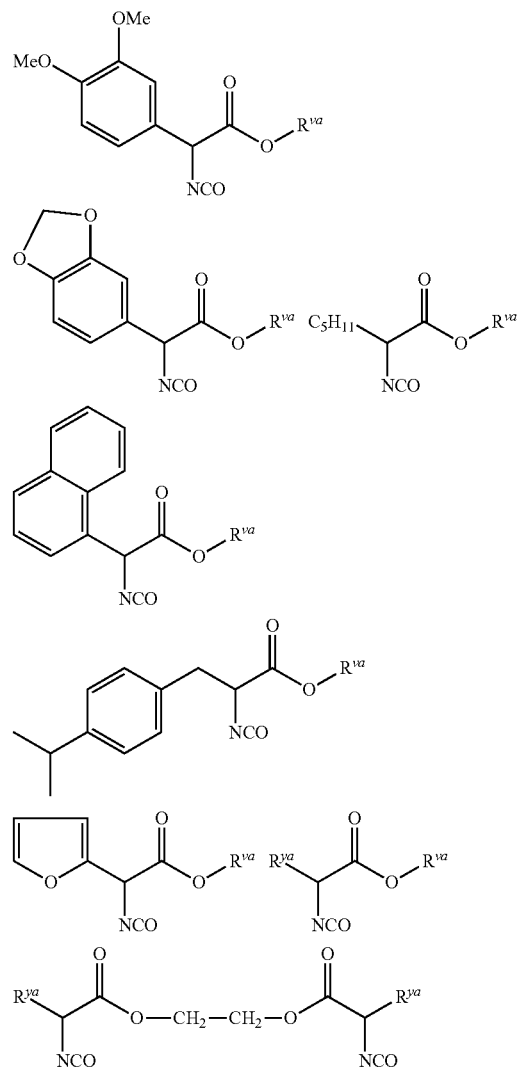

-continued

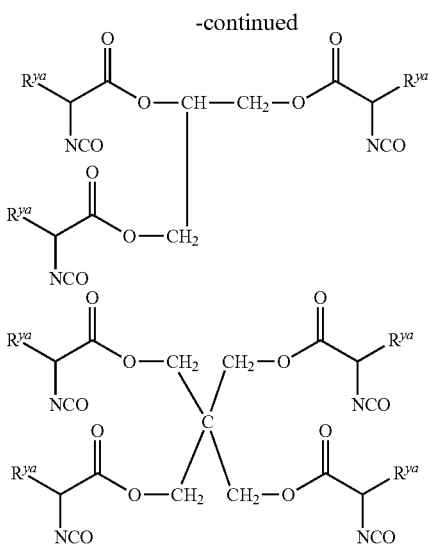

In the formulae, $R^{va}$ and $R^{ya}$ each represents a group defined in the formula (A-2). $R^{Va}$ preferably represents a C1-6 aliphatic group which may have an isocyanate group. $R^{ya}$ preferably represents a C1-6 aliphatic group which may have an isocyanate group.

Each steps are explained below.

[Step of Preparing a Mixture Liquid]

The step is a step of preparing a mixture liquid containing a carbamate and a polyisocyanate compound. The carbamate used as a starting material according to the present embodiment is preferably a carbamate derived from a carbonic acid ester, obtained by reacting the below-mentioned carbonic acid ester and an amine compound. An inactive solvent and a polyisocyanate compound used in the step will be described below.

The mixture liquid of a polyisocyanate compound and a carbamate according to the present embodiment is prepared such that the amount of the carbamate, relative to the total mass of the mixture liquid, becomes 1% by mass to 90% by mass, preferably 3% by mass to 70% by mass, more preferably 5% by mass to 50% by mass, and even more preferably 10% by mass to 50% by mass.

In the case where the amount of the carbamate is the lower limit or more, there is a tendency in which the space time yield of an isocyanate is further improved, and an advantage is provided at the time of industrial operation. In the case where the amount of the carbamate is the upper limit or lower, there is a tendency in which the occurrence of a side reaction is further suppressed at the time of thermal decomposition.

In contrast, the mixture liquid is prepared such that the amount of the polyisocyanate compound, relative to the total mass of the mixture liquid, becomes 10% by mass to 99% by mass, preferably 20% by mass to 80% by mass, and more preferably 20% by mass to 70% by mass.

The mixture liquid preferably contains an inactive solvent. The presence of the inactive solvent exhibits effects of suppressing reaction in which an isocyanate produced by the thermal decomposition reaction of a carbamate recombines with a hydroxy compound to form a carbamate.

In the case where an inactive solvent is contained in the mixture liquid, the mixture liquid is prepared such that the amount of the inactive solvent, relative to the total mass of the mixture liquid, becomes 1% by mass to 80% by mass, preferably 3% by mass to 70% by mass, and more preferably 5% by mass to 60% by mass.

[Step of Conducting Thermal Decomposition Reaction]

The step is a step in which a carbamate is introduced continuously into a thermal decomposition reactor to subject the carbamate to a thermal decomposition reaction to obtain an isocyanate, and in which the isocyanate and a hydroxy compound (preferably an aromatic hydroxy compound) are produced from the carbamate. The step is preferably conducted in a liquid phase.

The reaction temperature is usually within a range of 100° C. to 350° C. Although the temperature is preferably high so as to increase the reaction rate, the temperature is preferably within a range of 150° C. to 300° C. from the viewpoint of further suppressing the side reaction caused by a carbamic acid ester and/or a resultant isocyanate.

The reactor may be equipped with a conventionally-known cooler or heater so as to maintain a constant reaction temperature.

Although the reaction pressure depends on the kinds of compounds to be used or the reaction temperature, any of reduced pressure, ordinary pressure, and increased pressure may be adopted, and the reaction pressure is generally 1 Pa to $1 \times 10^6$ Pa (absolute pressure).

The reaction time (retention time) is not particularly limited, and it is preferable that the reaction time be generally 0.001 hours to 100 hours, more preferably 0.005 hours to 50 hours, and even more preferably 0.01 hours to 10 hours.

Although the form of the thermal decomposition reactor is not particularly limited, conventionally known distillation equipment is preferably used, and the thermal decomposition reactor is preferably composed of at least one reactor selected from the group consisting of an evaporator, a continuous multistage distillation column, a packed column, a thin-film evaporator and a falling-film evaporator, so as to collect a gas phase component efficiently.

In addition, various conventionally known methods, such as a method in which a reactor containing any of a distillation column, a multistage distillation column, a multitubular reactor, a reactor internally equipped with a support, a forced circulation reactor, a falling-film evaporator, and a falling-drop evaporator is used, or a method in which these are combined may be adopted.

From the viewpoint of extracting continuously and promptly a low-boiling-point decomposition product having a standard boiling point lower than the polyisocyanate compound from the reaction system, a packed column or a tubular reactor is preferable, a tubular reactor is more preferable, a reactor such as a tubular thin-film evaporator or a tubular falling-film evaporator is even more preferable, and a structure having a large gas-liquid contact area that realizes prompt move of the produced low-boiling decomposition component to the gas phase is more preferable.

In the case where a packed column is used, a filler content which is generally used in a distillation column or an absorption tower may be appropriately used as a solid filler content. Preferable examples thereof include Raschig ring, Lessing ring, Spiral ring, Pall ring, Intalox saddle, Stedman packing, McMahon packing, Dixon packing, helix packing, coil packing, and heat pipe packing.

A material of the filler content is not particularly limited, and may be porcelain, metallic, or the like. In the present embodiment, a filler content made of a material having a high thermal conductivity is preferable.

The kind of the carbamation-reactor used in the below-mentioned step of preparing carbamate and the kind of the thermal decomposition reactor may be identical to or different from each other.

Although the thermal decomposition reactor or lines may be formed by any of conventionally known materials, unless the materials exert harmful effects on carbamic acid esters, resultant hydroxy compounds (aromatic hydroxy compound), or isocyanates, SUS 304, SUS 316, or SUS 316L is preferably used because of the low prices thereof.

In the present embodiment, a catalyst is not always required, but the catalyst may be used without problems so as to decrease the reaction temperature or terminate the reaction promptly. The catalyst may be used in an amount of 0.01% by mass to 30% by mass, and more preferably 0.5% by mass to 20% by mass, relative to the mass of the carbamate.

Examples of the catalyst include: Lewis acids, transition metal compounds that generate Lewis acids, organic tin compounds, and copper group metal compounds, zinc compounds, and iron group metal compounds, and specific examples thereof include Lewis acids such as $AlX^a_3$, $TiX^a_3$, $TiX^a_4$, $VOX^a_3$, $VX^a_5$, $ZnX^a_2$, $FeX^a_3$, $SnX^a_4$ (in the formulae, $X^a$ represents a halogen, an acetoxy group, an alkoxy group, or an aryloxy group), and transition metal compounds that generate Lewis acids; organic tin compounds such as $(CH_3)_3SnOCOCH_3$, $(C_2H_5)SnOCOC_6H_5$, $Bu_3SnOCOCH_3$, $Ph_3SnOCOCH_3$, $Bu_2Sn(OCOCH_3)_2$, $Bu_2Sn(OCOC_{11}H_{23})_2$, $Ph_3SnOCH_3$, $(C_2H_5)_3SnOPh$, $Bu_2Sn(OCH_3)_2$, $Bu_2Sn(OC_2H_5)_2$, $Bu_2Sn(OPh)_2$, $Ph_2Sn(CH_3)_2$, $(C_2H_5)_3SnOH$, $PhSnOH$, $Bu_2SnO$, $(C_8H_{17})_2SnO$, $Bu_2SnCl_2$, and $BuSnO(OH)$; copper group metal compounds such as $CuCl$, $CuCl_2$, $CuBr$, $CuBr_2$, $CuI$, $CuI_2$, $Cu(OAc)_2$, $Cu(acac)_2$, copper oleate, $Bu_2Cu$, $(CH_3O)_2Cu$, $AgNO_3$, $AgBr$, silver picrate, and $AgC_6H_6ClO_4$; zinc compounds such as $Zn(acac)_2$; and iron group metal compounds such as $Fe(C_{10}H_5)(CO)_5$, $Fe(CO)_5$, $Fe(C_4H_6)(CO)_3$, $Co(mesitylene)_2(PEt_2Ph_2)$, $CoC_5F_5(CO)_7$, and ferrocene. (Bu represents a butyl group, Ph represents a phenyl group, and acac represents an acetylacetone chelate ligand.) Amines such as 1,4-diazabicyclo[2,2,2]octane, triethylene diamine, or triethyl amine may be used. Among these, organic metal catalysts such as dibutyltin dilaurate, lead octylate, and stannous octoate are preferable. These compounds may be used alone or in combination of at least two kinds thereof.

[Step of Collecting Low-Boiling Decomposition Product (First Collecting Step)]

The step is a step in which a low-boiling decomposition product produced by decomposing a carbamate by heat is extracted continuously in a gaseous state from a thermal decomposition reactor, together with an inactive solvent when the inactive solvent is used. Among an isocyanate and a hydroxy compound that are produced by the thermal decomposition reaction of the carbamate, the term "low-boiling decomposition product" refers to a compound having a standard boiling point lower than a polyisocyanate compound supplied to the thermal decomposition reactor, preferably refers to at least one of the hydroxy compound and the isocyanate, and more preferably refers to both the hydroxy compound and the isocyanate.

In order to collect the components in a gaseous state, it is preferable that the temperature, the pressure, and other conditions under which the step is conducted be determined depending on used compounds or resultant compounds produced by thermal decomposition of a carbamate.

In addition, a carrier agent may be introduced to collect the low-boiling decomposition product promptly. Examples of the carrier agent include: inactive gases such as nitrogen, argon, helium, carbonic acid gas, methane, ethane, and propane; and hydrocarbon gases. Among these, inactive gases such as nitrogen are preferably used.

Examples of an agent that exhibits a similar effect include low-boiling organic solvents such as halogenated hydrocarbons such as dichloromethane, chloroform, and carbon tetrachloride; lower hydrocarbons such as pentane, hexane, heptane, and benzene; and ethers such a tetrahydrofuran, and dioxane. These carrier agents may be used alone or in combination of at least two kinds thereof. In addition, these carrier agents may be preheated to be used.

The gaseous low-boiling decomposition product and inactive solvent that are collected from the thermal decomposition reactor may be directly introduced into a cooler and then collected partially or entirely in a liquid state. The purification and separation may be conducted by supplying, to a distillation column, the low-boiling decomposition product and inactive solvent, in a gaseous state, or in a liquid state after being introduced into the cooler.

[Step of Collecting High-Boiling Component (Second Collecting Step)]

In the step of collecting a high-boiling component, a liquid phase component that is not collected in a gaseous state in the step of collecting the low-boiling decomposition product is extracted continuously from the reactor to be collected. Since the compound having a standard boiling point lower than a standard boiling point of the polyisocyanate compound supplied to the thermal decomposition reactor and the inactive solvent are collected in a gaseous state in the step of collecting the low-boiling decomposition product, it is understood that the high-boiling component to be collected in the step is a liquid phase component that is not collected in a gaseous state in the step of collecting the low-boiling decomposition product, and that has a standard boiling point equal to or higher than the standard boiling point of the polyisocyanate compound supplied to the thermal decomposition reaction. The high-boiling component often contains side reaction products caused by an isocyanate produced by thermal decomposition of a carbamate and the carbamate, side reaction products caused by the isocyanate, side reaction products caused by the carbamate, or compounds caused by reaction of these side reaction products. There are many cases in which the compounds are not collected in a gaseous state in the step of collecting the low-boiling decomposition product, and the compounds often cause adhesion thereof to the reactor surface, which results in occlusion. Thus, the continuous collection of the liquid phase component from the thermal decomposition reactor with a polyisocyanate compound supplied to the thermal decomposition reaction suppresses adhesion to the reactor surface.

The step of conducting the thermal decomposition reaction, the step of collecting the low-boiling decomposition product, and the step of collecting the high-boiling component may be conducted separately using plural devices, or conducted simultaneously using one device.

<Example of the Case in which Plural Reactors are Used>

In addition to the above-mentioned methods, the below-mentioned methods may also be conducted, for example. Although a mixture liquid containing a carbamate, an inactive solvent, and a polyisocyanate compound is used in the below-shown examples, the inactive solvent may not be used.

The step of conducting the thermal decomposition reaction preferably includes:

a step of preparing the liquid phase component in which the mixture liquid is introduced continuously into a first reactor composed by a vertical tubular reactor to conduct a first decomposition reaction while allowing the mixture liquid to fall down inside the first reactor, and the liquid phase component is obtained from the bottom of the first reactor; and a decomposition step in which the liquid phase component is introduced into a second reactor composed of a tank reactor and a second decomposition reaction is conducted to decompose the carbamate contained in the liquid phase component into an isocyanate and a hydroxy compound.

[Step of Preparing Liquid Phase Component]

The mixture liquid containing a polyisocyanate compound and a carbamate is introduced continuously from the top of the first reactor composed of a vertical tubular reactor to allow the mixture liquid to fall down inside the reactor to conduct the first decomposition reaction, and a liquid phase component (reaction mixture) is obtained from the bottom of the reactor. In the present embodiment, the first reactor is preferably preheated at a temperature equal to or lower than the reaction temperature before introducing the mixture liquid.

It is preferable that the mixture liquid further contain an inactive solvent. The mixture liquid is preferably introduced into a reactor as a solution or in a melting state, or may be introduced in a suspension state.

In the present embodiment, there is no particular limitation on a tubular reactor available as the first reactor, provided that the inside temperature can be maintained at an appropriate temperature between 140° C. and 380° C. during the thermal decomposition reaction.

In addition, the cross-sectional form of the tubular reactor is also not particularly limited, and a circular form is preferable.

The length of the tubular reactor may be appropriately determined depending on the kind or the concentration of carbamate, the decomposition reaction temperature, the pressure, the presence or absence of a filler content, the kind of the filler content, the presence or absence of a tray, the kind of the tray, or other reaction conditions.

For example, the length of the tubular reactor is preferably 50 cm to 15 m, and more preferably 1 m to 7 m. In the case where the cross-sectional form is a circular form, the diameter thereof is preferably 1 cm to 3 m, and more preferably 2 cm to 50 cm.

In the present embodiment, the tubular reactor is preferably a tubular reactor filled with either a solid filler content or a solid catalyst or both thereof.

As a solid filler content, the solid filler content mentioned in the above [a step of conducting thermal decomposition reaction] may be used.

A packed solid filler content increases the surface area of the liquid-form component falling down, and thereby increasing the residence time. In addition, the packed solid filler content becomes a favorable medium that provides the liquid-form component with the decomposition reaction heat.

In the case where a solid catalyst is packed, there is no need to conduct separation procedures from a reaction liquid unlike homogeneous catalysts, and therefore the case is preferable from the viewpoint of industrial operation.

The solid catalyst is useful to decrease the decomposition temperature or increase the reaction temperature. A solid catalyst having a favorable thermal conductivity is preferable from the viewpoint of supplying the thermal decomposition reaction heat.

As such a solid catalyst, a catalyst disclosed in Japanese Unexamined Patent Application, First Publication No. Sho 57-158746, Japanese Unexamined Patent Application, First Publication No. Sho 57-158747, Japanese Unexamined Patent Application, First Publication No. Sho 57-158748, or Japanese Unexamined Patent Application, First Publication No. Sho 57-159751 may be used.

For example, an elemental substance of a rare-earth element, an antimony, or a bismuth, an oxide, a sulfide or a salt thereof; an elemental substance of boron, or a boron compound, a metal belonging to the copper group, the zinc group, the aluminium group, the carbon group, or the titanium group in the periodic series, a metal oxide or a metal sulfide thereof, or a carbide or a nitride of an element belonging to the carbon group excepting carbon, the titanium group, the vanadium group, or the chrome group in the periodic series is preferable.

In the present embodiment, the first reactor is preferably a packed-type tubular reactor in which either a liquid distributor or a liquid redistributor or both thereof is disposed.

The liquid distributor is disposed at the top of a packed-bed and is configured to distribute the liquid into the packed-bed uniformly. The form of the liquid distributor is not particularly limited. Examples thereof include a ring-type distributor, a barrage flow-type distributor, a trough-type distributor, and an orifice-type distributor, that are usually used in a packed column.

The liquid redistributor can prevent drift from generating when the liquid component falls down in the packed-bed. The use of the liquid redistributor not only contributes to realization of uniform distribution of the liquid, but also can narrow the distribution width of the residence time of the reaction liquid. When the distribution width of the residence time of the reaction liquid is narrowed, undecomposed carbamates do not remain, the generation of polymeric by-products caused by a side reaction of the resultant isocyanate is suppressed, and thus a high-quality isocyanate can be obtained. Such a liquid redistributor is preferably disposed at every approximate height of the packed-bed. The material or the form of the liquid redistributor is not particularly limited.

In the present embodiment, a tray is preferably disposed inside the tubular reactor of the first reactor. The term "tray" means a stage used in usual shelf-type distillation equipment, such as a bubble cap tray, a unifrax tray, a porous plate tray, or a baffle tray. Such a tray exhibits a similar effect to a liquid redistributor disposed in a packed-type reaction tube, and can narrow the distribution width of the residence time of the reaction liquid.

In the present embodiment, a tubular reactor in which a tray is disposed and which is filled with either a solid filler content or a solid catalyst or both thereof is preferably used as the first reactor.

The temperature in the first reactor is not particularly limited, provided that the temperature allows the carbamate to be decomposed, and the temperature, for example, is maintained at an appropriate temperature ($T1°$ C.) within a range of 140° C. to 380° C. Although the temperature depends on the kind of the carbamate used, the temperature is preferably 160° C. to 350° C., and more preferably 180° C. to 330° C.

Although the temperature is preferably high so as to increase the decomposition reaction rate, the temperature is preferably low from the viewpoint of suppressing the side reaction. The temperature may be appropriately controlled depending on the kind of the carbamate used. The temperature distribution of the reaction tube may be uniform from the top to the bottom thereof, or the thermal gradient may be generated.

The pressure in the first reactor is preferably controlled such that the reaction temperature becomes equal to or lower than the standard boiling point of the polyisocyanate compound and the low-boiling component which is any of an isocyanate and a hydroxyl compound that are decomposition products is vaporized at the reaction temperature.

The average residence time in the first reactor is preferably 0.5 minutes to 150 minutes, more preferably 1 minute to 90 minutes, and even more preferably 10 minutes to 30 minutes.

The mixture liquid containing: a carbamate introduced continuously from the top of the tubular first reactor; an inactive solvent; and a polyisocyanate compound is decomposed to an isocyanate and a hydroxy compound while falling down the first reactor (first decomposition reaction). After the first decomposition reaction, the resultant low-boiling decomposition product and the inactive solvent are vaporized and the step of collecting the low-boiling decomposition product in which the resultant low-boiling decomposition product and the inactive solvent are extracted continuously in a gaseous state from the top of the first reactor (mentioned below) may be conducted simultaneously. The gas extracted from the top of the first reactor may contain the polyisocyanate compound partially.

The low-boiling decomposition product has a standard boiling point lower than the standard boiling point of the polyisocyanate compound, and is preferably at least one of the hydroxy compound and the isocyanate, and more preferably both the hydroxy compound and the isocyanate.

Although most carbamates contained in the mixture liquid are decomposed into an isocyanate and a hydroxyl compound in the first reactor, a partial carbamate may remain in a liquid phase component without reacting.

There is a need to further increase the reaction temperature or elongate the residence time, so as to decompose completely the undecomposed carbamates or/and isocyanate compounds having undecomposed carbamate groups in the tubular first reactor. However, when the reaction conditions are further tightened, the side reaction may easily occur, and polymeric by-products may be generated. Accordingly, it is also preferable that the remaining carbamate and the like be extracted continuously in a liquid state from the bottom of the first reactor as liquid phase components with a high-boiling product (having a standard boiling point equal to or higher than the standard boiling point of the polyisocyanate compound) and the polyisocyanate compound, without complete decomposition of the carbamate in the tubular first reactor.

In the present specification, the top of the reactor (reaction tube) and the bottom thereof refer to, respectively, the position located at approximately one third or less from the top edge of the reactor tube, and the position located at approximately one third or less from the bottom edge of the reaction tube.

[Decomposition Step]

The liquid phase component (reaction mixture) extracted in a liquid state from the bottom of the first reactor is introduced into a second reactor connected to the first reactor and composed of a tank reactor. In the second reactor, the carbamate is further decomposed into an isocyanate and a hydroxy compound (second decomposition reaction). The liquid phase component introduced into the second reactor may contain the low-boiling decomposition product or the inactive solvent obtained in the first reactor.

Although the temperature in the second reactor may be appropriately controlled depending on the decomposition degree in the first reactor or the kind of the carbamate, it is preferable that the temperature allow the carbamate to decompose and the difference from the temperature in the first reactor (T1° C.) to be 50° C. or less, that is, the temperature in the second reactor be within a range of (T1−50)° C. to (T1+50)° C., and more preferably (T1−20)° C. to (T1+30)° C.

[Step of Collecting Low-Boiling Decomposition Product (First Collecting Step)]

The low-boiling decomposition product (having a standard boiling point lower than that of a polyisocyanate compound, and preferably being a hydroxy compound and/or an isocyanate) generated in the step of preparing the liquid phase component and the inactive solvent are vaporized, and then extracted continuously in a gaseous state from the top of the first reactor. The gas component extracted from the top of the first reactor may contain partial polyisocyanate compounds.

The low-boiling decomposition product generated in the second reactor is also extracted continuously in a gaseous state from the top of the second reactor. In this case, the gas extracted from the top of the second reactor may contain partial polyisocyanate compounds.

The gas component extracted from the second reactor is preferably introduced from the top of the second reactor into the bottom of the first reactor. In this case, it is preferable that the gas component introduced into the first reactor contain a polyisocyanate compound in addition to the low-boiling decomposition product.

The second reactor may be a single tank or a multistage tank composed of 2 or more tanks.

The low-boiling decomposition product thus prepared in the first reactor and the second reactor in a gaseous state may be directly introduced into a cooler to be collected in a liquid state, may be separated from the solvent to be collected, or may be supplied to a distillation column to conduct distillation purification.

[Step of Collecting High-Boiling Component (Second Collecting Step)]

A high-boiling component that is not collected in the step of collecting the low-boiling decomposition product is extracted continuously from the second reactor with the inactive solvent and/or the polyisocyanate compound to obtain the high-boiling component continuously. In the case where the high-boiling component contains an isocyanate, and the isocyanate is separated by distillation, the distillation is preferably conducted at a temperature being as low as possible, and more preferably at 150° C. or less.

[Recycle Step]

A gas component composed of the low-boiling decomposition product extracted continuously from the top of the first reactor, or each of the top of the first reactor and the second reactor, and an inactive solvent vapor may be introduced into a partial condenser, the temperature of which is maintained at a temperature in which the vapor of the inactive solvent and/or the polyisocyanate compound is condensed partially, mostly or entirely, but in which the low-boiling decomposition product (preferably a hydroxy compound) is not condensed mostly or entirely, to separate the gas component into a low-boiling decomposition product in a gaseous state, accounting for a most or entire portion of the resultant, and a liquid-form component consisting primarily of the inactive solvent, and then a partial or entire portion of the liquid-form component is brought back to the first reactor, or both the first reactor and the second reactor, respectively.

The method is particularly effective to suppress the side reaction. The gas components composed of the low-boiling decomposition product and the inactive solvent vapor, extracted from the top of the second reactor, are preferably introduced from the bottom of the reaction tube into the first reactor.

[Introduction of Carrier Agent]

A carrier agent is preferably introduced from the bottom of either the first reactor or the second reactor or both thereof so as to extract promptly a low-boiling decomposition product produced in the first reactor and the second reactor from the reactors. The carrier agent is preferably preheated to be introduced into the reactors.

The gas components containing the carrier agent, the low-boiling decomposition product, and the solvent vapor, extracted from at least one of the reactor and the partial condenser, may be separated into each components by partial condensation or other methods, to be reused for circulation.

In an embodiment, it is preferable that the carrier agent be introduced into the liquid in the second reactor, and then introduced into the bottom of the first reactor with the produced low-boiling decomposition product and solvent vapor.

It is preferable that the carrier agent be substantially inactive and in a gaseous state under thermal decomposition reaction conditions.

As the carrier agent, an inactive gas such as nitrogen, argon, helium, carbonic acid gas, methane, ethane, or propane, or a hydrocarbon gas may be used, and an inactive gas such as nitrogen, argon, or helium is preferably used.

Examples of an agent that exhibits a similar effect include low-boiling organic solvents such as halogenated hydrocarbons such as dichloromethane, chloroform, and carbon tetrachloride; lower hydrocarbons such as pentane, hexane, heptane, and benzene; and ethers such a tetrahydrofuran, and dioxane. These carrier agents may be used alone or in combination of at least two kinds thereof.

[Step of Preparing Carbamate]

A carbamate available as a starting material according to the present embodiment is preferably prepared by the below-mentioned carbamate preparation step.

The carbamate preparation step is a step in which a carbonic acid ester and an amine compound are reacted to obtain a reaction mixture containing a carbamate derived from the carbonic acid ester, a hydroxy compound derived from the carbonic acid ester, and the carbonic acid ester.

The carbonic acid ester and the amine compound may be reacted in a reaction solvent, and preferable examples of the reaction solvent include: alkanes such as hexane (each isomer), heptane (each isomer), octane (each isomer), nonane (each isomer), and decane (each isomer); aromatic hydrocarbons and alkyl-substituted aromatic hydrocarbons such as benzene, toluene, xylene (each isomer), ethyl benzene, diisopropyl benzene (each isomer), dibutyl benzene (each isomer), and naphthalene; alcohols such as methanol, ethanol, propanol (each isomer), butanol (each isomer), pentanol (each isomer), hexanol (each isomer), heptanol (each isomer), octanol (each isomer), and nonanol (each isomer); aromatic compounds substituted with (a) halogen or nitro group(s), such as chlorobenzene, dichlorobenzene (each isomer), bromobenzene, dibromobenzene (each isomer), chloronaphthalene, bromonaphthalene, nitrobenzene, and nitronaphthalene; polycyclic hydrocarbon compounds such as diphenyl, substituted diphenyl, diphenylmethane, terphenyl, anthracene, and dibenzyltoluene (each isomer); aromatic hydroxy compounds such as phenol, methylphenol (each isomer), ethylphenol (each isomer), butylphenol (each isomer), pentylphenol (each isomer), dimethylphenol (each isomer), diethylphenol (each isomer), dibutylphenol (each isomer), and dipentylphenol (each isomer); aliphatic hydrocarbons such as cyclohexane, cyclopentane, cyclooctane, and ethylcyclohexane; alicyclic alcohols such as cyclohexanol, cyclopentanol, and cyclooctanol; ketones such as methyl ethyl ketone, and acetophenone; esters such as dibutyl phthalate, dihexyl phthalate, dioctyl phthalate, and benzyl butyl phthalate; ethers and thioethers such as diphenyl ether, and diphenyl sulfide; and sulfoxides such as dimethyl sulfoxide, and diphenyl sulfoxide. Among these, an aromatic hydrocarbon such as benzene, toluene, or xylene is preferably used.

The solvents may be used alone or in combination of at least two thereof. The carbonic acid ester used in an excessive amount relative to an amino group of the amine compound is preferably used as a solvent in the reaction.

The reaction is also preferably conducted in the presence of an aromatic hydroxy compound as a reaction solvent.

As the aromatic hydroxy compound, a compound having one hydroxyl group directly bonded to an aromatic hydrocarbon ring constituting the aromatic hydroxy compound is preferable. Specific examples of the aromatic hydroxy compound available in the present embodiment are mentioned below.

The amine compound is preferably supplied in a liquid state to a reactor in which a carbamate is prepared.

In the present embodiment, the amine compound is preferably mixed with an alcohol, water, or a carbonic acid ester to be supplied thereto.

Although the reaction conditions of the carbonic acid ester and the amine compound depend on the kinds of compounds to be reacted, the stoichiometric proportion of the carbonic acid ester, relative to an amino group of the amine compound, is preferably 1 or more, and more preferably within a range of 1- to 1000-fold. Although the stoichiometric proportion of the carbonic acid ester, relative to an amino group of the amine compound, is preferably an excessive amount, so as to increase the reaction rate to terminate promptly the reaction, the stoichiometric proportion is preferably within a range of 1.1- to 50-fold, and more preferably within a range of 1.5- to 10-fold, in view of the size of the reactor.

The stoichiometric proportion of the aromatic hydroxy compound used, relative to an amino group of the amine compound, is preferably within a range of 1- to 100-fold, more preferably 1.2- to 50-fold, and even more preferably 1.5- to 10-fold.

The reaction temperature is preferably 0° C. to 150° C. Although the temperature is preferably high so as to increase the reaction rate, the temperature is more preferably within a range of 10° C. to 100° C., because an unfavorable reaction may occur at a high temperature. The reactor may be provided with a conventionally-known cooler or heater so as to maintain the reaction temperature at a constant level.

Although the reaction pressure depends on the kinds of compounds to be used or the reaction temperature, any of reduced pressure, ordinary pressure, and increased pressure may be adopted, and the reaction pressure is generally 20 Pa to $1 \times 10^6$ Pa. The reaction time (retention time in the case of a continuous method) is not particularly limited, and it is preferable that the reaction time be generally 0.001 hours to 50 hours, more preferably 0.01 hours to 20 hours, and even more preferably 0.1 hours to 10 hours. In addition, the reaction may be terminated after the reaction liquid is collected and then the production of the predetermined amount of the carbamate is confirmed by liquid chromatography, for example.

In the present embodiment, a catalyst may be used or may not be used in the reaction of the carbonic acid ester and the amine compound. In the case where no catalyst is used, thermal denaturation of the carbamate, caused by a metal component derived from a catalyst, can be prevented.

In the case where a catalyst is used, the reaction can be terminated promptly, and the reaction temperature can be lowered.

In the case where a catalyst is used, an organic compound or an inorganic compound of metal such as tin, lead, copper, or titanium, or a basic catalyst, such as an alcoholate of alkali metal or alkaline-earth metal, such as methylate, ethylate, or butylate (each isomer) of lithium, sodium, potassium, calcium, or barium, may be used.

Particularly, in the case where a used compound forms a salt with an inorganic acid or an organic acid, a basic compound is also preferably used.

Examples of the basic compound include inorganic bases such as alkali metal hydroxides and alkaline-earth metal hydroxides, and organic bases such as ammonia, amines, and phosphazenes. Among these, amines are preferable, and in the case of aliphatic amines, secondary aliphatic amines and tertiary aliphatic amines are preferable.

The aliphatic amine is an amine having at least one aliphatic group, and the carbon number of the aliphatic group is preferably 1 to 12.

Examples of the aliphatic amine include amines formed by substituting at least one hydrogen atom of ammonia $NH_3$ with an alkyl group or a hydroxy alkyl group, the carbon number of which is 12 or less (alkylamine or alkyl alcohol amine) and cyclic amines.

Specific examples of the alkylamine and the alkyl alcohol amine include: monoalkylamines such as n-hexylamine, n-heptylamine, n-octylamine, n-nonylamine, and n-decylamine; dialkylamines such as diethylamine, di-n-propylamine, di-n-heptylamine, di-n-octylamine, and dicyclohexylamine; trialkylamines such as trimethylamine, triethylamine, tri-n-propylamine, tri-n-butylamine, tri-n-pentylamine (triamylamine), tri-n-hexylamine, tri-n-heptylamine, tri-n-octylamine, tri-n-nonylamine, tri-n-decylamine, and tri-n-dodecylamine; alkyl alcohol amines such as diethanolamine, triethanolamine, diisopropanolamine, triisopropanolamine, di-n-octanolamine, and tri-n-octanolamine. Among these, a C5-10 trialkylamine is further preferable, and triethylamine, tri-n-pentylamine or tri-n-octylamine is particularly preferable.

Examples of the cyclic amine include heterocyclic compounds containing a nitrogen atom as a hetero atom. The heterocyclic compounds may be monocyclic (aliphatic monocyclic amines), or polycyclic (aliphatic polycyclic amines). Specific examples of the aliphatic monocyclic amine include piperidine and piperazine. The aliphatic polycyclic amine preferably has a carbon number of 6 to 10, and specific examples thereof include 1,5-diazabicyclo[4.3.0]-5-nonene, 1,8-diazabicyclo[5.4.0]-7-undecene, hexamethylenetetramine, and 1,4-diazabicyclo[2.2.2]octane.

An aromatic amine may be used as an amine. Examples of the aromatic amine include 4-dimethylaminopyridine, pyrrole, indole, pyrazole, imidazole or derivatives thereof, tribenzylamine, 2,6-diisopropylaniline, and N-tert-butoxycarbonylpyrrolidine.

Although the used amount of the basic compound is appropriately determined depending on used compounds, the stoichiometric proportion of the basic compound to be used, relative to an amino group of an inorganic amino acid salt of an amino acid alkyl ester, is preferably 0.001-fold or more, and more preferably within a range of 0.01- to 100-fold.

Although a conventionally-known tank reactor, column reactor, or distillation column may be used as a reactor to be used in reaction of a carbonic acid ester and an amine compound, and the reactor and lines may be formed by any of conventionally known materials, unless the materials exert harmful effects on starting materials or reaction products, SUS 304, SUS 316, or SUS 316L is preferably used because of the low prices thereof.

(Carbamate)

The reaction mixture containing a carbamate, a redundant carbonic acid ester, and a hydroxy compound derived from the carbonic acid ester is obtained by the above-mentioned method.

The carbamate obtained by the above-mentioned method is preferably a carbamate of formula (20) shown below.

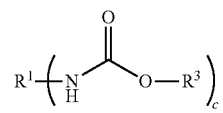

(20)

In the formula (20), c represents the number defined in the formula (2), $R^1$ represents a group defined in the formula (2), and $R^3$ represents a residual group obtained by removing one hydroxy group from the hydroxy compound. Each of plural $R^3$ in the formula (20) may be identical to or different from each other.

The carbamate of the formula (20) is not only a carbamate prepared in the below-mentioned [step of preparing carbamate], but also a carbamate used in the present embodiment.

In the formula (20), $R^3$ preferably represents a C1-20 aliphatic hydrocarbon group or a C6-20 aromatic group.

In the case where $R^3$ is a C1-20 aliphatic hydrocarbon group, the hydrocarbon group may be linear or branched.

Examples of the aliphatic hydrocarbon group as $R^3$ include alkyl groups. The carbon number of a linear alkyl group is preferably 1 to 5, more preferably 1 to 4, and even more preferably 1 or 2. Specific examples thereof include a methyl group, an ethyl group, a n-propyl group, a n-butyl group, and a n-pentyl group. The carbon number of a branched alkyl group is preferably 3 to 10, and more preferably 3 to 5. Specific examples thereof include an isopropyl group, an isobutyl group, a tert-butyl group, an isopentyl group, a neopentyl group, a 1,1-diethylpropyl group, and a 2,2-dimethylbutyl group. Among these, an ethyl group, a n-butyl group, and an isopentyl group are preferable.

An alicyclic hydrocarbon group may be polycyclic or monocyclic. Examples of a monocyclic alicyclic hydrocarbon group include a cyclopentyl group, and a cyclohexyl group. Examples of a polycyclic alicyclic hydrocarbon group include an adamantyl group, a norbornyl group, an isonorbornyl group, a tricyclodecyl group, and a tetracyclododecyl group. Among these, a cyclohexyl group is preferable.

As $R^3$ in the formula (20), a C6-20 aromatic hydrocarbon group is preferable, and a C6-12 aromatic hydrocarbon group is more preferable. Although a diaryl carbonate in which $R^3$ is an aromatic hydrocarbon group having a carbon number of 21 or more may be used, the carbon number constituting $R^3$ is preferably 20 or less from the viewpoint of making the separation from an isocyanate produced by a thermal decomposition reaction of a carbamic acid ester easy.

Examples of $R^3$ include a phenyl group, a methylphenyl group (each isomer), an ethylphenyl group (each isomer), a propylphenyl group (each isomer), a butylphenyl group (each isomer), a pentylphenyl group (each isomer), a hexylphenyl group (each isomer), a dimethylphenyl group (each isomer), a methylethylphenyl group (each isomer), a methylpropylphenyl group (each isomer), a methylbutylphenyl group (each isomer), methylpentylphenyl group (each isomer), a diethylphenyl group (each isomer), an ethylpropylphenyl group (each isomer), an ethylbutylphenyl group (each isomer), a dipropylphenyl group (each isomer), a trimethylphenyl group (each isomer), a triethylphenyl group (each isomer), and a naphthyl group (each isomer). Among these, a phenyl group, a 2,6-dimethylphenyl group, a 4-(1,1,3,3-tetramethylbutyl)phenyl group, a 4-(α,α-dimethylbenzyl)phenyl group, a 4-phenoxyphenyl group, a 4-methylphenyl group, and a 4-ethyl phenyl group are preferable.

In the formula (20), $R^1$ preferably represents an aliphatic hydrocarbon group, an aromatic hydrocarbon group, or a group formed by bonding a single kind or plural kinds of aliphatic hydrocarbon groups and/or aromatic hydrocarbon groups via an ether bond (—O—), a thioether bond (—S—), an ester bond (—COO—), or an amide bond (—CONH—), and more preferably represents an aliphatic hydrocarbon group, an aromatic hydrocarbon group, or a group formed by bonding a single kind or plural kinds of aliphatic hydrocarbon groups and/or aromatic hydrocarbon groups via an ester bond.

The number of carbon atoms constituting $R^1$ is preferably 1 to 30.

In the case where $R^1$ is an aliphatic hydrocarbon group, the carbon number of $R^1$ is preferably 3 to 85, more preferably 3 to 30, and even more preferably 5 to 13. Examples of the aliphatic hydrocarbon group as $R^1$ include alkyl groups. The carbon number of a linear alkyl group is preferably 1 to 15, more preferably 3 to 10, and even more preferably 5 or 6. The carbon number of a branched alkyl group is preferably 3 to 15, and more preferably 8 to 13.

Specific examples of a monovalent $R^1$ group include a methyl group, an ethyl group, a n-propyl group, a n-butyl group, a n-pentyl group, a n-hexyl group, an isopropyl group, an isobutyl group, a tert-butyl group, an isopentyl group, a neopentyl group, and a 1,1-diethylpropyl group.

Specific preferable examples of a divalent $R^1$ group include a methylene group, an ethylene group, a n-trimethylene group, a n-tetramethylene group, a n-pentamethylene group, and a n-hexamethylene group. Among these, a n-pentamethylene group and n-hexamethylene group are preferable.

Specific preferable examples of a trivalent $R^1$ group include an octamethylenediyl-4-methyl group.

In the case where $R^1$ is an alicyclic hydrocarbon group, the number of carbon atoms of $R^1$ is preferably 5 to 85, more preferably 5 to 30, and even more preferably 8 to 13. The alicyclic hydrocarbon group may be polycyclic or monocyclic. The alicyclic hydrocarbon group is preferably a divalent group, and specific preferable examples thereof include a cyclohexane-1,2-dimethylene group, a 3,5,5-trimethyl-3-methyl-1-yl group, and a 4,4'-dicyclohexylmethyl group.

In the case where $R^1$ is an aromatic hydrocarbon group, the number of carbon atoms of $R^1$ is preferably 6 to 20, and more preferably 7 to 13. The aromatic hydrocarbon group may be polycyclic or monocyclic. The aromatic hydrocarbon group is preferably a divalent group, and specific preferable examples thereof include a toluene-2,4-diyl group, a benzene-1,2-dimethylene group, and a 4,4'-diphenylmethyl group.

In the case where $R^1$ is a group formed by binding (an) aliphatic hydrocarbon group(s) and/or (an) aromatic hydrocarbon group(s) via an ether bond (—O—), a thioether bond (—S—), an ester bond (—COO—), or an amide bond (—CONH—), a group of the below-shown formula (20-1) is preferable.

(20-0)

In the formula (20-0), $R^{20}$ represents a group having a valency of c, and * represents a binding position to a carbamate group.

A group of the below-shown formula (20-1) or formula (20-2) is preferable as a monovalent $R^{20}$, a group of the below-shown formula (20-3), formula (20-4), formula (20-5) or formula (20-6) is preferable as a divalent $R^{20}$, a group of the below-shown formula (20-7), formula (20-8) or formula (20-9) is preferable as a trivalent $R^{20}$, a group of the below-shown formula (20-10), formula (20-11), formula (20-12) or formula (20-13) is preferable as a tetravalent $R^{20}$.

(20-1)

(20-2)

(20-3)

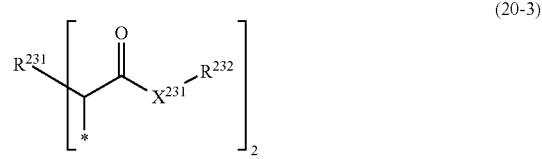
(20-4)

(20-5)

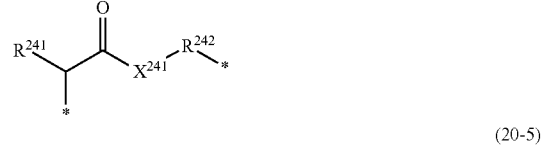

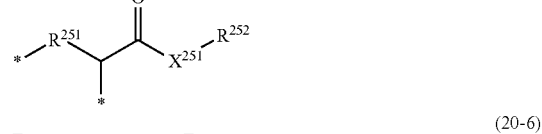
(20-6)

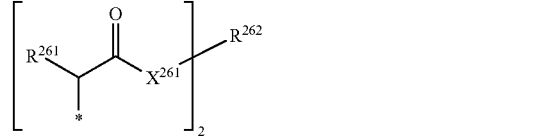
(20-7)

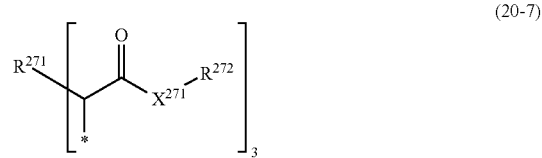

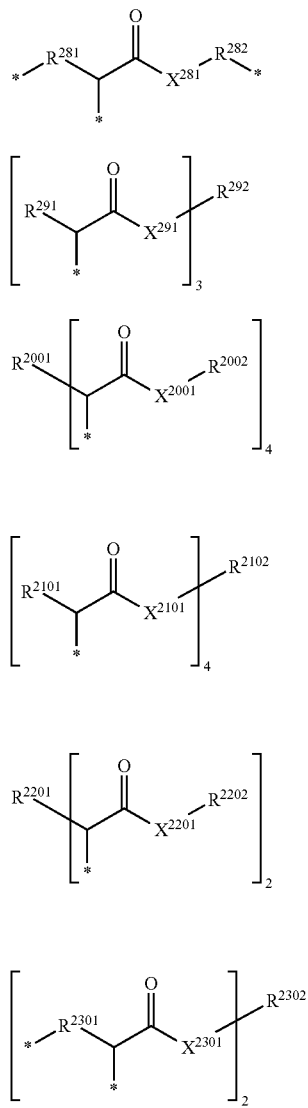

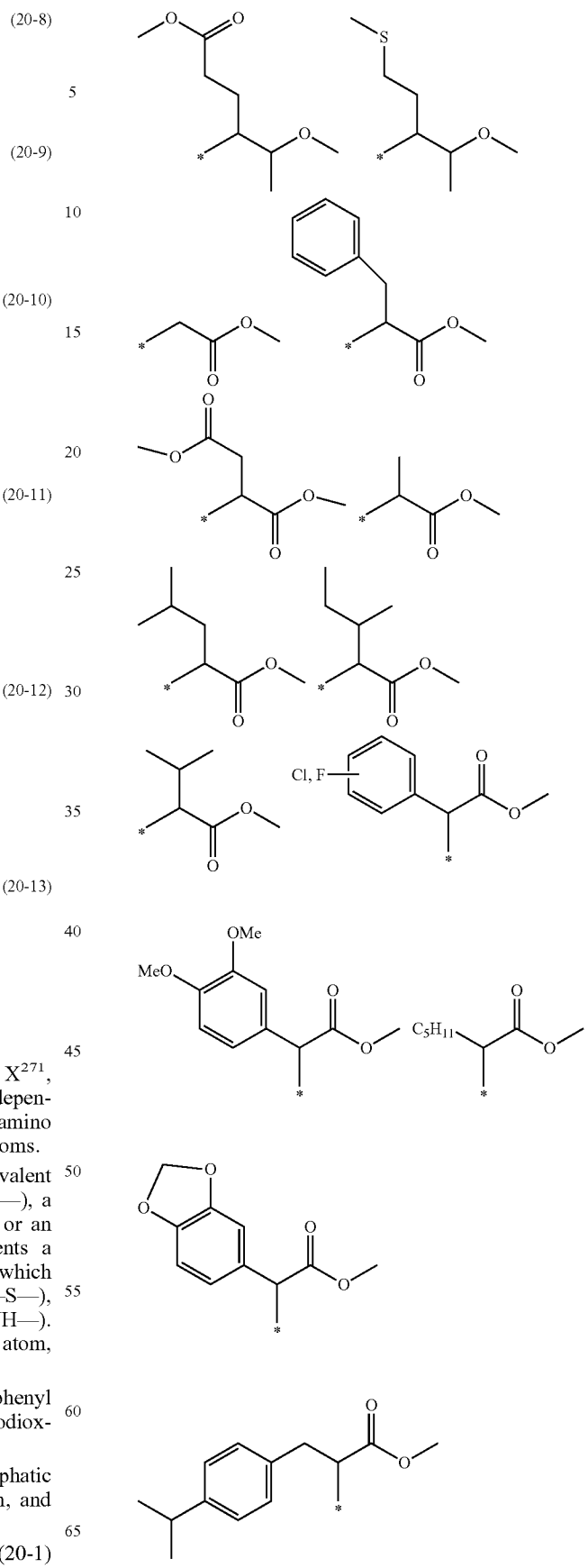

In the formulae, $X^{211}$, $X^{221}$, $X^{231}$, $X^{241}$, $X^{251}$, $X^{261}$, $X^{271}$, $X^{281}$, $X^{291}$, $X^{2001}$, $X^{2101}$, $X^{2201}$, and $X^{2301}$ each independently represent an oxygen atom or a secondary amino group (—NH—), and preferably represent oxygen atoms.

In the formula (20-1), $R^{211}$ represents a monovalent organic group which may have an ether bond (—O—), a thioether bond (—S—), an ester bond (—COO—), or an amide bond (—CONH—), and preferably represents a C1-15 aliphatic group or a C6-15 aromatic group, which may have an ether bond (—O—), a thioether bond (—S—), an ester bond (—COO—), or an amide bond (—CONH—). The aromatic group may be substituted with a halogen atom, a C1-6 alkyl group, and/or a C1-6 alkoxy group.

Examples of the C6-15 aromatic group include a phenyl group, a naphthyl group, a furanyl group, and a benzodioxolyl group.

In the formula (20-1), $R^{212}$ represents a C1-15 aliphatic group, a C6-15 aromatic group or a hydrogen atom, and preferably represents a C1-6 alkyl group.

Preferable examples of the group of the formula (20-1) include groups of the below-shown formulae.

-continued

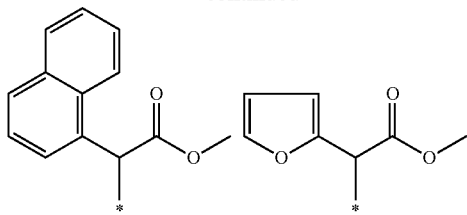

In the formulae, * represents a binding position to a carbamate group.

In the formula (20-2), $R^{221}$ represents a monovalent organic group which may have an ether bond (—O—), a thioether bond (—S—), an ester bond (—COO—), or an amide bond (—CONH—), preferably represents a C1-15 aliphatic group or a C6-15 aromatic group, which may have an ether bond (—O—), a thioether bond (—S—), an ester bond (—COO—), or an amide bond (—CONH—), more preferably represents a C1-15 unsaturated hydrocarbon group, even more preferably represents a C1-5 alkenyl group, and sill more preferably represents an isopropenyl group.

In the formula (20-2), $R^{222}$ represents a C1-15 aliphatic group or a C6-15 aromatic group, preferably represents a C1-5 aliphatic hydrocarbon group, and more preferably represents an ethylene group.

Preferable example of the group of the formula (20-2) include a group of the below-shown formula.

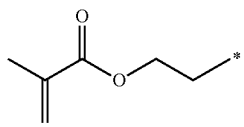

In the formula, * represents a binding position to a carbamate group.

In the formula (20-3), $R^{231}$ represents a divalent organic group which may have an ether bond (—O—), a thioether bond (—S—), an ester bond (—COO—), or an amide bond (—CONH—), and preferably represents a C1-15 aliphatic group or a C6-15 aromatic group, which may have an ether bond (—O—), a thioether bond (—S—), an ester bond (—COO—), or an amide bond (—CONH—).

In the formula (20-3), $R^{232}$ is a group identical to $R^{212}$.

Preferable examples of the group of formula (20-3) include groups of the below-shown formulae.

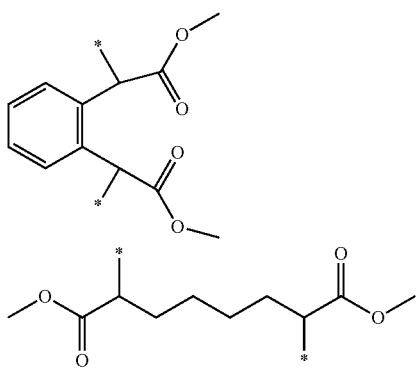

In the formulae, * represents a binding position to a carbamate group.

In the formula (20-4), $R^{241}$ represents a monovalent organic group which may have an ether bond (—O—), a thioether bond (—S—), an ester bond (—COO—), or an amide bond (—CONH—), and more preferably represents a C1-15 aliphatic group or a C6-15 aromatic group, which may have a thioether bond (—S—) and may be substituted with a C6-15 aromatic group. Examples of the aromatic group include a phenyl group, an imidazolyl group, and an indolyl group.

In the formula (20-4), $R^{242}$ represents a C1-15 aliphatic group or a C6-15 aromatic group, preferably represents a C1-6 alkylene group, and more preferably represents an ethylene group.

Preferable examples of the group of the formula (20-4) include groups of the below-shown formulae.

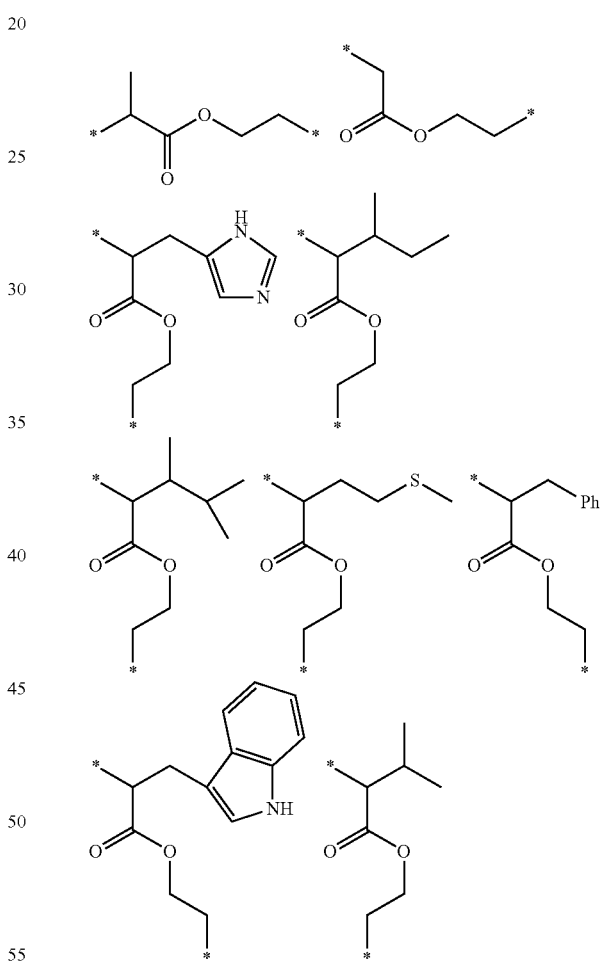

In the formulae, * represents a binding position to a carbamate group.

In the formula (20-5), $R^{251}$ represents a monovalent organic group which may have an ether bond (—O—), a thioether bond (—S—), an ester bond (—COO—), or an amide bond (—CONH—), preferably represents a C1-15 aliphatic group or a C6-15 aromatic group, which may have an ether bond (—O—), a thioether bond (—S—), an ester bond (—COO—), or an amide bond (—CONH—), and more preferably represents a C1-6 alkylene group.

In the formula (20-5), $R^{252}$ is the same group as $R^{212}$.

Preferable examples of the group of the formula (20-5) include groups of the below-shown formulae.

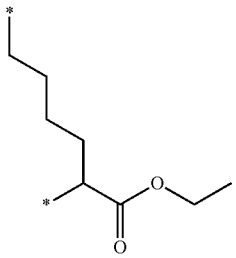

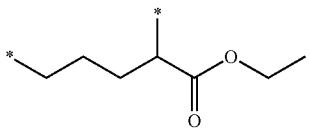

In the formulae, * represents a binding position to a carbamate group.

In the formula (20-6), $R^{261}$ represents the same group as $R^{211}$, and preferably represents a C2-10 alkylene group which has an ester bond (—COO—).

In the formula (20-6), $R^{262}$ is a divalent group and represents a C1-15 aliphatic group or a C6-15 aromatic group, preferably represents a C1-6 alkylene group, and more preferably represents an ethylene group.

Preferable examples of the group of the formula (20-6) include a group of the below-shown formula.

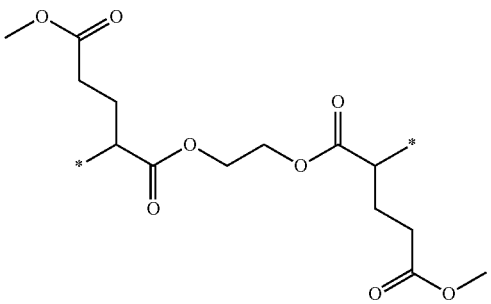

In the formula, * represents a binding position to a carbamate group.

In the formula (20-7), $R^{271}$ represents a trivalent organic group which may have an ether bond (—O—), a thioether bond (—S—), an ester bond (—COO—), or an amide bond (—CONH—), preferably represents a C1-15 aliphatic group or a C6-15 aromatic group, which may have an ether bond (—O—), a thioether bond (—S—), an ester bond (—COO—), or an amide bond (—CONH—), and more preferably represents a C6 aromatic hydrocarbon group.

In the formula (20-7), $R^{272}$ represents the same group as $R^{212}$, and preferably represents a C1-6 alkyl group.

Preferable examples of the group of the formula (20-7) include a group of the below-shown formula.

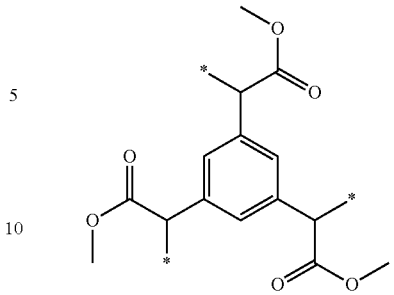

In the formula, * represents a binding position to a carbamate group.

In the formula (20-8), $R^{281}$ represents a monovalent organic group which may have an ether bond (—O—), a thioether bond (—S—), an ester bond (—COO—), or an amide bond (—CONH—), and preferably represents a C1-15 aliphatic group which may have an ester bond (—COO—).

$R^{282}$ represents a C1-15 aliphatic group or a C6-15 aromatic group, and preferably represents a C1-6 alkylene group.

Preferable examples of the group of the formula (20-8) include groups of the below-shown formulae.

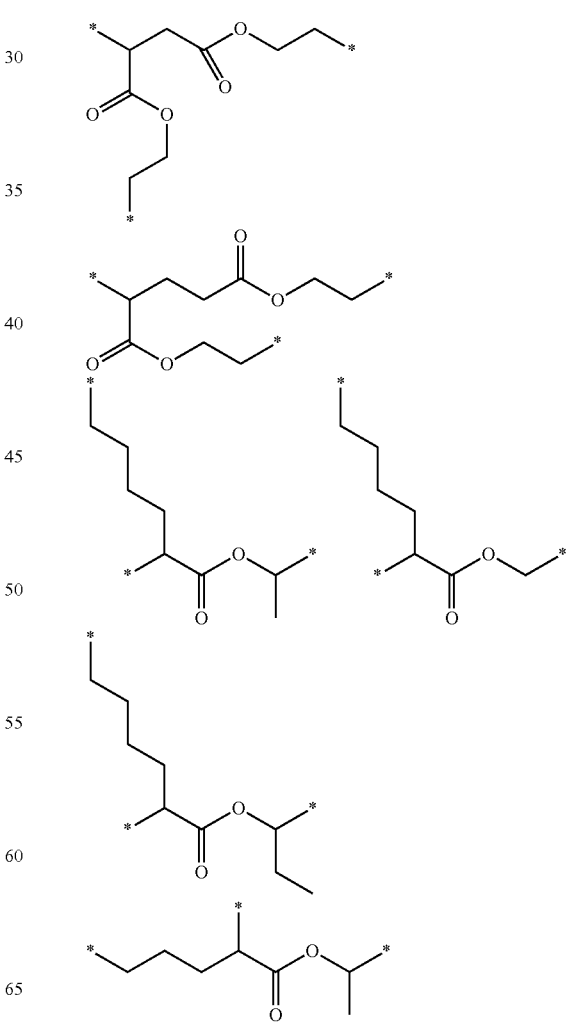

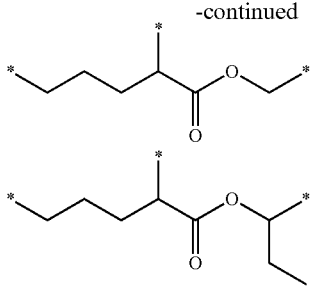

In the formulae, * represents a binding position to a carbamate group.

In the formula (20-9), $R^{291}$ represents the same group as $R^{211}$.

In the formula (20-9), $R^{292}$ is a trivalent group, and represents a C1-15 aliphatic group or a C6-15 aromatic group.

In the formula (20-10), $R^{2001}$ represents a tetravalent organic group which may have an ether bond (—O—), a thioether bond (—S—), an ester bond (—COO—), or an amide bond (—CONH—), and preferably represents a C1-15 aliphatic group or a C6-15 aromatic group, which may have an ether bond (—O—), a thioether bond (—S—), an ester bond (—COO—), or an amide bond (—CONH—).

In the formula (20-10), $R^{2002}$ is the same group as $R^{212}$.

In the formula (20-11), $R^{2101}$ represents a monovalent organic group which may have an ether bond (—O—), a thioether bond (—S—), an ester bond (—COO—), or an amide bond (—CONH—), preferably represents a C1-15 aliphatic group which may have a thioether bond (—S—), and more preferably represents a C1-6 aliphatic group which has a thioether bond (—S—).

In the formula (20-11), $R^{2102}$ is a tetravalent group, and represents a C1-15 aliphatic group, a C6-15 aromatic group or a hydrogen atom, and preferably represents a C5-10 aliphatic saturated hydrocarbon group.

Preferable examples of the group of the formula (20-11) include groups of the below-shown formulae.

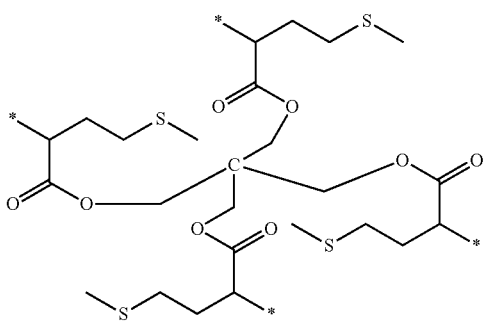 [SMILES: *C(CCSC)C(=O)OCC(COC(=O)C(*)CCSC)(COC(=O)C(*)CCSC)COC(=O)C(*)CCSC]

In the formula, * represents a binding position to a carbamate group.

In the formula (20-12), $R^{2201}$ represents the same group as $R^{231}$, and $R^{2202}$ represents the same group as $R^{242}$.

In the formula (20-13), $R^{2301}$ represents a monovalent organic group which may have an ether bond (—O—), a thioether bond (—S—), an ester bond (—COO—), or an amide bond (—CONH—), preferably represents a C1-15 aliphatic group, and more preferably represents a C1-6 alkylene group.

$R^{2302}$ represents a C1-15 aliphatic group or a C6-15 aromatic group, and preferably represents a C1-6 alkylene group.

Preferable examples of the group of the formula (20-13) include groups of the below-shown formulae.

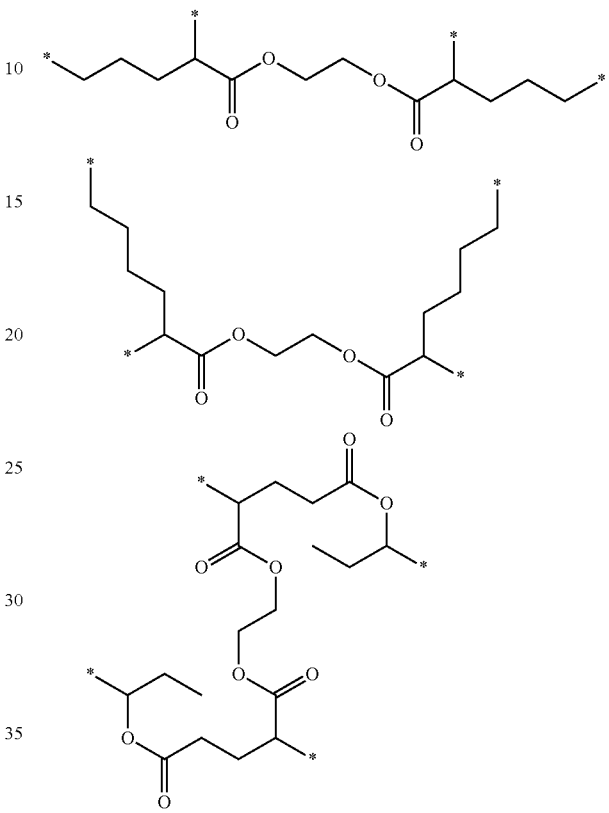

In the formulae, * represents a binding position to a carbamate group.

Examples of a monofunctional carbamate in which c in the formula (20) is 1 include aliphatic carbamates in which the carbon number of $R^1$ in the formula (20) is 1 to 30, alicyclic carbamates in which the carbon number of $R^1$ in the formula (20) is 6 to 30, and C6-30 carbamates having an aromatic group.

In addition, the monofunctional carbamate in which c in the formula (20) is 1 may be a carbamate having an ester bond or an amide bond of formula (B-2), the carbamate being an isocyanate having one carbamate group, which may be 2-((phenoxycarbonyl)amino)ethyl methacrylate.

Examples of a difunctional carbamate in which c in the formula (20) is 2 include C4-30 aliphatic dicarbamates, C8-30 alicyclic dicarbamates, and C8-30 dicarbamates having an aromatic group.

Specific examples of C4-30 aliphatic dicarbamates include 1,4-tetramethylene di(carbamic acid methyl ester), 1,5-pentamethylene di(carbamic acid methyl ester), 1,4-di(carbamic acid methyl ester) 2-methylbutane, 1,6-hexamethylene di(carbamic acid methyl ester), 1,6-di(carbamic acid methyl ester) 2,5-dimethylhexane, 2,2,4-trimethyl-1,6-hexamethylene di(carbamic acid methyl ester), lysine methyl ester di(carbamic acid methyl ester), lysine ethyl ester di(carbamic acid methyl ester), 1,4-tetramethylene di(carbamic acid ethyl ester), 1,5-pentamethylene di(carbamic acid ethyl ester), 1,4-di(carbamic acid ethyl ester)

2-ethyl butane, 1,6-hexamethylene di(carbamic acid ethyl ester), 1,6-di(carbamic acid ethyl ester) 2,5-diethyl hexane, 2,2,4-triethyl 1,6-hexamethylene di(carbamic acid ethyl ester), lysine ethyl ester di(carbamic acid ethyl ester), lysine ethyl ester di(carbamic acid ethyl ester), 1,4-tetramethylene di(carbamic acid butyl ester), 1,5-pentamethylene di(carbamic acid butyl ester), 1,4-di(carbamic acid butyl ester) 2-butylbutane, 1,6-hexamethylene di(carbamic acid butyl ester), 1,6-di(carbamic acid butyl ester) 2,5-dibutylhexane, 2,2,4-tributyl 1,6-hexamethylene di(carbamic acid butyl ester), lysine butyl ester di(carbamic acid butyl ester), lysine butyl ester di(carbamic acid butyl ester), 1,4-tetramethylene di(carbamic acid phenyl ester), 1,5-pentamethylene di(carbamic acid phenyl ester), 1,4-di(carbamic acid phenyl ester) 2-phenylbutane, 1,6-hexamethylene di(carbamic acid phenyl ester), 1,6-di(carbamic acid phenyl ester) 2,5-diphenylhexane, 2,2,4-triphenyl 1,6-hexamethylene di(carbamic acid phenyl ester), lysine phenyl ester di(carbamic acid phenyl ester), lysine phenyl ester di(carbamic acid phenyl ester), 1,4-tetramethylene di(carbamic acid dimethylphenyl ester), 1,5-pentamethylene di(carbamic acid dimethylphenyl ester), 1,4-di(carbamic acid dimethylphenyl ester) 2-dimethylphenyl butane, 1,6-hexamethylene di(carbamic acid dimethylphenyl ester), 1,6-di(carbamic acid dimethylphenyl ester) 2,5-didimethylphenylhexane, 2,2,4-tridimethylphenyl 1,6-hexamethylene di(carbamic acid dimethylphenyl ester), lysine dimethylphenyl ester di(carbamic acid dimethylphenyl ester), lysine dimethylphenyl ester di(carbamic acid dimethylphenyl ester), 1,4-tetramethylene di(carbamic acid dibutyl phenyl ester), 1,5-pentamethylene di(carbamic acid dibutylphenyl ester), 1,4-di(carbamic acid dibutyl phenyl ester) 2-dibutylphenyl butane, 1,6-hexamethylene di(carbamic acid dibutylphenyl ester), 1,6-di(carbamic acid dibutylphenyl ester) 2,5-didibutylphenyl hexane, 2,2,4-tridibutylphenyl 1,6-hexamethylene di(carbamic acid dibutylphenyl ester), lysine dibutylphenyl ester di(carbamic acid dibutylphenyl ester), lysine dibutylphenyl ester di(carbamic acid dibutylphenyl ester), 3-(phenoxycarbonylaminomethyl)-3,5,5-trimethylcyclohexylcarbamic acid phenyl ester, N,N'-(4,4'-methanediyl-dicyclohexyl)-biscarbamic acid diphenyl ester, cyclohexane-1,2-diyl bis(methylene) dicarbamic acid diphenyl, 1,6-hexamethylene di(carbamic acid (3-methylbutyl)ester), cyclohexane-1,2-diyl bis(methylene) dicarbamic acid di(4-(1,1,3,3-tetramethylbutyl)phenyl), 3-((2,6-dimethylphenoxy)carbonylamino-methyl)-3,5,5-trimethylcyclohexyl carbamic acid (2,6-dimethylphenyl) ester, and cyclohexane-1,2-diyl bis(methylene) dicarbamic acid di(4-phenoxyphenyl).

Among these, 1,6-hexamethylene di(carbamic acid phenyl ester), 1,5-pentamethylene di(carbamic acid phenyl ester), 3-(phenoxycarbonylamino-methyl)-3,5,5-trimethylcyclohexyl carbamic acid phenyl ester, N,N'-(4,4'-methanediyl dicyclohexyl)-biscarbamic acid diphenyl ester, cyclohexane-1,2-diyl bis(methylene) dicarbamic acid diphenyl, 1,6-hexamethylene di(carbamic acid ethyl ester), 1,6-hexamethylene di(carbamic acid (3-methylbutyl)ester), 1,5-pentamethylene di(carbamic acid butyl ester), cyclohexane-1,2-diyl bis(methylene) dicarbamic acid di(4-(1,1,3,3-tetramethylbutyl)phenyl), 3-((2,6-dimethylphenoxy)carbonylamino-methyl)-3,5,5-trimethylcyclohexyl carbamic acid (2,6-dimethylphenyl)ester, and cyclohexane-1,2-diyl bis(methylene) dicarbamic acid di(4-phenoxyphenyl) are preferable.

Specific examples of C8-30 alicyclic dicarbamates include isophorone di(carbamic acid methyl ester), 1,3-bis((carbamic acid methyl ester)methyl)-cyclohexane, 4,4'-dicyclohexylmethane di(carbamic acid methyl ester), hydrogenated tetramethylxylylene di(carbamic acid methyl ester), norbornene di(carbamic acid methyl ester), isophorone di(carbamic acid ethyl ester), 1,3-bis((carbamic acid ethyl ester)ethyl)-cyclohexane, 4,4'-dicyclohexylmethane di(carbamic acid ethyl ester), hydrogenated tetraethyl xylylene di(carbamic acid ethyl ester), norbornene di(carbamic acid ethyl ester), isophorone di(carbamic acid butyl ester), 1,3-bis((carbamic acid butyl ester)butyl)-cyclohexane, 4,4'-dicyclohexylmethane di(carbamic acid butyl ester), hydrogenated tetrabutyl xylylene di(carbamic acid butyl ester), norbornene di(carbamic acid butyl ester), isophorone di(carbamic acid phenyl ester), 1,3-bis((carbamic acid phenyl ester)phenyl)-cyclohexane, 4,4'-dicyclohexylmethane di(carbamic acid phenyl ester), hydrogenated tetraphenylxylylene di(carbamic acid phenyl ester), norbornene di(carbamic acid phenyl ester), isophorone di(carbamic acid dimethylphenyl ester), 1,3-bis((carbamic acid dimethylphenyl ester)dimethylphenyl)-cyclohexane, 4,4'-dicyclohexylmethane di(carbamic acid dimethylphenyl ester), hydrogenated tetradimethylphenylxylylene di(carbamic acid dimethylphenyl ester), and norbornene di(carbamic acid dimethylphenyl ester).

Examples of C8-30 dicarbamates having an aromatic group include 4,4'-diphenylmethane di(carbamic acid methyl ester), 2,6-tolylene di(carbamic acid methyl ester), xylylene di(carbamic acid methyl ester), tetramethylxylylene di(carbamic acid methyl ester), naphthalene di(carbamic acid methyl ester), 4,4'-diphenylmethane di(carbamic acid ethyl ester), 2,6-tolylene di(carbamic acid ethyl ester), xylylene di(carbamic acid ethyl ester), tetraethyl xylylene di(carbamic acid ethyl ester), naphthalene di(carbamic acid ethyl ester), 4,4'-diphenylmethane di(carbamic acid butyl ester), 2,6-tolylene di(carbamic acid butyl ester), xylylene di(carbamic acid butyl ester), tetrabutyl xylylene di(carbamic acid butyl ester), naphthalene di(carbamic acid butyl ester), 4,4'-diphenylmethane di(carbamic acid phenyl ester), 2,6-tolylene di(carbamic acid phenyl ester), xylylene di(carbamic acid phenyl ester), tetraphenylxylylene di(carbamic acid phenyl ester), naphthalene di(carbamic acid phenyl ester), 4,4'-dimethylphenylmethane di(carbamic acid dimethylphenyl ester), 2,6-tolylene di(carbamic acid dimethylphenyl ester), xylylene di(carbamic acid dimethylphenyl ester), tetradimethylphenylxylylene di(carbamic acid dimethylphenyl ester), naphthalene di(carbamic acid dimethylphenyl ester), N,N'-(4,4'-methanediyl-diphenyl)-biscarbamic acid diphenyl ester, benzene-1,2-diyl bis(methylene) dicarbamic acid diphenyl), toluene-2,4-dicarbamic acid diphenyl ester, N,N'-(4,4'-methanediyl diphenyl)-biscarbamic acid diethyl ester, and toluene-2,4-dicarbamic acid dicyclohexyl ester.

Among these, N,N'-(4,4'-methanediyl diphenyl)-biscarbamic acid diphenyl ester, benzene-1,2-diyl bis(methylene) dicarbamic acid diphenyl), toluene-2,4-dicarbamic acid diphenyl ester, N,N'-(4,4'-methanediyl-diphenyl)-biscarbamic acid diethyl ester, and toluene-2,4-dicarbamic acid dicyclohexyl ester are preferable.

In the case where the above-mentioned compound has structural isomers, the structural isomers are encompassed in the above-mentioned examples.

The difunctional dicarbamate in which c in the formula (20) is 2 may be a carbamate having an ester bond or an amide bond of the below-mentioned formula (B-1) or formula (B-2), and two carbamate groups.

As a trifunctional carbamate in which c in the formula (20) is 3, a carbamate of the below-shown formula (21) is preferably used.

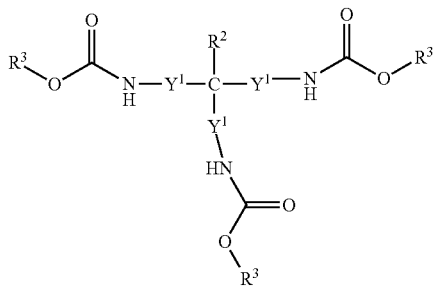

(21)

In the formula (21), plural $Y^1$ each independently represent a single bond, or a C1-20 divalent hydrocarbon group which may have an ester bond and/or an ether bond, $R^2$ represents a hydrogen atom or a C1-12 monovalent hydrocarbon group, and $R^3$ represents a group defined in the formula (20).

In the formula (21), $R^2$ preferably represents a C1-10 aliphatic group, or a C6-10 aromatic group, and specific examples thereof include: aliphatic groups such as a methyl group, an ethyl group, a propyl group, a butyl group, a pentyl group, a hexyl group, and a decyl group; and aromatic groups such as a phenyl group, a methylphenyl group, an ethylphenyl group, a butylphenyl group, a dimethylphenyl group, and a diethylphenyl group.

In the formula (21), $Y^1$ preferably represents a C1-20 divalent aliphatic group, a C6-20 divalent aromatic group, a C2-20 divalent group formed by bonding an aliphatic group and an aliphatic group via an ester bond, a C2-20 divalent group formed by bonding an aliphatic group and an aliphatic group via an ether bond, a C7-20 divalent group formed by bonding an aliphatic group and an aromatic group via an ester bond, a C7-20 divalent group formed by bonding an aliphatic group and an aromatic group via an ether bond, a C14-20 divalent group formed by bonding an aromatic group and an aromatic group via an ester bond, or a C14-20 divalent group formed by bonding an aromatic group and an aromatic group via an ether bond.

Specific examples of the carbamate of the formula (21) include compounds in which $Y^1$ in the formula (21) is a C1-20 divalent aliphatic group, or a C6-20 divalent aromatic group, compounds of the below-shown formula (22), (23) or (24), and carbamates having an ester bond or an amide bond of the below-shown formula (B-2) and three carbamate groups.

Examples of the compounds in which $Y^1$ in the formula (21) is a C1-20 divalent aliphatic group or a C6-20 divalent aromatic group include 1,8-di(carbamic acid methyl ester) 4-(carbamic acid methyl ester)methyloctane, 1,3,6-tri(carbamic acid methyl ester)hexane, 1,8-di(carbamic acid methyl ester) 4-((carbamic acid methyl ester)methyl)-2,4,7-trimethyloctane, 1,5-di(carbamic acid methyl ester) 3-((carbamic acid methyl ester)methyl)pentane, 1,6,11-tri(carbamic acid methyl ester)undecan, 1,4,7-tri(carbamic acid methyl ester)heptane, 1,2,2-tri(carbamic acid methyl ester)butane, 1,2,6-tri(carbamic acid methyl ester)hexane, 1-(carbamic acid methyl ester) 2,2-bis((carbamic acid methyl ester)methyl)butane, 1,3,5-tri(carbamic acid methyl ester)cyclohexane, 1,7-di(carbamic acid methyl ester) 4-(3-(carbamic acid methyl ester)propyl)heptane, 1,3-di(carbamic acid methyl ester) 2-((carbamic acid methyl ester)methyl)-2-methylpropane, 1,3,5-tri(carbamic acid methyl ester)benzene, 1,3,5-tri(carbamic acid methyl ester) 2-methylbenzene, 1,3,5-tris(1-(carbamic acid methyl ester)propane-2-yl)benzene, 1,3,5-tris(1-(carbamic acid methyl ester)propane-2-yl)-2-methylbenzene, 1,3,5-tris(1-(carbamic acid methyl ester)methyl)-2-methylbenzene, 2,2'-((2-(carbamic acid methyl ester) 1,3-phenylene)bis(methylene)) bis((carbamic acid methyl ester)benzene), 1,8-di(carbamic acid ethyl ester) 4-(carbamic acid ethyl ester)ethyl octane, 1,3,6-tri(carbamic acid ethyl ester)hexane, 1,8-di(carbamic acid ethyl ester) 4-((carbamic acid ethyl ester)ethyl)-2,4,7-triethyl octane, 1,5-di(carbamic acid ethyl ester) 3-((carbamic acid ethyl ester)ethyl)pentane, 1,6,11-tri(carbamic acid ethyl ester)undecan, 1,4,7-tri(carbamic acid ethyl ester)heptane, 1,2,2-tri(carbamic acid ethyl ester)butane, 1,2,6-tri(carbamic acid ethyl ester)hexane, 1-(carbamic acid ethyl ester) 2,2-bis((carbamic acid ethyl ester)ethyl)butane, 1,3,5-tri(carbamic acid ethyl ester)cyclohexane, 1,7-di(carbamic acid ethyl ester) 4-(3-(carbamic acid ethyl ester)propyl)heptane, 1,3-di(carbamic acid ethyl ester) 2-((carbamic acid ethyl ester)ethyl)-2-ethyl propane, 1,3,5-tri(carbamic acid ethyl ester)benzene, 1,3,5-tri(carbamic acid ethyl ester) 2-ethylbenzene, 1,3,5-tris(1-(carbamic acid ethyl ester) propane-2-yl)benzene, 1,3,5-tris(1-(carbamic acid ethyl ester) propane-2-yl)-2-ethylbenzene, 1,3,5-tris(1-(carbamic acid ethyl ester) ethyl)-2-ethylbenzene, 2,2'-((2-(carbamic acid ethyl ester) 1,3-phenylene)bis(methylene)) bis((carbamic acid ethyl ester)benzene), 1,8-di(carbamic acid butyl ester) 4-(carbamic acid butyl ester)butyloctane, 1,3,6-tri(carbamic acid butyl ester)hexane, 1,8-di(carbamic acid butyl ester) 4-((carbamic acid butyl ester)butyl)-2,4,7-tributyloctane, 1,5-di(carbamic acid butyl ester) 3-((carbamic acid butyl ester)butyl)pentane, 1,6,11-tri(carbamic acid butyl ester)undecan, 1,4,7-tri(carbamic acid butyl ester)heptane, 1,2,2-tri(carbamic acid butyl ester)butane, 1,2,6-tri(carbamic acid butyl ester)hexane, 1-(carbamic acid butyl ester) 2,2-bis((carbamic acid butyl ester)butyl)butane, 1,3,5-tri(carbamic acid butyl ester)cyclohexane, 1,7-di(carbamic acid butyl ester) 4-(3-(carbamic acid butyl ester)propyl)heptane, 1,3-di(carbamic acid butyl ester) 2-((carbamic acid butyl ester)butyl)-2-butylpropane, 1,3,5-tri(carbamic acid butyl ester)benzene, 1,3,5-tri(carbamic acid butyl ester) 2-butylbenzene, 1,3,5-tris(1-(carbamic acid butyl ester)propane-2-yl)benzene, 1,3,5-tris(1-(carbamic acid butyl ester)propane-2-yl)-2-butylbenzene, 1,3,5-tris(1-(carbamic acid butyl ester)butyl)-2-butylbenzene, 2,2'-((2-(carbamic acid butyl ester) 1,3-phenylene) bis(methylene)) bis((carbamic acid butyl ester)benzene), 1,8-di(carbamic acid phenyl ester) 4-(carbamic acid phenyl ester) phenyloctane, 1,3,6-tri(carbamic acid phenyl ester)hexane, 1,8-di(carbamic acid phenyl ester) 4-((carbamic acid phenyl ester)phenyl)-2,4,7-triphenyloctane, 1,5-di(carbamic acid phenyl ester)-3-((carbamic acid phenyl ester)phenyl)pentane, 1,6,11-tri(carbamic acid phenyl ester)undecan, 1,4,7-tri(carbamic acid phenyl ester)heptane, 1,2,2-tri(carbamic acid phenyl ester)butane, 1,2,6-tri(carbamic acid phenyl ester)hexane, 1-(carbamic acid phenyl ester) 2,2-bis((carbamic acid phenyl ester)phenyl) butane, 1,3,5-tri(carbamic acid phenyl ester)cyclohexane, 1,7-di(carbamic acid phenyl ester) 4-(3-(carbamic acid phenyl ester)propyl)heptane, 1,3-di(carbamic acid phenyl ester) 2-((carbamic acid phenyl ester)phenyl)-2-phenylpropane, 1,3,5-tri(carbamic acid phenyl ester)benzene, 1,3,5-tri(carbamic acid phenyl ester) 2-phenylbenzene, 1,3,5-tris(1-(carbamic acid phenyl ester)propane-2-yl)benzene, 1,3,5-tris(1-(carbamic acid phenyl ester)propane-2-yl)-2-phenylbenzene, 1,3,5-tris(1-(carbamic acid phenyl ester) phenyl)-2-phenylbenzene, 2,2'-((2-(carbamic acid phenyl ester) 1,3-phenylene)bis(methylene)) bis((carbamic acid phenyl ester)benzene), 1,8-di(carbamic acid dimethylphenyl ester) 4-(carbamic acid dimethylphenyl ester) dimethylphenyloctane, 1,3,6-tri(carbamic acid dimethylphenyl ester) hexane, 1,8-di(carbamic acid dimethylphenyl ester) 4-((carbamic acid dimethylphenyl ester) dimethylphenyl)-2,4,7-tridimethylphenyloctane, 1,5-di(carbamic acid dimethylphenyl ester) 3-((carbamic acid dimethylphenyl ester) dimethylphenyl)pentane, 1,6,11-tri(carbamic acid dimethylphenyl ester)undecan, 1,4,7-tri(carbamic acid dimethylphenyl ester)heptane, 1,2,2-tri(carbamic acid dimethylphenyl ester)butane, 1,2,6-tri(carbamic acid dimethylphenyl ester)hexane, 1-(carbamic acid dimethylphenyl ester) 2,2-bis((carbamic acid dimethylphenyl ester)dimethylphenyl)butane, 1,3,5-tri(carbamic acid dimethylphenyl ester) cyclohexane, 1,7-di(carbamic acid dimethylphenyl ester) 4-(3-(carbamic acid dimethylphenyl ester)propyl)heptane, 1,3-di(carbamic acid dimethylphenyl ester) 2-((carbamic acid dimethylphenyl ester) dimethylphenyl)-2-dimethylphenylpropane, 1,3,5-tri(carbamic acid dimethylphenyl ester) benzene, 1,3,5-tri(carbamic acid dimethylphenyl ester) 2-dimethylphenylbenzene, 1,3,5-tris(1-(carbamic acid dimethylphenyl ester) propane-2-yl)benzene, 1,3,5-tris(1-(carbamic acid dimethylphenyl ester)propane-2-yl)-2-dimethylphenylbenzene, 1,3,5-tris(1-(carbamic acid dimethylphenyl ester)dimethylphenyl)-2-dimethylphenylbenzene, 2,2'-((2-(carbamic acid dimethylphenyl ester) 1,3-phenylene) bis(methylene)) bis((carbamic acid dimethylphenyl ester)benzene), 1,8-di(carbamic acid phenyl ester) 4-(carbamic acid phenyl ester)methyloctane, and 1,8-di(carbamic acid (methylphenyl)ester) 4-(carbamic acid (methylphenyl) ester)methyloctane. Among these, 1,8-di(carbamic acid phenyl ester) 4-(carbamic acid phenyl ester)methyloctane, and 1,8-di(carbamic acid (methylphenyl)ester) 4-(carbamic acid (methylphenyl)ester)methyloctane are preferable.

2-(carbamic acid phenyl ester)ethyl-2,5-di(carbamic acid phenyl ester)pentanoate, and 2-(carbamic acid dimethylphenyl ester)ethyl-2,5-di(carbamic acid dimethylphenyl ester) pentanoate;

compounds in which e is 4, f and h are 0, $R^g$ is an ethylene group, j and l are 0, and k is 1, such as 2-(carbamic acid methyl ester)ethyl-2,6-di(carbamic acid methyl ester) hexanoate, 2-(carbamic acid ethyl ester)ethyl-2,6-di(carbamic acid ethyl ester)hexanoate, 2-(carbamic acid butyl ester)ethyl-2,6-di(carbamic acid butyl ester)hexanoate, 2-(carbamic acid phenyl ester)ethyl-2,6-di(carbamic acid phenyl ester)hexanoate, 2-(carbamic acid dimethylphenyl ester)ethyl-2,6-di(carbamic acid dimethylphenyl ester) hexanoate, compounds in which d is 2, $R^g$ is an ethylene group, e is 1, f and h are 0, j and k are 1, and l is 0, such as bis(2-(carbamic acid ethyl ester)ethyl)-2-(carbamic acid ethyl ester)butanedioate, bis(2-(carbamic acid methyl ester)ethyl)-2-(carbamic acid methyl ester)butanedioate, bis(2-(carbamic acid butyl ester)ethyl)-2-(carbamic acid butyl ester)butanedioate, and bis(2-(carbamic acid phenyl ester)ethyl)-2-(carbamic acid phenyl ester) butanedioate, compounds in which d is 2, $R^g$ is an ethylene group, e is 2, f and h are 0, j and k are 1, and l is 0, such as bis(2-(carbamic acid ethyl ester)ethyl)-2-(carbamic acid ethyl ester)pentanedioate, bis(2-(carbamic acid methyl ester)ethyl)-2-(carbamic acid methyl ester)pentanedioate, bis(2-(carbamic acid butyl ester)ethyl)-2-(carbamic acid butyl ester)pentanedioate, and bis(2-(carbamic acid phenyl) ethyl)-2-(carbamic acid phenyl)pentanedioate, and compounds in which d and i are 2, $R^9$ is an ethylene group, j, k and l are 1, e is 3, f is 2, and h is 0, such as

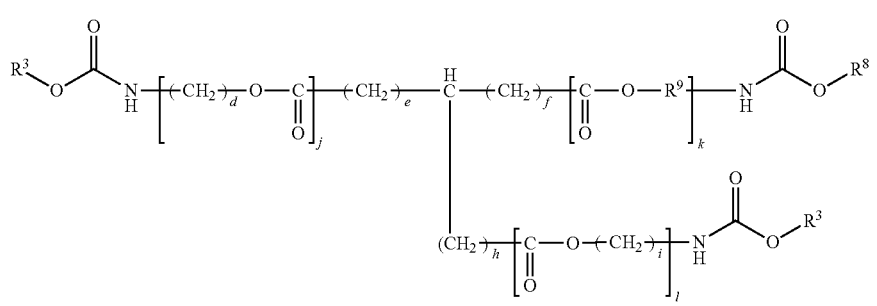

(22)

In the formula (22), $R^9$ represents a C1-10 aliphatic hydrocarbon group (preferably a C1-6 linear or branched alkylene group), d and i each independently represent an integer of 1 to 4, e, f, and h each independently represent an integer of 0 to 5, j, k and l each independently represent 0 or 1, the sum of j, k, and l is 1 to 3, and $R^3$ represents a group of the formula (20) (preferably a phenyl group).

Specific examples of the compound of the formula (22) include: compounds in which e is 3, f and h are 0, j and l are 0, k is 1, and $R^g$ is an ethylene group, such as 2-(carbamic acid ethyl ester) ethyl-2,5-di(carbamic acid ethyl ester) pentanoate, 2-(carbamic acid methyl ester)ethyl-2,5-di(carbamic acid methyl ester)pentanoate, 2-(carbamic acid butyl ester)ethyl-2,5-di(carbamic acid butyl ester)pentanoate, tris(2-(carbamic acid ethyl ester)ethyl)hexane-1,3,6-tricarboxylate, tris(2-(carbamic acid methyl)ethyl)hexane-1,3,6-tricarboxylate, tris(2-(carbamic acid butyl ester)ethyl) hexane-1,3,6-tricarboxylate, and tris(2-(carbamic acid phenyl ester)ethyl)hexane-1,3,6-tricarboxylate.

Additional examples thereof include 2-((phenoxycarbonyl)amino)ethyl (phenoxy carbonyl)glutaminate, bis(2-((phenoxy carbonyl)amino)ethyl) (phenoxycarbonyl)aspartate, and 2-((phenoxycarbonyl)amino) ethyl 2,5-bis ((phenoxycarbonyl)amino)pentanoate.

Among these, a carbamate of the below-shown formula (II) is also preferable.

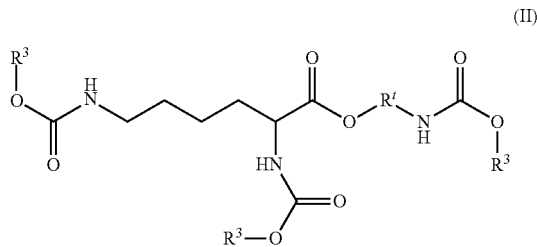

(II)

In the formula, $R'$ represents an alkylene group as defined in the formula (I), and $R^3$ represents a group defined in the formula (20).

$R^3$ preferably represents a phenyl group.

and an aliphatic group via an ester bond, a C2-20 divalent group formed by bonding an aliphatic group and an aliphatic group via an ether bond, a C7-20 divalent group formed by bonding an aliphatic group and an aromatic group via an ester bond, a C7-20 divalent group formed by bonding an aliphatic group and an aromatic group via an ether bond, a C14-20 divalent group formed by bonding an aromatic group and an aromatic group via an ester bond, or a C14-20 divalent group formed by bonding an aromatic group and an aromatic group via an ether bond, more preferably represents a single bond or a C1-20 divalent aliphatic group, or a C6-20 divalent aromatic group, and even more preferably represents a single bond.

$R^3$ preferably represents a C1-6 alkyl group.

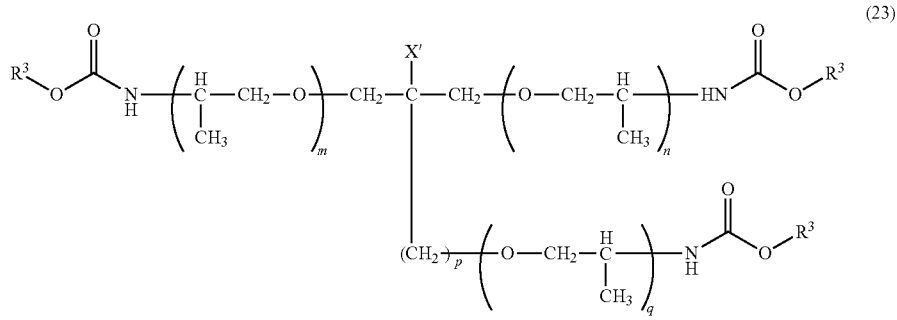

(23)

In the formula (23), X' represents a C1-4 hydrocarbon group, m, n, and q each represents an integer of 1 or more, the sum of m, n and q is 3 to 99, p represents an integer of 0 to 3, and $R^3$ represents a group defined in the formula (20).

A compound of the below-shown formula (24) may also be used preferably as a carbamate according to the present embodiment.

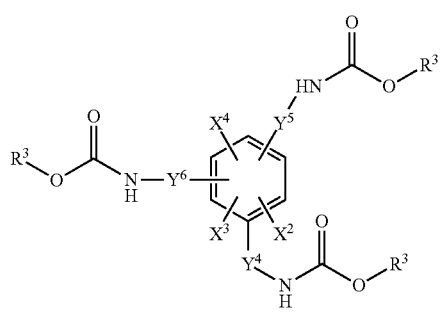

(24)

In the formula (24), $X^2$ to $X^4$ each independently represent a hydrogen atom or a C1-12 monovalent hydrocarbon group, $Y^4$ to $Y^6$ each independently represent a C1-20 divalent hydrocarbon group which may have an ester bond and/or an ether bond or a single bond, and $R^3$ represents a group defined in the formula (20).

In the formula (24), $X^2$ to $X^4$ preferably represents a group defined as $R^2$ in the formula (16), and more preferably represents a hydrogen atom.

$Y^4$ to $Y^6$ each preferably represent a single bond, a C1-20 divalent aliphatic group, a C6-20 divalent aromatic group, a C2-20 divalent group formed by bonding an aliphatic group In addition, compounds formed by trimerizing three molecules of the difunctional carbamate via an isocyanurate-ring structure or a biuret bond may be used as a trifunctional carbamate.

Specific examples of the compound of the formula (24) include 1,3,5-tri(carbamic acid methyl ester)benzene, 1,3,5-tri(carbamic acid methyl ester) 2-methylbenzene, 1,3,5-tris (1-(carbamic acid methyl ester)propane-2-yl)benzene, 1,3,5-tris(1-(carbamic acid methyl ester)propane-2-yl)-2-methylbenzene, 1,3,5-tris(1-(carbamic acid methyl ester)methyl)-2-methylbenzene, 2,2'-((2-(carbamic acid methyl ester) 1,3-phenylene)bis(methylene)) bis((carbamic acid methyl ester)benzene), 1,3,5-tri(carbamic acid ethyl ester)benzene, 1,3,5-tri(carbamic acid ethyl ester) 2-methylbenzene, 1,3,5-tris(1-(carbamic acid ethyl ester)propane-2-yl)benzene, 1,3,5-tris(1-(carbamic acid ethyl ester)propane-2-yl)-2-methylbenzene, 1,3,5-tris(1-(carbamic acid ethyl ester)methyl)-2-methylbenzene, 2,2'-((2-(carbamic acid ethyl ester) 1,3-phenylene) bis(methylene)) bis((carbamic acid ethyl ester)benzene), 1,3,5-tri(carbamic acid butyl ester)benzene, 1,3,5-tri(carbamic acid butyl ester) 2-methylbenzene, 1,3,5-tris(1-(carbamic acid butyl ester) propane-2-yl)benzene, 1,3,5-tris(1-(carbamic acid butyl ester)propane-2-yl)-2-methylbenzene, 1,3,5-tris(1-(carbamic acid butyl ester)methyl)-2-methylbenzene, 2,2'-((2-(carbamic acid butyl ester) 1,3-phenylene) bis(methylene)) bis((carbamic acid butyl ester)benzene), 1,3,5-tri(carbamic acid phenyl ester)benzene, 1,3,5-tri(carbamic acid phenyl ester) 2-methylbenzene, 1,3,5-tris(1-(carbamic acid phenyl ester)propane-2-yl)benzene, 1,3,5-tris(1-(carbamic acid phenyl ester)propane-2-yl)-2-methylbenzene, 1,3,5-tris(1-(carbamic acid phenyl ester) methyl)-2-methylbenzene, 2,2'-((2-(carbamic acid phenyl ester) 1,3-phenylene) bis(methylene)) bis((carbamic acid phenyl ester)benzene), 1,3,5-tri(carbamic acid dimethylphenyl ester)benzene, 1,3,5-tri(carbamic acid dimethylphenyl ester) 2-methylbenzene, 1,3,5-tris(1-(carbamic acid dimethylphenyl ester)propane-2-yl)benzene, 1,3,5-tris(1-(carbamic acid dimethylphenyl ester)propane-2-yl) 2-methylbenzene, 1,3,5-tris(1-(carbamic acid dimethylphenyl ester)methyl)-2-methylbenzene, and 2,2'-((2-(carbamic acid dimethylphenyl ester) 1,3-phenylene) bis(methylene)) bis((carbamic acid dimethylphenyl ester)benzene).

In addition, a compound of the below-shown formula (B-1) or (B-2) may be used as a polyfunctional carbamate.

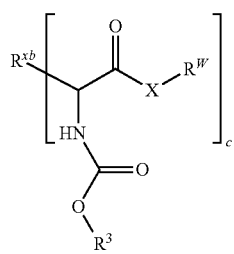
(B-1)

In the formula, X represents a group defined in the formula (A-1).

$R^{xb}$ represents an aliphatic group having a carbon number of 1 or more or an aromatic group having a carbon number of 6 or more, which may contain a carbamate group, a sulfur atom, an oxygen atom, or a halogen atom.

$R^3$ represents a group defined in the formula (20), and preferably represents a phenyl group.

$R^w$ represents a C1-15 aliphatic group, a C6-15 aromatic group or a hydrogen atom, and preferably represents a C1-6 alkyl group.

c represents 2 or 3.

In the formula (B-1), $R^{xb}$ preferably has a structure formed by removing a —NHCOOH group from an amino acid, and preferably represents a C1-15 aliphatic group or a C6-15 aromatic group.

Preferable examples of the compound of the formula (B-1) include compounds of the below-shown formulae.

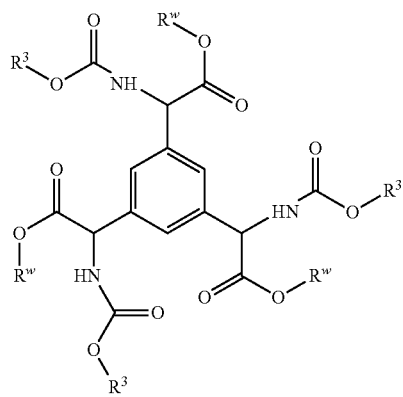
(B-2)

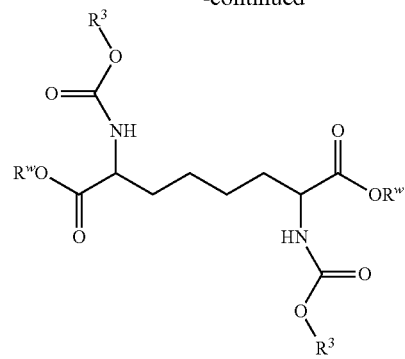
-continued

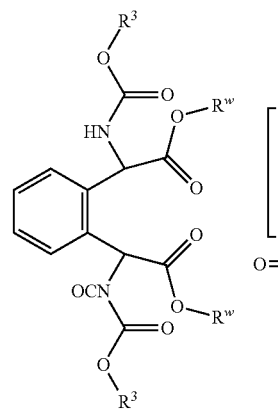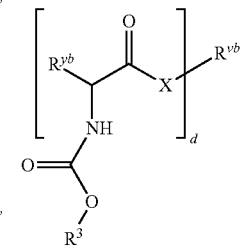

In the formula, X and $R^3$ each represent a group defined in the formula (B-1).

$R^{yb}$ represents an aliphatic group having a carbon number of 1 or more or an aromatic group having a carbon number of 6 or more, which may contain a carbamate group, a sulfur atom, an oxygen atom, or a halogen atom, or a hydrogen atom.

$R^{vb}$ represents a C1-15 aliphatic group or a C6-15 aromatic group, which may have a carbamate group, or a hydrogen atom.

d represents an integer of 1 to 4.

In the formula (B-2), $R^{yb}$ represents a C1-15 aliphatic group which may have a group selected from the group consisting of groups of the below-shown formulae (i-2) to (ii-2) and (iii-2) to (iv-2), a C6-15 aromatic group which may have a group selected from the group consisting of groups of the below-shown formula (i-2) to (ii-2) and (iii-2) to (iv-2), a C7-15 group which is formed by bonding an aliphatic group and an aromatic group and which may have a group selected from the group consisting of groups of the below-shown formula (i-2) to (ii-2) and (iii-2) to (iv-2), a group of any one of the below-shown formulae (IV-2) to (V-2), or a hydrogen atom.

—O— (i-2)

—S— (ii-2)

 (iii-2)

—S—S— (iv-2)

In the formula (iii-2), $R^3$ represents a group defined in the formula (B-2).

In the formulae (i-2) to (iv-2), an atom to which a nitrogen atom or a sulfur atom is bonded is a carbon atom.

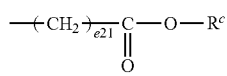
(IV-2)

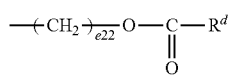
(V-2)

In the formula (IV-2), e21 represents an integer of 0 to 5, and $R^c$ represents a group of the below-shown formula (1-2), (11-2), or (111-2), or a C1-10 aliphatic hydrocarbon group.

In the formula (V-2), e22 represents an integer of 0 to 5, and $R^d$ represents a C1-15 aliphatic hydrocarbon group or a C6-15 aromatic hydrocarbon group.

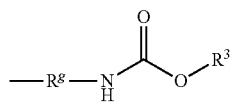
(I-2)

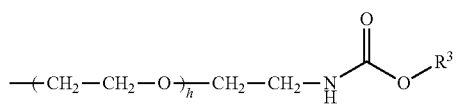
(II-2)

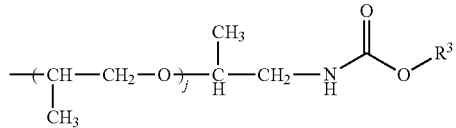
(III-2)

In the formulae, $R^g$ represents a C1-10 aliphatic hydrocarbon group, h represents an integer of 1 to 9, j represents an integer of 0 to 9, and $R^3$ represents a group defined in the formula (B-2).

In the formula (IV-2), $R^c$ preferably represents a group defined in the formula (I-1).

Examples of the carbamate according to the present embodiment include compounds of the below-shown formulae.

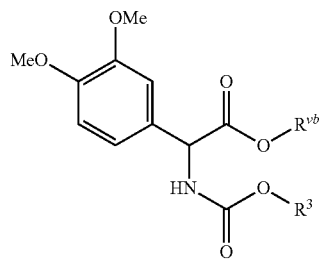

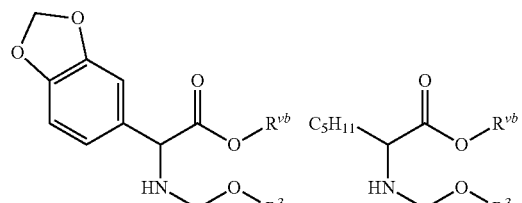

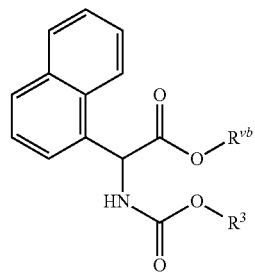

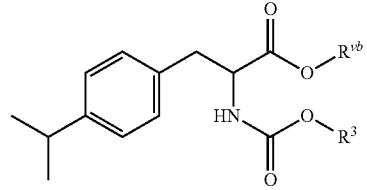

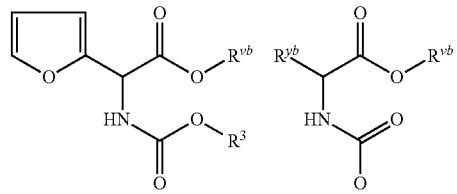

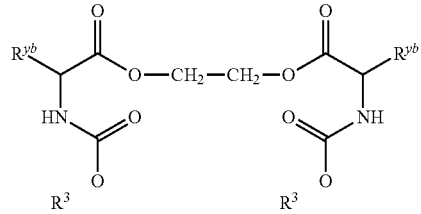

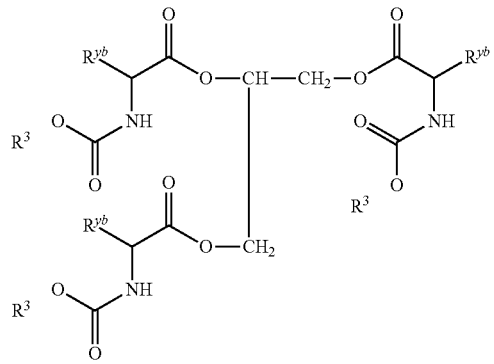

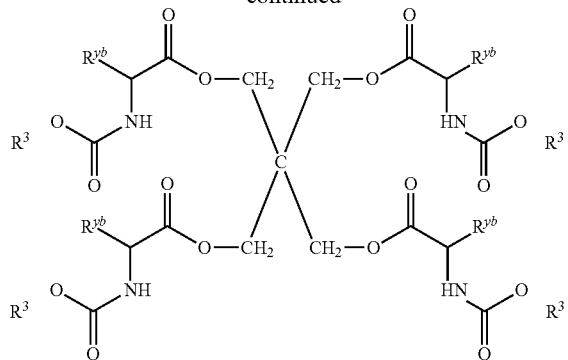

In the formulae, $R^{yb}$, $R^{vb}$ and $R^3$ are as defined as above. $R^{yb}$ preferably represents a C1-6 aliphatic group which may have a carbamate group, and $R^3$ preferably represents a phenyl group.

Specific examples of the carbamate of the formula (B-2) include 2-((phenoxy carbonyl)amino)ethyl (phenoxy carbonyl)alaninate, 2-((phenoxy carbonyl)amino)ethyl (phenoxy carbonyl)alginate, 2-((phenoxycarbonyl)amino)ethyl $N^2,N^4$-bis(phenoxycarbonyl)asparaginate, 2-((phenoxycarbonyl)amino)ethyl (phenoxycarbonyl)glycinate, 2-(phenoxy carbonyl)amino)ethyl (phenoxy carbonyl)histidinate, 2-((phenoxy carbonyl)amino)ethyl 3-methyl-2-((phenoxycarbonyl)amino)pentanoate, 2-((phenoxy carbonyl)amino) ethyl (phenoxy carbonyl)leucinate, 2-(phenoxy carbonyl) amino)ethyl (phenoxy carbonyl)methioninate, 2-((phenoxy carbonyl)amino)ethyl (phenoxy carbonyl)phenylalaninate, 2-((phenoxy carbonyl)amino)ethyl (phenoxy carbonyl)tryptophanate, 2-((phenylcarbonyl)amino)ethyl (phenoxycarbonyl)valinate, methyl N2,N6-bis(phenoxy carbonyl)lysinate, O'1,O1-(ethane-1,2-diyl)-5,5'-dimethyl bis(2-((phenoxy carbonyl)amino)pentanedioate), dimethyl(phenoxy carbonyl) glutamate, methyl(phenoxycarbonyl)methioninate, methyl (phenoxy carbonyl)glycinate, methyl(phenoxy carbonyl) phenylalaninate, dimethyl(phenoxy carbonyl)aspartate, methyl(phenoxy carbonyl)alaninate, methyl(phenoxycarbonyl)leucinate, methyl(phenoxycarbonyl) isoleucinate, methyl(phenoxycarbonyl)valinate, ethyl $N^2,N^6$-bis(phenoxycarbonyl)isoleucsinate, ethane-1,2-diyl-bis(2,6-bis((phenoxycarbonyl)amino)hexanoate, 2,2-bis(((N2,N6-bis (phenoxy carbonyl)lysyl)oxy)methyl)propane-1,3-diyl-bis (2,6-bis((phenoxycarbonyl)amino)hexanoate, ethyl-2,5-bis ((phenoxy carbonyl)amino)pentanoate, ethane-1,2-diyl-bis (2,5-bis((phenoxy carbonyl)amino)pentanoate), 2,2-bis(((2, 5-bis((phenoxycarbonyl)amino)pentanoyl)oxy)methyl) propane-1,3-diyl-bis(2,5-bis((phenoxycarbonyl)amino)pentanoate), ethyl (phenoxy carbonyl)methioninate, 1-((phenoxy carbonyl)amino)ethyl (phenoxy carbonyl)methioninate, 1-((phenoxy carbonyl)amino)propyl (phenoxycarbonyl)methioninate, ethane-1,2-diyl-bis(4-(methylthio)-2-((phenoxy carbonyl)amino)butanoate, 2,2-bis((((phenoxy carbonyl)methionyl)oxy)methyl)propane-1, 3-diyl-bis(4-methylthio)-2-((phenoxycarbonyl)amino) butanoate), diethyl (phenoxy carbonyl)glutamate, bis(1-((phenoxy carbonyl)amino)ethyl)(phenoxy carbonyl) glutamate, bis(1-((phenoxy carbonyl)amino)propyl) (phenoxy carbonyl)glutamate, O'1,O1-(ethane-1,2-diyl)-5, 5'-bis(1-((phenoxy carbonyl)amino)propyl) bis(2-((phenoxy carbonyl)amino)pentanedioate, O'1,O1-(2,2-bis(((5-oxo-2-((phenoxy carbonyl)amino)-5-(1-((phenoxy carbonyl) amino)propoxy)pentanoyl)oxy)methyl)propane-1,3-diyl) 5,5'-bis(1-((phenoxy carbonyl)amino)propyl) bis(2-((phenoxy carbonyl)amino)pentanedioate, 1-((phenoxy carbonyl) amino)propane-2-yl (phenoxy carbonyl)alaninate, methyl 3-methyl-2-(((4-(2-phenylpropane-2-yl)phenoxy)carbonyl) amino) pentanoate, dibutyl (phenoxycarbonyl)glutamate, 5-((phenoxycarbonyl)amino)hexyl 3-methyl-2-((phenoxycarbonyl)amino) pentanoate, 2-(((2,6-dimethylphenoxy)carbonyl)amino)ethyl-((2,6-dimethylphenoxy) carbonyl)phenyl alaninate, 2-(((4-ethyl phenoxy)carbonyl)amino)ethyl ((4-ethyl phenoxy)carbonyl)triptophanate, and methyl((4-(2,4,4-trimethylpentane-2-yl)phenoxy)carbonyl)valinate.

<Each Material>

Each material used in the present embodiment will be described below.

<<Inactive Solvent>>

An inactive solvent available in the present embodiment is substantially inactive under reaction conditions, and is not particularly limited, provided that the boiling point thereof is between the boiling point of the resultant isocyanate and that of the resultant hydroxyl compound.

Examples of such a thermally-decomposable solvent include aliphatic compounds, alicyclic compounds, aromatic compounds that may have a substituent, unsubstituted hydrocarbons and mixtures thereof.

Additional examples thereof include compounds that may have an oxygen atom, such as ethers, ketones, and esters, and compounds that may have a sulfur atom, such as thioethers, sulfoxides, and sulfones.

In the present embodiment, alkanes such as hexane, heptane, octane, nonane, decane, n-dodecane, tetradecane, n-pentadecane, n-hexadecane, n-octadecane, eicosane, and squalene, and ketones corresponding to the alkanes; alkanes substituted by halogen, such as chlorododecane; aromatic hydrocarbons and alkyl-substituted aromatic hydrocarbons such as benzene, toluene, xylene, ethylbenzene, hexylbenzene, cumene, diisopropyl benzene, dibutyl benzene, triethyl benzene, naphthalene, lower alkyl-substituted naphthalene, and dodecyl benzene; aromatic compounds substituted with a nitro group, a halogen or both a halogen and a lower alkyl group, such as chlorobenzene, dichlorobenzene, trichlorobenzene, methylbenzyl chloride, bromobenzene, dibromobenzene, chloronaphthalene, bromonaphthalene, nitrobenzene, and nitronaphthalene; polycyclic aromatic hydrocarbon compounds such as diphenyl, substituted diphenyl, diphenylmethane, diphenylethane, terphenyl, anthracene, fluorene, phenanthrene, benzyltoluene, isomers of benzyltoluene, and triphenylmethane; heteropolycyclic compounds such as xanthene; alicyclic hydrocarbons such as cyclohexane, ethylcyclohexane, cyclododecane, and decalin; ketones such as methylethyl ketone, and acetophenone; esters such as dibutyl phthalate, dihexyl phthalate, dioctyl phthalate, triacetin, and diethyl phthalate; ethers and thioethers such as dibutyl cellosolve, dibenzyl ether, diphenyl ether, anisole, thioanisole, ethyl phenyl sulfide, and diphenyl sulfide; sulfoxides such as dimethyl sulfoxide, and diphenyl sulfoxide; sulfones such as dimethyl sulfone, diethyl sulfone, diphenyl sulfone, and sulfolane; silicones such as decamethyltetrasiloxane, decamethylcyclopentasiloxane; silicone oil; and amines such as tributyl amine can be mentioned. Among these, aromatic compounds substituted with (a) nitro group(s) or (a) halogen(s), such as chlorobenzene, dichlorobenzene, trichlorobenzene, bromobenzene, dibromobenzene, chloronaphthalene, bromonaphthalene, nitrobenzene, and nitronaphthalene are preferable, and benzenes substituted with halogen, such as chlorobenzene and dichlorobenzene are more preferable. The term "lower" means that the carbon number is 1 to 6.

<<Polyisocyanate Compound>>

As a polyisocyanate compound available in the present embodiment, a polyisocyanate compound obtained by polymerizing isocyanates is preferable, and, a polyisocyanate compound obtained by polymerizing diisocyanates in which c in the formula (2) is 2 by a conventionally-known method, and having a unit of the below-shown formula (A) and at least one unit selected from the group consisting of units of the below-shown formulae (25) to (29), in which a group bonded to $R^5$ in the below-shown formula (25) to (29) is a group of the below-shown formula (B) or a group of the below-shown formula (30) is more preferable. A nitrogen atom constituting the polyisocyanate compound is bonded to a carbon atom.

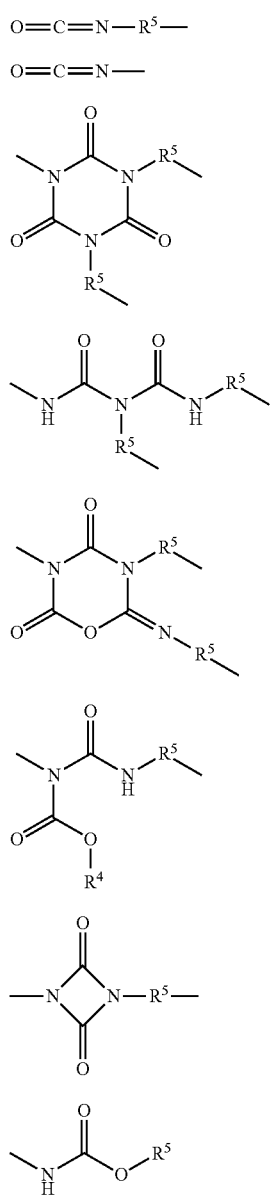

In the formulae (A), (B) and (25) to (30) $R^4$ represents a C1-15 monovalent organic group, preferably represents a C1-15 aliphatic group or a C6-15 aromatic group, and specifically represents a methyl group, an ethyl group, a propyl group, a butyl group, a pentyl group, a hexyl group, an octyl group, a cyclopentyl group, a cyclohexyl group, a residual group formed by removing one hydrogen atom from adamantane, norbornane, isobornane, tricyclodecane, or tetracyclododecane, a phenyl group, a methylphenyl group, an ethylphenyl group, a propylphenyl group, a butylphenyl group, a pentylphenyl group, a hexylphenyl group, a dimethylphenyl group, a methylethylphenyl group, a methylpropylphenyl group, a methylbutylphenyl group, a methylpentylphenyl group, a diethylphenyl group, an ethylpropylphenyl group, an ethylbutylphenyl group, a dipropylphenyl group, a trimethylphenyl group, a triethylphenyl group, or a naphthyl group.

$R^5$ each independently represents a residual group formed by removing two isocyanate groups from the isocyanate mentioned in the paragraph relating to the "isocyanate", and, from the standpoint of industrial use or the like, preferably represents a residual group formed removing two isocyanate groups from an aliphatic diisocyanate and/or an aromatic diisocyanate, and more preferably represents a residual group formed by removing two isocyanate group from at least one diisocyanate selected from the group consisting of hexamethylene diisocyanate, isophorone diisocyanate, 4,4'-dicyclohexylmethane diisocyanate, 2,4-toluenediisocyanate, 2,6-toluenediisocyanate, and 4,4'-diphenylmethane diisocyanate.

$R^6$ each independently represent a C1-15 monovalent organic group, preferably represents a C1-15 aliphatic group or a C6-15 aromatic group, and specifically represents a methyl group, an ethyl group, a propyl group, a butyl group, a pentyl group, a hexyl group, an octyl group, a cyclopentyl group, a cyclohexyl group, a residual group formed by removing one hydrogen atom from adamantane, norbornane, isobornane, tricyclodecane, or tetracyclododecane, a phenyl group, a methylphenyl group, an ethylphenyl group, a propylphenyl group, a butylphenyl group, a pentylphenyl group, a hexylphenyl group, a dimethylphenyl group, a methylethylphenyl group, a methylpropylphenyl group, a methylbutylphenyl group, a methylpentylphenyl group, a diethylphenyl group, an ethylpropylphenyl group, an ethylbutylphenyl group, a dipropylphenyl group, a trimethylphenyl group, a triethylphenyl group, or a naphthyl group.

$R^4$ in the formula (28) and $R^6$ in the formula (30) depend of compounds used to prepare the polyisocyanate compound, and, in the case where an alcohol is used, for example, the groups often represent residual groups each formed by removing a hydroxy group (OH group) from the alcohol.

The polyisocyanate compound according to the present embodiment has at least one structure selected from the group consisting of units of the above-shown formulae (25) to (29), preferably has 1 unit to 10 units, more preferably has 1 unit to 5 units, an even more preferably has 1 unit to 3 units. The number of the above-mentioned structural units contained in the polyisocyanate compound may be calculated by $^1$H NMR analysis or the like, or calculated from a molecular weight calculated by gel permeation chromatography or the like. The polyisocyanate compound may constitute a homologous composition constituted by single compounds having the same number of a unit selected from the group consisting of units of the above-shown formulae (25) to (29), or a composite composition constituted by plural compounds having different numbers of the unit.

Although the structure of the polyisocyanate compound according to the present embodiment depends of the used isocyanate compound, formulation of an isocyanate composition, reaction conditions, or the like, preferable examples of the structure thereof include structures of the below-shown formulae.

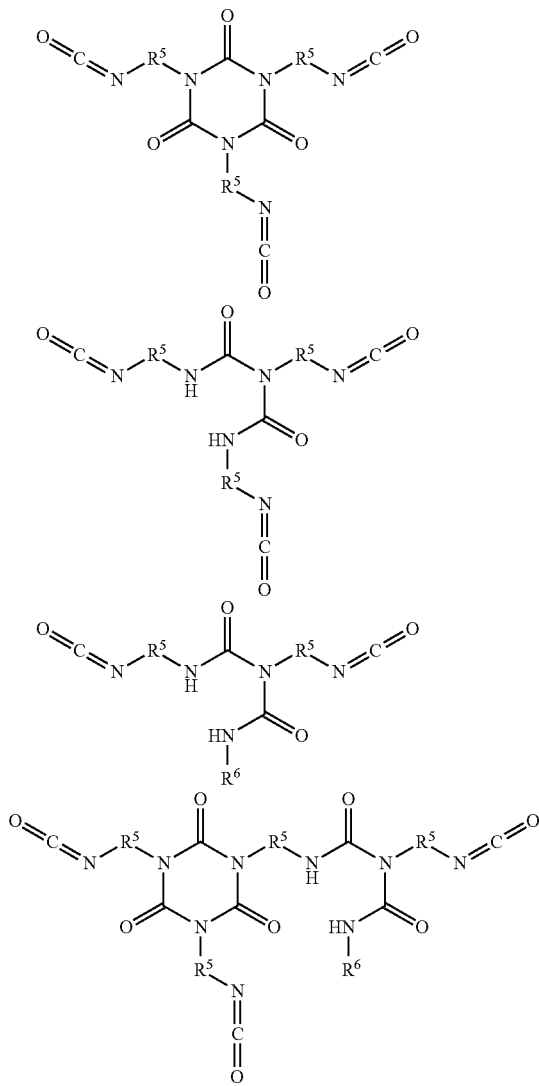

In the formulae, $R^5$ and $R^6$ are defined in the formulae (A) and (25) to (30).

<<Carbonic Acid Ester>>

A carbonic acid ester available in the production method according to the present embodiment is preferably a compound of the below-shown formula (32).

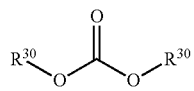

(32)

In the formula, $R^{30}$ each independently represents a C1-20 aliphatic hydrocarbon group or a C6-20 aromatic group.

In the case where $R^{30}$ is a C1-20 aliphatic hydrocarbon group, the hydrocarbon group may be linear or branched.

Examples of the aliphatic hydrocarbon group as $R^{30}$ include alkyl groups. The carbon number of the linear alkyl group is preferably 1 to 5, more preferably 1 to 4, and even more preferably 1 or 2. Specific examples thereof include a methyl group, an ethyl group, a n-propyl group, a n-butyl group, and a n-pentyl group. The carbon number of the branched alkyl group is preferably 3 to 10, and more preferably 3 to 5. Specific examples thereof include an isopropyl group, an isobutyl group, a tert-butyl group, an isopentyl group, a neopentyl group, a 1,1-diethylpropyl group, and a 2,2-dimethylbutyl group.

The alicyclic hydrocarbon group may be polycyclic or monocyclic. Specific examples of the monocyclic alicyclic hydrocarbon group include cyclopentane and cyclohexane. Specific examples of the polycyclic alicyclic hydrocarbon group include adamantane, norbornane, isobornane, tricyclodecane, and tetracyclododecane.

$R^{30}$ in the formula (32) is preferably a C6-20 aromatic hydrocarbon group, and more preferably a C6-12 aromatic hydrocarbon group. Although a diaryl carbonate in which $R^{30}$ is an aromatic hydrocarbon group having a carbon number of 21 or more may be used, the number of carbons constituting $R^{30}$ is preferably 20 or less, from the viewpoint of facilitation of separation from an isocyanate produced by the thermal decomposition reaction of a carbamic acid ester.

Examples of $R^{30}$ include a phenyl group, a methylphenyl group (each isomer), an ethylphenyl group (each isomer), a propylphenyl group (each isomer), a butylphenyl group (each isomer), a pentylphenyl group (each isomer), a hexylphenyl group (each isomer), a dimethylphenyl group (each isomer), a methylethyl phenyl group (each isomer), a methylpropylphenyl group (each isomer), a methylbutylphenyl group (each isomer), a methylpentylphenyl group (each isomer), a diethylphenyl group (each isomer), an ethylpropylphenyl group (each isomer), an ethylbutylphenyl group (each isomer), a dipropylphenyl group (each isomer), a trimethylphenyl group (each isomer), a triethylphenyl group (each isomer), and a naphthyl group (each isomer).

Among these carbonic acid esters, diaryl carbonates in which $R^{30}$ is a C6-8 aromatic hydrocarbon group are preferable, and examples of such diaryl carbonates include diphenyl carbonate, di(methylphenyl) carbonate (each isomer), di(diethyl phenyl) carbonate (each isomer), and di(methylethylphenyl) carbonate (each isomer).

In the present embodiment, the compound of the formula (32) is preferably a diaryl carbonate of the below-shown formula (2).

(33)

In the formula, $R^{30a}$ each independently represents a C6-20 aromatic hydrocarbon group.

$R^{30a}$ in the formula (33) is a C6-20 aromatic hydrocarbon group, preferably a C6-12 aromatic hydrocarbon group, and more preferably a phenyl group.

The carbonic acid ester or the diaryl carbonate preferably contain a metal atom in an amount, relative to the total mass of the carbonic acid ester or the diaryl carbonate, of 0.001 ppm by mass to 10% by mass, more preferably 0.001 ppm by mass to 5% by mass, and even more preferably 0.002 ppm by mass to 3% by mass.

The metal atom may be present as a metal ion or as an elemental substance of the metal atom. As the metal atom, metal atoms having a valence of 2 to 4 are preferable, and, among these, one kind or plural kinds of metals selected from the group consisting of iron, cobalt, nickel, zinc, tin, copper, and titanium is(are) more preferable.

As the production method of the carbonic acid ester or the diaryl carbonate, a conventionally-known method may be used. As an example thereof, a method, disclosed in International Patent Application, Publication No. WO2009/139061, in which an organic tin compound having a tin-oxygen-carbon bond and a carbon dioxide are reacted to obtain a carbonic acid ester, followed by producing a diaryl carbonate from the carbonic acid ester and an aromatic hydroxy compound.

<<Aromatic Hydroxy Compound>>

Examples of the aromatic hydroxy compound available as a reaction solvent according to the present embodiment include phenol, and monosubstituted phenol such as methylphenol (each isomer), ethylphenol (each isomer), propylphenol (each isomer), butylphenol (each isomer), pentylphenol (each isomer), hexylphenol (each isomer), heptylphenol (each isomer), octylphenol (each isomer), nonylphenol (each isomer), decylphenol (each isomer), dodecylphenol (each isomer), phenylphenol (each isomer), phenoxyphenol (each isomer), and cumylphenol (each isomer). Among these aromatic hydroxy compounds, compounds corresponding to compounds ArOH formed by adding a hydrogen atom to a group ArO (in which Ar is an aromatic group and O is an oxygen atom), that constitutes a diaryl carbonate, are more preferably used. The compounds make it possible to decrease the kind of compounds in the reaction mixture obtained by reaction of a diaryl carbonate and an amine compound and simplify separation procedures.

The carbonic acid ester and the aromatic hydroxy compound may be produced using a manufacturing equipment described in International Patent Application, Publication No. WO2009/139061, for example.

<<Amine Compound>>

An amine compound of the below-shown formula (34) is preferable as an amine compound available as a starting material according to the present embodiment.

$$R^1\text{-}(NH_2)_c \tag{34}$$

In the formula (34), c and $R^1$ are defined in the formula (2).

In formula (34), $R^1$ preferably represents a C3-85 organic group, and more preferably represents a C3-30 organic group.

$R^1$ preferably represents an aliphatic group, an aromatic group, or a group formed by bonding an aliphatic group and an aromatic group. Specific examples of $R^1$ include: cyclic groups such as cyclic hydrocarbon groups (monocyclic hydrocarbon groups, condensed polycyclic hydrocarbon groups, cross-linked cyclic hydrocarbon groups, spiro hydrocarbon groups, ring-assembly hydrocarbon groups, side chain-containing cyclic hydrocarbon groups), heterocyclic groups, heterocyclic spiro groups, and hetero cross-linked cyclic groups; acyclic hydrocarbon groups, groups formed by bonding an acyclic hydrocarbon group and at least one cyclic group, and groups formed by bonding the above-mentioned group and a specific nonmetallic atom (carbon, oxygen, nitrogen, sulfur or silicon) via a covalent bond.

The covalent bond with the specific nonmetallic atom may generate the state, for example, in which the above-mentioned group is bonded with any of groups of formulae (3) to (15).

In the amine composition according to the present embodiment, an amine compound in which c in the formula (34) is an integer of 2 to 5, more preferably 2 or 3, and even more preferably 3, is preferable, in view of the ease of production or handling. Among amine compounds having a bonding of formula (3) to (15), an amine compound having a bonding of formula (3) to (5), (7), (9), (11), or (12), is preferable, and an amine compound having a bonding of formula (7), (9) or (12) is more preferable.

Among these, $R^1$ preferably represents an aliphatic hydrocarbon group, an aromatic hydrocarbon group, or a group formed by bonding a single kind or plural kinds of aliphatic hydrocarbon groups and/or aromatic hydrocarbon groups via an ether bond (—O—), a thioether bond (—S—), an ester bond (—COO—), or an amide bond (—CONH—), and more preferably represents an aliphatic hydrocarbon group, an aromatic hydrocarbon group, or a group formed by bonding a single kind or plural kinds of aliphatic hydrocarbon groups and/or aromatic hydrocarbon groups via an ester bond. The number of carbon atoms constituting $R^1$ is preferably 1 to 30.

Examples of a monofunctional amine compound in which c in the formula (34) is 1 include C1-30 aliphatic amine compounds, C6-30 alicyclic amine compound, and C6-30 amine compounds having an aromatic group.

The monofunctional amine compound in which c in the formula (34) is 1 may be an amine compound having an ester bond or an amide bond of the below-shown formula (C-2), and one amino group.

Examples of a difunctional diamine compound in which c in the formula (34) is 2 include C4-30 aliphatic diamines, C8-30 alicyclic diamines, and C8-30 diamines having an aromatic group.

Specific examples of the C4-30 aliphatic diamines include 1,4-tetramethylene diamine, 1,5-pentamethylene diamine, 1,4-diamino-2-methylbutane, 1,6-hexamethylene diamine, 1,6-diamino-2,5-dimethylhexane, 2,2,4-trimethyl-1,6-hexamethylene diamine, lysine methyl ester diamine, and lysine ethyl ester diamine.

Specific examples of the C8-30 alicyclic diamines include isophorone diamine, 1,3-bis(amine methyl)-cyclohexane, 4,4'-dicyclohexylmethane diamine, hydrogenated tetramethylxylylene diamine, and norbornene diamine.

Specific examples of the C8-30 diamines having an aromatic group include 4,4'-diphenylmethane diamine, 2,6-tolylene diamine, xylylene diamine, tetramethylxylylene diamine, and naphthalene diamine.

In the case where the above-mentioned compound has structural isomers, the structural isomers are encompassed in the above-mentioned examples.

The difunctional diamine compound in which c in the formula (34) is 2 may be an amine compound having an ester bond or an amide bond of the below-shown formula (C-1) or (C-2) and two amino groups.

As a trifunctional amine in which c in the formula (34) is 3, an amine compound of the below-shown formula (35) may be preferably used.

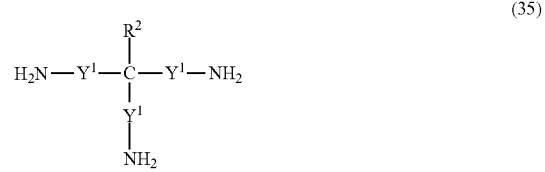

$$\tag{35}$$

In the formula (35), plural $Y^1$ each independently represent a single bond, or a C1-20 divalent hydrocarbon group which may have a bond selected from the group consisting of an ester bond, an ether bond and an amide bond, and $R^2$ represents a hydrogen atom or a C1-12 monovalent hydrocarbon group.

In the formula (35), $R^2$ preferably represents a C1-10 aliphatic group or a C6-10 aromatic group, and specific examples thereof include: aliphatic groups such as a methyl group, an ethyl group, a propyl group, a butyl group, a pentyl group, a hexyl group, and a decyl group; and aromatic groups such as a phenyl group, a methylphenyl group, an ethylphenyl group, a butylphenyl group, a dimethylphenyl group, and a diethylphenyl group.

In the formula (35), $Y^1$ preferably represents a C1-20 divalent aliphatic group, a C6-20 divalent aromatic group, a C2-20 divalent group formed by bonding an aliphatic group and an aliphatic group via an ester bond, a C2-20 divalent group formed by bonding an aliphatic group and an aliphatic group via an ether bond, a C7-20 divalent group formed by bonding an aliphatic group and an aromatic group via an ester bond, a C7-20 divalent group formed by bonding an aliphatic group and an aromatic group via an ether bond, a C14-20 divalent group formed by bonding an aromatic group and an aromatic group via an ester bond, or a C14-20 divalent group formed by bonding an aromatic group and an aromatic group via an ether bond.

Specific examples of the amine compound of the formula (35) include compounds in which $Y^1$ in the formula (35) is a C1-20 divalent aliphatic group, or a C6-20 divalent aromatic group, compounds of the below-shown formula (36), (37) or (38), and amine compounds having an ester bond or an amide bond of the below-shown formula (C-2) and three amino groups. Examples of the compounds in which $Y^1$ in the formula (35) is a C1-20 divalent aliphatic group and/or a C6-20 divalent aromatic group include 1,2,3-propane triamine, 1,8-diamine 4-amine methyloctane, 1,3,6-triamine hexane, 1,8-diamino 4-(aminomethyl)-2,4,7-trimethyloctane, 1,5-diamino 3-(aminomethyl)pentane, 1,6,11-triaminoundecan, 1,4,7-triaminoheptane, 1,2,2-triaminobutane, 1,2,6-triaminohexane, 1-amino 2,2-bis(aminomethyl) butane, 1,3,5-triaminocyclohexane, 1,7-diamino 4-(3-aminopropyl)heptane, 1,3-diamino 2-(aminomethyl)-2-methylpropane, 1,3,5-triaminobenzene, 1,3,5-triamino 2-methylbenzene, 1,3,5-tris(1-aminopropane-2-yl)benzene, 1,3,5-tris(1-aminopropane-2-yl)-2-methylbenzene, 1,3,5-tris(1-aminomethyl)-2-methylbenzene, and 2,2'-((2-amino 1,3-phenylene)bis(methylene))bis(amine benzene).

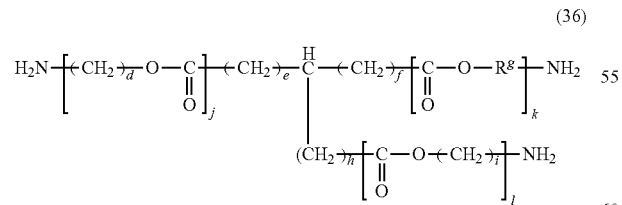

(36)

In the formula (36), $R^9$ represents a C1-10 aliphatic hydrocarbon group (preferably a C1-6 linear or branched alkylene group), d and i each independently represent an integer of 1 to 4, e, f, and h each independently represent an integer of 0 to 5, j, k, and l each independently represent 0 or 1, and the sum of j, k, and l is 1 to 3.

Specific examples of the compound of the formula (36) include: 2-aminoethyl-2,5-diaminopentanoate in which e is 3, f and h are 0, j and l are 0, k is 1, and $R^9$ represents an ethylene group; 2-aminoethyl-2,6-diaminohexanoate in which e is 4, f and h are 0, $R^9$ represents an ethylene group, j and l are 0, and k is 1; bis(2-aminoethyl)-2-aminobutanedioate in which d is 2, $R^9$ represents an ethylene group, e is 1, f and h are 0, j and k are 1, and l is 0; bis(2-aminoethyl)-2-aminopentanedioate in which d is 2, $R^9$ represents an ethylene group, e is 2, f and h are 0, j and k are 1, and l is 0; and tris(2-aminoethyl)hexane-1,3,6-tricarboxylate in which d and i are 2, $R^9$ represents an ethylene group, j, k and l are 1, e is 3, f is 2, and h is 0.

Among these, an aliphatic amine of the below-shown formula (III) is preferable.

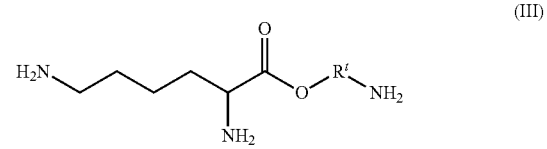

(III)

In the formula (III), $R^t$ represents an alkylene group as defined in the formula (I).

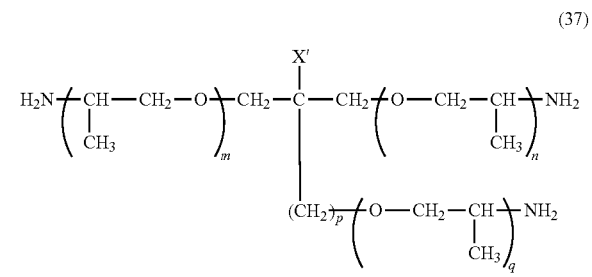

(37)

In the formula (37), X' represents a C1-4 hydrocarbon group, m, n, and q each represent an integer of 1 or more, the sum of m, n, and q is 3 to 99, and p represents an integer of 0 to 3.

A compound of the below-shown formula (38) is also preferably used as an amine compound according to the present embodiment.

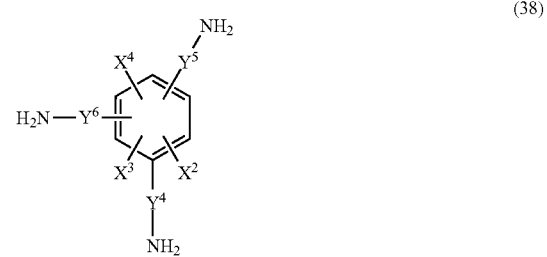

(38)

In the formula (38), $X^2$ to $X^4$ each independently represent a hydrogen atom or a C1-12 monovalent hydrocarbon group, and $Y^4$ to $Y^6$ each independently represent a C1-20 divalent hydrocarbon which may have an ester bond and/or an ether bond or a single bond.

In the formula (38), $X^2$ to $X^4$ each preferably represent a group defined as $R^2$ in the formula (16), and more preferably represent a hydrogen atom.

$Y^4$ to $Y^6$ each preferably represent a single bond, a C1-20 divalent aliphatic group, C6-20 divalent aromatic group, a C2-20 divalent group formed by bonding an aliphatic group and an aliphatic group via an ester bond, a C2-20 divalent group formed by bonding an aliphatic group and an aliphatic group via an ether bond, a C7-20 divalent group formed by bonding an aliphatic group and an aromatic group via an ester bond, a C7-20 divalent group formed by bonding an aliphatic group and an aromatic group via an ether bond, a C14-20 divalent group formed by bonding an aromatic group and an aromatic group via an ester bond, or a C14-20 divalent group formed by bonding an aromatic group and an aromatic group via an ether bond, more preferably represent a single bond, a C1-20 divalent aliphatic group, or a C6-20 divalent aromatic group, and even more preferably a single bond.

In addition, a compound formed by trimerization of three molecules of difunctional amines via an isocyanurate ring structure or a biuret bond may be used as a trifunctional amine.

Specific examples of the compound of the formula (38) include 1,3,5-triaminobenzene, 1,3,5-triamino-2-methylbenzene, 1,3,5-tris(1-aminopropane-2-yl)benzene, 1,3,5-tris(1-aminopropane-2-yl)-2-methylbenzene, 1,3,5-tris(1-aminomethyl)-2-methylbenzene, and 2,2'-((2-amino 1,3-phenylene)bis(methylene))bis(amine benzene).

In addition, a compound of the below-shown formula (C-1) or (C-2) may be used as an amine compound.

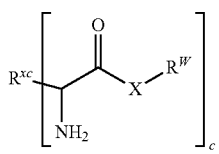

(C-1)

In the formula, X represents a group defined in the formula (B-1).

$R^{xc}$ represents an aliphatic group having a carbon number of 1 or more or an aromatic group having a carbon number of 6 or more, which may contain a primary amino group, a sulfur atom, an oxygen atom, or a halogen atom.

$R^w$ represents a C1-15 aliphatic group, a C6-15 aromatic group or a hydrogen atom, and preferably represents a C1-6 alkyl group, and c represents 2 or 3.

In the formula (C-1), $R^{xc}$ preferably has a structure formed by removing a —NHCOOH group from an amino acid, and more preferably represents a C1-15 aliphatic group or a C6-15 aromatic group.

Preferable examples of the compound of the formula (C-1) include compounds of the below-shown formulae.

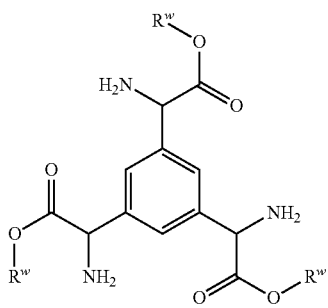

(C-2)

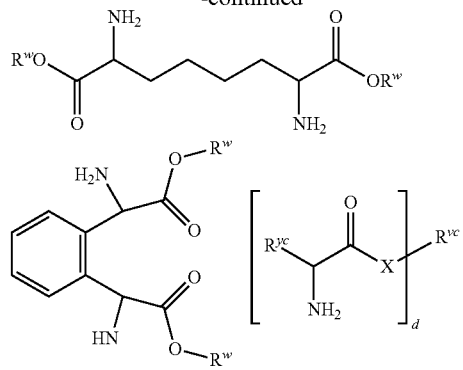

In the formula, X represents a group defined in the formula (C-1).

$R^{yc}$ represents an aliphatic group having a carbon number of 1 or more or an aromatic group having a carbon number of 6 or more, which may contain a primary amino group, a sulfur atom, an oxygen atom, or a halogen atom, or a hydrogen atom.

$R^{vc}$ represents a C1-15 aliphatic group or a C6-15 aromatic group, which may have a primary amino group, or a hydrogen atom, and d represents an integer of 1 to 4.

In the formula (C-2), $R^{yc}$ represents a C1-15 aliphatic group which may have a group selected from the group consisting of groups of the below-shown formulae (i-3) to (ii-3) and (iii-3) to (iv-3); a C6-15 aromatic group which may have a group selected from the group consisting of groups of the below-shown formulae (i-3) to (ii-3) and (iii-3) to (iv-3); a C7-15 group formed by bonding an aliphatic group and an aromatic group, which may have a group selected from the group consisting of groups of the below-shown formulae (i-3) to (ii-3) and (iii-3) to (iv-3); a group of the below-shown formula (IV-3) to (V-3); or a hydrogen atom.

—O— (i-3)

—S— (ii-3)

—NH$_2$ (iii-3)

—S—S— (iv-3)

In the formulae (i-3) to (iv-3), an atom to which a nitrogen atom or a sulfur atom is bonded is a carbon atom.

(IV-3)

(V-3)

In the formula (IV-3), e31 represents an integer of 0 to 5, $R^c$ represents a group represented by one of the below-shown formulae (1-3) to (111-3), or a C1-10 aliphatic hydrocarbon group.

In the formula (V-3), e32 represents an integer of 0 to 5, and $R^d$ represents a C1-15 aliphatic hydrocarbon group or a C6-15 aromatic hydrocarbon group.

—R$^g$—NH$_2$ (I-3)

—(CH$_2$—CH$_2$—O)$_h$—CH$_2$—CH$_2$—NH$_2$ (II-3)

—(CH—CH$_2$—O)$_j$—C(CH$_3$)(H)—CH$_2$—NH$_2$ (III-3)
  |
  CH$_3$

In the formulae, R$^9$ represents a C1-10 aliphatic hydrocarbon group, h represents an integer of 1 to 9, and j represents an integer of 0 to 9.

Examples of the amine compound according to the present embodiment include compounds of the below-shown formulae.

[Chemical structures: methyl-dimethoxyphenyl glycine ester; methylenedioxyphenyl glycine ester; C$_5$H$_{11}$ amino acid ester; naphthyl glycine ester; p-isopropylphenyl alanine ester; furyl glycine ester; R$^{ya}$ amino acid ester; bis-ester with —O—CH$_2$—CH$_2$—O— linker bearing two NH$_2$ groups]

-continued

[Chemical structures: bis-ester with —O—CH—CH$_2$—O— linker (NH$_2$ groups); mono-ester with —O—CH$_2$—; tetra-ester of pentaerythritol-like core with four R$^{yc}$ groups and four NH$_2$ groups]

In the formulae, R$^{vc}$ and R$^{yc}$ are defined above, R$^{vc}$ preferably represents a C1-6 aliphatic group which may have a primary amino group, and R$^{yc}$ preferably represents a C1-6 aliphatic group which may have a primary amino group.

EXAMPLES

Next, the present invention will be explained further specifically by showing specific examples and comparative examples. However, the present invention is not be intended to be limited to the examples or comparative examples, unless it exceeds the gist thereof.

<Analysis Methods>

1) NMR Analysis Method

Equipment: JNM-A400 FT NMR system manufactured by JEOL Ltd., Japan.

(1) Preparation of Samples of 1H and 13C-NMR Analysis

Approximately 0.3 g of a sample solution was weighed, and then approximately 0.7 g of deuterated chloroform (manufactured by Aldrich, United States, 99.8%) and 0.05 g of tetramethylsilane as an internal standard substance (manufactured by Wako Pure Chemical Corporation, Japan, Wako 1$^{st}$ grade) were added to the sample solution, followed by mixing the resultant uniformly to obtain a NMR analysis sample.

(2) Quantitative Analysis Method

Each standard substances were subjected to analysis to prepare a standard curve, and the quantitative analysis of each analysis sample solution was conducted based on the standard curve.

2) Liquid Chromatography Analysis Method

Equipment: LC-10AT system manufactured by Shimadzu Corporation, Japan.

Column: Silica-60 column manufactured by TOSOH CORPORATION, Japan, two columns were series-connected.

Developing solvent: mixture liquid of hexane/tetrahydrofuran=80/20 (volume ratio)

Solvent flow rate: 2 mL/minute

Column temperature: 35° C.

Detector: R.I. (Refractometer)

(1) Liquid Chromatography Analysis Sample

Approximately 0.1 g of a sample was weighed, and then approximately 1 g of tetrahydrofuran (manufactured by Wako Pure Chemical Corporation, Japan, anhydrated) and approximately 0.02 g of bisphenol A (manufactured by Wako Pure Chemical Corporation, Japan, 1$^{st}$ grade) as an internal standard substance were added to the sample, followed by mixing the resultant uniformly to obtain a liquid chromatography analysis sample.

(2) Quantitative Analysis Method

Each standard substances were subjected to analysis to prepare a standard curve, and the quantitative analysis of each analysis sample solution was conducted based on the standard curve.

3) Gas Chromatography Analysis Method

Equipment: GC-2010 manufactured by Shimadzu Corporation, Japan

Column: DB-1 manufactured by Agilent Technologies, United States, and having a length of 30 m, an inner diameter of 0.250 mm, and a film thickness of 1.00 m.

Column temperature: maintained at 50° C. for 5 minutes, raised at a rate of 10° C./minute until 200° C., maintained at 200° C. for 5 minutes, and then raised at a rate of 10° C./minute until 300° C.

Detector: FID (1) Gas Chromatography Analysis Sample

Approximately 0.05 g of a sample was weighed, and then approximately 1 g of acetone (manufactured by Wako Pure Chemical Corporation, Japan, anhydrated) and approximately 0.02 g of toluene (manufactured by Wako Pure Chemical Corporation, Japan, anhydrated) as an internal standard substance were added to the sample, followed by mixing the resultant uniformly to obtain a gas chromatography analysis sample.

(2) Quantitative Analysis Method

Each standard substances were subjected to analysis to prepare a standard curve, and the quantitative analysis of each analysis sample solution was conducted based on the standard curve.

4) Inductively Coupled Plasma Mass Spectrometry Method

Equipment: SPQ-8000 manufactured by Seiko Instrument Inc., Japan (1) Inductively Coupled Plasma Mass Analysis Sample Approximately 0.15 g of a sample was subjected to ashing with diluted sulfuric acid, and then dissolved in diluted nitric acid.

(2) Quantitative Analysis Method

Each standard substances were subjected to analysis to prepare a standard curve, and the quantitative analysis of each analysis sample solution was conducted based on the standard curve.

Example 1

(Step of Preparing a Mixture Solvent)

A mixture solvent composed of: 10% by mass N,N'-hexanediyl bis-carbamic acid diphenyl ester (hereinafter, abbreviated as carbamate derivative), obtained by a conventionally-known method; 60% by mass of ortho dichlorobenzene; and 30% by mass of polyisocyanate (manufactured by Asahi Kasei Corporation, polyisocyanate (trade name: DURANATE) grade: TPA-100) was obtained.

(Step of Preparing a Liquid Phase Component, Decomposition Step, Step of Collecting a Low-Boiling Decomposition Product, and Step of Collecting High-Boiling Solvent)

The mixture solvent obtained above was introduced continuously into a thermal decomposition reactor shown in FIG. 1. Specifically, a starting material preheater 1 was preheated at 160° C., and the mixture solvent was introduced continuously into the top of a tubular first reactor 2 via the starting material preheater 1 at a flow rate of 600 g/hr.

The inner diameter of the tubular first reactor 2 was 5 cm, the tubular first reactor 2 was equipped with a distributor configured to distribute uniformly the starting material mixture introduced into the top thereof, and a packed-bed filled with a Raschig ring formed by stainless steel was provided inside the tubular first reactor 2. In addition, the packed-bed was equipped with liquid redistributors at every 15 cm interval.

A liquid phase component extracted from the bottom of the tubular first reactor 2 was introduced continuously at a flow rate of 300 g/hr into a second reactor 3 composed of a tank reactor. At the time, a dry nitrogen gas preheated at 250° C. was introduced continuously into a liquid in the second reactor 3 composed of a tank reactor at 200 NL/hr as a carrier agent.

The temperature at both the tubular first reactor 2 and the tank second reactor 3 was maintained at 250° C., and the pressure therein was maintained at 8 kg/cm$^2$.

The average residence time of the reaction liquid was 20 minutes in the tubular first reactor 2 and 15 minutes in the tank second reactor.

The vapor of phenol and ortho dichlorobenzene generated at the tank second reactor 3 was extracted from the top of the tank second reactor 3 with a nitrogen gas as a carrier agent, and then introduced into the tubular first reactor 2.

The gas component extracted from the top of the tubular first reactor 2 was passed through a partial condenser 4 maintained at 150° C., to separate the gas component into a liquid component composed of a large part of ortho dichlorobenzene and a gas component composed of: a phenol vapor containing a small amount of ortho dichlorobenzene vapor; and a nitrogen gas.

The liquid component separated by the partial condenser 4 was brought back directly to the tubular first reactor 2 from the top thereof, and the gas component was introduced into a cooler to separate continuously a liquid component composed of phenol containing a small amount of ortho dichlorobenzene from a nitrogen gas.

An ortho dichlorobenzene-polyisocyanate solution containing hexamethylene diisocyanate was extracted continuously from the bottom of the tank second reactor 3. After the reaction achieved a steady state, the ortho dichlorobenzene-polyisocyanate solution was analyzed to confirm that undecomposed carbamate and reaction intermediate were absent, and hexamethylene diisocyanate was produced at a selectivity of 85% or more. When the decomposition reaction was carried out continuously for 200 hours, hexamethylene diisocyanate was produced stably without causing adhesion of polymeric by-products inside the reactor.

Examples 2 to 11

Isocyanates corresponding to starting carbamate derivatives were obtained by conducting the same procedures as those in Example 1, except that each carbamates shown in the below tables were used instead of the carbamate derivative used in Example 1. When the decomposition reaction was carried out continuously for 200 hours, isocyanates corresponding to the starting materials were produced stably without causing adhesion of polymeric by-products inside the reactor.

In the below-shown tables, the term "low boiling solvent" means "inactive solvent", and the term "high boiling solvent" means "polyisocyanate compound".

TABLE 1

| | Reactor | Starting material to conduct thermal decomposition and resultant isocyanate | | Formulation of starting material mixture (% by mass) | | | | Temperature Condition (° C.) | | Thermal decomposition yield (%) |
| --- | --- | --- | --- | --- | --- | --- | --- | --- | --- | --- |
| | | Carbamate | Resultant isocyanate | Low-boiling solvent | High-boiling solvent | Conc. of carbamate | Conc. of low-boiling solvent | Conc. of high-boiling solvent | Temperature at first reactor | Temperature at second reactor | |
| Ex. 1 | FIG. 1 | PhO-C(O)-NH-(CH₂)₆-NH-C(O)-OPh | OCN-(CH₂)₆-NCO | ODB | TPA | 10 | 60 | 30 | 250 | 250 | 85 |
| Ex. 2 | FIG. 1 | PhO-C(O)-NH-(CH₂)₅-NH-C(O)-OPh | OCN-(CH₂)₅-NCO | ODB | TPA | 10 | 60 | 30 | 250 | 250 | 86 |
| Ex. 3 | FIG. 1 | isophorone bis-phenylcarbamate | isophorone diisocyanate | ODB | TPA | 10 | 60 | 30 | 250 | 250 | 81 |
| Ex. 4 | FIG. 1 | 4,4'-methylenebis(phenyl phenylcarbamate) | 4,4'-methylenebis(phenyl isocyanate) | ODB | TPA | 10 | 60 | 30 | 250 | 250 | 84 |
| Ex. 5 | FIG. 1 | 4,4'-methylenebis(cyclohexyl phenylcarbamate) | 4,4'-methylenebis(cyclohexyl isocyanate) | ODB | TPA | 10 | 60 | 30 | 250 | 250 | 83 |
| Ex. 6 | FIG. 1 | isoamyl N-(6-isocyanatohexyl)carbamate | OCN-(CH₂)₆-NCO | ODB | TPA | 10 | 60 | 30 | 250 | 250 | 84 |

TABLE 2

| | Reactor | Starting material to conduct thermal decomposition ad resultant isocyanate | | Formulation of starting material mixture (% by mass) | | | | Temperature Condition (° C.) | | Thermal decomposition yield (%) |
|---|---|---|---|---|---|---|---|---|---|---|
| | | Carbamate | Resultant isocyanate | Low-boiling solvent | High-boiling solvent | Conc. of carbamate | Conc. of low-boiling solvent | Conc. of high-boiling solvent | Temperature at first reactor | Temperature at second reactor | |
| Ex. 7 | FIG. 1 | | | ODB | TPA | 10 | 60 | 30 | 250 | 250 | 82 |
| Ex. 8 | FIG. 1 | | | ODB | TPA | 10 | 60 | 30 | 250 | 250 | 83 |
| Ex. 9 | FIG. 1 | | | ODB | TPA | 10 | 60 | 30 | 250 | 250 | 84 |

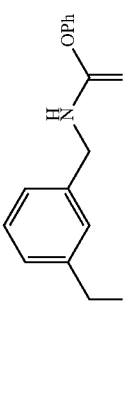
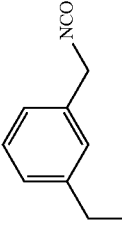
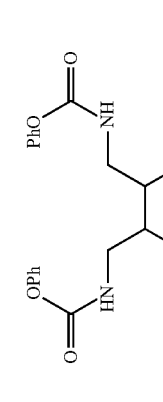
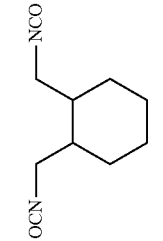
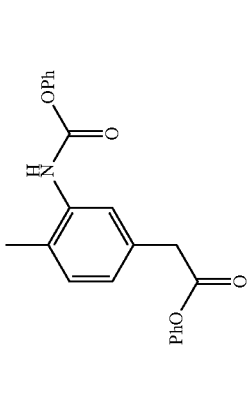
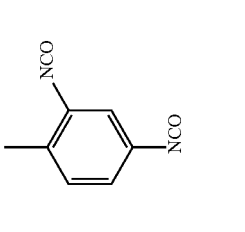

TABLE 2-continued

| | Reactor | Starting material to conduct thermal decomposition ad resultant isocyanate | | Formulation of starting material mixture (% by mass) | | | | Temperature Condition (° C.) | | Thermal decomposition yield (%) |
|---|---|---|---|---|---|---|---|---|---|---|
| | | Carbamate | Resultant isocyanate | Low-boiling solvent | High-boiling solvent | Conc. of carbamate | Conc. of low-boiling solvent | Conc. of high-boiling solvent | Temperature at first reactor | Temperature at second reactor | |
| Ex. 10 | FIG. 1 | (carbamate structure with PhO–C(=O)–NH– groups) | (isocyanate structure with NCO groups) | ODB | TPA | 10 | 60 | 30 | 250 | 250 | 81 |
| Ex. 11 | FIG. 1 | (methacrylate carbamate structure with OPh group) | (methacrylate isocyanate with NCO) | ODB | TPA | 10 | 60 | 30 | 250 | 250 | 82 |

[Reference Example 1] Preparation of Carbamate 510 g (2.4 mol) of diphenyl carbonate, 136 g (1.35 mol) of triethyl amine, and 150 g (0.34 mol) of lysine β-aminoethyl ester trihydrochloride were reacted in toluene at 50° C. for 8 hours in a 1 L four-necked flask equipped with a stirrer under a nitrogen atmosphere. The reaction liquid was subjected to sampling, and then analyzed by liquid chromatography, as a result of which it was confirmed that approximately 82% by mol of the target carbamate was produced, relative to lysine β-aminoethyl ester trihydrochloride.

1 mol/L of hydrochloric acid was added to the reaction liquid, and then stirred, followed by collecting an organic layer, and then washing the organic layer with ion-exchanged water.

Toluene was distilled off from the organic layer using a rotary evaporator to obtain a solid, and then the solid was analyzed by $^1$H-NMR, and, as a result of which, it was confirmed that the solid was 2-((phenoxycarbonyl)amino)ethyl-2,6-bis((phenoxycarbonyl)amino) hexanoate.

Example 12

(Step of Preparing Mixture Solvent)

A mixture solvent composed of 10% by mass of 2-((phenoxycarbonyl)amino)ethyl-2,6-bis((phenoxycarbonyl)amino) hexanoate (hereinafter, which may be abbreviated as carbamate), 60% by mass of ortho dichlorobenzene, and 30% by mass of polyisocyanate (manufactured by Asahi Kasei Corporation, polyisocyanate (trade name: DURANATE) grade: TPA-100) was obtained.

(Step of Preparing Liquid Phase Component, Decomposition Step, Step of Collecting Low-Boiling Decomposition Product and Step of Collecting High-Boiling Solvent)

The mixture solvent obtained above was introduced continuously into a thermal decomposition reactor shown in FIG. 1. Specifically, a starting material preheater 1 was preheated at 160° C., and the mixture solvent was introduced continuously into the top of a tubular first reactor 2 via the starting material preheater 1 at a flow rate of 600 g/hr.

The inner diameter of the tubular first reactor 2 was 5 cm, the tubular first reactor 2 was equipped with a distributor configured to distribute uniformly the starting material mixture introduced into the top thereof, and, a packed-bed filled with a Raschig ring formed by stainless steel was provided inside the tubular first reactor 2. In addition, the packed-bed was equipped with liquid redistributors at every 15 cm interval.

A liquid phase component extracted from the bottom of the tubular first reactor 2 was introduced continuously at a flow rate of 400 g/hr into a second reactor 3 composed of a tank reactor. At the time, a dry nitrogen gas preheated at 250° C. was introduced continuously into a liquid in the second reactor 3 at 200 NL/hr as a carrier agent.

The temperature at both the tubular first reactor 2 and the tank second reactor 3 was maintained at 250° C., and the pressure therein was maintained at 8 kg/cm².

The average residence time of the reaction liquid was 20 minutes in the tubular first reactor 2 and 15 minutes in the tank second reactor.

The vapor of phenol and ortho dichlorobenzene generated at the tank second reactor 3 was extracted from the top of the tank second reactor 3 with a nitrogen gas as a carrier agent, and then introduced into the tubular first reactor 2.

The gas component extracted from the top of the tubular first reactor 2 was passed through a partial condenser 4 maintained at 150° C., to separate the gas component into a liquid component composed of a large part of ortho dichlorobenzene and a gas component composed of: a phenol vapor containing a small amount of ortho dichlorobenzene vapor; and a nitrogen gas.

The liquid component separated by the partial condenser 4 was brought back directly to the tubular first reactor 2 from the top thereof, and the gas component was introduced into a cooler to separate continuously a liquid component composed of phenol containing a small amount of ortho dichlorobenzene from a nitrogen gas.

An ortho dichlorobenzene-polyisocyanate solution containing lysine ester triisocyanate was extracted continuously from the bottom of the tank second reactor 3. After the reaction achieved a steady state, the ortho dichlorobenzene-polyisocyanate solution was analyzed to confirm that undecomposed carbamate and reaction intermediate were absent, and lysine ester triisocyanate was produced at a selectivity of 85% or more. When the decomposition reaction was carried out continuously for 200 hours, lysine ester triisocyanate was produced stably without causing adhesion of polymeric by-products inside the reactor.

Examples 13 to 48

Isocyanates corresponding to starting carbamate derivatives were obtained by conducting the same procedures as those in Example 12, except that each starting materials to produce carbamates or conduct thermal decomposition shown in the below tables were used. When the decomposition reaction was carried out continuously for 200 hours, isocyanates corresponding to the starting materials were produced stably without causing adhesion of polymeric by-products inside the reactor. In the case where an arginine was used, the arginine was hydrolyzed to an ornithine by a conventionally-known method to be used. In the case where a glutamine or an asparagine was used, the glutamine or the asparagine was hydrolyzed to a glutamic acid or an aspargic acid, respectively, by a conventionally-known method to be used.

Examples 49 to 68

Isocyanates corresponding to starting carbamate derivatives were obtained by conducting the same procedures as those in Example 12, except that each starting materials to produce carbamates or conduct thermal decomposition shown in the below tables were used. When the decomposition reaction was carried out continuously for 200 hours, isocyanates corresponding to the starting materials were produced stably without causing adhesion of polymeric by-products inside the reactor.

Examples 69 to 80

The same procedures as those in Example 12 were conducted, except that each amino acids or amino acid derivatives shown in the below tables were introduced instead of an amino acid group of the lysine aminoethyl ester hydrochloride used in Example 1, or polyisocyanates were used in the step of preparing a mixture solvent. As the polyisocyanates shown in the tables, polyisocyanates manufactured by Asahi Kasei Corporation, (trade name: DURANATE, grade: TKA-100, 24A-100, and TLA-100) were used. Isocyanates corresponding to starting carbamate derivatives were obtained by the procedures. When the decomposition reaction was carried out continuously for 200 hours, isocyanates corresponding to the starting materials were produced stably without causing adhesion of polymeric by-products inside the reactor.

TABLE 3

| Reactor | FIG. | Starting material to produce carbamate | | | Starting material to conduct thermal decomposition ad resultant isocyanate | | | Formulation of starting material mixture (% by mass) | | | Temperature Condition (°C.) | | Thermal decomposition yield (%) |
|---|---|---|---|---|---|---|---|---|---|---|---|---|---|
| | | Amino acid, amino acid derivative | Amino acid formula | Alkanol amine | Carbamate | Low-boiling solvent | High-boiling solvent | Conc. of carbamate | Conc. of low-boiling solvent | Conc. of high-boiling solvent | Temperature at first reactor | Temperature at second reactor | |
| Ex. 12 | 1 | Lysine | (H₂N-(CH₂)₄-CH(NH₂)-COOH structure) | Mono-ethanol amine | (PhO-C(=O)-NH-(CH₂)₄-CH(NH-C(=O)-OPh)-C(=O)-O-CH₂-CH₂-NH-C(=O)-OPh structure) | ODB | TPA | 10 | 60 | 30 | 250 | 250 | 79 |
| Ex. 13 | 1 | Alanine | (CH₃-CH(NH₂)-COOH structure) | Mono-ethanol amine | (PhO-C(=O)-NH-CH(CH₃)-C(=O)-O-CH₂-CH₂-NH-C(=O)-OPh structure) | ODB | TPA | 10 | 60 | 30 | 250 | 250 | 81 |

Resultant isocyanate (Ex. 12): OCN-(CH₂)₄-CH(NCO)-C(=O)-O-CH₂-CH₂-NCO

Resultant isocyanate (Ex. 13): OCN-CH(CH₃)-C(=O)-O-CH₂-CH₂-NCO

TABLE 3-continued

| Reactor | FIG. | Starting material to produce carbamate | | | Starting material to conduct thermal decomposition ad resultant isocyanate | | | Formulation of starting material mixture (% by mass) | | | Temperature Condition (° C.) | | Thermal decomposition yield (%) |
|---|---|---|---|---|---|---|---|---|---|---|---|---|---|
| | | Amino acid, amino acid derivative | Amino acid formula | Alkanol amine | Carbamate | Low-boiling solvent | High-boiling solvent | Conc. of carbamate | Conc. of low-boiling solvent | Conc. of high-boiling solvent | Temperature at first reactor | Temperature at second reactor | |
| Ex. 14 | 1 | Arginine | (structure) | Monoethanolamine | (structure) | ODB | TPA | 10 | 60 | 30 | 250 | 250 | 83 |
| Ex. 15 | 1 | Asparagine | (structure) | Monoethanolamine | (structure) | ODB | TPA | 10 | 60 | 30 | 250 | 250 | 82 |

TABLE 4

| | Reactor | Starting material to produce carbamate | | | Starting material to conduct thermal decomposition and resultant isocyanate |
|---|---|---|---|---|---|
| | | Amino acid, amino acid derivative | Amino acid formula | Alkanol amine | |
| Ex. 16 | FIG. 1 | Glutamine | H₂N-CH(COOH)-CH₂-CH₂-C(=O)-NH₂ | Mono-ethanol amine | PhO-C(=O)-NH-CH(-C(=O)-O-CH₂CH₂-NH-C(=O)-OPh)-CH₂-CH₂-C(=O)-O-CH₂CH₂-NH-C(=O)-OPh |
| Ex. 17 | FIG. 1 | Glycine | H₂N-CH₂-COOH | Mono-ethanol amine | PhO-C(=O)-NH-CH₂-C(=O)-O-CH₂CH₂-NH-C(=O)-OPh |
| Ex. 18 | FIG. 1 | Asparaginic acid | H₂N-CH(COOH)-CH₂-COOH | Mono-ethanol amine | PhO-C(=O)-NH-CH(-C(=O)-O-CH₂CH₂-NH-C(=O)-OPh)-CH₂-C(=O)-O-CH₂CH₂-NH-C(=O)-OPh |
| Ex. 19 | FIG. 1 | Glutamic acid | H₂N-CH(COOH)-CH₂-CH₂-COOH | Mono-ethanol amine | PhO-C(=O)-NH-CH(-C(=O)-O-CH₂CH₂-NH-C(=O)-OPh)-CH₂-CH₂-C(=O)-O-CH₂CH₂-NH-C(=O)-OPh |

| | Starting material to conduct thermal decomposition and resultant isocyanate | | Formulation of starting material mixture (% by mass) | | | Temperature Condition (°C.) | | Termal decomposition yield (%) |
|---|---|---|---|---|---|---|---|---|
| | Resultant isocyanate | Low-boiling solvent | High-boiling solvent | Conc. of carbamate | Conc. of low-boiling solvent | Conc. of high-boiling solvent | Temperature at first reactor | Temperature at second reactor | |
| Ex. 16 | OCN-CH(-C(=O)-O-CH₂CH₂-NCO)-CH₂-CH₂-C(=O)-O-CH₂CH₂-NCO | ODB | TPA | 10 | 60 | 30 | 250 | 250 | 79 |
| Ex. 17 | OCN-CH₂-C(=O)-O-CH₂CH₂-NCO | ODB | TPA | 10 | 60 | 30 | 250 | 250 | 78 |
| Ex. 18 | OCN-CH(-C(=O)-O-CH₂CH₂-NCO)-CH₂-C(=O)-O-CH₂CH₂-NCO | ODB | TPA | 10 | 60 | 30 | 250 | 250 | 79 |

TABLE 4-continued
| Ex. 19 | 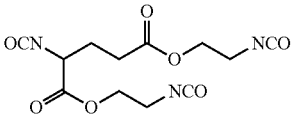 | ODB | TPA | 10 | 60 | 30 | 250 | 250 | 76 |
TABLE 5
| | | Starting material to produce carbamate | | | Starting material to conduct |
| Reactor | Amino acid, amino acid derivative | Amino acid formula | Alkanol amine | thermal decomposition and resultant isocyanate |
|---|---|---|---|---|---|
| Ex. 20 | FIG. 1 | Histadine | 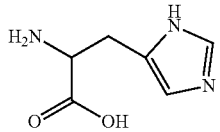 [SMILES: NC(Cc1cnc[nH]1)C(=O)O] | Mono-ethanol amine | 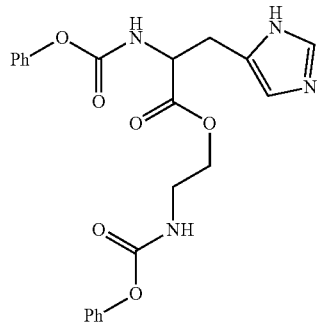 [SMILES: O=C(NCCOC(=O)C(Cc1cnc[nH]1)NC(=O)Oc1ccccc1)Oc1ccccc1] |
| Ex. 21 | FIG. 1 | Isoleucine | 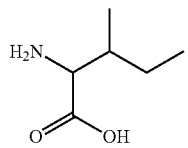 | Mono-ethanol amine | 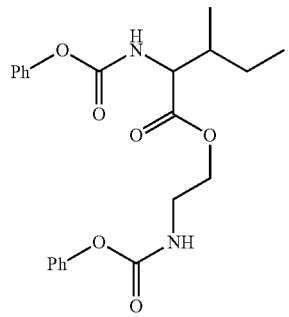 [SMILES: CCC(C)C(NC(=O)Oc1ccccc1)C(=O)OCCNC(=O)Oc1ccccc1] |
| Ex. 22 | FIG. 1 | Leucine | 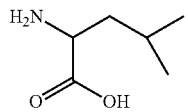 | Mono-ethanol amine | 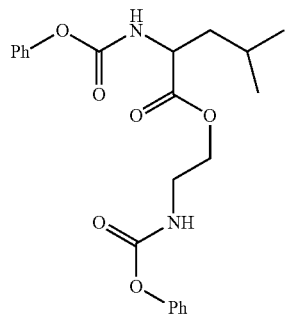 [SMILES: CC(C)CC(NC(=O)Oc1ccccc1)C(=O)OCCNC(=O)Oc1ccccc1] |

TABLE 5-continued

| Starting material to conduct thermal decomposition and resultant isocyanate | | Formulation of starting material mixture (% by mass) | | | Temperature Condition (° C.) | | Termal decomposition yield (%) |
|---|---|---|---|---|---|---|---|
| Resultant isocyanate | Low-boiling solvent | High-boiling solvent | Conc. of carbamate | Conc. of low-boiling solvent | Conc. of high-boiling solvent | Temperature at first reactor | Temperature at second reactor | |

| | Resultant isocyanate | Low-boiling solvent | High-boiling solvent | Conc. of carbamate | Conc. of low-boiling solvent | Conc. of high-boiling solvent | Temperature at first reactor | Temperature at second reactor | Termal decomposition yield (%) |
|---|---|---|---|---|---|---|---|---|---|
| Ex. 20 | OCN-CH(CH₂-imidazole)-C(=O)-O-CH₂CH₂-NCO | ODB | TPA | 10 | 60 | 30 | 250 | 250 | 79 |
| Ex. 21 | OCN-CH(CH(CH₃)CH₂CH₃)-C(=O)-O-CH₂CH₂-NCO | ODB | TPA | 10 | 60 | 30 | 250 | 250 | 75 |
| Ex. 22 | OCN-CH(CH₂CH(CH₃)₂)-C(=O)-O-CH₂CH₂-NCO | ODB | TPA | 10 | 60 | 30 | 250 | 250 | 79 |

TABLE 6

| | Reactor | Starting material to produce carbamate | | | Starting material to conduct thermal decomposition and resultant isocyanate |
|---|---|---|---|---|---|
| | | Amino acid, amino acid derivative | Amino acid formula | Alkanol amine | |
| Ex. 23 | FIG. 1 | Methionine | H₂N-CH(CH₂CH₂SCH₃)-C(=O)-OH | Monoethanol amine | PhO-C(=O)-NH-CH(CH₂CH₂SCH₃)-C(=O)-O-CH₂CH₂-NH-C(=O)-OPh |

TABLE 6-continued

| Ex. | | Amino acid | Structure | Amine | Carbamate Structure |
|---|---|---|---|---|---|
| Ex. 24 | FIG. 1 | Phenyl alanine | H₂N-CH(CH₂Ph)-COOH | Mono-ethanol amine | PhO-C(=O)-NH-CH(CH₂Ph)-C(=O)-O-CH₂CH₂-NH-C(=O)-O-Ph |
| Ex. 25 | FIG. 1 | Triptophan | H₂N-CH(CH₂-indolyl)-COOH | Mono-ethanol amine | PhO-C(=O)-NH-CH(CH₂-indolyl)-C(=O)-O-CH₂CH₂-NH-C(=O)-O-Ph |

| | Starting material to conduct thermal decomposition and resultant isocyanate | | Formulation of starting material mixture (% by mass) | | | Temperature Condition (° C.) | | Termal decom- position yield (%) |
|---|---|---|---|---|---|---|---|---|
| | Resultant isocyanate | Low- boiling solvent | High- boiling solvent | Conc. of carbamate | Conc. of low- boiling solvent | Conc. of high- boiling solvent | Tempera- ture at first reactor | Tempera- ture at second reactor | |
| Ex. 23 | OCN-CH(CH₂CH₂SCH₃)-C(=O)-O-CH₂CH₂-NCO | ODB | TPA | 10 | 60 | 30 | 250 | 250 | 74 |
| Ex. 24 | OCN-CH(CH₂Ph)-C(=O)-O-CH₂CH₂-NCO | ODB | TPA | 10 | 60 | 30 | 250 | 250 | 73 |
| Ex. 25 | OCN-CH(CH₂-indolyl)-C(=O)-O-CH₂CH₂-NCO | ODB | TPA | 10 | 60 | 30 | 250 | 250 | 74 |

TABLE 7

| Reactor | | Starting material to produce carbamate | | | |
|---|---|---|---|---|---|
| | | Amino acid, amino acid derivative | Amino acid formula | Alkanol amine | Starting material to conduct thermal decomposition and resultant isocyanate |
| Ex. 26 | FIG. 1 | Valine | (H$_2$N-CH(iPr)-COOH structure) | Monoethanol amine | (Ph-O-CO-NH-CH(iPr)-CO-O-CH$_2$CH$_2$-NH-CO-O-Ph structure) |
| Ex. 27 | FIG. 1 | Ornithine | (H$_2$N-(CH$_2$)$_3$-CH(NH$_2$)-COOH structure) | Monoethanol amine | (Ph-O-CO-NH-(CH$_2$)$_3$-CH(NH-CO-O-Ph)-CO-O-CH$_2$CH$_2$-NH-CO-O-Ph structure) |

| | Starting material to conduct thermal decomposition and resultant isocyanate | | | Formulation of starting material mixture (% by mass) | | | Temperature Condition (° C.) | | Termal decomposition yield (%) |
|---|---|---|---|---|---|---|---|---|---|
| | Resultant isocyanate | Low-boiling solvent | High-boiling solvent | Conc. of carbamate | Conc. of low-boiling solvent | Conc. of high-boiling solvent | Temperature at first reactor | Temperature at second reactor | |
| Ex. 26 | (OCN-CH(iPr)-CO-O-CH$_2$CH$_2$-NCO structure) | ODB | TPA | 10 | 60 | 30 | 250 | 250 | 78 |
| Ex. 27 | (OCN-(CH$_2$)$_3$-CH(NCO)-CO-O-CH$_2$CH$_2$-NCO structure) | ODB | TPA | 10 | 60 | 30 | 250 | 250 | 74 |

TABLE 8

| | Reactor | Amino acid, amino acid derivative | Amino acid formula | X | Ra | Rb | Explanation of formula |
|---|---|---|---|---|---|---|---|
| Ex. 28 | FIG. 1 | Lysine derivative | [Structure: lysine ester with NH₂, H₂N, C(=O)O-R$^a$]$_x$ | 1 | Me | — | Ra and Rb each independenly represents an aliphatic group, an aromatic group, or a hydrogen atom. X = 1-4 (excepting that Ra represents a hydrogen atom). When both Ra and Rb represent hydrogen atoms, X represens 1. |
| Ex. 29 | FIG. 1 | Glutamic acid derivative | [Structure: glutamic acid diester with R$^b$O-C(=O), H₂N, C(=O)O-R$^a$]$_x$ | 2 | Et | Me | Ra and Rb each independenly represents an aliphatic group, an aromatic group, or a hydrogen atom. X = 1-4 (excepting that Ra represents a hydrogen atom). When both Ra and Rb represent hydrogen atoms, X represens 1. |
| Ex. 30 | FIG. 1 | Glutamic acid derivative | [Structure: glutamic acid diester with R$^a$O-C(=O), H₂N, C(=O)O-R$^b$]$_x$ | 1 | Me | Me | Ra and Rb each independenly represents an aliphatic group, an aromatic group, or a hydrogen atom. X = 1-4 (excepting that Ra represents a hydrogen atom). When both Ra and Rb represent hydrogen atoms, X represens 1. |
| Ex. 31 | FIG. 1 | Methionine derivative | [Structure: methionine ester with S, H₂N, C(=O)O-R$^a$]$_x$ | 1 | Me | — | Ra and Rb each independenly represents an aliphatic group, an aromatic group, or a hydrogen atom. X = 1-4 (excepting that Ra represents a hydrogen atom). When both Ra and Rb represent hydrogen atoms, X represens 1. |
| Ex. 32 | FIG. 1 | Glycine derivative | [Structure: glycine ester with H₂N, C(=O)O-R$^a$]$_x$ | 1 | Me | — | Ra and Rb each independenly represents an aliphatic group, an aromatic group, or a hydrogen atom. X = 1-4 (excepting that Ra represents a hydrogen atom). When both Ra and Rb represent hydrogen atoms, X represens 1. |

TABLE 9

Starting material to conduct thermal decomposition and resultant isocyanate

| | Carbamate | Resultant isocyanate | Low-boiling solvent | High-boiling solvent |
|---|---|---|---|---|
| Ex. 28 | [Lysine dicarbamate structure with two Ph-O-C(O)-NH groups and ester -O-$R^a$], subscript $x$ | [Lysine diisocyanate structure with two NCO/OCN groups and ester -O-$R^a$], subscript $x$ | ODB | TPA |
| Ex. 29 | [Glutamate dicarbamate: $R^a$-O-C(O)- side chain, Ph-O-C(O)-NH-, ester -O-$R^b$], subscript $x$ | [Glutamate diisocyanate: $R^a$-O-C(O)- side chain, OCN-, ester -O-$R^b$], subscript $x$ | ODB | TPA |
| Ex. 30 | [Glutamate dicarbamate: $R^a$-O-C(O)- side chain, Ph-O-C(O)-NH-, ester -O-$R^b$], subscript $x$ | [Glutamate diisocyanate: $R^a$-O-C(O)- side chain, OCN-, ester -O-$R^b$], subscript $x$ | ODB | TPA |
| Ex. 31 | [Methionine carbamate with -S-CH$_3$ side chain, Ph-O-C(O)-NH-, ester -O-$R^a$], subscript $x$ | [Methionine isocyanate with -S- side chain, OCN-, ester -O-$R^a$], subscript $x$ | ODB | TPA |
| Ex. 32 | [Glycine carbamate: Ph-O-C(O)-NH-CH$_2$-C(O)-O-$R^a$], subscript $x$ | [Glycine isocyanate: OCN-CH$_2$-C(O)-O-$R^a$], subscript $x$ | ODB | TPA |

TABLE 10

| | Reactor | Starting material to produce carbamate | | | | | |
|---|---|---|---|---|---|---|---|
| | | Amino acid, amino acid derivative | Amino acid formula | x | Ra | Rb | Explanation of formula |
| Ex. 33 | FIG. 1 | Phenylalanine derivative | [structure] | 1 | Me | — | Ra and Rb each independenly represents an aliphatic group, an aromatic group, or a hydrogen atom, X = 1-4 (excepting that Ra represents a hydrogen atom). When both Ra and Rb represent hydrogen atoms, X represens 1. |
| Ex. 34 | FIG. 1 | Asparagin derivative | [structure] | 1 | Me | Me | Ra and Rb each independenly represents an aliphatic group, an aromatic group, or a hydrogen atom, X = 1-4 (excepting that Ra represents a hydrogen atom). When both Ra and Rb represent hydrogen atoms, X represens 1. |
| Ex. 35 | FIG. 1 | Alanine derivative | [structure] | 1 | Me | — | Ra and Rb each independenly represents an aliphatic group, an aromatic group, or a hydrogen atom, X = 1-4 (excepting that Ra represents a hydrogen atom). When both Ra and Rb represent hydrogen atoms, X represens 1. |
| Ex. 36 | FIG. 1 | Leucine derivative | [structure] | 1 | Me | — | Ra and Rb each independenly represents an aliphatic group, an aromatic group, or a hydrogen atom, X = 1-4 (excepting that Ra represents a hydrogen atom). When both Ra and Rb represent hydrogen atoms, X represens 1. |
| Ex. 37 | FIG. 1 | Isoleucine derivative | [structure] | 1 | Me | — | Ra and Rb each independenly represents an aliphatic group, an aromatic group, or a hydrogen atom, X = 1-4 (excepting that Ra represents a hydrogen atom). When both Ra and Rb represent hydrogen atoms, X represens 1. |

TABLE 11

Starting material to conduct thermal decomposition and resultant isocyanate

| | Carbamate | Resultant isocyanate | Low-boiling solvent | High-boiling solvent |
|---|---|---|---|---|
| Ex. 33 | [Phenylalanine-derived phenyl carbamate structure with R$^a$] | [Phenylalanine-derived isocyanate structure with R$^a$] | ODB | TPA |
| Ex. 34 | [Aspartate-derived phenyl carbamate structure with R$^a$, R$^b$] | [Aspartate-derived isocyanate structure with R$^a$, R$^b$] | ODB | TPA |
| Ex. 35 | [Alanine-derived phenyl carbamate structure with R$^a$] | [Alanine-derived isocyanate structure with R$^a$] | ODB | TPA |
| Ex. 36 | [Leucine-derived phenyl carbamate structure with R$^a$] | [Leucine-derived isocyanate structure with R$^a$] | ODB | TPA |
| Ex. 37 | [Isoleucine-derived phenyl carbamate structure with R$^a$] | [Isoleucine-derived isocyanate structure with R$^a$] | ODB | TPA |

TABLE 12

| | Reactor | Amino acid, amino acid derivative | Amino acid formula | x | Ra | Rb | Explanation of formula |
|---|---|---|---|---|---|---|---|
| Ex. 38 | FIG. 1 | Valine derivative | [structure: H$_2$N-CH(iPr)-C(=O)-O-R$^a$]$_x$ | 1 | Me | — | Ra and Rb each independenly represents an aliphatic group, an aromatic group, or a hydrogen atom, X = 1-4 (excepting that Ra represents a hydrogen atom). When both Ra and Rb represent hydrogen atoms, X represens 1. |
| Ex. 39 | FIG. 1 | Synthesized amino acid | [structure: 1,3,5-trisubstituted benzene with three -CH(NH$_2$)-C(=O)-O-R$^a$ groups] | — | Me | — | Ra and Rb each independenly represents an aliphatic group, an aromatic group, or a hydrogen atom, X = 1-4 (excepting that Ra represents a hydrogen atom). When both Ra and Rb represent hydrogen atoms, X represens 1. |
| Ex. 40 | FIG. 1 | Synthesized amino acid | [structure: R$^a$O-C(=O)-CH(NH$_2$)-(CH$_2$)$_4$-CH(NH$_2$)-C(=O)-OR$^a$] | — | Me | — | Ra and Rb each independenly represents an aliphatic group, an aromatic group, or a hydrogen atom, X = 1-4 (excepting that Ra represents a hydrogen atom). When both Ra and Rb represent hydrogen atoms, X represens 1. |
| Ex. 41 | FIG. 1 | Synthesized amino acid | [structure: Cl,F-substituted phenyl-CH(NH$_2$)-C(=O)-O-R$^a$] | — | Me | — | Ra and Rb each independenly represents an aliphatic group, an aromatic group, or a hydrogen atom, X = 1-4 (excepting that Ra represents a hydrogen atom). When both Ra and Rb represent hydrogen atoms, X represens 1. |
| Ex. 42 | FIG. 1 | Synthesized amino acid | [structure: 3,4-dimethoxyphenyl-CH(NH$_2$)-C(=O)-O-R$^a$] | — | Me | — | Ra and Rb each independenly represents an aliphatic group, an aromatic group, or a hydrogen atom, X = 1-4 (excepting that Ra represents a hydrogen atom). When both Ra and Rb represent hydrogen atoms, X represens 1. |

TABLE 12-continued

Starting material to produce carbamate

| | Reactor | Amino acid, amino acid derivative | Amino acid formula | x | Ra | Rb | Explanation of formula |
|---|---|---|---|---|---|---|---|
| Ex. 43 | FIG. 1 | Synthesized amino acid | 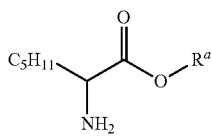 | — | Me | — | Ra and Rb each independently represents an aliphatic group, an aromatic group, or a hydrogen atom, X = 1-4 (excepting that Ra represents a hydrogen atom). When both Ra and Rb represent hydrogen atoms, X represens 1. |

TABLE 13

Starting material to conduct thermal decomposition and resultant isocyanate

| | Carbamate | Resultant isocyanate | Low-boiling solvent | High-boiling solvent |
|---|---|---|---|---|
| Ex. 38 | 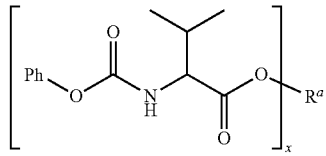 | 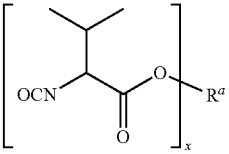 | ODB | TPA |
| Ex. 39 | 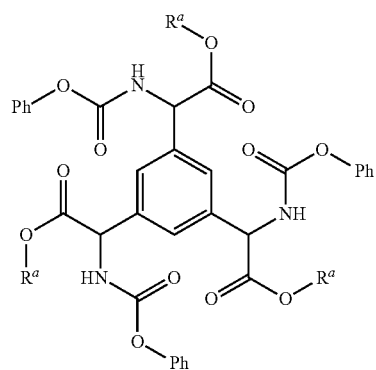 | 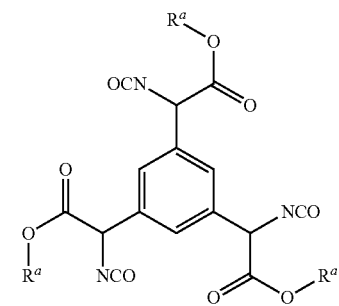 | ODB | TPA |
| Ex. 40 | 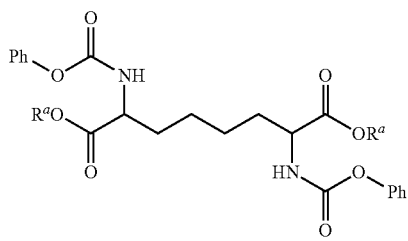 | 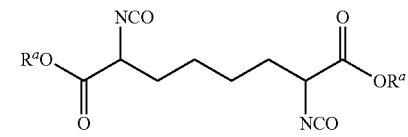 | ODB | TPA |
| Ex. 41 | 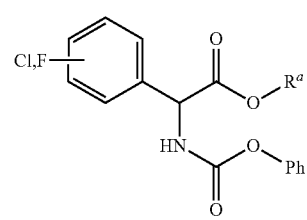 | 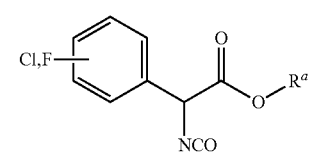 | ODB | TPA |

TABLE 13-continued

Starting material to conduct thermal decomposition and resultant isocyanate

| | Carbamate | Resultant isocyanate | Low-boiling solvent | High-boiling solvent |
|---|---|---|---|---|
| Ex. 42 | 4-MeO, 3-MeO-phenyl-CH(NHC(O)OPh)-C(O)O-R$^a$ | 4-MeO, 3-MeO-phenyl-CH(NCO)-C(O)O-R$^a$ | ODB | TPA |
| Ex. 43 | $C_5H_{11}$-CH(NHC(O)OPh)-C(O)O-R$^a$ | $C_5H_{11}$-CH(NCO)-C(O)O-R$^a$ | ODB | TPA |

TABLE 14

| | Reactor | Amino acid, amino acid derivative | Amino acid formula | x | Ra | Rb | Explanation of formula |
|---|---|---|---|---|---|---|---|
| Ex. 44 | FIG. 1 | Synthesized amino acid | 3,4-methylenedioxyphenyl-CH(NH$_2$)-C(O)O-R$^a$ | — | Me | — | Ra and Rb each independently represents an aliphatic group, an aromatic group, or a hydrogen atom, X = 1-4 (excepting that Ra represents a hydrogen atom). When both Ra and Rb, represent hydrogen atoms, X represens 1. |
| Ex. 45 | FIG. 1 | Synthesized amino acid | 4-isopropylphenyl-CH$_2$-CH(NH$_2$)-C(O)O-R$^a$ | — | Me | — | Ra and Rb each independently represents an aliphatic group, an aromatic group, or a hydrogen atom, X = 1-4 (excepting that Ra represents a hydrogen atom). When both Ra and Rb, represent hydrogen atoms, X represens 1. |
| Ex. 46 | FIG. 1 | Synthesized amino acid | 1-naphthyl-CH(NH$_2$)-C(O)O-R$^a$ | — | Me | — | Ra and Rb each independently represents an aliphatic group, an aromatic group, or a hydrogen atom, X = 1-4 (excepting that Ra represents a hydrogen atom). When both Ra and Rb, represent hydrogen atoms, X represens 1. |

TABLE 14-continued

Starting material to produce carbamate

| | Reactor | Amino acid, amino acid derivative | Amino acid formula | x | Ra | Rb | Explanation of formula |
|---|---|---|---|---|---|---|---|
| Ex. 47 | FIG. 1 | Synthesized amino acid | [structure: benzene ring with two -CH(NH$_2$)-C(=O)-O-R$^a$ groups ortho] | — | Me | — | Ra and Rb each independenly represents an aliphatic group, an aromatic group, or a hydrogen atom, X = 1-4 (excepting that Ra represents a hydrogen atom). When both Ra and Rb, represent hydrogen atoms, X represens 1. |
| Ex. 48 | FIG. 1 | Synthesized amino acid | [structure: furan-2-yl-CH(NH$_2$)-C(=O)-O-R$^a$] | — | Me | — | Ra and Rb each independenly represents an aliphatic group, an aromatic group, or a hydrogen atom, X = 1-4 (excepting that Ra represents a hydrogen atom). When both Ra and Rb, represent hydrogen atoms, X represens 1. |

TABLE 15

Starting material conduct thermal decomposition and resultant isocyanate

| | Carbamate | Resultant isocyanate | Low-boiling solvent | High-boiling solvent |
|---|---|---|---|---|
| Ex. 44 | [structure: benzodioxole-CH(NHC(=O)OPh)-C(=O)-O-R$^a$] | [structure: benzodioxole-CH(NCO)-C(=O)-O-R$^a$] | ODB | TPA |
| Ex. 45 | [structure: 4-isopropylphenyl-CH$_2$-CH(NHC(=O)OPh)-C(=O)-O-R$^a$] | [structure: 4-isopropylphenyl-CH$_2$-CH(NCO)-C(=O)-O-R$^a$] | ODB | TPA |
| Ex. 46 | [structure: naphthyl-CH(NHC(=O)OPh)-C(=O)-O-R$^a$] | [structure: naphthyl-CH(NCO)-C(=O)-O-R$^a$] | ODB | TPA |

TABLE 15-continued

Starting material conduct thermal decomposition and resultant isocyanate

| | Carbamate | Resultant isocyanate | Low-boiling solvent | High-boiling solvent |
|---|---|---|---|---|
| Ex. 47 | [bis-phenyl carbamate of benzene-1,2-diyl diester with $R^a$ groups] | [bis-isocyanate of benzene-1,2-diyl diester with $R^a$ groups] | ODB | TPA |
| Ex. 48 | [furan-2-yl acetate ester with $R^a$ bearing HN-C(O)-O-Ph carbamate] | [furan-2-yl acetate ester with $R^a$ bearing NCO group] | ODB | TPA |

TABLE 16

| | Formulation of starting material mixture (% by mass) | | | Temperature Condition (° C.) | | Thermal decomposition yield (%) |
|---|---|---|---|---|---|---|
| | Conc. of carbamate | Conc. of low-boiling solvent | Conc. of high-boiling solvent | Temperature at first reactor | Temperature at second reactor | |
| Ex. 28 | 10 | 60 | 30 | 250 | 250 | 75 |
| Ex. 29 | 10 | 60 | 30 | 250 | 250 | 71 |
| Ex. 30 | 10 | 60 | 30 | 250 | 250 | 74 |
| Ex. 31 | 10 | 60 | 30 | 250 | 250 | 72 |
| Ex. 32 | 10 | 60 | 30 | 250 | 250 | 70 |
| Ex. 33 | 10 | 50 | 30 | 250 | 250 | 78 |
| Ex. 34 | 10 | 60 | 30 | 250 | 250 | 77 |
| Ex. 35 | 10 | 60 | 30 | 250 | 250 | 75 |
| Ex. 36 | 10 | 60 | 30 | 250 | 250 | 74 |
| Ex. 37 | 10 | 60 | 30 | 250 | 250 | 73 |
| Ex. 38 | 10 | 60 | 30 | 250 | 250 | 72 |
| Ex. 39 | 10 | 60 | 30 | 250 | 250 | 75 |
| Ex. 40 | 10 | 60 | 30 | 250 | 250 | 71 |
| Ex. 41 | 10 | 60 | 30 | 250 | 250 | 76 |
| Ex. 42 | 10 | 60 | 30 | 250 | 250 | 74 |
| Ex. 43 | 10 | 60 | 30 | 250 | 250 | 72 |
| Ex. 44 | 10 | 60 | 30 | 250 | 250 | 74 |
| Ex. 45 | 10 | 60 | 30 | 250 | 250 | 71 |
| Ex. 46 | 10 | 60 | 30 | 250 | 250 | 73 |
| Ex. 47 | 10 | 60 | 30 | 250 | 250 | 71 |
| Ex. 48 | 10 | 60 | 30 | 250 | 250 | 74 |

TABLE 17

| | | Starting material to produce carbamate | | Starting material to conduct thermal decomposition and resultant isocyanate | | | |
|---|---|---|---|---|---|---|---|
| | Reactor | Amino acid, amino acid derivative | Alkanol amine, Alcohol | Carbamate | Resultant isocyanate | Low-boiling solvent | High-boiling solvent |
| Ex. 49 | FIG. 1 | Lysine | EtOH | *(structure)* | *(structure)* | ODB | TPA |
| Ex. 50 | FIG. 1 | Lysine | 1-amino-2-PrOH | *(structure)* | *(structure)* | ODB | TPA |
| Ex. 51 | FIG. 1 | Lysine | 2-amino-1-BuOH | *(structure)* | *(structure)* | ODB | TPA |
| Ex. 52 | FIG. 1 | Lysine | Glycerin | *(structure)* | *(structure)* | ODB | TPA |

TABLE 17-continued

| | Reactor | Starting material to produce carbamate | | Starting material to conduct thermal decomposition and resultant isocyanate | | Low-boiling solvent | High-boiling solvent |
|---|---|---|---|---|---|---|---|
| | | Amino acid, amino acid derivative | Alkanol amine, Alcohol | Carbamate | Resultant isocyanate | | |
| Ex. 53 | FIG. 1 | Lysine | Pentaerythritol | *(structure)* | *(structure)* | ODB | TPA |

TABLE 18

| | Reactor | Starting material to produce carbamate | | Starting material to conduct thermal decomposition and resultant isocyanate | | Low-boiling solvent | High-boiling solvent |
|---|---|---|---|---|---|---|---|
| | | Amino acid, amino acid derivative | Alkanol amine, Alcohol | Carbamate | Resultant isocyanate | | |
| Ex. 54 | FIG. 1 | Ornithine | EtOH | *(structure)* | *(structure)* | ODB | TPA |
| Ex. 55 | FIG. 1 | Ornithine | 1-amino-2-PrOH | *(structure)* | *(structure)* | ODB | TPA |
| Ex. 56 | FIG. 1 | Ornithine | 2-amino-1-BuOH | *(structure)* | *(structure)* | ODB | TPA |

TABLE 18-continued

| | Reactor | Starting material to produce carbamate | | Starting material to conduct thermal decomposition and resultant isocyanate | | Low-boiling solvent | High-boiling solvent |
|---|---|---|---|---|---|---|---|
| | | Amino acid, amino acid derivative | Alkanol amine, Alcohol | Carbamate | Resultant isocyanate | | |
| Ex. 57 | FIG. 1 | Ornithine | Glycerin | *(structure)* | *(structure)* | ODB | TPA |
| Ex. 58 | FIG. 1 | Ornithine | Pentaerythritol | *(structure)* | *(structure)* | ODB | TPA |

TABLE 19

| | Reactor | Starting material to produce carbamate | | Starting material to conduct thermal decomposition and resultant isocyanate | | Low-boiling solvent | High-boiling solvent |
|---|---|---|---|---|---|---|---|
| | | Amino acid, amino acid derivative | Alkanol amine, Alcohol | Carbamate | Resultant isocyanate | | |
| Ex. 59 | FIG. 1 | Methionine | EtOH | *(structure)* | *(structure)* | ODB | TPA |
| Ex. 60 | FIG. 1 | Methionine | 1-amino-2-PrOH | *(structure)* | *(structure)* | ODB | TPA |
| Ex. 61 | FIG. 1 | Methionine | 2-amino-1-BuOH | *(structure)* | *(structure)* | ODB | TPA |

TABLE 19-continued

| | Reactor | Starting material to produce carbamate | | Starting material to conduct thermal decomposition and resultant isocyanate | | Low-boiling solvent | High-boiling solvent |
|---|---|---|---|---|---|---|---|
| | | Amino acid, amino acid derivative | Alkanol amine, Alcohol | Carbamate | Resultant isocyanate | | |
| Ex. 62 | FIG. 1 | Methionine | Glycerin | *(structure)* | *(structure)* | ODB | TPA |
| Ex. 63 | FIG. 1 | Methionine | Pentaerythritol | *(structure)* | *(structure)* | ODB | TPA |
| Ex. 64 | FIG. 1 | Glutamic acid | EtOH | *(structure)* | *(structure)* | ODB | TPA |

TABLE 20
| | Starting material to produce carbamate | | Starting material to conduct thermal decomposition and resultant isocyanate | | | |
|---|---|---|---|---|---|---|
| | Amino acid, | | | | | |
| Reactor | amino acid derivative | Alkanol amine, Alcohol | Carbamate | Resultant isocyanate | Low-boiling solvent | High-boiling solvent |
| Ex. 65 FIG. 1 | Glutamic acid | 1-amino-2-PrOH | 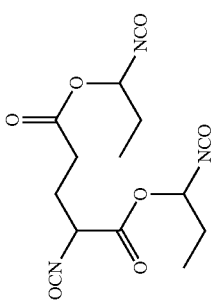 | 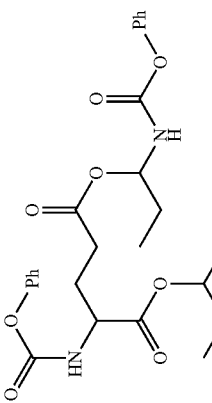 | ODB | TPA |
| Ex. 66 FIG. 1 | Glutamic acid | 2-amino-1-BuOH | | | OBD | TPA |

TABLE 20-continued

| | Starting material to produce carbamate | | Starting material to conduct thermal decomposition and resultant isocyanate | | | |
|---|---|---|---|---|---|---|
| Reactor | Amino acid, amino acid derivative | Alkanol amine, Alcohol | Carbamate | Resultant isocyanate | Low-boiling solvent | High-boiling solvent |
| Ex. FIG. 67  1 | Glutamic acid | Glycerin | | | ODB | TPA |

TABLE 20-continued

| | Starting material to produce carbamate | | Starting material to conduct thermal decomposition and resultant isocyanate | | |
|---|---|---|---|---|---|
| Reactor | Amino acid, amino acid derivative | Alkanol amine, Alcohol | Carbamate | Resultant isocyanate | Low-boiling solvent | High-boiling solvent |
| Ex. 68 FIG. 1 | Glutamic acid | Pentaerythritol | (structure) | (structure) | ODB | TPA |

TABLE 21

| | Formulation of starting material mixture (% by mass) | | | Temperature Condition (° C.) | | Thermal decomposition yield (%) |
|---|---|---|---|---|---|---|
| | Conc. of carbamate | Conc. of low-boiling solvent | Conc. of high-boiling solvent | Temperature at first reactor | Temperature at second reactor | |
| Ex. 49 | 10 | 60 | 30 | 250 | 250 | 80 |
| Ex. 50 | 10 | 60 | 30 | 250 | 250 | 78 |
| Ex. 51 | 10 | 60 | 30 | 250 | 250 | 76 |
| Ex. 52 | 10 | 60 | 30 | 250 | 250 | 76 |
| Ex. 53 | 10 | 60 | 30 | 250 | 250 | 77 |
| Ex. 54 | 10 | 60 | 30 | 200 | 250 | 79 |
| Ex. 55 | 10 | 60 | 30 | 250 | 250 | 76 |
| Ex. 56 | 10 | 60 | 30 | 250 | 250 | 74 |
| Ex. 57 | 10 | 60 | 30 | 250 | 250 | 71 |
| Ex. 58 | 10 | 60 | 30 | 250 | 250 | 76 |
| Ex. 59 | 10 | 60 | 30 | 250 | 250 | 74 |
| Ex. 60 | 10 | 60 | 30 | 250 | 250 | 72 |
| Ex. 61 | 10 | 60 | 30 | 250 | 250 | 77 |
| Ex. 62 | 10 | 60 | 30 | 250 | 250 | 76 |
| Ex. 63 | 10 | 60 | 30 | 250 | 250 | 74 |
| Ex. 64 | 10 | 60 | 30 | 250 | 250 | 75 |
| Ex. 65 | 10 | 60 | 30 | 250 | 250 | 72 |
| Ex. 66 | 10 | 60 | 30 | 250 | 250 | 76 |
| Ex. 67 | 10 | 60 | 30 | 250 | 250 | 74 |
| Ex. 68 | 10 | 60 | 30 | 250 | 250 | 77 |

TABLE 22

| | Reactor | Starting material to produce carbamate | | Starting material to conduct thermal decomposition and resultant isocyanate | | Low-boiling solvent | High-boiling solvent |
|---|---|---|---|---|---|---|---|
| | | Amino acid, amino acid derivative | Alkanol amine, Alcohol | Carbamate | Resultant isocyanate | | |
| Ex. 69 | FIG. 1 | Lysine | Mono-ethanol amine | [structure] | [structure] | ODB | TKA-100 |
| Ex. 70 | FIG. 1 | Lysine | Mono-ethanol amine | [structure] | [structure] | ODB | 24A-100 |
| Ex. 71 | FIG. 1 | Lysine | Mono-ethanol amine | [structure] | [structure] | ODB | TLA-100 |

TABLE 22-continued

| | | Starting material to produce carbamate | | Starting material to conduct thermal decomposition and resultant isocyanate | | | |
|---|---|---|---|---|---|---|---|
| | Reactor | Amino acid, amino acid derivative | Alkanol amine, Alcohol | Carbamate | Resultant isocyanate | Low-boiling solvent | High-boiling solvent |
| Ex. 72 | FIG. 1 | Ornithine | Mono-ethanol amine | [structure] | [structure] | ODB | TKA-100 |
| Ex. 73 | FIG. 1 | Ornithine | Mono-ethanol amine | [structure] | [structure] | ODB | 24A-100 |
| Ex. 74 | FIG. 1 | Ornithine | Mono-ethanol amine | [structure] | [structure] | ODB | TLA-100 |
| Ex. 75 | FIG. 1 | Methionine | Mono-ethanol amine | [structure] | [structure] | ODB | TKA-100 |

TABLE 23

| | Reactor | Starting material to produce carbamate — Amino acid, amino acid derivative | Alkanol amine, Alcohol | Starting material to conduct thermal decomposition and resultant isocyanate — Carbamate | Resultant isocyanate | Low-boiling solvent | High-boiling solvent |
|---|---|---|---|---|---|---|---|
| Ex. 76 | FIG. 1 | Methionine | Mono-ethanol amine | [structure] | [structure] | ODB | 24A-100 |
| Ex. 77 | FIG. 1 | Methionine | Mono-ethanol amine | [structure] | [structure] | ODB | TLA-100 |
| Ex. 78 | FIG. 1 | Glutamic acid | Mono-ethanol amine | [structure] | [structure] | ODB | TKA-100 |
| Ex. 79 | FIG. 1 | Glutamic acid | Mono-ethanol amine | [structure] | [structure] | ODB | 24A-100 |
| Ex. 80 | FIG. 1 | Glutamic acid | Mono-ethanol amine | [structure] | [structure] | ODB | TLA-100 |

TABLE 24

| | Formulation of starting material mixture (% by mass) | | | Temperature Condition (° C.) | | Thermal decomposition yield (%) |
| --- | --- | --- | --- | --- | --- | --- |
| | Conc. of carbamate | Conc. of low-boiling solvent | Conc. of high-boiling solvent | Temperature at first reactor | Temperature at second reactor | |
| Ex. 69 | 10 | 60 | 30 | 250 | 250 | 76 |
| Ex. 70 | 10 | 60 | 30 | 250 | 250 | 74 |
| Ex. 71 | 10 | 60 | 30 | 250 | 250 | 79 |
| Ex. 72 | 10 | 60 | 30 | 250 | 250 | 76 |
| Ex. 73 | 10 | 60 | 30 | 250 | 250 | 74 |
| Ex. 74 | 10 | 60 | 30 | 250 | 250 | 73 |
| Ex. 75 | 10 | 60 | 30 | 250 | 250 | 79 |
| Ex. 76 | 10 | 60 | 30 | 250 | 250 | 74 |
| Ex. 77 | 10 | 60 | 30 | 250 | 250 | 75 |
| Ex. 78 | 10 | 60 | 30 | 250 | 250 | 76 |
| Ex. 79 | 10 | 60 | 30 | 250 | 250 | 78 |
| Ex. 80 | 10 | 60 | 30 | 250 | 250 | 79 |

Example 81

The below-mentioned step was conducted instead of the steps conducted after the preparation step in Example 1.

The mixture liquid obtained in the "step of preparing a mixture liquid" was introduced into a first storage tank 101. An ortho dichlorobenzene and a polyisocyanate (manufactured by Asahi Kasei Corporation, polyisocyanate (trade name: DURANATE) grade: TPA-100) were introduced into a reactor 100 equipped with a heat medium jacket composed of a first packed-bed 106, a second packed-bed 107, and a third packed-bed 108.

The temperature of a heat medium passing through the heat medium jacket was set at 270° C., and the state in which the ortho dichlorobenzene was refluxed through a sixth line 16, a third partial condenser 115, a third storage tank 103, a fourth solution-sending pump 112 and a seventh line 17, that were provided at the top of the third packed-bed 108, was realized while controlling the inner pressure. In a similar manner, the state in which the ortho dichlorobenzene was refluxed through a fourth line 14, a second partial condenser 114, a fourth storage tank 104, a third solution-sending pump 111, and a fifth line 15, that were provided at the top of the second packed-bed 107, was realized. In a similar manner, the state in which the ortho dichlorobenzene was refluxed through a second line 12, a first partial condenser 113, a fifth storage tank 105, a second solution-sending pump 110 and a third line 13, that were provided at the top of the first packed-bed 106, was realized.

The mixture liquid was supplied at 500 g/hr to the reactor 100 from a first storage tank 101 through a first line 10 and a fifth solution-sending pump 116 to conduct thermal decomposition of N,N'-hexanediyl-bis-carbamic acid diphenyl ester. A mixture liquid containing a phenol produced by the thermal decomposition and the ortho dichlorobenzene was collected in the third storage tank 103 through the sixth line 16 and the third partial condenser 115, provided at the top of the third packed-bed 108. At the same time, a mixture liquid containing a hexamethylene diisocyanate produced by the thermal decomposition and the ortho dichlorobenzene was collected in the fourth storage tank 104 through the fourth line 14 and the second partial condenser 114, provided at the top of the second packed-bed 107. At the same time, a mixture liquid containing the hexamethylene diisocyanate produced by the thermal decomposition and the ortho dichlorobenzene was collected in the fifth storage tank 105 through the second line 12 and the first partial condenser 113, provided at the top of the first packed-bed 106. On the other hand, a reaction liquid containing a polyisocyanate was extracted from the bottom of the reactor 100 through an eighth line 11 and a first solution-sending pump to be collected in the second storage tank 102, so as to make the liquid surface in the reactor 100 became constant. The yield of the hexamethylene diisocyanate collected in the fourth storage tank 104 was 58%. The above-mentioned operations could be conducted continuously for 200 hours.

Examples 82 to 91

The same procedures as those used in Example 81 were used except that the carbamate derivative used in Example 81 was replaced with each carbamate shown in the below tables to obtain isocyanates corresponding to the starting carbamate derivatives. When the decomposition reaction was conducted for 200 hours continuously, no adhesion of polymeric by-products was confirmed inside the reactor, and the isocyanates corresponding to the starting materials were obtained stably.

Examples 92 to 128

The same procedures as those used in Example 81 were used except that starting materials to produce carbamates and starting materials to conduct a thermal decomposition reaction, shown in the below tables, were used to obtain isocyanates corresponding to the starting carbamate derivatives. When the decomposition reaction was conducted for 200 hours continuously, no adhesion of polymeric by-products was confirmed inside the reactor, and the isocyanates corresponding to the starting materials were obtained stably. In the case where an arginine was used, the arginine was hydrolyzed to an ornithine by a conventionally-known method. In the case where a glutamine or an asparagine was used, the glutamine or the asparagine was hydrolyzed to a glutamic acid or an asparagic acid, respectively, to be used.

Examples 129 to 148

The same procedures as those used in Example 92 were used except that starting materials to produce carbamates and starting materials to conduct thermal decomposition reaction, shown in the below tables, were used to obtain isocyanates corresponding to the starting carbamate derivatives. When the decomposition reaction was conducted for 200 hours continuously, no adhesion of polymeric by-products was confirmed inside the reactor, and the isocyanates corresponding to the starting materials were obtained stably.

Examples 149 to 160

The same procedures as those used in Example 92 were used except that each amino acids or amino acid derivatives shown in the below tables were introduced instead of an amino acid group of the lysine aminoethyl ester hydrochloride used in Example 92, or polyisocyanates shown in the below tables were used instead of the polyisocyanate used in the step of preparing a mixture solvent. As the polyisocyanates shown in the tables, polyisocyanates manufactured by Asahi Kasei Corporation, (trade name: DURANATE, grade: TKA-100, 24A-100, and TLA-100) were used. Isocyanates corresponding to starting carbamate derivatives were obtained by the procedures. When the decomposition reaction was carried out continuously for 200 hours, no adhesion of polymeric by-products was confirmed inside the reactor, and the isocyanates corresponding to the starting materials were obtained stably.

TABLE 25

Starting material to conduct thermal decomposition and resultant isocyanate

Figure 2:
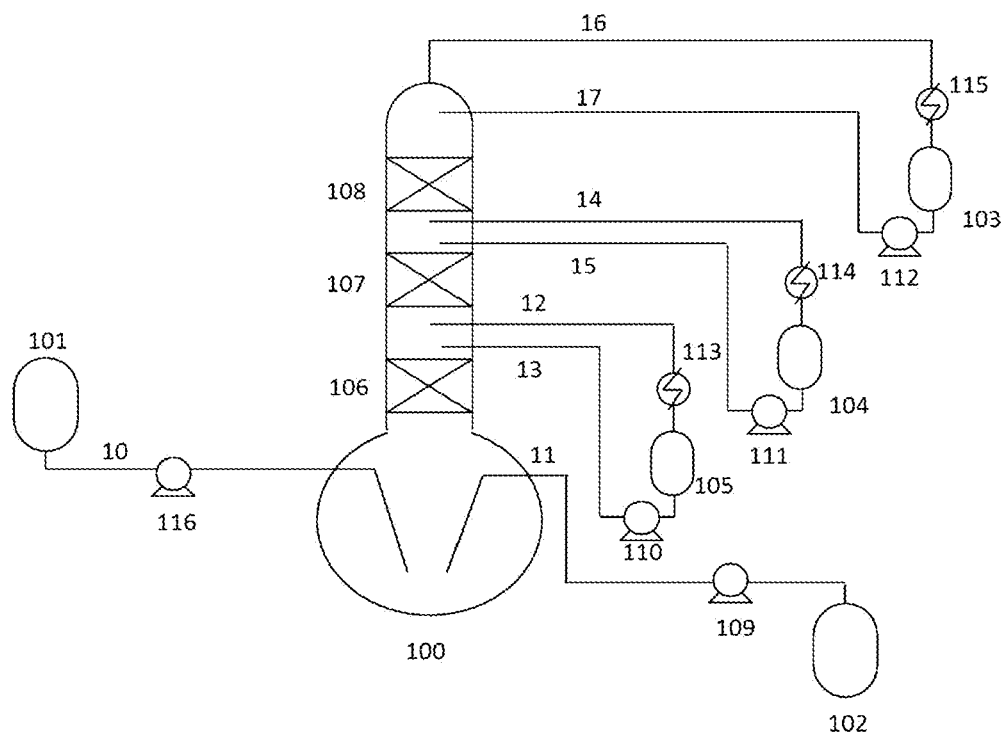

| Reactor | Carbamate | Resultant isocyanate | Low-boiling solvent | High-boiling solvent |
|---|---|---|---|---|
| Ex. 81 FIG. 2 | PhO-C(=O)-NH-(CH₂)₆-NH-C(=O)-OPh | OCN-(CH₂)₆-NCO | ODB | TPA |
| Ex. 82 FIG. 2 | PhO-C(=O)-NH-(CH₂)₅-NH-C(=O)-OPh | OCN-(CH₂)₅-NCO | ODB | TPA |
| Ex. 83 FIG. 2 | PhO-C(=O)-NH-(isophorone)-CH₂-NH-C(=O)-OPh | OCN-(isophorone)-CH₂-NCO | ODB | TPA |
| Ex. 84 FIG. 2 | PhO-C(=O)-NH-C₆H₄-CH₂-C₆H₄-NH-C(=O)-OPh | OCN-C₆H₄-CH₂-C₆H₄-NCO | ODB | TPA |
| Ex. 85 FIG. 2 | PhO-C(=O)-NH-C₆H₁₀-CH₂-C₆H₁₀-NH-C(=O)-OPh | OCN-C₆H₁₀-CH₂-C₆H₁₀-NCO | ODB | TPA |
| Ex. 86 FIG. 2 | iBuO-C(=O)-NH-(CH₂)₆-NH-C(=O)-OiBu | OCN-(CH₂)₆-NCO | ODB | TPA |
| Ex. 87 FIG. 2 | 1,3-C₆H₄(CH₂-NH-C(=O)-OPh)₂ | 1,3-C₆H₄(CH₂-NCO)₂ | ODB | TPA |

TABLE 25-continued

Starting material to conduct thermal decomposition and resultant isocyanate

| Reactor | Carbamate | Resultant isocyanate | Low-boiling solvent | High-boiling solvent |
|---|---|---|---|---|
| Ex. 88 FIG. 2 | 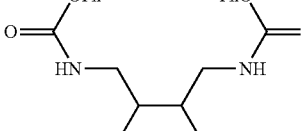 | 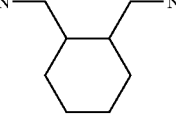 | ODB | TPA |
| Ex. 89 FIG. 2 | 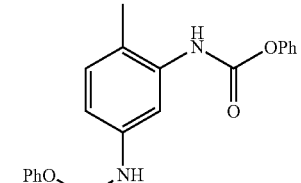 | 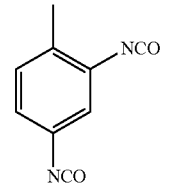 | ODB | TPA |
| Ex. 90 FIG. 2 | 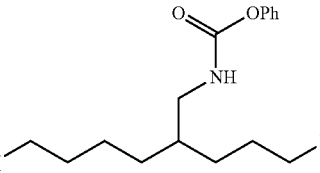 | 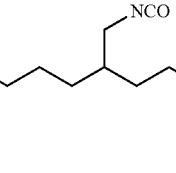 | ODB | TPA |

TABLE 26

| | | Starting material to produce carbamate | | Starting material to conduct thermal decomposition and resultant isocyanate | | | |
|---|---|---|---|---|---|---|---|
| | Reactor | Amino acid, amino acid derivative | Alkanol amine | Carbamate | Resultant isocyanate | Low-boiling solvent | High-boiling solvent |
| Ex. 91 | FIG. 2 | — | — |  |  | ODB | TPA |
| Ex. 92 | FIG. 2 | Lysine | Mono-ethanol amine | 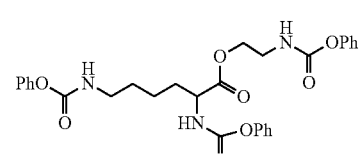 | 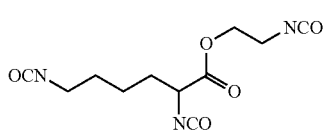 | ODB | TPA |
| Ex. 93 | FIG. 2 | Alanine | Mono-ethanol amine | 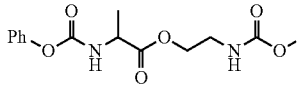 | 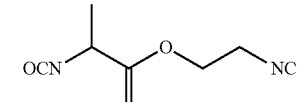 | ODB | TPA |

TABLE 26-continued

| | Reactor | Starting material to produce carbamate | | Starting material to conduct thermal decomposition and resultant isocyanate | | Low-boiling solvent | High-boiling solvent |
|---|---|---|---|---|---|---|---|
| | | Amino acid, amino acid derivative | Alkanol amine | Carbamate | Resultant isocyanate | | |
| Ex. 94 | FIG. 2 | Arginine | Monoethanolamine | (structure) | (structure) | ODB | TPA |
| Ex. 95 | FIG. 2 | Asparagine | Monoethanolamine | (structure) | (structure) | ODB | TPA |
| Ex. 96 | FIG. 2 | Glutamine | Monoethanolamine | (structure) | (structure) | ODB | TPA |
| Ex. 97 | FIG. 2 | Glycine | Monoethanolamine | (structure) | (structure) | ODB | TPA |

TABLE 27

| | Reactor | Starting material to produce carbamate | | Starting material to conduct thermal decomposition and resultant isocyanate | | Low-boiling solvent | High-boiling solvent |
|---|---|---|---|---|---|---|---|
| | | Amino acid, amino acid derivative | Alkanol amine | Carbamate | Resultant isocyanate | | |
| Ex. 98 | FIG. 2 | Asparaginic acid | Mono-ethanol amine | *(structure)* | *(structure)* | ODB | TPA |
| Ex. 99 | FIG. 2 | Glutamic acid | Mono-ethanol amine | *(structure)* | *(structure)* | ODB | TPA |
| Ex. 100 | FIG. 2 | Histidine | Mono-ethanol amine | *(structure)* | *(structure)* | ODB | TPA |
| Ex. 101 | FIG. 2 | Isoleucine | Mono-ethanol amine | *(structure)* | *(structure)* | ODB | TPA |
| Ex. 102 | FIG. 2 | Leucine | Mono-ethanol amine | *(structure)* | *(structure)* | ODB | TPA |

TABLE 27-continued

| | | Starting material to produce carbamate | | | | | |
|---|---|---|---|---|---|---|---|
| | | Amino acid, amino acid derivative | Alkanol amine | Starting material to conduct thermal decomposition and resultant isocyanate | | Low-boiling solvent | High-boiling solvent |
| | Reactor | | | Carbamate | Resultant isocyanate | | |
| Ex. 103 | FIG. 2 | Methionine | Mono-ethanol amine | 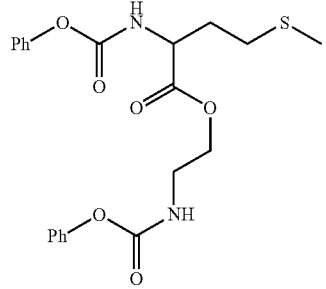 [SMILES: CSCCC(NC(=O)Oc1ccccc1)C(=O)OCCNC(=O)Oc1ccccc1] | 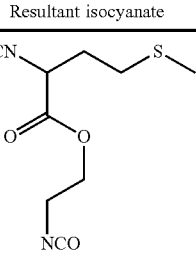 | ODB | TPA |

TABLE 28

| | | Starting material to produce carbamate | | | | | |
|---|---|---|---|---|---|---|---|
| | | Amino acid, amino acid derivative | Alkanol amine | Starting material to conduct thermal decomposition and resultant isocyanate | | Low-boiling solvent | High-boiling solvent |
| | Reactor | | | Carbamate | Resultant isocyanate | | |
| Ex. 104 | FIG. 2 | Phenyl alanine | Mono-ethanol amine | 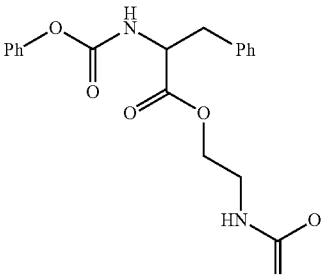 | 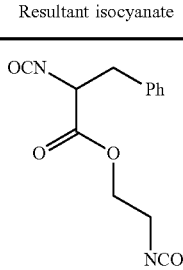 | ODB | TPA |
| Ex. 105 | FIG. 2 | Triptophan | Mono-ethanol amine | 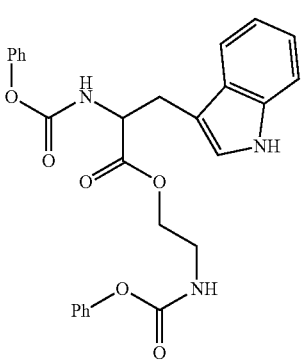 [SMILES: O=C(NCCOC(=O)C(Cc1c[nH]c2ccccc12)NC(=O)Oc1ccccc1)Oc1ccccc1] | 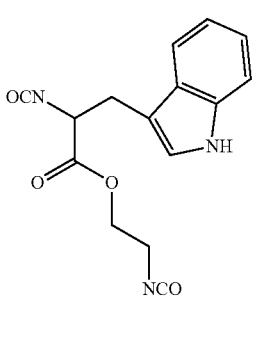 | ODB | TPA |

TABLE 28-continued

| Reactor | Starting material to produce carbamate | | Starting material to conduct thermal decomposition and resultant isocyanate | | Low-boiling solvent | High-boiling solvent |
|---|---|---|---|---|---|---|
| | Amino acid, amino acid derivative | Alkanol amine | Carbamate | Resultant isocyanate | | |
| Ex. 106 FIG. 2 | Valine | Mono-ethanol amine | [structure: Ph-O-C(=O)-NH-CH(iPr)-C(=O)-O-CH2-CH2-NH-C(=O)-O-Ph] | [structure: OCN-CH(iPr)-C(=O)-O-CH2-CH2-NCO] | ODB | TPA |

TABLE 29

| | Formulation of starting material mixture (% by mass) | | | Temperature Condition (° C.) | | Thermal decomposition yield (%) |
|---|---|---|---|---|---|---|
| | Conc. of carbamate | Conc. of low-boiling solvent | Conc. of high-boiling solvent | Temperature at first reactor | Temperature at second reactor | |
| Ex. 81 | 10 | 60 | 30 | 250 | 250 | 82 |
| Ex. 82 | 10 | 60 | 30 | 250 | 250 | 84 |
| Ex. 83 | 10 | 60 | 30 | 250 | 250 | 83 |
| Ex. 84 | 10 | 60 | 30 | 250 | 250 | 85 |
| Ex. 85 | 10 | 60 | 30 | 250 | 250 | 81 |
| Ex. 86 | 10 | 60 | 30 | 250 | 250 | 84 |
| Ex. 87 | 10 | 60 | 30 | 250 | 250 | 83 |
| Ex. 88 | 10 | 60 | 30 | 250 | 250 | 85 |
| Ex. 89 | 10 | 60 | 30 | 250 | 250 | 84 |
| Ex. 90 | 10 | 60 | 30 | 250 | 250 | 82 |
| Ex. 91 | 10 | 60 | 30 | 250 | 250 | 86 |
| Ex. 92 | 10 | 60 | 30 | 250 | 250 | 79 |
| Ex. 93 | 10 | 60 | 30 | 250 | 250 | 77 |
| Ex. 94 | 10 | 60 | 30 | 250 | 250 | 74 |
| Ex. 95 | 10 | 60 | 30 | 250 | 250 | 76 |
| Ex. 96 | 10 | 60 | 30 | 250 | 250 | 75 |
| Ex. 97 | 10 | 60 | 30 | 250 | 250 | 72 |
| Ex. 98 | 10 | 60 | 30 | 250 | 250 | 71 |
| Ex. 99 | 10 | 60 | 30 | 250 | 250 | 74 |
| Ex. 100 | 10 | 60 | 30 | 250 | 250 | 76 |
| Ex. 101 | 10 | 60 | 30 | 250 | 250 | 73 |
| Ex. 102 | 10 | 60 | 30 | 250 | 250 | 74 |
| Ex. 103 | 10 | 60 | 30 | 250 | 250 | 72 |
| Ex. 104 | 10 | 60 | 30 | 250 | 250 | 73 |
| Ex. 105 | 10 | 60 | 30 | 250 | 250 | 75 |
| Ex. 106 | 10 | 60 | 30 | 250 | 250 | 73 |

TABLE 30

| | Reactor | Amino acid, amino acid derivative | Amino acid formula | x | Ra | Rb | Explanation of formula | Alkanol amine |
|---|---|---|---|---|---|---|---|---|
| Ex. 107 | FIG. 2 | Ornithine | H₂N–(chain)–C(=O)OH with NH₂ | — | — | — | — | Mono-ethanol amine |
| Ex. 108 | FIG. 2 | Lysine derivative | [Rᵃ–O–C(=O)–...–CH(NH₂)–C(=O)–O–Rᵇ]ₓ | 1 | Me | Me | Ra and Rb each independently represents an aliphatic group, an aromatic group, or a hydrogen atom, X = 1-4 (excepting that Ra represents a hydrogen atom). When both Ra and Rb represent hydrogen atoms, X represens 1. | — |
| Ex. 109 | FIG. 2 | Lysine derivative | [Rᵃ–O–C(=O)–...–CH(NH₂)–C(=O)–O–Rᵇ]ₓ | 2 | —(CH2)2— | Me | Ra and Rb each independently represents an aliphatic group, an aromatic group, or a hydrogen atom, X = 1-4 (excepting that Ra represents a hydrogen atom). When both Ra and Rb represent hydrogen atoms, X represens 1. | — |
| Ex. 110 | FIG. 2 | Glutamine derivative | [Rᵃ–O–C(=O)–...–CH(NH₂)–C(=O)–O–Rᵇ]ₓ | 1 | Me | Me | Ra and Rb each independently represents an aliphatic group, an aromatic group, or a hydrogen atom, X = 1-4 (excepting that Ra represents a hydrogen atom). When both Ra and Rb represent hydrogen atoms, X represens 1. | — |
| Ex. 111 | FIG. 2 | Methionine derivative | [CH₃–S–...–CH(NH₂)–C(=O)–O–Rᵃ]ₓ | 1 | Me | — | Ra and Rb each independently represents an aliphatic group, an aromatic group, or a hydrogen atom, X = 1-4 (excepting that Ra represents a hydrogen atom). When both Ra and Rb represent hydrogen atoms, X represens 1. | — |
| Ex. 112 | FIG. 2 | Glycine derivative | [H₂N–CH₂–C(=O)–O–Rᵃ]ₓ | 1 | Me | — | Ra and Rb each independently represents an aliphatic group, an aromatic group, or a hydrogen atom, X = 1-4 (excepting that Ra represents a hydrogen atom). When both Ra and Rb represent hydrogen atoms, X represens 1. | — |
| Ex. 113 | FIG. 2 | Phenyl alanine derivative | [Ph–CH₂–CH(NH₂)–C(=O)–O–Rᵃ]ₓ | 1 | Me | — | Ra and Rb each independently represents an aliphatic group, an aromatic group, or a hydrogen atom, X = 1-4 (excepting that Ra represents a hydrogen atom). When both Ra and Rb represent hydrogen atoms, X represens 1. | — |

TABLE 30-continued

| | Reactor | Amino acid, amino acid derivative | Amino acid formula | x | Ra | Rb | Explanation of formula | Alkanol amine |
|---|---|---|---|---|---|---|---|---|
| Ex. 114 | FIG. 2 | Asparagine derivative | (structure shown) | 1 | Me | H | Ra and Rb each independenly represents an aliphatic group, an aromatic group, or a hydrogen atom, X = 1-4 (excepting that Ra represents a hydrogen atom). When both Ra and Rb represent hydrogen atoms, X represens 1. | — |

TABLE 31

Starting material to conduct thermal decomposition and resultant isocyanate

| | Carbamate | Resultant isocyanate | Low-boiling solvent | High-boiling solvent |
|---|---|---|---|---|
| Ex. 107 | (structure) | (structure) | ODB | TPA |
| Ex. 108 | (structure) | (structure) | ODB | TPA |
| Ex. 109 | (structure) | (structure) | ODB | TPA |
| Ex. 110 | (structure) | (structure) | ODB | TPA |

TABLE 31-continued

Starting material to conduct thermal decomposition and resultant isocyanate

| | Carbamate | Resultant isocyanate | Low-boiling solvent | High-boiling solvent |
|---|---|---|---|---|
| Ex. 111 | [methionine-derived PhO-C(O)-NH-CH(CH₂CH₂SMe)-C(O)-O-Rᵃ]ₓ | [OCN-CH(CH₂CH₂SMe)-C(O)-O-Rᵃ]ₓ | ODB | TPA |
| Ex. 112 | [PhO-C(O)-NH-CH₂-C(O)-O-Rᵃ]ₓ | [OCN-CH₂-C(O)-O-Rᵃ]ₓ | ODB | TPA |
| Ex. 113 | [phenylalanine-derived PhO-C(O)-NH-CH(CH₂Ph)-C(O)-O-Rᵃ]ₓ | [OCN-CH(CH₂Ph)-C(O)-O-Rᵃ]ₓ | ODB | TPA |
| Ex. 114 | [aspartate-derived, Rᵇ-O-C(O)-CH₂-CH(NH-C(O)-O-Ph)-C(O)-O-Rᵃ]ₓ | [Rᵇ-O-C(O)-CH₂-CH(NCO)-C(O)-O-Rᵃ]ₓ | ODB | TPA |

TABLE 32

Starting material to produce carbamate

| | Reactor | Amino acid, amino acid derivative | Formula of Amino acid | x | Ra | Rb | Explanation of formula |
|---|---|---|---|---|---|---|---|
| Ex. 115 | FIG. 2 | Alanine derivative | [H₂N-CH(CH₃)-C(O)-O-Rᵃ]ₓ | 1 | Me | — | Ra and Rb each independenly represents an aliphatic group, an aromatic group, or a hydrogen atom, X = 1-4 (excepting that Ra represents a hydrogen atom). When both Ra and Rb represent hydrogen atoms, X represens 1. |
| Ex. 116 | FIG. 2 | Leucine derivative | [H₂N-CH(CH₂CH(CH₃)₂)-C(O)-O-Rᵃ]ₓ | 1 | Me | — | Ra and Rb each independenly represents an aliphatic group, an aromatic group, or a hydrogen atom, X = 1-4 (excepting that Ra represents a hydrogen atom). When both Ra and Rb represent hydrogen atoms, X represens 1. |

TABLE 32-continued

| | Reactor | Amino acid, amino acid derivative | Formula of Amino acid | x | Ra | Rb | Explanation of formula |
|---|---|---|---|---|---|---|---|
| Ex. 117 | FIG. 2 | Iso-leucine derivative | [structure: H₂N-CH(CH(CH₃)CH₂CH₃)-C(=O)-O-Rᵃ]ₓ | 1 | Me | — | Ra and Rb each independenly represents an aliphatic group, an aromatic group, or a hydrogen atom, X = 1-4 (excepting that Ra represents a hydrogen atom). When both Ra and Rb represent hydrogen atoms, X represens 1. |
| Ex. 118 | FIG. 2 | Valine derivative | [structure: H₂N-CH(CH(CH₃)₂)-C(=O)-O-Rᵃ]ₓ | 1 | Me | — | Ra and Rb each independenly represents an aliphatic group, an aromatic group, or a hydrogen atom, X = 1-4 (excepting that Ra represents a hydrogen atom). When both Ra and Rb represent hydrogen atoms, X represens 1. |
| Ex. 119 | FIG. 2 | Synthesized amino acid | [structure: 1,3,5-trisubstituted benzene with three -CH(NH₂)-C(=O)-O-Rᵃ groups] | — | Me | — | Ra and Rb each independenly represents an aliphatic group, an aromatic group, or a hydrogen atom, X = 1-4 (excepting that Ra represents a hydrogen atom). When both Ra and Rb represent hydrogen atoms, X represens 1. |
| Ex. 120 | FIG. 2 | Synthesized amino acid | [structure: RᵃO-C(=O)-CH(NH₂)-(CH₂)₄-CH(NH₂)-C(=O)-ORᵃ] | — | Me | — | Ra and Rb each independenly represents an aliphatic group, an aromatic group, or a hydrogen atom, X = 1-4 (excepting that Ra represents a hydrogen atom). When both Ra and Rb represent hydrogen atoms, X represens 1. |
| Ex. 121 | FIG. 2 | Synthesized amino acid | [structure: Cl, F-substituted phenyl-CH(NH₂)-C(=O)-O-Rᵃ] | — | Me | — | Ra and Rb each independenly represents an aliphatic group, an aromatic group, or a hydrogen atom, X = 1-4 (excepting that Ra represents a hydrogen atom). When both Ra and Rb represent hydrogen atoms, X represens 1. |

TABLE 33

| | Starting material to conduct thermal decomposition and resultant isocyanate | | Low-boiling solvent | Hight-boiling solvent |
|---|---|---|---|---|
| | Carbamate | Resultant isocyanate | | |
| Ex. 115 | [Ph-O-C(=O)-NH-CH(CH₃)-C(=O)-O-Rᵃ]ₓ | [OCN-CH(CH₃)-C(=O)-O-Rᵃ]ₓ | ODB | TPA |

TABLE 33-continued

Starting material to conduct thermal decomposition and resultant isocyanate

| | Carbamate | Resultant isocyanate | Low-boiling solvent | High-boiling solvent |
|---|---|---|---|---|
| Ex. 116 | (structure) | (structure) | ODB | TPA |
| Ex. 117 | (structure) | (structure) | ODB | TPA |
| Ex. 118 | (structure) | (structure) | ODB | TPA |
| Ex. 119 | (structure) | (structure) | ODB | TPA |
| Ex. 120 | (structure) | (structure) | ODB | TPA |
| Ex. 121 | (structure) | (structure) | ODB | TPA |

TABLE 34

| | Reactor | Amino acid, amino acid derivative | Formula of Amino acid | x | Ra | Rb | Explanation of formula |
|---|---|---|---|---|---|---|---|
| Ex. 122 | FIG. 2 | Synthesized amino acid | 3,4-dimethoxyphenylglycine ester (OMe, MeO on phenyl; CH(NH₂)C(O)O-Rᵃ) | — | Me | — | Ra and Rb each independenly represents an aliphatic group, an aromatic group, or a hydrogen atom, X = 1-4 (excepting that Ra represents a hydrogen atom). When both Ra and Rb represent hydrogen atoms, X represens 1. |
| Ex. 123 | FIG. 2 | Synthesized amino acid | R-CH(NH₂)-C(O)O-Rᵃ | — | Me | — | Ra and Rb each independenly represents an aliphatic group, an aromatic group, or a hydrogen atom, X = 1-4 (excepting that Ra represents a hydrogen atom). When both Ra and Rb represent hydrogen atoms, X represens 1. |
| Ex. 124 | FIG. 2 | Synthesized amino acid | 3,4-methylenedioxyphenylglycine ester | — | Me | — | Ra and Rb each independenly represents an aliphatic group, an aromatic group, or a hydrogen atom, X = 1-4 (excepting that Ra represents a hydrogen atom). When both Ra and Rb represent hydrogen atoms, X represens 1. |
| Ex. 125 | FIG. 2 | Synthesized amino acid | 4-isopropylphenylalanine ester | — | Me | — | Ra and Rb each independenly represents an aliphatic group, an aromatic group, or a hydrogen atom, X = 1-4 (excepting that Ra represents a hydrogen atom). When both Ra and Rb represent hydrogen atoms, X represens 1. |
| Ex. 126 | FIG. 2 | Synthesized amino acid | 1-naphthylglycine ester | — | Me | — | Ra and Rb each independenly represents an aliphatic group, an aromatic group, or a hydrogen atom, X = 1-4 (excepting that Ra represents a hydrogen atom). When both Ra and Rb represent hydrogen atoms, X represens 1. |
| Ex. 127 | FIG. 2 | Synthesized amino acid | 1,2-phenylenebis(glycine ester) (H₂N-CH(C(O)O-Rᵃ) groups on ortho phenyl) | — | Me | — | Ra and Rb each independenly represents an aliphatic group, an aromatic group, or a hydrogen atom, X = 1-4 (excepting that Ra represents a hydrogen atom). When both Ra and Rb represent hydrogen atoms, X represens 1. |
| Ex. 128 | FIG. 2 | Synthesized amino acid | 2-furylglycine ester | — | Me | — | Ra and Rb each independenly represents an aliphatic group, an aromatic group, or a hydrogen atom, X = 1-4 (excepting that Ra represents a hydrogen atom). When both Ra and Rb represent hydrogen atoms, X represens 1. |

TABLE 35

| | Starting material to conduct thermal decomposition and resultant isocyanate | | | |
|---|---|---|---|---|
| | Carbamate | Resultant isocyanate | Low-boiling solvent | High-boiling solvent |
| Ex. 122 | (3,4-dimethoxyphenyl)(phenoxycarbonylamino)acetic acid ester | (3,4-dimethoxyphenyl)(isocyanato)acetic acid ester | ODB | TPA |
| Ex. 123 | R-substituted (phenoxycarbonylamino)acetic acid ester | R-substituted isocyanatoacetic acid ester | ODB | TPA |
| Ex. 124 | (benzo[d][1,3]dioxol-5-yl)(phenoxycarbonylamino)acetic acid ester | (benzo[d][1,3]dioxol-5-yl)(isocyanato)acetic acid ester | ODB | TPA |
| Ex. 125 | 3-(4-isopropylphenyl)-2-(phenoxycarbonylamino)propanoic acid ester | 3-(4-isopropylphenyl)-2-isocyanatopropanoic acid ester | ODB | TPA |
| Ex. 126 | (naphthalen-1-yl)(phenoxycarbonylamino)acetic acid ester | (naphthalen-1-yl)(isocyanato)acetic acid ester | ODB | TPA |

TABLE 35-continued

Starting material to conduct thermal decomposition and resultant isocyanate

| | Carbamate | Resultant isocyanate | Low-boiling solvent | High-boiling solvent |
|---|---|---|---|---|
| Ex. 127 | (structure: benzene ring with two -CH(NHC(O)OPh)C(O)O-R$^a$ groups ortho) | (structure: benzene ring with two -CH(NCO)C(O)O-R$^a$ groups ortho) | ODB | TPA |
| Ex. 128 | (structure: furan-2-yl-CH(NHC(O)OPh)-C(O)O-R$^a$) | (structure: furan-2-yl-CH(NCO)-C(O)O-R$^a$) | ODB | TPA |

TABLE 36

| | Formulation of starting material mixture (% by mass) | | | Temperature Condition (° C.) | | Thermal decomposition yield (%) |
|---|---|---|---|---|---|---|
| | Conc. of carbamate | Conc. of low-boiling solvent | Conc. of high-boiling solvent | Temperature at first reactor | Temperature at second reactor | |
| Ex. 107 | 10 | 60 | 30 | 250 | 250 | 74 |
| Ex. 108 | 10 | 60 | 30 | 250 | 250 | 76 |
| Ex. 109 | 10 | 60 | 30 | 250 | 250 | 78 |
| Ex. 110 | 10 | 60 | 30 | 250 | 250 | 74 |
| Ex. 111 | 10 | 60 | 30 | 250 | 250 | 76 |
| Ex. 112 | 10 | 60 | 30 | 250 | 250 | 74 |
| Ex. 113 | 10 | 60 | 30 | 250 | 250 | 75 |
| Ex. 114 | 10 | 60 | 30 | 250 | 250 | 73 |
| Ex. 115 | 10 | 60 | 30 | 250 | 250 | 72 |
| Ex. 116 | 10 | 60 | 30 | 250 | 250 | 76 |
| Ex. 117 | 10 | 60 | 30 | 250 | 250 | 74 |
| Ex. 118 | 10 | 60 | 30 | 250 | 250 | 75 |
| Ex. 119 | 10 | 60 | 30 | 250 | 250 | 76 |
| Ex. 120 | 10 | 60 | 30 | 250 | 250 | 73 |
| Ex. 121 | 10 | 60 | 30 | 250 | 250 | 74 |
| Ex. 122 | 10 | 60 | 30 | 250 | 250 | 72 |
| Ex. 123 | 10 | 60 | 30 | 250 | 250 | 74 |
| Ex. 124 | 10 | 60 | 30 | 250 | 250 | 75 |
| Ex. 125 | 10 | 60 | 30 | 250 | 250 | 76 |
| Ex. 126 | 10 | 60 | 30 | 250 | 250 | 74 |
| Ex. 127 | 10 | 60 | 30 | 250 | 250 | 74 |
| Ex. 128 | 10 | 60 | 30 | 250 | 250 | 77 |

TABLE 37

| | Reactor | Starting material to produce carbamate | | Starting material to conduct thermal decomposition and resultant isocyanate | | | |
|---|---|---|---|---|---|---|---|
| | | Amino acid, amino acid derivative | Alkanol amine, Alcohol | Carbamate | Resultant isocyanate | Low-boiling solvent | High-boiling solvent |
| Ex. 129 | FIG. 2 | Lysine | EtOH | *structure* | *structure* | ODB | TPA |
| Ex. 130 | FIG. 2 | Lysine | 1-amino-2-PrOH | *structure* | *structure* | ODB | TPA |
| Ex. 131 | FIG. 2 | Lysine | 2-amino-1-BuOH | *structure* | *structure* | ODB | TPA |
| Ex. 132 | FIG. 2 | Lysine | Glycerin | *structure* | *structure* | ODB | TPA |

TABLE 37-continued

| | Starting material to produce carbamate | | Starting material to conduct thermal decomposition and resultant isocyanate | | | |
|---|---|---|---|---|---|---|
| Reactor | Amino acid, amino acid derivative | Alkanol amine, Alcohol | Carbamate | Resultant isocyanate | Low-boiling solvent | High-boiling solvent |
| Ex. 133 | FIG. 2 / Lysine | Penta-erythritol | (structure shown) | (structure shown) | ODB | TPA |

TABLE 38

| | Starting material to produce carbamate | | Starting material to conduct thermal decomposition and resultant isocyanate | | | |
|---|---|---|---|---|---|---|
| Reactor | Amino acid, amino acid derivative | Alkanol amine, Alcohol | Carbamate | Resultant isocynate | Low-boiling solvent | High-boiling solvent |
| Ex. 134 | FIG. 2 / Ornithine | EtOH | (structure shown) | (structure shown) | ODB | TPA |
| Ex. 135 | FIG. 2 / Ornithine | 1-amino-2-PrOH | (structure shown) | (structure shown) | ODB | TPA |

TABLE 38-continued

| Reactor | Starting material to produce carbamate | | Starting material to conduct thermal decomposition and resultant isocyanate | | Low-boiling solvent | High-boiling solvent |
|---|---|---|---|---|---|---|
| | Amino acid, amino acid derivative | Alkanol amine, Alcohol | Carbamate | Resultant isocynate | | |
| Ex. 136 | FIG. 2 Ornithine | 2-amino-1-BuOH | [structure] | [structure] | ODB | TPA |
| Ex. 137 | FIG. 2 Ornithine | Glycerin | [structure] | [structure] | ODB | TPA |
| Ex. 138 | FIG. 2 Ornithine | Pentaerythritol | [structure] | [structure] | ODB | TPA |
| Ex. 139 | FIG. 2 Methionine | EtOH | [structure] | [structure] | ODB | TPA |
| Ex. 140 | FIG. 2 Methionine | 1-amino-2-PrOH | [structure] | [structure] | ODB | TPA |
| Ex. 141 | FIG. 2 Methionine | 2-amino-1-BuOH | [structure] | [structure] | ODB | TPA |

TABLE 39

| | Starting material to produce carbamate | | Starting material to conduct thermal decomposition and resultant isocyanate | | | |
|---|---|---|---|---|---|---|
| Reactor | Amino acid, amino acid derivative | Alkanol amine, Alcohol | Carbamate | Resultant isocynate | Low-boiling solvent | High-boiling solvent |
| Ex. 142 / FIG. 2 | Methionine | Glycerin | | | ODB | TPA |
| Ex. 143 / FIG. 2 | Methionine | Pentaerythritol | | | ODB | TPA |
| Ex. 144 / FIG. 2 | Glutamic acid | EtOH | | | ODB | TPA |
| Ex. 145 / FIG. 2 | Glutamic acid | 1-amino-2-PrOH | | | ODB | TPA |
| Ex. 146 / FIG. 2 | Glutamic acid | 2-amino-1-BuOH | | | ODB | TPA |

TABLE 39-continued

| Reactor | Starting material to produce carbamate | | Starting material to conduct thermal decomposition and resultant isocyanate | | Low-boiling solvent | High-boiling solvent |
|---|---|---|---|---|---|---|
| | Amino acid, amino acid derivative | Alkanol amine, Alcohol | Carbamate | Resultant isocynate | | |
| Ex. 147 | FIG. 2 Glutamic acid | Glyceryn | 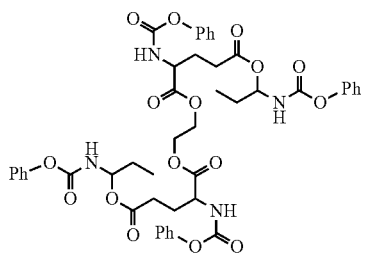 [SMILES: CCC(NC(=O)Oc1ccccc1)OC(=O)CCC(NC(=O)Oc1ccccc1)C(=O)OCCOC(=O)C(CCC(=O)OC(CC)NC(=O)Oc1ccccc1)NC(=O)Oc1ccccc1] | 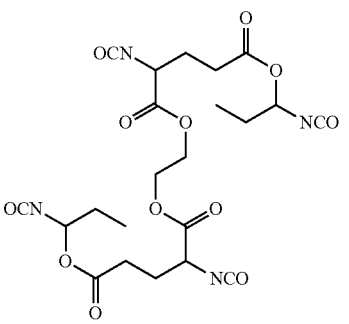 | ODB | TPA |

TABLE 40

| Reactor | Starting material to produce carbamate | | Starting material to conduct thermal decomposition and resultant isocyanate | | Low-boiling solvent | High-boiling solvent |
|---|---|---|---|---|---|---|
| | Amino acid, amino acid derivative | Alkanol amine, Alcohol | Carbamate | Resultant isocynate | | |
| Ex. 148 | FIG. 2 Glutamic acid | Pentaerythritol | 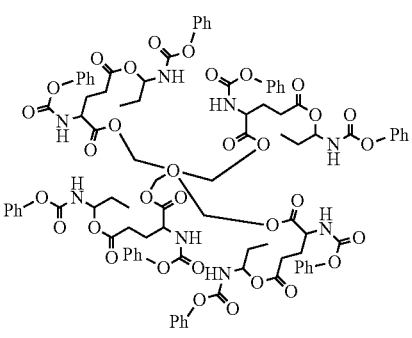 | | ODB | TPA |
| Ex. 149 | FIG. 2 Lysine | Monoethanol amine | 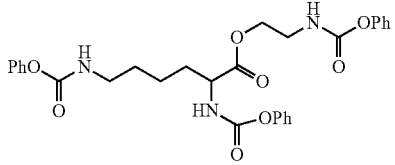 [SMILES: O=C(NCCCCC(NC(=O)Oc1ccccc1)C(=O)OCCNC(=O)Oc1ccccc1)Oc1ccccc1] | | ODB | TKA-100 |
| Ex. 150 | FIG. 2 Lysine | Monoethanol amine | 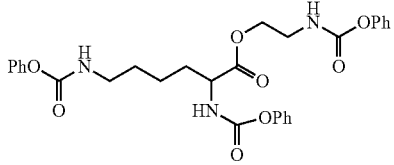 [SMILES: O=C(NCCCCC(NC(=O)Oc1ccccc1)C(=O)OCCNC(=O)Oc1ccccc1)Oc1ccccc1] | | ODB | 24A-100 |

TABLE 40-continued

| Reactor | Starting material to produce carbamate | | Starting material to conduct thermal decomposition and resultant isocyanate | | Low-boiling solvent | High-boiling solvent |
| --- | --- | --- | --- | --- | --- | --- |
| | Amino acid, amino acid derivative | Alkanol amine, Alcohol | Carbamate | Resultant isocynate | | |
| Ex. 151 | FIG. 2 | Lysine | Monoethanol amine | [structure] | [structure] | ODB | TLA-100 |
| Ex. 152 | FIG. 2 | Ornithine | Monoethanol amine | [structure] | [structure] | ODB | TKA-100 |
| Ex. 153 | FIG. 2 | Ornithine | Monoethanol amine | [structure] | [structure] | ODB | 24A-100 |
| Ex. 154 | FIG. 2 | Ornithine | Monoethanol amine | [structure] | [structure] | ODB | TLA-100 |

TABLE 41

| Reactor | Starting material to produce carbamate | | Starting material to conduct thermal decomposition and resultant isocyanate | | Low-boiling solvent | High-boiling solvent |
| --- | --- | --- | --- | --- | --- | --- |
| | Amino acid, amino acid derivative | Alkanol amine | Carbamate | Resultant isocynate | | |
| Ex. 155 | FIG. 2 | Methionine | Monoethanol amine | [structure] | [structure] | ODB | TKA-100 |

TABLE 41-continued

| | | Starting material to produce carbamate | | Starting material to conduct thermal decomposition and resultant isocyanate | | | |
|---|---|---|---|---|---|---|---|
| | Reactor | Amino acid, amino acid derivative | Alkanol amine | Carbamate | Resultant isocynate | Low-boiling solvent | High-boiling solvent |
| Ex. 156 | FIG. 2 | Methionine | Monoethanol amine | *(structure)* | *(structure)* | ODB | 24A-100 |
| Ex. 157 | FIG. 2 | Methionine | Monoethanol amine | *(structure)* | *(structure)* | ODB | TLA-100 |
| Ex. 158 | FIG. 2 | Glutamic acid | Monoethanol amine | *(structure)* | *(structure)* | ODB | TKA-100 |
| Ex. 159 | FIG. 2 | Glutamic acid | Monoethanol amine | *(structure)* | *(structure)* | ODB | 24A-100 |
| Ex. 160 | FIG. 2 | Glutamic acid | Monoethanol amine | *(structure)* | *(structure)* | ODB | TLA-100 |

TABLE 42

|  | Formulation of starting material mixture (% by mass) | | | Temperature Condition (° C.) | | Thermal decomposition yield (%) |
|---|---|---|---|---|---|---|
|  | Conc. of carbamate | Conc. of low-boiling solvent | Conc. of high-boiling solvent | Temperature at first reactor | Temperature at second reactor |  |
| Ex. 129 | 10 | 60 | 30 | 250 | 250 | 80 |
| Ex. 130 | 10 | 60 | 30 | 250 | 250 | 76 |
| Ex. 131 | 10 | 60 | 30 | 250 | 250 | 78 |
| Ex. 132 | 10 | 60 | 30 | 250 | 250 | 74 |
| Ex. 133 | 10 | 60 | 30 | 250 | 250 | 76 |
| Ex. 134 | 10 | 60 | 30 | 250 | 250 | 79 |
| Ex. 135 | 10 | 60 | 30 | 250 | 250 | 80 |
| Ex. 136 | 10 | 60 | 30 | 250 | 250 | 76 |
| Ex. 137 | 10 | 60 | 30 | 250 | 250 | 74 |
| Ex. 138 | 10 | 60 | 30 | 250 | 250 | 75 |
| Ex. 139 | 10 | 60 | 30 | 250 | 250 | 74 |
| Ex. 140 | 10 | 60 | 30 | 250 | 250 | 76 |
| Ex. 141 | 10 | 60 | 30 | 250 | 250 | 74 |
| Ex. 142 | 10 | 60 | 30 | 250 | 250 | 74 |
| Ex. 143 | 10 | 60 | 30 | 250 | 250 | 72 |
| Ex. 144 | 10 | 60 | 30 | 250 | 250 | 73 |
| Ex. 145 | 10 | 60 | 30 | 250 | 250 | 71 |
| Ex. 146 | 10 | 60 | 30 | 250 | 250 | 76 |
| Ex. 147 | 10 | 60 | 30 | 250 | 250 | 74 |
| Ex. 148 | 10 | 60 | 30 | 250 | 250 | 76 |
| Ex. 149 | 10 | 60 | 30 | 250 | 250 | 74 |
| Ex. 150 | 10 | 60 | 30 | 250 | 250 | 76 |
| Ex. 151 | 10 | 60 | 30 | 250 | 250 | 75 |
| Ex. 152 | 10 | 60 | 30 | 250 | 250 | 77 |
| Ex. 153 | 10 | 60 | 30 | 250 | 250 | 76 |
| Ex. 154 | 10 | 60 | 30 | 250 | 250 | 74 |
| Ex. 155 | 10 | 60 | 30 | 250 | 250 | 73 |
| Ex. 156 | 10 | 60 | 30 | 250 | 250 | 75 |
| Ex. 157 | 10 | 60 | 30 | 250 | 250 | 74 |
| Ex. 158 | 10 | 60 | 30 | 250 | 250 | 76 |
| Ex. 159 | 10 | 60 | 30 | 250 | 250 | 74 |
| Ex. 160 | 10 | 60 | 30 | 250 | 250 | 77 |

Example 161

The below-mentioned step was conducted instead of the steps conducted after the preparation step in Example 81.
(Thermal Decomposition of Carbamate)

The mixture liquid obtained in the "step of preparing a mixture liquid" was introduced into a tenth storage tank 201. An ortho dichlorobenzene was introduced into a packed column 210, the temperature of a reboiler 206 was set at 200° C., and the ortho dichlorobenzene was circulated through a fifteenth line 25, a seventh solution-sending pump 208, and a sixteenth line. At the same time, the state in which the ortho dichlorobenzene was refluxed through a thirteenth line 23, a fourth partial condenser 205, a twelfth storage tank 203, an eighth solution-sending pump 209, and a fourteenth line 24, provided at the top of the packed column 210, was realized, while controlling the inner pressure of the packed column 210.

The mixture liquid was supplied to a falling-film type reactor 200 preheated at 250° C. from a tenth storage tank 201 through a tenth line 20 and a sixth solution-sending pump 207 at 500 g/hr to conduct thermal decomposition of N,N'-hexanediyl-bis-carbamic acid diphenyl ester. A gas containing a phenol and a hexamethylene diisocyanate, produced by the thermal decomposition, and the ortho dichlorobenzene, was supplied to the packed column 210 through a twelfth line 22. On the other hand, a polyisocyanate containing a by-product was collected in an eleventh storage tank 202 from the bottom of the falling-film type reactor 200 through the eleventh line 21. The gas component collected through the twelfth line 22 was subjected to separation by distillation in the packed column 210, and the mixture liquid containing the phenol and the ortho dichlorobenzene was collected in the twelfth storage tank 203 through the thirteenth line 23 and the fourth partial condenser 205. On the other hand, a mixture liquid containing the hexamethylene diisocyanate, the ortho dichlorobenzene, and a small amount of the polyisocyanate was collected in a thirteenth storage tank 204 through a seventeenth line 27. The yield of the hexamethylene diisocyanate collected in the thirteenth storage tank 204 was 88%. The operations could be conducted continuously for 200 hours.

Examples 162 to 171

The same procedures as those used in Example 161 were used except that the carbamate derivative used in Example 161 was replaced with each carbamate shown in the below tables to obtain isocyanates corresponding to the starting carbamate derivatives. When the decomposition reaction was conducted for 200 hours continuously, no adhesion of polymeric by-products was confirmed inside the reactor, and the isocyanates corresponding to the starting materials were obtained stably.

Examples 172-208

The same procedures as those used in Example 161 were used except that starting materials to produce carbamates and starting materials to conduct thermal decomposition reaction, shown in the below tables, were used to obtain isocyanates corresponding to the starting carbamate derivatives. When the decomposition reaction was conducted for 200 hours continuously, no adhesion of polymeric by-products was confirmed inside the reactor, and the isocyanates corresponding to the starting materials were obtained stably. In the case where an arginine was used, the arginine was hydrolyzed to an ornithine by a conventionally-known method. In the case where a glutamine or an asparagine was used, the glutamine or the asparagine was hydrolyzed to a glutamic acid or an asparagic acid, respectively, to be used.

Examples 209 to 228

The same procedures as those used in Example 172 were used except that starting materials to produce carbamates and starting materials to conduct thermal decomposition reaction, shown in the below tables, were used to obtain isocyanates corresponding to the starting carbamate derivatives. When the decomposition reaction was conducted for 200 hours continuously, no adhesion of polymeric by-products was confirmed inside the reactor, and the isocyanates corresponding to the starting materials were obtained stably.

Examples 229 to 240

The same procedures as those used in Example 172 were used except that each amino acids or amino acid derivatives shown in the below tables were introduced instead of an amino acid group of the lysine aminoethyl ester hydrochloride used in Example 172, or polyisocyanates shown in the below tables were used instead of the polyisocyanate used in the step of preparing a mixture solvent. As the polyisocyanates shown in the tables, polyisocyanates manufactured by Asahi Kasei Corporation, (trade name: DURANATE, grade: TKA-100, 24A-100, and TLA-100) were used.

Isocyanates corresponding to starting carbamate derivatives were obtained by the procedures. When the decomposition reaction was carried out continuously for 200 hours, no adhesion of polymeric by-products was confirmed inside the reactor, and the isocyanates corresponding to the starting materials were obtained stably.

TABLE 43

Starting material to conduct thermal decomposition and resultant isocyanate

Figure 3:
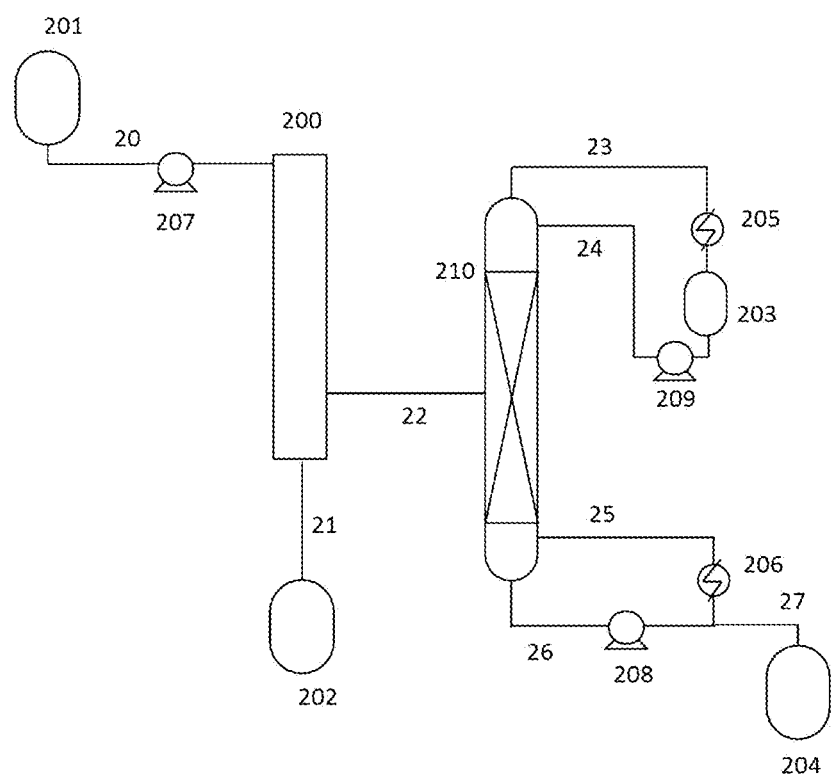

| Reactor | | Carbamate | Resultant isocynate | Low-boiling solvent | High-boiling solvent |
|---|---|---|---|---|---|
| Ex. 161 | FIG. 3 | [structure] | [structure] | ODB | TPA |
| Ex. 162 | FIG. 3 | [structure] | [structure] | ODB | TPA |
| Ex. 163 | FIG. 3 | [structure] | [structure] | ODB | TPA |
| Ex. 164 | FIG. 3 | [structure] | [structure] | ODB | TPA |
| Ex. 165 | FIG. 3 | [structure] | [structure] | ODB | TPA |
| Ex. 166 | FIG. 3 | [structure] | [structure] | ODB | TPA |

TABLE 43-continued

Starting material to conduct thermal decomposition and resultant isocyanate

| | Reactor | Carbamate | Resultant isocynate | Low-boiling solvent | High-boiling solvent |
|---|---|---|---|---|---|
| Ex. 167 | FIG. 3 | (carbamate structure) | (isocyanate structure) | ODB | TPA |
| Ex. 168 | FIG. 3 | (carbamate structure) | (isocyanate structure) | ODB | TPA |
| Ex. 169 | FIG. 3 | (carbamate structure) | (isocyanate structure) | ODB | TPA |

TABLE 44

| | | Starting material to produce carbamate | | Starting material to conduct thermal decomposition and resultant isocyanate | | | |
|---|---|---|---|---|---|---|---|
| | Reactor | Amino acid, amino acid derivative | Alkanol amine | Carbamate | Resultant isocynate | Low-boiling solvent | High-boiling solvent |
| Ex. 170 | FIG. 3 | — | — | (carbamate structure) | (isocyanate structure) | ODB | TPA |
| Ex. 171 | FIG. 3 | — | — | (carbamate structure) | (isocyanate structure) | ODB | TPA |
| Ex. 172 | FIG. 3 | Lysine | Monoethanolamine | (carbamate structure) | (isocyanate structure) | ODB | TPA |

TABLE 44-continued

| | | Starting material to produce carbamate | | Starting material to conduct thermal decomposition and resultant isocyanate | | | |
|---|---|---|---|---|---|---|---|
| Reactor | | Amino acid, amino acid derivative | Alkanol amine | Carbamate | Resultant isocynate | Low-boiling solvent | High-boiling solvent |
| Ex. 173 | FIG. 3 | Alanine | Monoethanolamine | (structure) | (structure) | ODB | TPA |
| Ex. 174 | FIG. 3 | Arginine | Monoethanolamine | (structure) | (structure) | ODB | TPA |
| Ex. 175 | FIG. 3 | Asparagine | Monoethanolamine | (structure) | (structure) | ODB | TPA |
| Ex. 176 | FIG. 3 | Glutamine | Monoethanolamine | (structure) | (structure) | ODB | TPA |

TABLE 45

| | | Starting material to produce carbamate | | Starting material to conduct thermal decomposition and resultant isocyanate | | | |
|---|---|---|---|---|---|---|---|
| Reactor | | Amino acid, amino acid derivative | Alkanol amine | Carbamate | Resultant isocynate | Low-boiling solvent | High-boiling solvent |
| Ex. 177 | FIG. 3 | Glycine | Monoethanolamine | (structure) | (structure) | ODB | TPA |

TABLE 45-continued

| | Starting material to produce carbamate | | Starting material to conduct thermal decomposition and resultant isocyanate | | | |
|---|---|---|---|---|---|---|
| Reactor | Amino acid, amino acid derivative | Alkanol amine | Carbamate | Resultant isocynate | Low-boiling solvent | High-boiling solvent |
| Ex. 178 FIG. 3 | Asparaginic acid | Monoethanol amine | | | ODB | TPA |
| Ex. 179 FIG. 3 | Glutamic acid | Monoethanol amine | | | ODB | TPA |
| Ex. 180 FIG. 3 | Histidine | Monoethanol amine | | | ODB | TPA |
| Ex. 181 FIG. 3 | Isoleucine | Monoethanol amine | | | ODB | TPA |
| Ex. 182 FIG. 3 | Leucine | Monoethanol amine | | | ODB | TPA |

TABLE 46

| | Reactor | Starting material to produce carbamate | | Starting material to conduct thermal decomposition and resultant isocyanate | | Low-boiling solvent | High-boiling solvent |
|---|---|---|---|---|---|---|---|
| | | Amino acid, amino acid derivative | Alkanol amine | Carbamate | Resultant isocynate | | |
| Ex. 183 | FIG. 3 | Methionine | Monoethanolamine | *(structure)* | *(structure)* | ODB | TPA |
| Ex. 184 | FIG. 3 | Phenylalanine | Monoethanolamine | *(structure)* | *(structure)* | ODB | TPA |
| Ex. 185 | FIG. 3 | Tryptophan | Monoethanolamine | *(structure)* | *(structure)* | ODB | TPA |
| Ex. 186 | FIG. 3 | Valine | Monoethanolamine | *(structure)* | *(structure)* | ODB | TPA |

TABLE 47

| | Formulation of starting material mixture (% by mass) | | | Temperature Condition (° C.) | | Thermal |
|---|---|---|---|---|---|---|
| | Conc. of carbamate | Conc. of low-boiling solvent | Conc. of high-boiling solvent | Temperature at first reactor | Temperature at second reactor | decomposition yield (%) |
| Ex. 161 | 10 | 60 | 30 | 250 | 250 | 85 |
| Ex. 162 | 10 | 60 | 30 | 250 | 250 | 86 |
| Ex. 163 | 10 | 60 | 30 | 250 | 250 | 84 |
| Ex. 164 | 10 | 60 | 30 | 250 | 250 | 86 |
| Ex. 165 | 10 | 60 | 30 | 250 | 250 | 84 |
| Ex. 166 | 10 | 60 | 30 | 250 | 250 | 84 |
| Ex. 167 | 10 | 60 | 30 | 250 | 250 | 85 |
| Ex. 168 | 10 | 60 | 30 | 250 | 250 | 86 |
| Ex. 169 | 10 | 60 | 30 | 250 | 250 | 84 |
| Ex. 170 | 10 | 60 | 30 | 250 | 250 | 82 |
| Ex. 171 | 10 | 60 | 30 | 250 | 250 | 83 |
| Ex. 172 | 10 | 60 | 30 | 250 | 250 | 82 |
| Ex. 173 | 10 | 60 | 30 | 250 | 250 | 81 |
| Ex. 174 | 10 | 60 | 30 | 250 | 250 | 83 |
| Ex. 175 | 10 | 60 | 30 | 250 | 250 | 82 |
| Ex. 176 | 10 | 60 | 30 | 250 | 250 | 81 |
| Ex. 177 | 10 | 60 | 30 | 250 | 250 | 84 |
| Ex. 178 | 10 | 60 | 30 | 250 | 250 | 83 |
| Ex. 179 | 10 | 60 | 30 | 250 | 250 | 86 |
| Ex. 180 | 10 | 60 | 30 | 250 | 250 | 82 |
| Ex. 181 | 10 | 60 | 30 | 250 | 250 | 81 |
| Ex. 182 | 10 | 60 | 30 | 250 | 250 | 82 |
| Ex. 183 | 10 | 60 | 30 | 250 | 250 | 84 |
| Ex. 184 | 10 | 60 | 30 | 250 | 250 | 84 |
| Ex. 185 | 10 | 60 | 30 | 250 | 250 | 85 |
| Ex. 186 | 10 | 50 | 30 | 250 | 250 | 86 |

TABLE 48

| | Reactor | Amino acid, amino acid derivative | Formula of Amino acid | X | Ra | Rb | Explanation of formula | Alkanol amine |
|---|---|---|---|---|---|---|---|---|
| Ex. 187 | FIG. 3 | Ornithine | H₂N-(CH₂)₃-CH(NH₂)-COOH | — | — | — | — | Monoethanolamine |
| Ex. 188 | FIG. 3 | Lysine derivative | [R$^a$-O-CO-(CH₂)₃-CH(NH₂)-CO-O-R$^b$]$_x$ | 1 | Me | Me | Ra and Rb each independently represents an aliphatic group, an aromatic group, or a hydrogen atom, X = 1-4 (excepting that Ra represents a hydrogen atom). When both Ra and Rb represent hydrogen atoms, X represens 1. | — |
| Ex. 189 | FIG. 3 | Lysine derivative | [R$^a$-O-CO-(CH₂)₃-CH(NH₂)-CO-O-R$^b$]$_x$ | 2 | —(CH2)2— | Me | Ra and Rb each independently represents an aliphatic group, an aromatic group, or a hydrogen atom, X = 1-4 (excepting that Ra represents a hydrogen atom). When both Ra and Rb represent hydrogen atoms, X represens 1. | — |

TABLE 48-continued

| Reactor | Amino acid, amino acid derivative | Formula of Amino acid | X | Ra | Rb | Explanation of formula | Alkanol amine |
|---|---|---|---|---|---|---|---|
| Ex. 190 | FIG. 3 | Glutamic acid derivative | (structure) | 1 | Me | Me | Ra and Rb each independently represents an aliphatic group, an aromatic group, or a hydrogen atom, X = 1-4 (excepting that Ra represents a hydrogen atom). When both Ra and Rb represent hydrogen atoms, X represens 1. | — |
| Ex. 191 | FIG. 3 | Methionine derivative | (structure) | 1 | Me | — | Ra and Rb each independently represents an aliphatic group, an aromatic group, or a hydrogen atom, X = 1-4 (excepting that Ra represents a hydrogen atom). When both Ra and Rb represent hydrogen atoms, X represens 1. | — |
| Ex. 192 | FIG. 3 | Glycine derivative | (structure) | 1 | Me | — | Ra and Rb each independently represents an aliphatic group, an aromatic group, or a hydrogen atom, X = 1-4 (excepting that Ra represents a hydrogen atom). When both Ra and Rb represent hydrogen atoms, X represens 1. | — |
| Ex. 193 | FIG. 3 | Phenyl alanine derivative | (structure) | 1 | Me | — | Ra and Rb each independently represents an aliphatic group, an aromatic group, or a hydrogen atom, X = 1-4 (excepting that Ra represents a hydrogen atom). When both Ra and Rb represent hydrogen atoms, X represens 1. | — |
| Ex. 194 | FIG. 3 | Asparagine derivative | (structure) | 1 | Me | H | Ra and Rb each independently represents an aliphatic group, an aromatic group, or a hydrogen atom, X = 1-4 (excepting that Ra represents a hydrogen atom). When both Ra and Rb represent hydrogen atoms, X represens 1. | — |
| Ex. 195 | FIG. 3 | Alanine derivative | (structure) | 1 | Me | — | Ra and Rb each independently represents an aliphatic group, an aromatic group, or a hydrogen atom, X = 1-4 (excepting that Ra represents a hydrogen atom). When both Ra and Rb represent hydrogen atoms, X represens 1. | — |

TABLE 49

| | Starting material to conduct thermal decomposition and resultant isocyanate | | Low-boiling solvent | High-boiling solvent |
|---|---|---|---|---|
| | Carbamate | Resultant isocynate | | |
| Ex. 187 | (structure) | (structure) | ODB | TPA |
| Ex. 188 | (structure) | (structure) | ODB | TPA |
| Ex. 189 | (structure) | (structure) | ODB | TPA |
| Ex. 190 | (structure) | (structure) | ODB | TPA |
| Ex. 191 | (structure) | (structure) | ODB | TPA |
| Ex. 192 | (structure) | (structure) | ODB | TPA |

TABLE 49-continued

Starting material to conduct thermal decomposition and resultant isocyanate

| | Carbamate | Resultant isocynate | Low-boiling solvent | High-boiling solvent |
|---|---|---|---|---|
| Ex. 193 | [Ph-O-C(=O)-NH-CH(CH₂Ph)-C(=O)-O-Rᵃ]ₓ | [OCN-CH(CH₂Ph)-C(=O)-O-Rᵃ]ₓ | ODB | TPA |
| Ex. 194 | [Rᵇ-O-C(=O)-CH₂-CH(NH-C(=O)-O-Ph)-C(=O)-O-Rᵃ]ₓ | [Rᵇ-O-C(=O)-CH₂-CH(NCO)-C(=O)-O-Rᵃ]ₓ | ODB | TPA |
| Ex. 195 | [Ph-O-C(=O)-NH-CH(CH₃)-C(=O)-O-Rᵃ]ₓ | [OCN-CH(CH₃)-C(=O)-O-Rᵃ]ₓ | ODB | TPA |

TABLE 50

| | Reactor | Amino acid, amino acid derivative | Formula of Amino acid | X | Ra | Rb | Explanation of formula |
|---|---|---|---|---|---|---|---|
| Ex. 196 | FIG. 3 | Leucine derivative | [H₂N-CH(CH₂CH(CH₃)₂)-C(=O)-O-Rᵃ]ₓ | 1 | Me | — | Ra and Rb each independently represents an aliphatic group, an aromatic group, or a hydrogen atom, X = 1-4 (excepting that Ra represents a hydrogen atom). When both Ra and Rb represent hydrogen atoms, X represens 1. |
| Ex. 197 | FIG. 3 | Iso-leucine derivative | [H₂N-CH(CH(CH₃)CH₂CH₃)-C(=O)-O-Rᵃ]ₓ | 1 | Me | — | Ra and Rb each independently represents an aliphatic group, an aromatic group, or a hydrogen atom, X = 1-4 (excepting that Ra represents a hydrogen atom). When both Ra and Rb represent hydrogen atoms, X represens 1. |
| Ex. 198 | FIG. 3 | Valine derivative | [H₂N-CH(CH(CH₃)₂)-C(=O)-O-Rᵃ]ₓ | 1 | Me | — | Ra and Rb each independently represents an aliphatic group, an aromatic group, or a hydrogen atom, X = 1-4 (excepting that Ra represents a hydrogen atom). When both Ra and Rb represent hydrogen atoms, X represens 1. |

TABLE 50-continued

| Reactor | Amino acid, amino acid derivative | Formula of Amino acid | X | Ra | Rb | Explanation of formula |
|---|---|---|---|---|---|---|
| Ex. 199 | FIG. 3 | Synthesized amino acid | 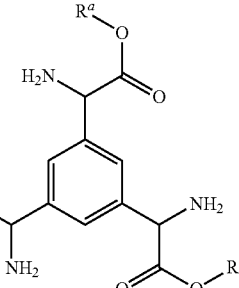 | — | Me | — | Ra and Rb each independently represents an aliphatic group, an aromatic group, or a hydrogen atom, X = 1-4 (excepting that Ra represents a hydrogen atom). When both Ra and Rb represent hydrogen atoms, X represens 1. |
| Ex. 200 | FIG. 3 | Synthesized amino acid | 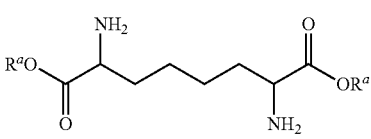 | — | Me | — | Ra and Rb each independently represents an aliphatic group, an aromatic group, or a hydrogen atom, X = 1-4 (excepting that Ra represents a hydrogen atom). When both Ra and Rb represent hydrogen atoms, X represens 1. |
| Ex. 201 | FIG. 3 | Synthesized amino acid | 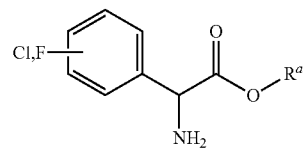 | — | Me | — | Ra and Rb each independently represents an aliphatic group, an aromatic group, or a hydrogen atom, X = 1-4 (excepting that Ra represents a hydrogen atom). When both Ra and Rb represent hydrogen atoms, X represens 1. |
| Ex. 202 | FIG. 3 | Synthesized amino acid | 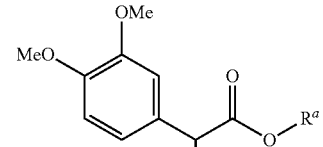 | — | Me | — | Ra and Rb each independently represents an aliphatic group, an aromatic group, or a hydrogen atom, X = 1-4 (excepting that Ra represents a hydrogen atom). When both Ra and Rb represent hydrogen atoms, X represens 1. |
| Ex. 203 | FIG. 3 | Synthesized amino acid | 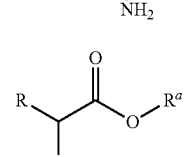 | — | Me | — | Ra and Rb each independently represents an aliphatic group, an aromatic group, or a hydrogen atom, X = 1-4 (excepting that Ra represents a hydrogen atom). When both Ra and Rb represent hydrogen atoms, X represens 1. |

TABLE 51

Starting material to conduct thermal decomposition and resultant isocyanate

| | Carbamate | Resultant isocynate | Low-boiling solvent | High-boiling solvent |
|---|---|---|---|---|
| Ex. 196 | | | ODB | TPA |

TABLE 51-continued

Starting material to conduct thermal decomposition and resultant isocyanate

| Carbamate | Resultant isocynate | Low-boiling solvent | High-boiling solvent |
|---|---|---|---|
| Ex. 197 | | ODB | TPA |
| Ex. 198 | | ODB | TPA |
| Ex. 199 | | ODB | TPA |
| Ex. 200 | | ODB | TPA |
| Ex. 201 | | ODB | TPA |
| Ex. 202 | | ODB | TPA |

TABLE 51-continued

Starting material to conduct thermal decomposition and resultant isocyanate

| | Carbamate | Resultant isocynate | Low-boiling solvent | High-boiling solvent |
|---|---|---|---|---|
| Ex. 203 | 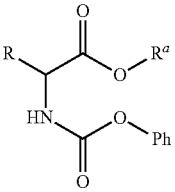 | 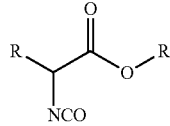 | ODB | TPA |

TABLE 52

| Reactor | Amino acid, amino acid derivative | Formula of Amino acid | X | Ra | Rb | Explanation of formula |
|---|---|---|---|---|---|---|
| Ex. 204 | FIG. 3 | Synthesized amino acid | 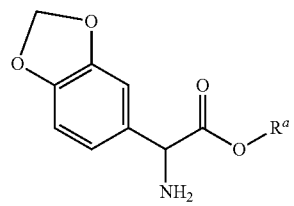 | — | Me | — | Ra and Rb each independently represents an aliphatic group, an aromatic group, or a hydrogen atom, X = 1-4 (excepting that Ra represents a hydrogen atom). When both Ra and Rb represent hydrogen atoms, X represens 1. |
| Ex. 205 | FIG. 3 | Synthesized amino acid | 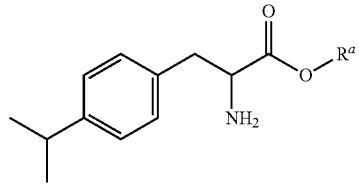 | — | Me | — | Ra and Rb each independently represents an aliphatic group, an aromatic group, or a hydrogen atom, X = 1-4 (excepting that Ra represents a hydrogen atom). When both Ra and Rb represent hydrogen atoms, X represens 1. |
| Ex. 206 | FIG. 3 | Synthesized amino acid | 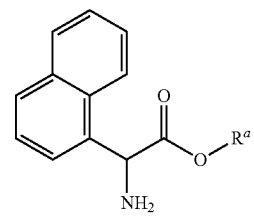 | — | Me | — | Ra and Rb each independently represents an aliphatic group, an aromatic group, or a hydrogen atom, X = 1-4 (excepting that Ra represents a hydrogen atom). When both Ra and Rb represent hydrogen atoms, X represens 1. |
| Ex. 207 | FIG. 3 | Synthesized amino acid | 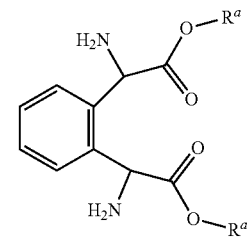 | — | Me | — | Ra and Rb each independently represents an aliphatic group, an aromatic group, or a hydrogen atom, X = 1-4 (excepting that Ra represents a hydrogen atom). When both Ra and Rb represent hydrogen atoms, X represens 1. |
| Ex. 208 | FIG. 3 | Synthesized amino acid | 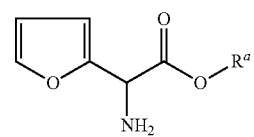 | — | Me | — | Ra and Rb each independently represents an aliphatic group, an aromatic group, or a hydrogen atom, X = 1-4 (excepting that Ra represents a hydrogen atom). When both Ra and Rb represent hydrogen atoms, X represens 1. |

TABLE 53

Starting material to conduct thermal decomposition and resultant isocyanate

| | Carbamate | Resultant isocynate | Low-boiling solvent | High-boiling solvent |
|---|---|---|---|---|
| Ex. 204 | benzo[d][1,3]dioxole with CH(NHC(O)OPh)C(O)O-$R^a$ | benzo[d][1,3]dioxole with CH(NCO)C(O)O-$R^a$ | ODB | TPA |
| Ex. 205 | 4-isopropylphenyl-CH$_2$-CH(NHC(O)OPh)C(O)O-$R^a$ | 4-isopropylphenyl-CH$_2$-CH(NCO)C(O)O-$R^a$ | ODB | TPA |
| Ex. 206 | naphthalen-1-yl-CH(NHC(O)OPh)C(O)O-$R^a$ | naphthalen-1-yl-CH(NCO)C(O)O-$R^a$ | ODB | TPA |
| Ex. 207 | 1,2-phenylene-bis[CH(NHC(O)OPh)C(O)O-$R^a$] | 1,2-phenylene-bis[CH(NCO)C(O)O-$R^a$] | ODB | TPA |
| Ex. 208 | furan-2-yl-CH(NHC(O)OPh)C(O)O-$R^a$ | furan-2-yl-CH(NCO)C(O)O-$R^a$ | ODB | TPA |

TABLE 54

| | Formulation of starting material mixture (% by mass) | | | Temperature Condition (° C.) | | Thermal decomposition yield (%) |
|---|---|---|---|---|---|---|
| | Conc. of carbamate | Conc. of low-boiling solvent | Conc. of high-boiling solvent | Temperature at first reactor | Temperature at second reactor | |
| Ex. 187 | 10 | 60 | 30 | 250 | 250 | 79 |
| Ex. 188 | 10 | 60 | 30 | 250 | 250 | 81 |
| Ex. 189 | 10 | 60 | 30 | 250 | 250 | 82 |
| Ex. 190 | 10 | 60 | 30 | 250 | 250 | 81 |
| Ex. 191 | 10 | 60 | 30 | 250 | 250 | 82 |
| Ex. 192 | 10 | 60 | 30 | 250 | 250 | 84 |
| Ex. 193 | 10 | 60 | 30 | 250 | 250 | 83 |
| Ex. 194 | 10 | 60 | 30 | 250 | 250 | 81 |
| Ex. 195 | 10 | 60 | 30 | 250 | 250 | 82 |
| Ex. 196 | 10 | 60 | 30 | 250 | 250 | 81 |
| Ex. 197 | 10 | 60 | 30 | 250 | 250 | 82 |
| Ex. 198 | 10 | 60 | 30 | 250 | 250 | 84 |
| Ex. 199 | 10 | 60 | 30 | 250 | 250 | 82 |
| Ex. 200 | 10 | 60 | 30 | 250 | 250 | 83 |
| Ex. 201 | 10 | 60 | 30 | 250 | 250 | 81 |
| Ex. 202 | 10 | 60 | 30 | 250 | 250 | 83 |
| Ex. 203 | 10 | 60 | 30 | 250 | 250 | 86 |
| Ex. 204 | 10 | 60 | 30 | 250 | 250 | 84 |
| Ex. 205 | 10 | 60 | 30 | 250 | 250 | 82 |
| Ex. 206 | 10 | 60 | 30 | 250 | 250 | 81 |
| Ex. 207 | 10 | 60 | 30 | 250 | 250 | 86 |
| Ex. 208 | 10 | 60 | 30 | 250 | 250 | 85 |

TABLE 55

| | | Starting material to produce carbamate | | Starting material to conduct thermal decomposition and resultant isocyanate | | | |
|---|---|---|---|---|---|---|---|
| | Reactor | Amino acid, amino acid derivative | Alkanol amine, Alcohol | Carbamate | Resultant isocynate | Low-boiling solvent | High-boiling solvent |
| Ex. 209 | FIG. 3 | Lysine | EtOH | 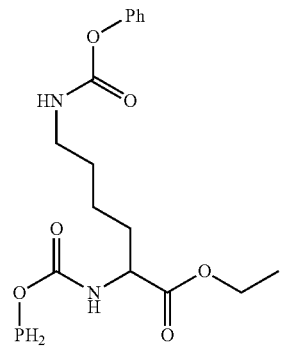 | 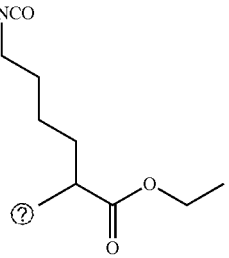 | ODB | TPA |

TABLE 55-continued

| | Starting material to produce carbamate | | Starting material to conduct thermal decomposition and resultant isocyanate | | | |
|---|---|---|---|---|---|---|
| Reactor | Amino acid, amino acid derivative | Alkanol amine, Alcohol | Carbamate | Resultant isocynate | Low-boiling solvent | High-boiling solvent |
| Ex. 210 | FIG. 3 Lysine | 1-amine-2-PrOH | 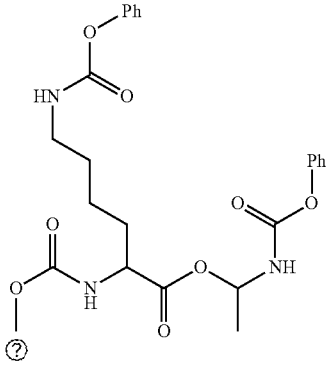 [SMILES: COC(=O)NC(CCCCNC(=O)Oc1ccccc1)C(=O)OC(C)NC(=O)Oc1ccccc1] | 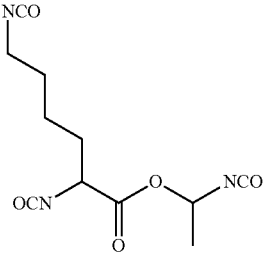 | ODB | TPA |
| Ex. 211 | FIG. 3 Lysine | 2-amino-1-BuOH | 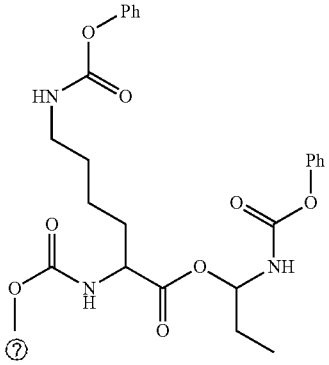 [SMILES: CCC(NC(=O)Oc1ccccc1)OC(=O)C(CCCCNC(=O)Oc1ccccc1)NC(=O)OC] | 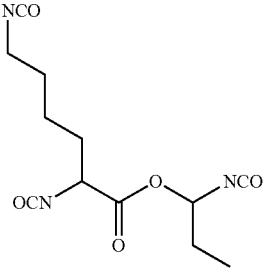 | ODB | TPA |
| Ex. 212 | FIG. 3 Lysine | Glycerin | 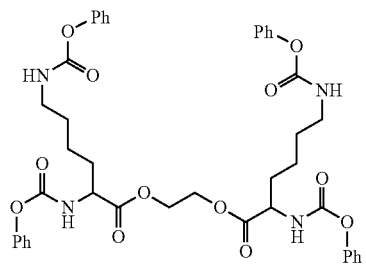 [SMILES: O=C(NCCCCC(NC(=O)Oc1ccccc1)C(=O)OCCOC(=O)C(CCCCNC(=O)Oc1ccccc1)NC(=O)Oc1ccccc1)Oc1ccccc1] | 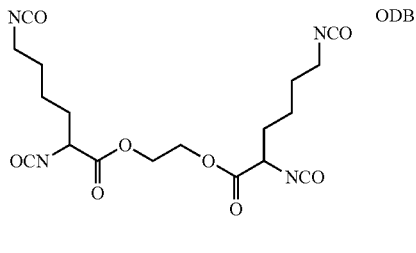 | ODB | TPA |

TABLE 55-continued
| Reactor | Starting material to produce carbamate | | Starting material to conduct thermal decomposition and resultant isocyanate | | Low-boiling solvent | High-boiling solvent |
|---|---|---|---|---|---|---|
| | Amino acid, amino acid derivative | Alkanol amine, Alcohol | Carbamate | Resultant isocynate | | |
| Ex. 213 | FIG. 3 Lysine | Pentaerythritol | 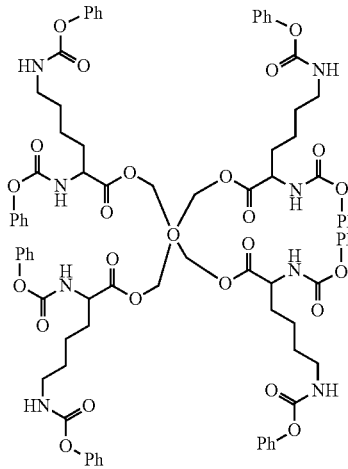 | 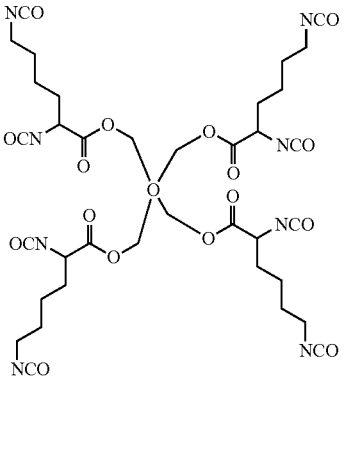 | ODB | TPA |

TABLE 56

| | Starting material to produce carbamate | | | Starting material to conduct thermal decomposition and resultant isocyanate | | | |
|---|---|---|---|---|---|---|---|
| | Amino acid, amino acid derivative | Alkanol amine, Alcohol | Reactor | Carbamate | Resultant isocyanate | Low-boiling solvent | High-boiling solvent |
| Ex. 214 | Ornithine | EtOH | FIG. 3 | (structure) | (structure) | ODB | TPA |
| Ex. 215 | Ornithine | 1-amino-2-PrOH | FIG. 3 | (structure) | (structure) | ODB | TPA |
| Ex. 216 | Ornithine | 2-amino-1-BuOH | FIG. 3 | (structure) | (structure) | ODB | TPA |

TABLE 56-continued

| | Starting material to produce carbamate | | Starting material to conduct thermal decomposition and resultant isocyanate | | |
|---|---|---|---|---|---|
| Reactor | Amino acid, amino acid derivative | Alkanol amine, Alcohol | Carbamate | Resultant isocyanate | Low-boiling solvent / High-boiling solvent |
| Ex. 217 FIG. 3 | Ornithine | Glycerin | (structure) | (structure) | ODB / TPA |
| Ex. 218 FIG. 3 | Ornithine | Pentaerythritol | (structure) | (structure) | ODB / TPA |

TABLE 57

| | Starting material to produce carbamate | | Starting material to conduct thermal decomposition and resultant isocyanate | | | |
|---|---|---|---|---|---|---|
| Re-actor | Amino acid, amino acid derivative | Alkanol amine, Alcohol | Carbamate | Resultant isocyanate | Low-boiling solvent | High-boiling solvent |
| Ex. 219 FIG. 3 | Methionine | EtOH | | | ODB | TPA |
| Ex. 220 FIG. 3 | Methionine | 1-amino-2-PrOH | | | ODB | TPA |
| Ex. 221 FIG. 3 | Methionine | 2-amino-1-BuOH | | | ODB | TPA |
| Ex. 222 FIG. 3 | Methionine | Glycerin | | | ODB | TPA |

TABLE 57-continued

Starting material to conduct thermal decomposition and resultant isocyanate

| Reactor | Starting material to produce carbamate | | Carbamate | Resultant isocyanate | Low-boiling solvent | High-boiling solvent |
|---|---|---|---|---|---|---|
| | Amino acid, amino acid derivative | Alkanol amine, Alcohol | | | | |
| Ex. 223 | FIG. 3 | Methionine | Pentaerythritol | (structure) | (structure) | ODB | TPA |
| Ex. 224 | FIG. 3 | Glutamic acid | EtOH | (structure) | (structure) | ODB | TPA |

TABLE 58

| | Starting material to produce carbamate | | Starting material to conduct thermal decomposition and resultant isocyanate | | | |
|---|---|---|---|---|---|---|
| Re-actor | Amino acid, amino acid derivative | Alkanol amine, Alcohol | Carbamate | Resultant isocyanate | Low-boiling solvent | High-boiling solvent |
| Ex. 225 FIG. 3 | Glutamic acid | 1-amino-2-PrOH | (structure) | (structure) | ODB | TPA |
| Ex. 226 FIG. 3 | Glutamic acid | 2-amino-1-BuOH | (structure) | (structure) | ODB | TPA |

TABLE 58-continued

Starting material to conduct thermal decomposition and resultant isocyanate

| Re-actor | | Starting material to produce carbamate | | Carbamate | Resultant isocyanate | Low-boiling solvent | High-boiling solvent |
|---|---|---|---|---|---|---|---|
| | | Amino acid, amino acid derivative | Alkanol amine, Alcohol | | | | |
| Ex. 227 | FIG. 3 | Glutamic acid | Glycerin | | | ODB | TPA |

TABLE 58-continued

Starting material to conduct thermal decomposition and resultant isocyanate

| Re-actor | Starting material to produce carbamate | | Carbamate | Resultant isocyanate | Low-boiling solvent | High-boiling solvent |
|---|---|---|---|---|---|---|
| | Amino acid, amino acid derivative | Alkanol amine, Alcohol | | | | |
| Ex. 228 FIG. 3 | Glutamic acid | Penta-erythritol | | | ODB | TPA |
| Ex. 229 FIG. 3 | Lysine | Mono-ethanol amine | | | ODB | TKA-100 |

TABLE 59

| | Starting material to produce carbamate | | Starting material to conduct thermal decomposition and resultant isocyanate | | | |
|---|---|---|---|---|---|---|
| Reactor | Amino acid, amino acid derivative | Alkanol amine, Alcohol | Carbamate | Resultant isocyanate | Low-boiling solvent | High-boiling solvent |
| Ex. 230 FIG. 3 | Lysine | Monoethanol amine | | | ODB | 24A-100 |
| Ex. 231 FIG. 3 | Lysine | Monoethanol amine | | | ODB | TLA-100 |
| Ex. 232 FIG. 3 | Ornithine | Monoethanol amine | | | ODB | TKA-100 |
| Ex. 233 FIG. 3 | Ornithine | Monoethanol amine | | | ODB | 24A-100 |

TABLE 59-continued

Starting material to conduct thermal decomposition and resultant isocyanate

| Reactor | Starting material to produce carbamate | | Carbamate | Resultant isocyanate | Low-boiling solvent | High-boiling solvent |
|---|---|---|---|---|---|---|
| | Amino acid, amino acid derivative | Alkanol amine, Alcohol | | | | |
| Ex. 234 FIG. 3 | Ornithine | Monoethanol amine | (carbamate structure) | (diisocyanate structure) | ODB | TLA-100 |
| Ex. 235 FIG. 3 | Methionine | Monoethanol amine | (carbamate structure) | (diisocyanate structure) | ODB | TKA-100 |

TABLE 60

| | Starting material to produce carbamate | | Starting material to conduct thermal decomposition and resultant isocyanate | | | |
|---|---|---|---|---|---|---|
| Reactor | Amino acid, amino acid derivative | Alkanol amine, Alcohol | Carbamate | Resultant isocyanate | Low-boiling solvent | High-boiling solvent |
| Ex. 236 FIG. 3 | Methionine | Monoethanol amine | | | ODB | 24A-100 |
| Ex. 237 FIG. 3 | Methionine | Monoethanol amine | | | ODB | TLA-100 |
| Ex. 238 FIG. 3 | Glutamic acid | Monoethanol amine | | | ODB | TKA-100 |

TABLE 60-continued

Starting material to conduct thermal decomposition and resultant isocyanate

| | Starting material to produce carbamate | | | | | |
|---|---|---|---|---|---|---|
| Reactor | Amino acid, amino acid derivative | Alkanol amine, Alcohol | Carbamate | Resultant isocyanate | Low-boiling solvent | High-boiling solvent |
| Ex. 239 | FIG. 3 | Glutamic acid | Monoethanol amine | [carbamate structure with Ph groups] | [isocyanate structure with NCO groups] | ODB | 24A-100 |
| Ex. 240 | FIG. 3 | Glutamic acid | Monoethanol amine | [carbamate structure with Ph groups] | [isocyanate structure with NCO groups] | ODB | TLA-100 |

TABLE 61

| | Formulation of starting material mixture (% by mass) | | | Temperature Condition (° C.) | | Thermal decomposition yield (%) |
| --- | --- | --- | --- | --- | --- | --- |
| | Conc. of carbamate | Conc. of low-boiling solvent | Conc. of high-boiling solvent | Temperature at first reactor | Temperature at second reactor | |
| Ex. 209 | 10 | 60 | 30 | 250 | 250 | 85 |
| Ex. 210 | 10 | 60 | 30 | 250 | 250 | 84 |
| Ex. 211 | 10 | 60 | 30 | 250 | 250 | 86 |
| Ex. 212 | 10 | 60 | 30 | 250 | 250 | 82 |
| Ex. 213 | 10 | 60 | 30 | 250 | 250 | 83 |
| Ex. 214 | 10 | 60 | 30 | 250 | 250 | 84 |
| Ex. 215 | 10 | 60 | 30 | 250 | 250 | 81 |
| Ex. 216 | 10 | 60 | 30 | 250 | 250 | 84 |
| Ex. 217 | 10 | 60 | 30 | 250 | 250 | 83 |
| Ex. 218 | 10 | 60 | 30 | 250 | 250 | 85 |
| Ex. 219 | 10 | 60 | 30 | 250 | 250 | 81 |
| Ex. 220 | 10 | 60 | 30 | 250 | 250 | 82 |
| Ex. 221 | 10 | 60 | 30 | 250 | 250 | 86 |
| Ex. 222 | 10 | 60 | 30 | 250 | 250 | 83 |
| Ex. 223 | 10 | 60 | 30 | 250 | 250 | 81 |
| Ex. 224 | 10 | 60 | 30 | 250 | 250 | 82 |
| Ex. 225 | 10 | 60 | 30 | 250 | 250 | 82 |
| Ex. 226 | 10 | 60 | 30 | 250 | 250 | 86 |
| Ex. 227 | 10 | 60 | 30 | 250 | 250 | 84 |
| Ex. 228 | 10 | 60 | 30 | 250 | 250 | 85 |
| Ex. 229 | 10 | 60 | 30 | 250 | 250 | 84 |
| Ex. 230 | 10 | 60 | 30 | 250 | 250 | 82 |
| Ex. 231 | 10 | 60 | 30 | 250 | 250 | 84 |
| Ex. 232 | 10 | 60 | 30 | 250 | 250 | 86 |
| Ex. 233 | 10 | 60 | 30 | 250 | 250 | 81 |
| Ex. 234 | 10 | 60 | 30 | 250 | 250 | 82 |
| Ex. 235 | 10 | 60 | 30 | 250 | 250 | 83 |
| Ex. 236 | 10 | 60 | 30 | 250 | 250 | 82 |
| Ex. 237 | 10 | 60 | 30 | 250 | 250 | 84 |
| Ex. 238 | 10 | 60 | 30 | 250 | 250 | 81 |
| Ex. 239 | 10 | 60 | 30 | 250 | 250 | 86 |
| Ex. 240 | 10 | 60 | 30 | 250 | 250 | 85 |

Comparative Example 1

The same procedures as those in Example 1 were conducted, except that the polyisocyanate used in Example 1 was not used. The state became approximately steady approximately 1 hour after the reaction was started. Approximately 5 hours thereafter, an ortho dichlorobenzene solution obtained from the bottom of the reaction tube was analyzed. As a result, it was confirmed that the reaction rate of the carbamate was 98%, but the selectivity of the hexamethylene diisocyanate was 62%, the content of polymeric by-products significantly increased, and the mass balance became unequilibrated, and therefore it was assumed that polymeric by-products adhered inside the reactor. Although the reaction was further continued for 3 hours, the mass balance became significantly unequilibrated, and therefore the reaction was disrupted, and the inside of the reaction tube was checked, and, as a result of which, it was confirmed that a large amount of polymeric substances were adhered to the bottom of the filler content, a support plate thereof, a liquid redistributor and an inner wall.

Comparative Example 2

The same procedures as those in Example 1 were conducted, except that β-phenethyl alcohol was used instead of the polyisocyanate used in Example 1. The state became approximately steady approximately 1 hour after the reaction was started. Approximately 5 hours thereafter, an ortho dichlorobenzene-β-phenethyl alcohol solution obtained from the bottom of the reaction tube was analyzed. As a result, it was confirmed that the reaction rate of the carbamate was 98%, but the selectivity of the hexamethylene diisocyanate was 64%, the content of polymeric by-products significantly increased, and the mass balance became unequilibrated, and therefore it was assumed that polymeric by-products adhered inside the reactor. Although the reaction was further continued for 2 hours, the mass balance became significantly unequilibrated, and therefore the reaction was disrupted, and the inside of the reaction tube was checked, and, as a result of which, it was confirmed that a large amount of polymeric substances were adhered to the bottom of the filler content, a support plate thereof, a liquid redistributor and an inner wall.

Comparative Example 3

The same procedures as those in Example 1 were conducted, except that phthalic acid was used instead of the polyisocyanate used in Example 1. The state became approximately steady approximately 1 hour after the reaction was started. Approximately 5 hours thereafter, an ortho dichlorobenzene-phthalic acid solution obtained from the bottom of the reaction tube was analyzed. As a result, it was confirmed that the reaction rate of the carbamate was 98%, but the selectivity of the hexamethylene diisocyanate was 54%, the content of polymeric by-products significantly increased, and the mass balance became unequilibrated, and therefore it was assumed that polymeric by-products adhered inside the reactor. Although the reaction was further continued for 2 hours, the mass balance became significantly unequilibrated, and therefore the reaction was disrupted, and the inside of the reaction tube was checked. As a result, it was confirmed that a large amount of polymeric substances were adhered to the bottom of the filler content, a support plate thereof, a liquid redistributor and an inner wall.

Comparative Example 4

The same procedures as those in Example 1 were conducted, except that flow passages between the tubular first reactor 2 and the partial condenser 4 were closed. Although the procedures were conducted for approximately 5 hours after the reaction started, the selectivity of the hexamethylene diisocyanate was 12%, and the reaction did not proceed efficiently. The content of polymeric by-products increased over time, the mass balance became unequilibrated, and therefore it was assumed that polymeric by-products adhered inside the reactor. Although the reaction was further continued for 4 hours, the mass balance became significantly unequilibrated, and therefore the reaction was disrupted, and the inside of the reaction tube was checked, and, as a result of which, it was confirmed that a large amount of polymeric substances were adhered to the bottom of the filler content, a support plate thereof, a liquid redistributor and an inner wall.

Comparative Example 5

The same procedures as those in Example 1 were conducted, except that an octylcarbamate synthesized by a conventionally-known method was used instead of the carbamate used in Example 1 and no polyisocyanate was used. The state became approximately steady approximately 1 hour after the reaction was started. Approximately 5 hours thereafter, an ortho dichlorobenzene solution obtained from the bottom of the reaction tube was analyzed. As a result, it was confirmed that the reaction rate of the carbamate was 98%, but the selectivity of the octylisocyanate was 50%, the content of polymeric by-products significantly increased, and the mass balance became unequilibrated, and therefore it was assumed that polymeric by-products adhered inside the reactor. Although the reaction was further continued for 5 hours, the mass balance became significantly unequilibrated, and therefore the reaction was disrupted, and the inside of the reaction tube was checked, and, as a result of which, it was confirmed that a large amount of polymeric substances were adhered to the bottom of the filler content, a support plate thereof, a liquid redistributor and an inner wall.

Comparative Example 6

The same procedures as those in Example 1 were conducted, except that an octylcarbamate synthesized by a conventionally-known method was used instead of the carbamate used in Example 1 and β-phenethyl alcohol was used instead of the polyisocyanate used in Example 1. The state became approximately steady approximately 5 hours after the reaction was started. Approximately 5 hours thereafter, an ortho dichlorobenzene-β-phenethyl alcohol solution obtained from the bottom of the reaction tube was analyzed. As a result, it was confirmed that the reaction rate of the carbamate was 98%, but the selectivity of the octylisocyanate was 52%, the content of polymeric by-products significantly increased, and the mass balance became unequilibrated, and therefore it was assumed that polymeric by-products adhered inside the reactor. Although the reaction was further continued for 5 hours, the mass balance became significantly unequilibrated, and therefore the reaction was disrupted, and the inside of the reaction tube was checked, and, as a result of which, it was confirmed that a large amount of polymeric substances were adhered to the bottom of the filler content, a support plate thereof, a liquid redistributor and an inner wall.

Comparative Example 7

The same procedures as those in Example 1 were conducted, except that an octylcarbamate synthesized by a conventionally-known method was used instead of the carbamate used in Example 1 and phthalic acid was used instead of the polyisocyanate used in Example 1. The state became approximately steady approximately 5 hours after the reaction was started. Approximately 5 hours thereafter, an ortho dichlorobenzene-phthalic acid solution obtained from the bottom of the reaction tube was analyzed. As a result, it was confirmed that the reaction rate of the carbamate was 98%, but the selectivity of the octylisocyanate was 42%, the content of polymeric by-products significantly increased, and the mass balance became unequilibrated, and therefore it was assumed that polymeric by-products adhered inside the reactor. Although the reaction was further continued for 5 hours, the mass balance became significantly unequilibrated, and therefore the reaction was disrupted, and the inside of the reaction tube was checked, and, as a result of which, it was confirmed that a large amount of polymeric substances were adhered to the bottom of the filler content, a support plate thereof, a liquid redistributor and an inner wall.

TABLE 62

| | | Starting material to conduct thermal decomposition and resultant isocyanate | | | |
|---|---|---|---|---|---|
| Reactor | | Carbamate | Resultant isocyanate | Low-boiling solvent | High-boiling solvent |
| C. Ex. 1 | FIG. 1 | PhO-C(=O)-NH-(CH₂)₆-NH-C(=O)-OPh | OCN-(CH₂)₆-NCO | ODB | No addition |

TABLE 62-continued

Starting material to conduct thermal decomposition and resultant isocyanate

| Reactor | | Carbamate | Resultant isocyanate | Low-boiling solvent | High-boiling solvent |
|---|---|---|---|---|---|
| C. Ex. 2 | FIG. 1 | PhO-C(=O)-NH-(CH2)6-NH-C(=O)-OPh | OCN-(CH2)6-NCO | ODB | β-phenethyl alchol |
| C. Ex. 3 | FIG. 1 | PhO-C(=O)-NH-(CH2)6-NH-C(=O)-OPh | OCN-(CH2)6-NCO | ODB | Phtalic acid |
| C. Ex. 4 | FIG. 1 | PhO-C(=O)-NH-(CH2)6-NH-C(=O)-OPh | OCN-(CH2)6-NCO | ODB | TPA |
| C. Ex. 5 | FIG. 1 | C8H17-NH-C(=O)-OPh | C8H17-NCO | ODB | No addition |
| C. Ex. 6 | FIG. 1 | C8H17-NH-C(=O)-OPh | C8H17-NCO | ODB | β-phenethyl alchol |
| C. Ex. 7 | FIG. 1 | C8H17-NH-C(=O)-OPh | C8H17-NCO | ODB | Phtalic acid |

TABLE 63

| | Formulation of starting material mixture (% by mass) | | | Temperature Condition (° C.) | | Thermal decomposition yield (%) |
|---|---|---|---|---|---|---|
| | Conc. of carbamate | Conc. of low-boiling solvent | Conc. of high-boiling solvent | Temperature at first reactor | Temperature at second reactor | |
| C. Ex. 1 | 10 | 60 | 30 | 250 | 250 | 62 |
| C. Ex. 2 | 10 | 60 | 30 | 250 | 250 | 64 |
| C. Ex. 3 | 10 | 60 | 30 | 250 | 250 | 54 |
| C. Ex. 4 | 10 | 60 | 30 | 250 | 250 | 12 |
| C. Ex. 5 | 10 | 60 | 30 | 250 | 250 | 50 |
| C. Ex. 6 | 10 | 60 | 30 | 250 | 250 | 52 |
| C. Ex. 7 | 10 | 60 | 30 | 250 | 250 | 42 |

Reference Example 2

1000 g of hexamethylene diisocyanate was charged in a glass four-necked flask equipped with a thermometer, a stirrer, and a nitrogen-sealed tube, the air in the flask was replaced with nitrogen, and the mixture was heated at 70° C. while conducting stirring. A catalyst (tetramethylammonium hydroxide) was added gradually to the reaction liquid until the degree of conversion of the hexamethylene diisocyanate, determined by refractive-index measurement of the reaction liquid, became 20%. When the degree of conversion became 20%, 0.5 g of 85% phosphoric acid aqueous solution was added to the reaction liquid to terminate the reaction. The amount of the catalyst required to achieve the degree of conversion of 20% was 220 ppm by mass, relative to the hexamethylene diisocyanate used in the reaction.

After the reaction, the reaction liquid was subjected to filtration, and then unreacted hexamethylene diisocyanate was removed using falling-film distillation equipment at 160° C. (27 Pa) for the first time and at 150° C. (13 Pa) for the second time to obtain an isocyanurate compound that was a polymer of hexamethylene diisocyanates.

Reference Example 3

1000 g of toluene diisocyanate (isomer mixture) was charged in a glass four-necked flask equipped with a thermometer, a stirrer, and a nitrogen-sealed tube, the air in the flask was replaced with nitrogen, and the mixture was heated at 70° C. while conducting stirring. A catalyst (tetramethylammonium hydroxide) was added gradually to the reaction liquid until the degree of conversion of the toluene diisocyanate, determined by refractive-index measurement of the reaction liquid, became 20%. When the degree of conversion became 20%, 0.5 g of 85% phosphoric acid aqueous solution was added to the reaction liquid to terminate the reaction.

After the reaction, the reaction liquid was subjected to filtration, and then unreacted toluene diisocyanate was removed using falling-film distillation equipment at 160° C. (27 Pa) for the first time and at 150° C. (13 Pa) for the second time to obtain an isocyanurate compound that was a polymer of toluene diisocyanates.

Reference Example 4

1000 g of isophorone diisocyanate (isomer mixture) was charged in a glass four-necked flask equipped with a thermometer, a stirrer, and a nitrogen-sealed tube, the air in the flask was replaced with nitrogen, and the mixture was heated at 70° C. while conducting stirring. A catalyst (tetramethylammonium hydroxide) was added gradually to the reaction liquid until the degree of conversion of the isophorone diisocyanate, determined by refractive-index measurement of the reaction liquid, became 20%. When the degree of conversion became 20%, 0.5 g of 85% phosphoric acid aqueous solution was added to the reaction liquid to terminate the reaction.

After the reaction, the reaction liquid was subjected to filtration, and then unreacted isophorone diisocyanate was removed using falling-film distillation equipment at 180° C. (10 Pa) for the first time and at 170° C. (10 Pa) for the second time to obtain an isocyanurate compound that was a polymer of isophorone diisocyanates.

Examples 241 to 243

The same procedures as those used in Example 1 were used except that starting materials to produce carbamates and starting materials to conduct thermal decomposition reaction, shown in the below tables, were used to obtain isocyanates corresponding to the starting carbamate derivatives. Although the decomposition reaction was conducted for 200 hours continuously, no adhesion of polymeric by-products was confirmed inside the reactor, and the isocyanates corresponding to the starting materials were obtained stably.

Examples 244 to 245

The same procedures as those used in Example 81 were used except that starting materials to produce carbamates and starting materials to conduct thermal decomposition reaction, shown in the below tables, were used to obtain isocyanates corresponding to the starting carbamate derivatives. Although the decomposition reaction was conducted for 200 hours continuously, no adhesion of polymeric by-products was confirmed inside the reactor, and the isocyanates corresponding to the starting materials were obtained stably.

Examples 246 to 251

The same procedures as those used in Example 161 were used except that starting materials to produce carbamates and starting materials to conduct thermal decomposition reaction, shown in the below tables, were used to obtain isocyanates corresponding to the starting carbamate derivatives. Although the decomposition reaction was conducted for 200 hours continuously, no adhesion of polymeric by-products was confirmed inside the reactor, and the isocyanates corresponding to the starting materials were obtained stably.

TABLE 64

| Reactor | Starting material to conduct thermal decomposition and resultant isocyanate | | Low-boiling solvent | High-boiling solvent |
|---|---|---|---|---|
| | Carbamate | Resultant isocyanate | | |
| Ex. 241 FIG. 1 | PhO-CO-NH-(CH₂)₆-NH-CO-OPh | OCN-(CH₂)₆-NCO | n-dodecane | TPA |
| Ex. 242 FIG. 1 | BuO-CO-NH-(CH₂)₆-NH-CO-OBu | OCN-(CH₂)₆-NCO | Toluene | TPA |
| Ex. 243 FIG. 1 | 2,6-dimethylphenyl carbamate of IPDA | IPDI | n-pentadecane | Polyisocyanate compound of Ref. Ex. 4 |
| Ex. 244 FIG. 2 | Ethyl carbamate of 4,4'-MDA | 4,4'-MDI | Tributyl amine | Polyisocyanate compound of Ref. Ex. 3 |
| Ex. 245 FIG. 2 | Phenyl carbamate of H12MDA | H12MDI | Dibenzyl ehter | TPA |
| Ex. 246 FIG. 3 | Isoamyl carbamate of HDA | HDI | o-dichlorobenzene | Polyisocyanate compound of Ref. Ex. 2 |

TABLE 64-continued
Starting material to conduct thermal decomposition and resultant isocyanate
| Reactor | Carbamate | Resultant isocyanate | Low-boiling solvent | High-boiling solvent |
|---|---|---|---|---|
| Ex. 247 FIG. 3 | 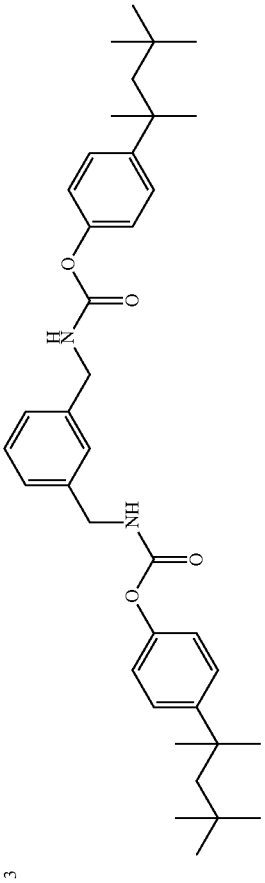 | 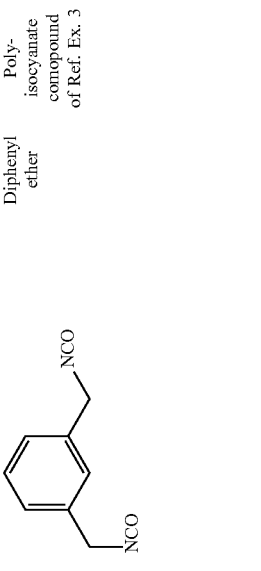 | Diphenyl ether | Polyisocyanate comopound of Ref. Ex. 3 |
| Ex. 248 FIG. 3 | 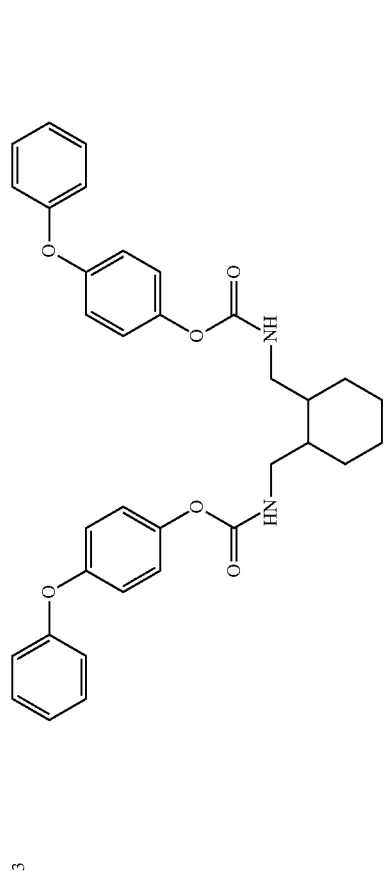 | 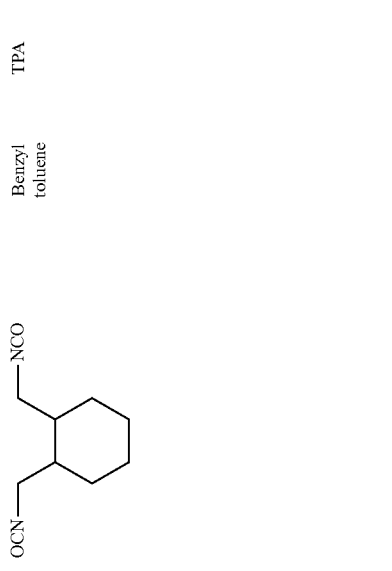 | Benzyl toluene | TPA |
| Ex. 249 FIG. 3 | 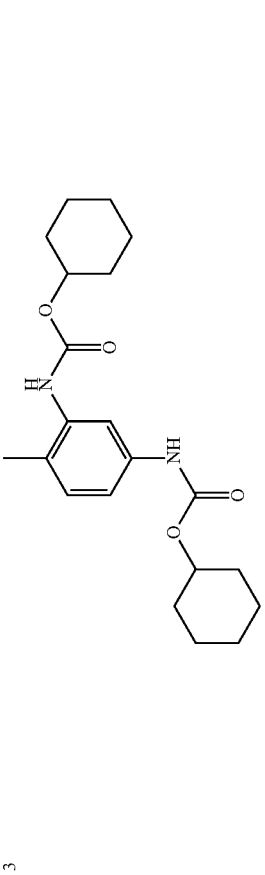 | 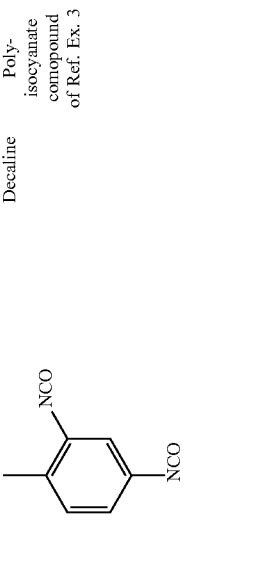 | Decaline | Polyisocyanate comopound of Ref. Ex. 3 |

TABLE 64-continued
Starting material to conduct thermal decomposition and resultant isocyanate
| Reactor | Carbamate | Resultant isocyanate | Low-boiling solvent | High-boiling solvent |
|---|---|---|---|---|
| Ex. 250 FIG. 3 | 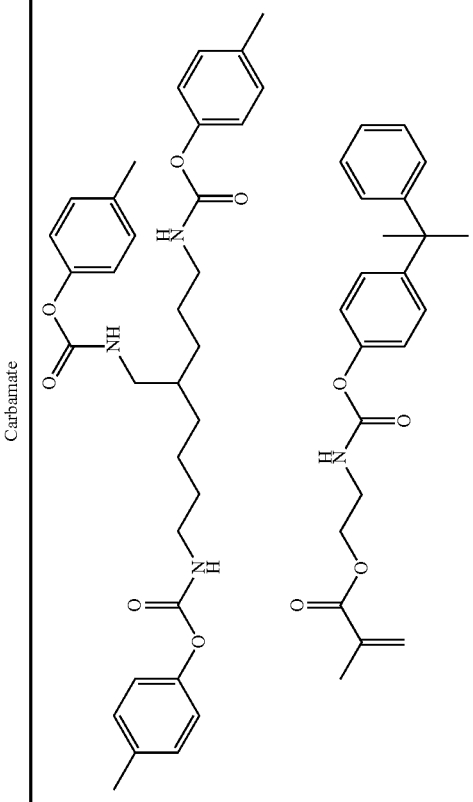 | 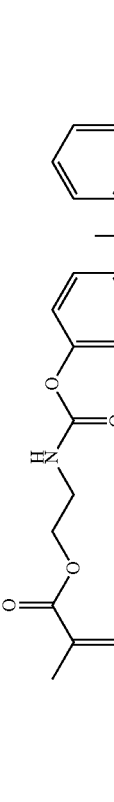 | Trichlorobenzene | Polyisocyanate comopound of Ref. Ex. 2 |
| Ex. 251 FIG. 3 | 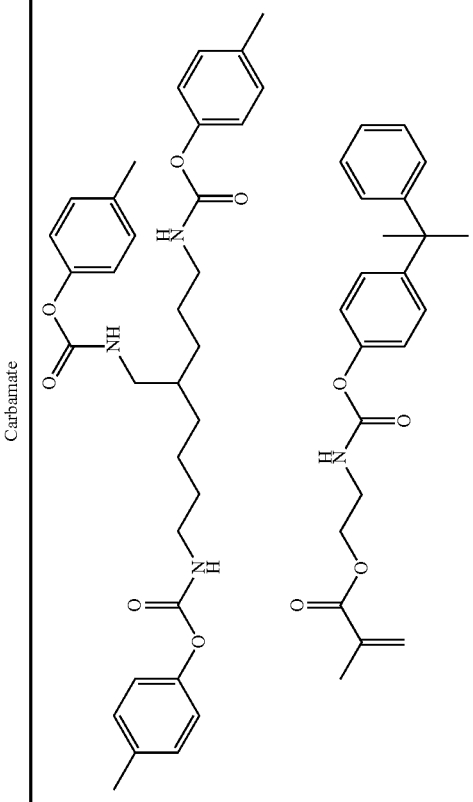 | 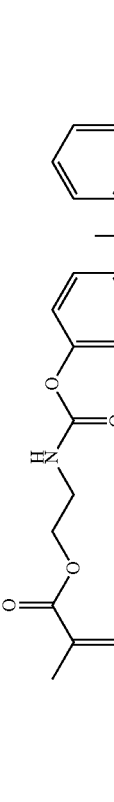 | 1-chlorododecane | Polyisocyanate comopound of Ref. Ex. 3 |

TABLE 65

| | Formulation of starting material mixture (% by mass) | | | Temperature Condition (° C.) | | Thermal decomposition yield (%) |
|---|---|---|---|---|---|---|
| | Conc. of carbamate | Conc. of middle-boiling solvent | Conc. of high-boiling solvent | Temperature at first reactor | Temperature at second reactor | |
| Ex. 241 | 10 | 30 | 60 | 250 | 250 | 90 |
| Ex. 242 | 20 | 40 | 40 | 250 | 250 | 94 |
| Ex. 243 | 20 | 60 | 20 | 250 | 250 | 90 |
| Ex. 244 | 30 | 30 | 40 | 250 | 250 | 92 |
| Ex. 245 | 10 | 40 | 50 | 250 | 250 | 88 |
| Ex. 246 | 10 | 40 | 50 | 250 | 250 | 91 |
| Ex. 247 | 20 | 40 | 40 | 250 | 250 | 87 |
| Ex. 248 | 30 | 40 | 30 | 250 | 250 | 90 |
| Ex. 249 | 20 | 60 | 20 | 250 | 250 | 91 |
| Ex. 250 | 30 | 30 | 40 | 250 | 250 | 87 |
| Ex. 251 | 10 | 60 | 30 | 250 | 250 | 88 |

Examples 252 to 254, 261 to 267, 271 to 274, and 279 to 320

The same procedures as those used in Example 161 were used except that starting materials to produce carbamates and starting materials to conduct thermal decomposition reaction, shown in the below tables, were used to obtain isocyanates corresponding to the starting carbamate derivatives. Although the decomposition reaction was conducted for 200 hours continuously, no adhesion of polymeric by-products was confirmed inside the reactor, and the isocyanates corresponding to the starting materials were obtained stably.

Examples 255 to 257, 268 to 270, and 275 to 278

The same procedures as those used in Example 12 were used except that starting materials to produce carbamates and starting materials to conduct thermal decomposition reaction, shown in the below tables, were used to obtain isocyanates corresponding to the starting carbamate derivatives. Although the decomposition reaction was conducted for 200 hours continuously, no adhesion of polymeric by-products was confirmed inside the reactor, and the isocyanates corresponding to the starting materials were obtained stably.

Examples 258 to 260

The same procedures as those used in Example 81 were used except that starting materials to produce carbamates and starting materials to conduct thermal decomposition reaction, shown in the below tables, were used to obtain isocyanates corresponding to the starting carbamate derivatives. Although the decomposition reaction was conducted for 200 hours continuously, no adhesion of polymeric by-products was confirmed inside the reactor, and the isocyanates corresponding to the starting materials were obtained stably.

TABLE 66

| | | Starting material to conduct thermal decomposition and resultant isocyanate | | |
|---|---|---|---|---|
| | Reactor | Amino acid, amino acid derivative | Formula of amino acid | Alkanol amine, or alcohol |
| Ex. 252 | FIG. 3 | Lysine | $H_2N$-(CH$_2$)$_4$-CH(NH$_2$)-COOH | $HO$-CH$_2$CH$_2$-$NH_2$ |
| Ex. 253 | FIG. 3 | Alanine | $H_2N$-CH(CH$_3$)-COOH | $HO$-CH(CH$_3$)-CH$_2$-$NH_2$ |

TABLE 66-continued
Starting material to conduct thermal decomposition and resultant isocyanate
| | Reactor | Amino acid, amino acid derivative | Formula of amino acid | Alkanol amine, or alcohol |
|---|---|---|---|---|
| Ex. 254 | FIG. 3 | Glycine | 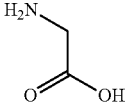 | $CH_3$—OH |
| Ex. 255 | FIG. 1 | Iso-leucine | 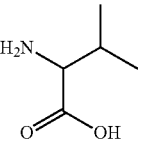 | $CH_3$—OH |
| Ex. 256 | FIG. 1 | Glutamic acid | 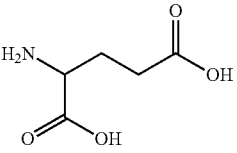 | HO~~~NH$_2$ |
| Ex. 257 | FIG. 1 | Glycine | 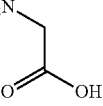 | HO~~~NH$_2$ |

TABLE 67

| | Starting material to conduct thermal decomposition and resultant isocyanate | | Low-boiling solvent | High-boiling solvent |
|---|---|---|---|---|
| | Carbamate | Resultant isocyanate | | |
| Ex. 252 | [structure] | [structure] | Fluorene | Polyisocyanate comopound of Ref. Ex. 3 |
| Ex. 253 | [structure] | [structure] | 1,3,5-triethyl benzene | TPA |
| Ex. 254 | [structure] | [structure] | n-dodecane | TPA |
| Ex. 255 | [structure] | [structure] | Benzyl toluene | Polyisocyanate comopound of Ref. Ex. 2 |

TABLE 67-continued

Starting material to conduct thermal decomposition and resultant isocyanate

| | Carbamate | Resultant isocyanate | Low-boiling solvent | High-boiling solvent |
|---|---|---|---|---|
| Ex. 256 | (carbamate structure with two phenyl carbamate groups linked via ester) | (diisocyanate structure) | Diphenyl ethane | Polyisocyanate compound of Ref. Ex. 3 |
| Ex. 257 | (phenyl carbamate-glycinate-ethyl phenyl carbamate structure) | OCN–CH$_2$–C(=O)–O–CH$_2$CH$_2$–NCO | Dibutyl cellosolve | TPA |

TABLE 68

Starting material to conduct thermal decomposition and resultant isocyanate

| Reactor | | Amino acid, amino acid derivative | Formula of amino acid | Alkanol amine, or alcohol |
|---|---|---|---|---|
| Ex. 258 | FIG. 2 | Asparaginic acid | H₂N-CH(CH₂COOH)-COOH (structure) | HO-CH₂CH₂-NH₂ |
| Ex. 259 | FIG. 2 | Glutamic acid | H₂N-CH(CH₂COOH)-COOH (structure) | C₄H₉—OH |
| Ex. 260 | FIG. 2 | Histidine | histidine structure | HO-CH₂CH₂-NH₂ |
| Ex. 261 | FIG. 3 | Iso-leocine | isoleucine structure | HO-C(CH₃)₂-CH₂CH₂CH₂-CH(CH₃)-NH₂ |
| Ex. 262 | FIG. 3 | Leucine | leucine structure | HO-CH₂CH₂-NH₂ |

Starting material to conduct thermal decomposition and resultant isocyanate

| | Carbamate | Resultant isocyanate | Low-boiling solvent | High-boiling solvent |
|---|---|---|---|---|
| Ex. 258 | (carbamate structure with three PhOC(O)NH groups) | (triisocyanate structure with three NCO groups) | Hexyl benzene | Poly-isocyanate compoound of Ref. Ex. 4 |
| Ex. 259 | (phenoxycarbonyl glutamic acid dibutyl ester structure) | (isocyanato glutaric acid dibutyl ester structure) | Decamethyl tetrasiloxane | Poly-isocyanate comopound of Ref. Ex. 2 |

-continued

| | Starting material to conduct thermal decomposition and resultant isocyanate | | Low-boiling solvent | High-boiling solvent |
|---|---|---|---|---|
| | Carbamate | Resultant isocyanate | | |
| Ex. 260 | [structure: phenyl carbamate of histidine ethyl ester with phenyl carbamate on ethyl side chain] | [structure: isocyanate of histidine ethyl ester with NCO] | Triacetin | TPA |
| Ex. 261 | [structure: bis-phenyl carbamate derivative with branched alkyl chain] | [structure: bis-isocyanate with branched alkyl chain] | Decamethyl cyclopenta-siloxane | Poly-isocyanate comopound of Ref. Ex. 4 |
| Ex. 262 | [structure: phenyl carbamate of leucine ethyl ester with phenyl carbamate] | [structure: isocyanate of leucine ethyl ester with NCO] | Trichloro benzase | TPA |

| | Reactor | Starting material to conduct thermal decomposition and resultant isocyanate | | |
|---|---|---|---|---|
| | | Amino acid, amino acid derivative | Formula of amino acid | Alkanol amine, or alcohol |
| Ex. 263 | FIG. 3 | Methionine | [structure: H$_2$N-CH(CH$_2$CH$_2$SCH$_3$)-COOH] | [structure: HO-CH$_2$CH$_2$-NH$_2$] |

-continued

| | Reactor | Amino acid, amino acid derivative | Formula of amino acid | Alkanol amine, or alcohol |
|---|---|---|---|---|
| Ex. 264 | FIG. 3 | Phenyl alanine | H₂N–CH(CH₂Ph)–COOH | HO–CH₂CH₂–NH₂ |
| Ex. 265 | FIG. 3 | Triptophan | H₂N–CH(CH₂-indol-3-yl)–COOH | HO–CH₂CH₂–NH₂ |
| Ex. 266 | FIG. 3 | Valine | H₂N–CH(CH(CH₃)CH₂CH₃)–COOH | CH₃–OH |
| Ex. 267 | FIG. 3 | Ornithine | H₂N–(CH₂)₃–CH(NH₂)–COOH | HO–CH₂CH₂–NH₂ |

TABLE 71

Starting material to conduct thermal decomposition and resultant isocyanate

| | Carbamate | Resultant isocyanate | Low-boiling solvent | High-boiling solvent |
|---|---|---|---|---|
| Ex. 263 | (structure: phenyl carbamate of methionine-derived ethyl carbamate with methylthio group) | OCN–CH(CH₂CH₂SMe)–C(=O)–O–CH₂CH₂–NCO | Ethyl phenyl sulfide | Polyisocyanate comopound of Ref. Ex. 3 |
| Ex. 264 | (structure: 2,6-dimethylphenyl carbamate of phenylalanine-derived ethyl carbamate) | OCN–CH(CH₂Ph)–C(=O)–O–CH₂CH₂–NCO | Tetradecane | Polyisocyanate comopound of Ref. Ex. 2 |

TABLE 71-continued

Starting material to conduct thermal decomposition and resultant isocyanate

| | Carbamate | Resultant isocyanate | Low-boiling solvent | High-boiling solvent |
|---|---|---|---|---|
| Ex. 265 | (structure shown) | (structure shown) | Cyclododecane | Polyisocyanate compound of Ref. Ex. 3 |
| Ex. 266 | (structure shown) | (structure shown) | Triacetin | Polyisocyanate compound of Ref. Ex. 2 |
| Ex. 267 | (structure shown) | (structure shown) | Benzyl toluene | TPA |

TABLE 72

| | Formulation of starting material mixture (% by mass) | | | Temperature Condition (° C.) | | Thermal decomposition yield (%) |
|---|---|---|---|---|---|---|
| | Conc. of carbamate | Conc. of middle-boiling solvent | Conc. of high-boiling solvent | Temperature at first reactor | Temperature at second reactor | |
| Ex. 252 | 10 | 30 | 60 | 250 | 250 | 84 |
| Ex. 253 | 20 | 60 | 20 | 250 | 250 | 91 |
| Ex. 254 | 20 | 60 | 20 | 250 | 250 | 92 |
| Ex. 255 | 20 | 60 | 20 | 250 | 290 | 87 |
| Ex. 256 | 20 | 60 | 20 | 250 | 250 | 86 |
| Ex. 257 | 10 | 30 | 60 | 250 | 250 | 88 |
| Ex. 258 | 10 | 30 | 60 | 250 | 250 | 85 |
| Ex. 259 | 20 | 50 | 30 | 250 | 250 | 85 |
| Ex. 260 | 20 | 60 | 20 | 250 | 250 | 88 |
| Ex. 261 | 10 | 40 | 50 | 250 | 250 | 81 |
| Ex. 262 | 30 | 30 | 40 | 250 | 250 | 85 |
| Ex. 263 | 10 | 50 | 40 | 250 | 250 | 83 |
| Ex. 264 | 10 | 30 | 60 | 250 | 250 | 82 |
| Ex. 265 | 20 | 60 | 20 | 250 | 250 | 83 |
| Ex. 266 | 10 | 30 | 60 | 250 | 250 | 87 |
| Ex. 267 | 30 | 30 | 40 | 250 | 250 | 83 |

TABLE 73

| | | Starting material to produce carbamate | | | | |
|---|---|---|---|---|---|---|
| | Reactor | Amino acid, amino acid derivative | Formula of amino acid | x | Ra | Rb |
| Ex. 268 | FIG. 1 | Lysine derivative | $\left[\begin{array}{c}NH_2 \\ \vdots \\ H_2N \end{array} \diagdown O{-}R^a \right]_x$ | 1 | Me | — |
| Ex. 269 | FIG. 1 | Glutamic acid derivative | $\left[ R^a{-}O{-}C(=O){-}(CH_2)_2{-}CH(NH_2){-}C(=O){-}O{-}R^b \right]_x$ | 2 | —(CH2)2— | Me |
| Ex. 270 | FIG. 1 | Glutamic acid derivative | $\left[ R^a{-}O{-}C(=O){-}(CH_2)_2{-}CH(NH_2){-}C(=O){-}O{-}R^b \right]_x$ | 1 | Me | Me |

TABLE 73-continued

| | Reactor | Starting material to produce carbamate | | x | Ra | Rb |
| --- | --- | --- | --- | --- | --- | --- |
| | | Amino acid, amino acid derivative | Formula of amino acid | | | |
| Ex. 271 | FIG. 3 | Methionine derivative | [Methionine structure with H₂N, S, O, Rᵃ]ₓ | 1 | Me | — |
| Ex. 272 | FIG. 3 | Glycine derivative | [Glycine structure with H₂N, O, Rᵃ]ₓ | 1 | Me | — |
| Ex. 273 | FIG. 3 | Phenyl alanine derivative | [Phenylalanine structure with H₂N, O, Rᵃ]ₓ | 1 | Me | — |

TABLE 74

| | Starting material to conduct thermal decomposition and resultant isocyanate | | Low-boiling solvent | High-boiling solvent |
| --- | --- | --- | --- | --- |
| | Carbamate | Resultant isocyanate | | |
| Ex. 268 | [Lysine dicarbamate structure with Ph-O-C(=O)-NH groups]ₓ | [Lysine diisocyanate structure with NCO, OCN, Rᵃ]ₓ | Diphenyl ether | TPA |
| Ex. 269 | [Glutamic acid dicarbamate structure with Rᵃ, Ph-O-C(=O)-NH, Rᵇ]ₓ | [Glutamic acid diisocyanate structure with Rᵃ, OCN, Rᵇ]ₓ | Trichloro benzene | TPA |

TABLE 74-continued

Starting material to conduct thermal decomposition and resultant isocyanate

| | Carbamate | Resultant isocyanate | Low-boiling solvent | High-boiling solvent |
|---|---|---|---|---|
| Ex. 270 | Glutamate carbamate with Ph-O-C(=O)-NH- group and $R^a$, $R^b$ substituents | Corresponding isocyanate with OCN- group | Tributyl amine | Poly-isocyanate comopound of Ref. Ex. 2 |
| Ex. 271 | Methionine-derived carbamate with Ph-O-C(=O)-NH- group, methylthio side chain, and $R^a$ substituent | Corresponding isocyanate with OCN- group | Hexyl benzene | Poly-isocyanate comopound of Ref. Ex. 2 |
| Ex. 272 | Glycine-derived carbamate with Ph-O-C(=O)-NH- and $R^a$ substituent | Corresponding isocyanate with OCN- group | Triethyl benzene | Poly-isocyanate comopound of Ref. Ex. 3 |
| Ex. 273 | Phenylalanine-derived carbamate with Ph-O-C(=O)-NH- and $R^a$ substituent | Corresponding isocyanate with OCN- group | n-dodecane | Poly-isocyanate comopound of Ref. Ex. 2 |

TABLE 75

Starting material to produce carbamate

| | Reactor | Amino acid, amino acid derivative | Formula of amino acid | x | Ra | Rb |
|---|---|---|---|---|---|---|
| Ex. 274 | FIG. 3 | Asparagine derivative | Asparagine-derived structure with $R^b$, $R^a$, and H$_2$N- groups | 1 | Me | Me |
| Ex. 275 | FIG. 1 | Alanine derivative | Alanine-derived structure with H$_2$N- and $R^a$ group | 1 | Me | — |

TABLE 75-continued

| | | Starting material to produce carbamate | | | | |
|---|---|---|---|---|---|---|
| | Reactor | Amino acid, amino acid derivative | Formula of amino acid | x | Ra | Rb |
| Ex. 276 | FIG. 1 | Leucine derivative | [H$_2$N-CH(CH$_2$CH(CH$_3$)$_2$)-C(=O)-O-R$^a$]$_x$ | 1 | Me | — |
| Ex. 277 | FIG. 1 | Isoluecine derivative | [H$_2$N-CH(CH(CH$_3$)CH$_2$CH$_3$)-C(=O)-O-R$^a$]$_x$ | 1 | Me | — |
| Ex. 278 | FIG. 1 | Valine derivative | [H$_2$N-CH(CH(CH$_3$)$_2$)-C(=O)-O-R$^a$]$_x$ | 1 | Me | — |
| Ex. 279 | FIG 3 | Synthesized amino acid | 1,3,5-benzene-tris[CH(NH$_2$)-C(=O)-O-R$^a$] | — | Me | — |

TABLE 76

| | Starting material to conduct thermal decomposition and resultant isocyanate | | | |
|---|---|---|---|---|
| | Carbamate | Resultant isocyanate | Low-boiling solvent | High-boiling solvent |
| Ex. 274 | [R$^b$-O-C(=O)-CH$_2$-CH(NH-C(=O)-O-Ph)-C(=O)-O-R$^a$]$_x$ | [R$^b$-O-C(=O)-CH$_2$-CH(NCO)-C(=O)-O-R$^a$]$_x$ | Decamethyl-cyclopenta-siloxane | Poly-isocyanate comopound of Ref. Ex. 3 |

TABLE 76-continued

Starting material to conduct thermal decomposition and resultant isocyanate

| | Carbamate | Resultant isocyanate | Low-boiling solvent | High-boiling solvent |
|---|---|---|---|---|
| Ex. 275 | | | Xanthene | TPA |
| Ex. 276 | | | Chlorobenzene | TPA |
| Ex. 277 | | | Anisole | Polyisocyanate comopound of Ref. Ex. 4 |
| Ex. 278 | | | Ethyl phenyl sulfide | Polyisocyanate comopound of Ref. Ex. 3 |
| Ex. 279 | | | Benzyl toluene | TPA |

TABLE 77

| | Reactor | Amino acid, amino acid derivative | Formula of amino acid | x | Ra | Rb |
|---|---|---|---|---|---|---|
| Ex. 280 | FIG. 3 | Synthesized amino acid | ![structure: 2,7-diaminosuberic acid diester with R$^a$O-C(=O)-CH(NH$_2$)-(CH$_2$)$_4$-CH(NH$_2$)-C(=O)-OR$^a$] | — | Me | — |
| Ex. 281 | FIG. 3 | Synthesized amino acid | ![structure: chlorophenylglycine ester, Cl-C$_6$H$_4$-CH(NH$_2$)-C(=O)-O-R$^a$] | — | Me | — |
| Ex. 282 | FIG. 3 | Synthesized amino acid | ![structure: 3,4-dimethoxyphenylglycine ester] | — | Me | — |
| Ex. 283 | FIG. 3 | Synthesized amino acid | ![structure: C$_5$H$_{11}$-CH(NH$_2$)-C(=O)-O-R$^a$] | — | Me | — |
| Ex. 284 | FIG. 3 | Synthesized amino acid | ![structure: 3,4-methylenedioxyphenylglycine ester] | — | Me | — |
| Ex. 285 | FIG. 3 | Synthesized amino acid | ![structure: 4-isopropylphenylalanine ester] | — | Me | — |

TABLE 78

Starting material to conduct thermal decomposition and resultant isocyanate

| | Carbamate | Resultant isocyanate | Low-boiling solvent | High-boiling solvent |
|---|---|---|---|---|
| Ex. 280 | | | 1,3,5-triethyl benzene | TPA |
| Ex. 281 | | | p-xylene | Polyisocyanate comopound of Ref. Ex. 3 |
| Ex. 282 | | | Tetradecane | TPA |
| Ex. 283 | | | n-dodecane | TPA |
| Ex. 284 | | | Hexyl benzene | Polyisocyanate comopound of Ref. Ex. 4 |
| Ex. 285 | | | Ethyl phenyl sulfide | Polyisocyanate comopound of Ref. Ex. 2 |

TABLE 79

| | Reactor | Starting material to produce carbamate | | x | Ra | Rb |
|---|---|---|---|---|---|---|
| | | Amino acid, amino acid derivative | Formula of amino acid | | | |
| Ex. 286 | FIG. 3 | Synthesized amino acid | 1-naphthyl-CH(NH₂)-C(O)O-Rᵃ | — | Me | — |
| Ex. 287 | FIG. 3 | Synthesized amino acid | 1,2-C₆H₄[CH(NH₂)C(O)O-Rᵃ]₂ | — | Me | — |
| Ex. 288 | FIG. 3 | Synthesized amino acid | 2-furyl-CH(NH₂)-C(O)O-Rᵃ | — | Me | — |

TABLE 80

Starting material to conduct thermal decomposition and resultant isocyanate

| | Carbamate | Resultant isocyanate | Low-boiling solvent | High-boiling solvent |
|---|---|---|---|---|
| Ex. 286 | 1-naphthyl-CH(NHC(O)OPh)-C(O)O-Rᵃ | 1-naphthyl-CH(NCO)-C(O)O-Rᵃ | 1,3,5-triethyl benzene | Polyisocyanate compound of Ref. Ex. 3 |
| Ex. 287 | 1,2-C₆H₄[CH(NHC(O)OPh)C(O)O-Rᵃ]₂ | 1,2-C₆H₄[CH(NCO)C(O)O-Rᵃ]₂ | Decamethyl tetrasiloxane | TPA |

TABLE 80-continued

Starting material to conduct thermal decomposition and resultant isocyanate

| | Carbamate | Resultant isocyanate | Low-boiling solvent | High-boiling solvent |
|---|---|---|---|---|
| Ex. 288 | furan-CH(NHC(O)OPh)-C(O)O-R$^a$ | furan-CH(NCO)-C(O)O-R$^a$ | 4-methyl benzyl chloride | TPA |

TABLE 81

| | Formulation of starting material mixture (% by mass) | | | Temperature Condition (° C.) | | Thermal decomposition yield (%) |
|---|---|---|---|---|---|---|
| | Conc. of carbamate | Conc. of middle-boiling solvent | Conc. of high-boiling solvent | Temperature at first reactor | Temperature at second reactor | |
| Ex. 268 | 10 | 30 | 60 | 250 | 250 | 80 |
| Ex. 269 | 10 | 30 | 60 | 250 | 250 | 78 |
| Ex. 270 | 10 | 30 | 60 | 250 | 250 | 81 |
| Ex. 271 | 10 | 30 | 60 | 250 | 250 | 82 |
| Ex. 272 | 20 | 30 | 50 | 250 | 250 | 76 |
| Ex. 273 | 20 | 30 | 50 | 250 | 250 | 84 |
| Ex. 274 | 30 | 30 | 40 | 250 | 250 | 86 |
| Ex. 275 | 20 | 30 | 50 | 250 | 250 | 84 |
| Ex. 276 | 40 | 40 | 20 | 250 | 250 | 82 |
| Ex. 277 | 10 | 50 | 40 | 250 | 250 | 82 |
| Ex. 278 | 20 | 60 | 20 | 250 | 250 | 80 |
| Ex. 279 | 20 | 40 | 40 | 250 | 250 | 85 |
| Ex. 280 | 20 | 30 | 50 | 250 | 250 | 80 |
| Ex. 281 | 10 | 60 | 30 | 250 | 250 | 84 |
| Ex. 282 | 20 | 60 | 20 | 250 | 250 | 82 |
| Ex. 283 | 30 | 50 | 20 | 250 | 250 | 81 |
| Ex. 284 | 10 | 80 | 10 | 250 | 250 | 79 |
| Ex. 285 | 20 | 30 | 50 | 250 | 250 | 76 |
| Ex. 286 | 20 | 30 | 50 | 250 | 250 | 79 |
| Ex. 287 | 20 | 30 | 90 | 250 | 250 | 81 |
| Ex. 288 | 40 | 30 | 30 | 250 | 250 | 83 |

TABLE 82

| | | Starting material to produce carbamate | | Starting material to conduct thermal decomposition and resultant isocyanate | | | |
|---|---|---|---|---|---|---|---|
| Reactor | | Amino acid, amino acid derivative | Alkanol amine, Alcohol | Carbamate | Resultant isocyanate | Low-boiling solvent | High-boiling solvent |
| Ex. 289 | FIG. 3 | Lysine | EtOH | 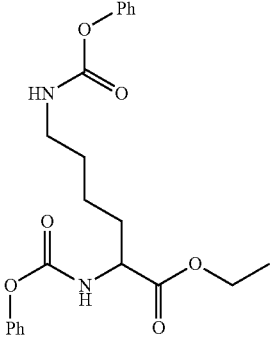 [SMILES: CCOC(=O)C(CCCCNC(=O)Oc1ccccc1)NC(=O)Oc1ccccc1] | 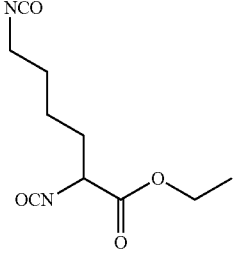 | n-pentadecane | TPA |
| Ex. 290 | FIG. 3 | Lysine | 1-amino-2-PrOH | 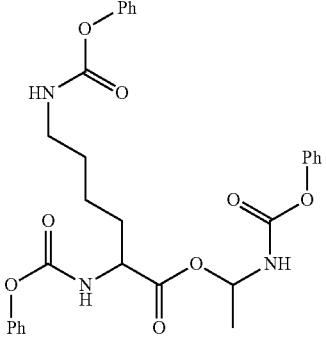 [SMILES: CC(NC(=O)Oc1ccccc1)OC(=O)C(CCCCNC(=O)Oc1ccccc1)NC(=O)Oc1ccccc1] | 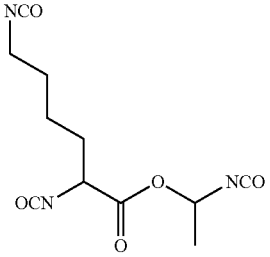 | 1-chlorododecane | TPA |
| Ex. 201 | FIG. 3 | Lysine | 2-amino-1-BuOH | 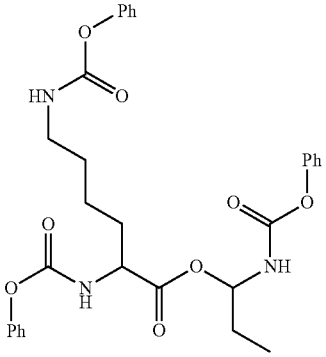 [SMILES: CCC(NC(=O)Oc1ccccc1)OC(=O)C(CCCCNC(=O)Oc1ccccc1)NC(=O)Oc1ccccc1] | 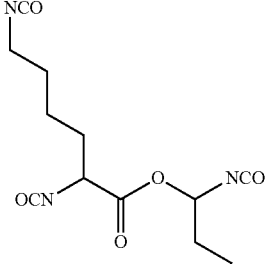 | Benzyl toluene | Polyisocyanate comopound of Ref. Ex. 2 |
| Ex. 292 | FIG. 3 | Lysine | Glycerin | 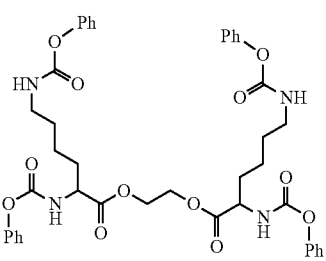 [SMILES: O=C(NCCCCC(NC(=O)Oc1ccccc1)C(=O)OCCOC(=O)C(CCCCNC(=O)Oc1ccccc1)NC(=O)Oc1ccccc1)Oc1ccccc1] | 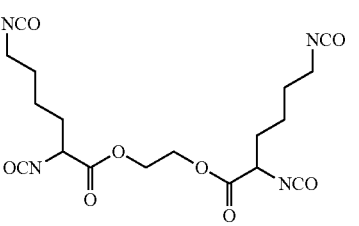 | 1,3,5-triethyl benzene | Polyisocyanate comopound of Ref. Ex. 2 |

TABLE 82-continued

| Reactor | | Starting material to produce carbamate | | Starting material to conduct thermal decomposition and resultant isocyanate | | | |
|---|---|---|---|---|---|---|---|
| | | Amino acid, amino acid derivative | Alkanol amine, Alcohol | Carbamate | Resultant isocyanate | Low-boiling solvent | High-boiling solvent |
| Ex. 293 | FIG. 3 | Lysine | Penta-erythritol | 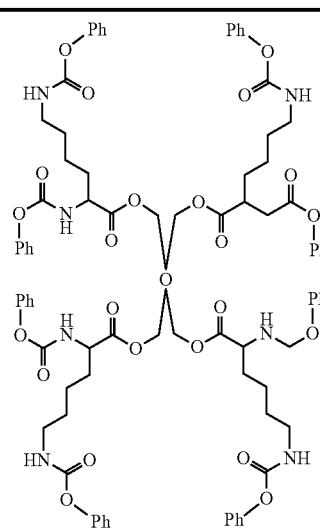 | 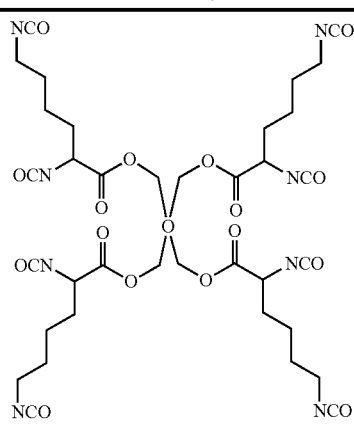 | Diethyl phthalate | TPA |

TABLE 83

| Reactor | | Starting material to produce carbamate | | Starting material to conduct thermal decomposition and resultant isocyanate | | | |
|---|---|---|---|---|---|---|---|
| | | Amino acid, amino acid derivative | Alkanol amine, Alcohol | Carbamate | Resultant isocyanate | Low-boiling solvent | High-boiling solvent |
| Ex. 294 | FIG. 3 | Ornithine | EtOH | 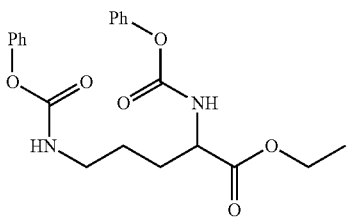 [SMILES: CCOC(=O)C(CCCNC(=O)Oc1ccccc1)NC(=O)Oc1ccccc1] | 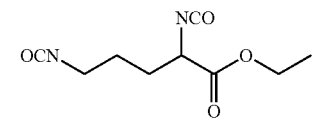 | n-dodecane | Polyisocyanate comopound of Ref. Ex. 4 |
| Ex. 295 | FIG. 3 | Ornithine | 1-amino-2-PrOH | 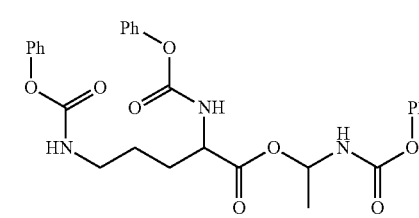 | 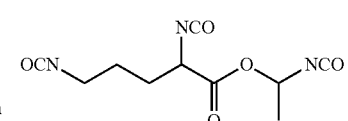 | Hexyl benzene | Polyisocyanate comopound of Ref. Ex. 2 |

TABLE 83-continued

| Re-actor | Starting material to produce carbamate | | Starting material to conduct thermal decomposition and resultant isocyanate | | | |
|---|---|---|---|---|---|---|
| | Amino acid, amino acid derivative | Alkanol amine, Alcohol | Carbamate | Resultant isocyanate | Low-boiling solvent | High-boiling solvent |
| Ex. 296 | FIG. 3 Ornithine | 2-amino-1-BuOH | | | Ethyl phenyl sulfide | TPA |
| Ex. 297 | FIG. 3 Ornithine | Glycerin | | | Trichlorobenzene | TPA |
| Ex. 298 | FIG. 3 Ornithine | Pentaerythritol | | | Triacetin | Polyisocyanate compound of Ref. Ex. 2 |
| Ex. 299 | FIG. 3 Methionine | EtOH | | | Diphenyl ether | Polyisocyanate compound of Ref. Ex. 4 |

TABLE 84

| Reactor | | Starting material to produce carbamate | | Starting material to conduct thermal decomposition and resultant isocyanate | | | |
|---|---|---|---|---|---|---|---|
| | | Amino acid, amino acid derivative | Alkanol amine, Alcohol | Carbamate | Resultant isocyanate | Low-boiling solvent | High-boiling solvent |
| Ex. 300 | FIG. 3 | Methionine | 1-amino-2-PrOH | 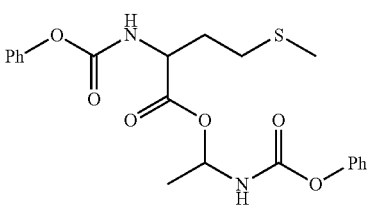 [SMILES: CSCCC(NC(=O)Oc1ccccc1)C(=O)OC(C)NC(=O)Oc1ccccc1] | 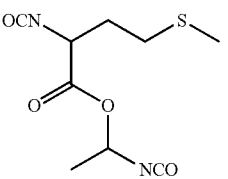 | Decamethyl cyclopentasiloxane | Polyisocyanate comopound of Ref. Ex. 3 |
| Ex. 301 | FIG. 3 | Methionine | 2-amino-1-BuOH | 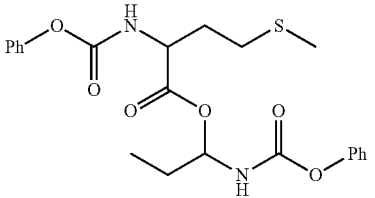 [SMILES: CCC(NC(=O)Oc1ccccc1)OC(=O)C(CCSC)NC(=O)Oc1ccccc1] | 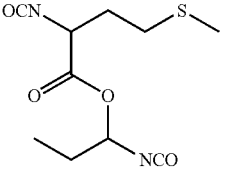 | Cyclododecane | Polyisocyanate comopound of Ref. Ex. 3 |
| Ex. 302 | FIG. 3 | Methionine | Glycerin | 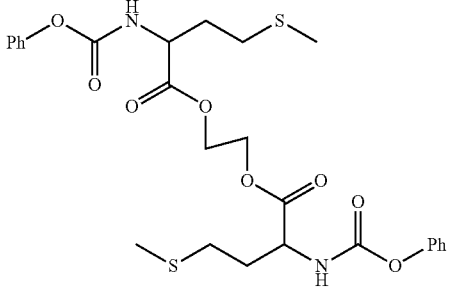 [SMILES: CSCCC(NC(=O)Oc1ccccc1)C(=O)OCCOC(=O)C(CCSC)NC(=O)Oc1ccccc1] | 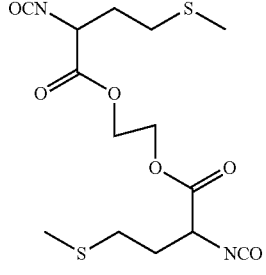 | Tetradecane | Polyisocyanate comopound of Ref. Ex. 2 |
| Ex. 303 | FIG. 3 | Methionine | Pentaerythritol | 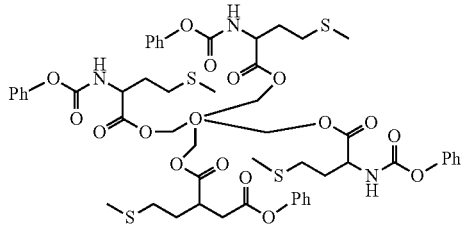 | 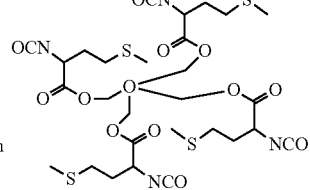 | Trichlorobenzene | Polyisocyanate comopound of Ref. Ex. 4 |
| Ex. 304 | FIG. 3 | Glutamic acid | EtOH | 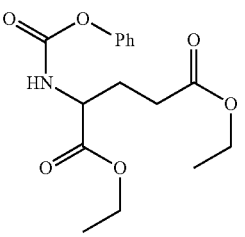 [SMILES: CCOC(=O)CCC(NC(=O)Oc1ccccc1)C(=O)OCC] | 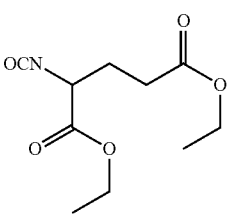 | 1,3,5-triethyl benzene | TPA |

TABLE 84-continued

| | Reactor | Starting material to produce carbamate | | Starting material to conduct thermal decomposition and resultant isocyanate | | Low-boiling solvent | High-boiling solvent |
|---|---|---|---|---|---|---|---|
| | | Amino acid, amino acid derivative | Alkanol amine, Alcohol | Carbamate | Resultant isocyanate | | |
| Ex. 305 | FIG. 3 | Glutamic acid | 1-amino-2-PrOH | (structure) | (structure) | n-pentadecane | Polyisocyanate compound of Ref. Ex. 2 |

TABLE 85

| | Reactor | Starting material to produce carbamate | | Starting material to conduct thermal decomposition and resultant isocyanate | | Low-boiling solvent | High-boiling solvent |
|---|---|---|---|---|---|---|---|
| | | Amino acid, amino acid derivative | Alkanol amine, Alcohol | Carbamate | Resultant isocyanate | | |
| Ex. 306 | FIG. 3 | Glutamic acid | 2-amino-1-BuOH | (structure) | (structure) | Triacetin | Polyisocyanate compound of Ref. Ex. 2 |
| Ex. 307 | FIG. 3 | Glutamic acid | Glycerin | (structure) | (structure) | Ethyl phenyl sulfide | TPA |

TABLE 85-continued

| | | Starting material to produce carbamate | | Starting material to conduct thermal decomposition and resultant isocyanate | | | |
|---|---|---|---|---|---|---|---|
| Reactor | FIG. | Amino acid, amino acid derivative | Alkanol amine, Alcohol | Carbamate | Resultant isocyanate | Low-boiling solvent | High-boiling solvent |
| Ex. 308 | FIG. 3 | Glutamic acid | Pentaerythritol | | | Thioanisole | TPA |
| Ex. 309 | FIG. 3 | Lysine | Monoethanolamine | | | Dibenzyl ether | TKA-100 |
| Ex. 310 | FIG. 3 | Lysine | Monoethanolamine | | | Dibenzyl ether | 24A-100 |
| Ex. 311 | FIG. 3 | Lysine | Monoethanolamine | | | Dibenzyl ether | TLA-100 |

TABLE 86

| Reactor | Starting material to produce carbamate | | Starting material to conduct thermal decomposition and resultant isocyanate | | Low-boiling solvent | High-boiling solvent |
|---|---|---|---|---|---|---|
| | Amino acid, amino acid derivative | Alkanol amine, Alcohol | Carbamate | Resultant isocyanate | | |
| Ex. 312 | FIG. 2 / Ornithine | Monoethanolamine | (structure) | (structure) | Diethyl phthalate | TKA-100 |
| Ex. 313 | FIG. 2 / Ornithine | Monoethanolamine | (structure) | (structure) | Diethyl phthalate | 24A-100 |
| Ex. 314 | FIG. 2 / Ornithine | Monoethanolamine | (structure) | (structure) | Diethyl phthalate | TLA-100 |
| Ex. 315 | FIG. 3 / Methionine | Monoethanolamine | (structure) | (structure) | Tetradecane | TKA-100 |
| Ex. 316 | FIG. 3 / Methionine | Monoethanolamine | (structure) | (structure) | Tetradecane | 24A-100 |

TABLE 86-continued

| Reactor | Starting material to produce carbamate | | | Starting material to conduct thermal decomposition and resultant isocyanate | | Low-boiling solvent | High-boiling solvent |
|---|---|---|---|---|---|---|---|
| | Amino acid, amino acid derivative | Alkanol amine, Alcohol | Carbamate | | Resultant isocyanate | | |
| Ex. 317 | FIG. 3 | Methionine | Monoethanol amine | *(structure)* | *(structure)* | Tetradecane | TLA-100 |
| Ex. 318 | FIG. 3 | Glutamic acid | Monoethanol amine | *(structure)* | *(structure)* | Xanthene | TKA-100 |
| Ex. 319 | FIG. 3 | Glutamic acid | Monoethanol amine | *(structure)* | *(structure)* | Xanthene | 24A-100 |
| Ex. 320 | FIG. 3 | Glutamic acid | Monoethanol amine | *(structure)* | *(structure)* | Xanthene | TLA-100 |

TABLE 87

| | Formulation of starting material mixture (% by mass) | | | Temperature Condition (° C.) | | Thermal decomposition yield (%) |
|---|---|---|---|---|---|---|
| | Conc. of carbamate | Conc. of middle-boiling solvent | Conc. of high-boiling solvent | Temperature at first reactor | Temperature at second reactor | |
| Ex. 289 | 50 | 40 | 10 | 250 | 250 | 85 |
| Ex. 290 | 20 | 30 | 50 | 250 | 250 | 84 |
| Ex. 291 | 20 | 30 | 50 | 250 | 250 | 84 |
| Ex. 292 | 10 | 40 | 50 | 250 | 250 | 85 |
| Ex. 293 | 30 | 50 | 20 | 250 | 250 | 85 |
| Ex. 294 | 20 | 30 | 50 | 250 | 250 | 88 |
| Ex. 295 | 20 | 30 | 50 | 250 | 250 | 85 |
| Ex. 296 | 20 | 30 | 50 | 250 | 250 | 84 |
| Ex. 297 | 20 | 30 | 50 | 250 | 250 | 77 |

TABLE 87-continued

| | Formulation of starting material mixture (% by mass) | | | Temperature Condition (° C.) | | Thermal |
|---|---|---|---|---|---|---|
| | Conc. of carbamate | Conc. of middle-boiling solvent | Conc. of high-boiling solvent | Temperature at first reactor | Temperature at second reactor | decomposition yield (%) |
| Ex. 298 | 20 | 30 | 50 | 250 | 250 | 83 |
| Ex. 299 | 20 | 30 | 50 | 250 | 250 | 79 |
| Ex. 300 | 20 | 30 | 50 | 250 | 250 | 82 |
| Ex. 301 | 20 | 30 | 50 | 250 | 250 | 86 |
| Ex. 302 | 20 | 30 | 50 | 250 | 250 | 84 |
| Ex. 303 | 30 | 40 | 30 | 250 | 250 | 83 |
| Ex. 304 | 10 | 60 | 30 | 250 | 250 | 80 |
| Ex. 305 | 40 | 30 | 30 | 250 | 250 | 81 |
| Ex. 306 | 20 | 30 | 50 | 250 | 250 | 85 |
| Ex. 307 | 30 | 50 | 20 | 250 | 250 | 84 |
| Ex. 308 | 20 | 30 | 50 | 250 | 250 | 84 |
| Ex. 309 | 10 | 60 | 30 | 250 | 250 | 81 |
| Ex. 310 | 10 | 60 | 30 | 250 | 250 | 84 |
| Ex. 311 | 10 | 60 | 30 | 250 | 250 | 87 |
| Ex. 312 | 10 | 60 | 30 | 250 | 250 | 81 |
| Ex. 313 | 10 | 60 | 30 | 250 | 250 | 82 |
| Ex. 314 | 10 | 60 | 30 | 250 | 250 | 82 |
| Ex. 315 | 10 | 60 | 30 | 250 | 250 | 86 |
| Ex. 316 | 10 | 60 | 30 | 250 | 250 | 82 |
| Ex. 317 | 10 | 60 | 30 | 250 | 250 | 85 |
| Ex. 318 | 10 | 60 | 30 | 250 | 250 | 81 |
| Ex. 319 | 10 | 60 | 30 | 250 | 250 | 88 |
| Ex. 320 | 10 | 60 | 30 | 250 | 250 | 87 |

TABLE 88

| | | Starting material to produce carbamate | | | | | Starting material to conduct thermal decomposition and resultant isocyante | |
|---|---|---|---|---|---|---|---|---|
| | Reactor | Amino acid, amino acid derivative | Amino acid formula | x | $R^a$ | $R^b$ | Carbamate | Resultant isocyanate |
| Ex. 321 | FIG. 1 | Synthesized amino acid | $\left[ R^a {-} \underset{NH_2}{\overset{}{CH}} {-} \overset{O}{\underset{}{C}} {-} O {-} R^b \right]_x$ | 2 | Me | —(CH2)2— | $\left[ R^a {-} \underset{NH}{\overset{}{CH}} {-} \overset{O}{\underset{}{C}} {-} X {-} R^b \right]_x$ $O{=}\underset{O}{\overset{}{C}}{-}Ph$ | $\left[ R^a {-} \underset{NCO}{\overset{}{CH}} {-} \overset{O}{\underset{}{C}} {-} X {-} R^b \right]_x$ |

| | Starting material to conduct thermal decomposition and resultant isocyanate | | Formulation of starting material mixture (% by mass) | | | Temperature Condition (° C.) | | Thermal |
|---|---|---|---|---|---|---|---|---|
| | Low-boiling solvent | High-boing solvent | Conc. of carbamate | Conc. of low-boiling solvent | Conc. of high-boiling solvent | Temperature at first reactor | Temperature at second reactor | decomposition yield (%) |
| Ex. 321 | ODB | TPA | 10 | 60 | 30 | 250 | 250 | 75 |

As shown in the results, in the case where the present invention was adopted, a lysine ester triisocyanate could be continuously and stably prepared without generating by-products, as shown in Example 1. In contrast, in the case where the present invention was not adopted, by-products were generated and continuous production was difficult, as shown in Comparative Example 1.

INDUSTRIAL APPLICABILITY

According to the present invention, a method for producing an isocyanate continuously while suppressing a side reaction is provided.

DESCRIPTION OF THE REFERENCE NUMERALS

1: starting material preheater, 2: tubular first reactor, 3: tank second reactor, 4: partial condenser, 10: first line, 11: eighth line, 12: second line, 13: third line, 14: fourth line, 15: fifth line, 16: sixth line, 17: seventh line, 20: tenth line, 21: eleventh line, 22: twelfth line, 23: thirteenth line, 24: fourteenth line, 25: fifteenth line, 26: sixteenth line, 27: seventeenth line, 100: reactor, 101: first storage tank, 102: second storage tank, 103: third storage tank, 104: fourth storage tank, 105: fifth storage tank, 106: first packed-bed, 107: second packed-bed, 108: third packed-bed, 109: first solution-sending pump, 110: second solution-sending pump, 111: third solution-sending pump, 112: fourth solution-sending pump, 113: first partial condenser, 114: second partial condenser, 115: third partial condenser, 116: fifth solution-sending pump, 200: falling-film type reactor, 201: tenth storage tank, 202: eleventh storage tank, 203: twelfth storage tank, 204: thirteenth storage tank, 205: fourth partial condenser, 206: reboiler, 207: sixth solution-sending pump, 208: seventh solution-sending pump, 209: eighth solution-sending pump, 210: packed column

The invention claimed is:

1. An isocyanate production method in which an isocyanate is produced by thermal decomposition of a carbamate, comprising:
   a step of preparing a mixture liquid comprising the carbamate and a polyisocyanate compound;
   a step of conducting a thermal decomposition reaction of the carbamate by continuously introducing the mixture liquid into a thermal decomposition reactor:
   a step of collecting a low-boiling decomposition product by continuously extracting the low-boiling decomposition product in a gaseous state from the thermal decomposition reactor, the low-boiling decomposition product having a standard boiling point lower than the polyisocyanate compound and comprising the isocyanate; and
   a step of collecting a high-boiling component by continuously extracting, from the thermal decomposition reactor, a liquid phase component which is not collected in a gaseous state at the step of collecting the low-boiling decomposition product, as the high-boiling component.

2. The isocyanate production method according to claim 1, wherein the mixture liquid comprises an inactive solvent, the inactive solvent is continuously extracted in a gaseous state from the thermal decomposition reactor together with the low-boiling decomposition product having a boiling point lower than the polyisocyanate compound in the step of collecting the low-boiling decomposition product, and the inactive solvent is substantially inactive under thermal decomposition reaction conditions, and has a boiling point between a boiling point of the isocyanate produced by thermal decomposition and a boiling point of a hydroxy compound.

3. The method according to claim 1, wherein the carbamate is a carbamate of formula (20):

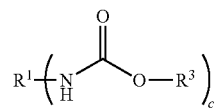

(20)

in the formula (20),
c represents an integer of 1 or more,
$R^1$ represents an aliphatic hydrocarbon group, an aromatic hydrocarbon group, or a group formed by bonding a single or plural of aliphatic hydrocarbon groups and/or aromatic hydrocarbon groups via an ether bond (—O—), a thioether bond (—S—), an ester bond (COO—), or an amide bond (—CONH—),
$R^3$ represents a C1-20 aliphatic hydrocarbon group or a C6-20 aromatic group, and plural $R^3$ are identical to or different from each other.

4. The method according to claim 1, wherein the thermal decomposition reactor is a tubular reactor.

5. The method according to claim 1, further comprising a step in which the low-boiling decomposition product is supplied in a gaseous state to a distillation column and the isocyanate is separated in the distillation column.

6. The method according to claim 2, wherein the step of conducting the thermal decomposition reaction comprises:
   a step of preparing the liquid phase component in which the mixture liquid is continuously introduced into a first reactor comprising a vertical tubular reactor to conduct a first decomposition reaction while allowing the mixture liquid to fall down inside the first reactor, and the liquid phase component is obtained from a bottom of the first reactor; and
   a decomposition step in which the liquid phase component is introduced into a second reactor comprising a tank reactor and a second decomposition reaction is conducted to decompose the carbamate into the isocyanate and a hydroxy compound;
   wherein, in the step of collecting the low-boiling decomposition product, the low-boiling decomposition product is extracted continuously in a gaseous state from the first reactor or both the first reactor and the second reactor,
   in the step of collecting the high-boiling component, the liquid phase component comprises a high-boiling decomposition product having a standard boiling point higher than a standard boiling point of the low-boiling decomposition product, and the high-boiling decomposition product is extracted continuously from the second reactor together with the polyisocyanate compound,
   the isocyanate is further comprised in the high-boiling decomposition product, and
   a difference between a temperature in the first reactor and a temperature in the second reactor is 50° C. or lower.

7. The isocyanate production method according to claim 6, further comprising a recycle step in which, in the step of collecting the low-boiling decomposition product, an inactive solvent vapor is extracted continuously in a gaseous state together with the low-boiling decomposition product from the first reactor or both the first reactor and the second reactor, the gas component extracted continuously is introduced into a partial condenser in which a temperature thereof is maintained at a temperature which allows partial or entire condensation of the inactive solvent vapor but does not allow partial or entire condensation of the low-boiling decomposition product to separate the gas component into a gaseous component mainly comprising the low-boiling decomposition product and a liquid-form component mainly comprising the inactive solvent, and then the liquid-form component is partially or entirely returned to the first reactor or both the first reactor and the second reactor.

8. The isocyanate production method according to claim 7, wherein a tubular reactor, an inside of which is filled with either a solid filler content or a solid catalyst or both thereof, is used as the first reactor.

9. The isocyanate production method according to claim 7, wherein a tubular reactor in which a tray is placed is used as the first reactor.

10. The isocyanate production method according to claim 7, wherein a tubular reactor in which a tray is placed, the tubular reactor being filled with either a solid filler content or a solid catalyst or both thereof, is used as the first reactor.

11. The isocyanate production method according to claim 6, wherein the gas component generated in the second reactor is introduced into the first reactor from a bottom thereof.

12. The isocyanate production method according to claim 6, wherein a carrier agent in a gaseous state, which is substantially inactive under thermal decomposition reaction conditions, is introduced into either the first reactor or the second reactor or both thereof from a bottom thereof, and a gas component is extracted from a top thereof.

13. The isocyanate production method according to claim 12, wherein the carrier agent is introduced into a liquid in the second reactor.

14. The method according to claim 3, wherein $R^1$ is the aliphatic hydrocarbon group having 3 to 85 carbon atoms.

15. The method according to claim 3, wherein $R^1$ is the aromatic hydrocarbon group having 6 to 20 carbon atoms.

16. The method according to claim 3, wherein $R^1$ is the group formed by bonding a single or plural of aliphatic hydrocarbon groups and/or aromatic hydrocarbon groups via an ether bond (—O—), a thioether bond (—S—), an ester bond (COO—), or an amide bond (—CONH—).

17. The method according to claim 16, wherein $R^1$ is a group represented by formula (20-1) or (20-2) when c is 1:

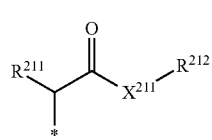
(20-1)

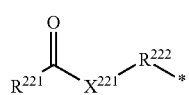
(20-2)

wherein:
$R^{211}$, $R^{212}$, $R^{221}$, and $R^{222}$ each independently represent an oxygen atom or a secondary amino group (—NH—).

18. The method according to claim 16, wherein $R^1$ is a group represented by formula (20-3), (20-4), (20-5), or (20-6) when c is 2:

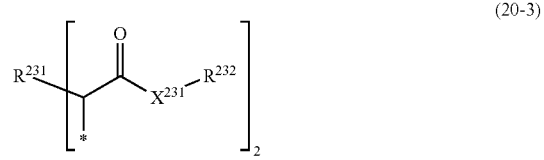
(20-3)

(20-4)

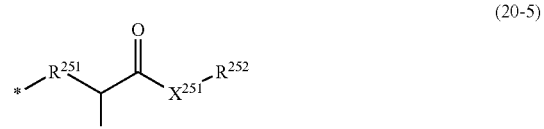
(20-5)

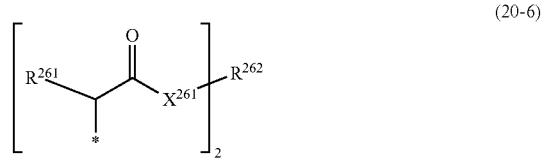
(20-6)

wherein:
$R^{231}$, $R^{232}$, $R^{241}$, $R^{242}$, $R^{251}$, $R^{252}$, $R^{261}$, and $R^{262}$ each independently represent an oxygen atom or a secondary amino group (—NH—).

19. The method according to claim 16, wherein $R^1$ is a group represented by formula (20-7), (20-8), or (20-9) when c is 3:

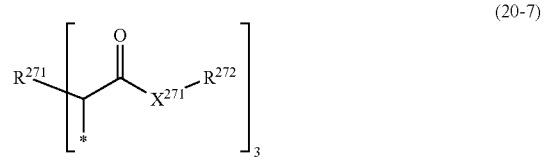
(20-7)

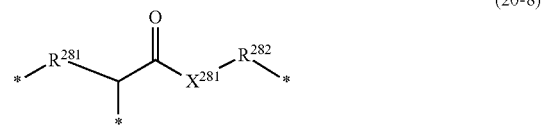
(20-8)

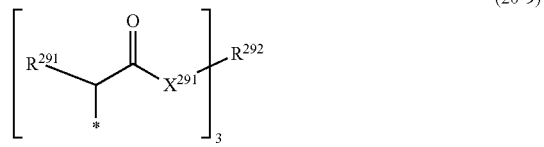
(20-9)

wherein:
$R^{271}$, $R^{272}$, $R^{281}$, $R^{282}$, $R^{291}$, and $R^{292}$ each independently represent an oxygen atom or a secondary amino group (—NH—).

* * * * *